US009486506B2

(12) United States Patent
Lau et al.

(10) Patent No.: US 9,486,506 B2
(45) Date of Patent: *Nov. 8, 2016

(54) GLUCAGON ANALOGUES

(71) Applicant: Novo Nordisk A/S, Bagsvaerd (DK)

(72) Inventors: Jesper F. Lau, Farum (DK); Thomas Kruse, Herlev (DK); Henning Thoegersen, Farum (DK); Ulrich Sensfuss, Copenhagen V (DK); Peter Kresten Nielsen, Holte (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/629,682

(22) Filed: Feb. 24, 2015

(65) Prior Publication Data

US 2015/0182594 A1 Jul. 2, 2015

Related U.S. Application Data

(63) Continuation of application No. 13/937,674, filed on Jul. 9, 2013, which is a continuation of application No. 13/624,387, filed on Sep. 21, 2012, now Pat. No. 8,541,368.

(60) Provisional application No. 61/539,148, filed on Sep. 26, 2011.

(30) Foreign Application Priority Data

Sep. 23, 2011 (EP) .................................. 11182476

(51) Int. Cl.
A61K 38/26 (2006.01)
A61K 38/00 (2006.01)
C07K 14/605 (2006.01)

(52) U.S. Cl.
CPC ............... *A61K 38/26* (2013.01); *A61K 38/00* (2013.01); *C07K 14/605* (2013.01)

(58) Field of Classification Search
CPC .................................................... A61K 38/26
See application file for complete search history.

(56) References Cited

U.S. PATENT DOCUMENTS

| | | | |
|---|---|---|---|
| 4,356,170 A | 10/1982 | Jennings et al. |
| 5,424,286 A | 6/1995 | Eng |
| 5,932,462 A | 8/1999 | Harris et al. |
| 7,157,277 B2 | 1/2007 | DeFrees et al. |
| 7,314,859 B2 | 1/2008 | Green et al. |
| 2007/0105755 A1 | 5/2007 | DeFrees et al. |
| 2013/0288958 A1 | 10/2013 | Lau et al. |
| 2015/0274801 A1 | 10/2015 | Lau et al. |
| 2015/0374794 A1 | 12/2015 | Sensfuss et al. |
| 2016/0002311 A1 | 1/2016 | Lau et al. |

FOREIGN PATENT DOCUMENTS

| | | |
|---|---|---|
| AU | 2011231503 A1 | 9/2012 |
| JP | H03254692 A | 11/1991 |
| JP | H09-510438 A | 10/1997 |
| WO | 9629342 A1 | 9/1996 |
| WO | 9808871 A1 | 3/1998 |
| WO | 03/031464 A2 | 4/2003 |
| WO | 03/062290 A1 | 7/2003 |
| WO | 2005/012347 A2 | 2/2005 |
| WO | 2005/016974 A1 | 2/2005 |
| WO | 2006/053299 A2 | 5/2006 |
| WO | 2006/090119 A1 | 8/2006 |
| WO | 2006097536 A2 | 9/2006 |
| WO | 2006/103298 A2 | 10/2006 |
| WO | 2006/134148 A2 | 12/2006 |
| WO | 2007/056362 A2 | 5/2007 |
| WO | 2007/087711 A1 | 8/2007 |
| WO | 2007/126808 A1 | 11/2007 |
| WO | 2008/011633 A2 | 1/2008 |
| WO | 2008/074032 A1 | 6/2008 |
| WO | 2008/086086 A2 | 7/2008 |
| WO | 2008/101017 A2 | 8/2008 |
| WO | 2008/151258 | 12/2008 |
| WO | 2008/151448 A1 | 12/2008 |
| WO | 2008/152403 A1 | 12/2008 |
| WO | 2009/030771 A1 | 3/2009 |
| WO | 2009033738 A2 | 3/2009 |
| WO | 2009/062100 A1 | 5/2009 |
| WO | 2009/089396 | 7/2009 |
| WO | 2009/108806 A1 | 9/2009 |
| WO | 2009/155257 A1 | 12/2009 |
| WO | 2009155258 A2 | 12/2009 |
| WO | 2010011439 A2 | 1/2010 |

(Continued)

OTHER PUBLICATIONS

Groner et al., Journal of Thrombosis and Haemostasis, "Abstracts From XXII ISTH Congress", 2009, vol. 7, No. SUPPL2, pp. 508-517.
Angata et al., Journal of Biological Chemistry, "ST8SIA II and ST8SIA IV Polysialyltransferases Exhibit Marked Differences in Utilizing Various Acceptors Containing Oligosialic Acid and Short Polysialic Acid", 2002, vol. 277, No. 39, pp. 36808-36817.
Bonora et al., Post-translational Modification of Protein Biopharmaceuticals, "Engineering in a PTM: Pegylation.", 2009, pp. 341-357.
"Cho, JW. et al., Proceedings of the National Academy of Sciences of the United Sta, "Polysialic Acid Engineering: Synthesis of Polysialylated Neoglycosphingolipids by Using the Polysialyltransferase From Neuroinvasive *Escherichia coli* K1", 1994, vol. 91, No. 24, pp. 11427-11431".

(Continued)

*Primary Examiner* — Gyan Chandra
(74) *Attorney, Agent, or Firm* — Leon Y. Lum

(57) ABSTRACT

The present invention relates to novel glucagon peptides, to the use of said glucagon peptides in therapy, to methods of treatment comprising administration of said glucagon peptides to patients in need thereof, and to the use of said glucagon peptides in the manufacture of medicaments. The glucagon peptides of the present invention are of particular interest in relation to the treatment of hyperglycemia, diabetes and obesity, as well as a variety of diseases or conditions associated with hyperglycemia, diabetes and obesity.

17 Claims, 2 Drawing Sheets

(56) References Cited

FOREIGN PATENT DOCUMENTS

| WO | 2010/014708 A2 | 2/2010 |
|---|---|---|
| WO | 2010016940 A2 | 2/2010 |
| WO | 2010/045568 A1 | 4/2010 |
| WO | 2010070251 A1 | 6/2010 |
| WO | 2010070252 A1 | 6/2010 |
| WO | 2010070253 A1 | 6/2010 |
| WO | 2010070255 A1 | 6/2010 |
| WO | 2010/102886 A1 | 9/2010 |
| WO | 2010148089 A1 | 12/2010 |
| WO | 2011006497 A1 | 1/2011 |
| WO | 2011075393 A2 | 6/2011 |
| WO | 2011/117416 A1 | 9/2011 |
| WO | 2011117415 A1 | 9/2011 |
| WO | 2011117417 A1 | 9/2011 |
| WO | 2011119657 A1 | 9/2011 |
| WO | 2011160630 A2 | 12/2011 |
| WO | 2011160633 A1 | 12/2011 |
| WO | 2011163473 A1 | 12/2011 |
| WO | 2012088116 A2 | 6/2012 |
| WO | 2012088379 A2 | 6/2012 |
| WO | 2012098462 A1 | 7/2012 |
| WO | 2012130866 A1 | 10/2012 |
| WO | 2012138941 A1 | 10/2012 |
| WO | 2012150503 A2 | 11/2012 |
| WO | 2012158962 A2 | 11/2012 |
| WO | 2012158965 A2 | 11/2012 |
| WO | 2012169798 A2 | 12/2012 |
| WO | 2012177443 A2 | 12/2012 |
| WO | 2012177444 A2 | 12/2012 |
| WO | 2013041678 A1 | 3/2013 |

OTHER PUBLICATIONS

Eckhardt et al., Nature, "Molecular Characterization of Eukaryotic Polysialyltransferase-1", 1995, vol. 373, pp. 715-718.

"Fernandes et al., Biochimica Et Biophysica Acta, "Synthesis, Characterization and Properties of Sialylated Catalase Synthesis, Characterization and Properties of Sialylated Catalase", 1996, vol. 1293, pp. 90-96".

Fontana et al., Advanced Drug Delivery Reviews, "Site-Specific Modification and Pegylation of Pharmaceutical Proteins Mediated by Transglutaminase", 2008, vol. 60, No. 1, pp. 13-28.

Gilbert et al., Journal of Biological Chemistry, "The Genetic Bases for the Variation in the Lipo-Oligosaccharide of the Mucosal Pathogen, Campylobacter jejuni", 2002, vol. 277, No. 1, pp. 327-337.

Glabe et al., Journal of Biological Chemistry, "Glycosylation of Ovalbumin Nascent Chains", 1980, vol. 255, No. 19, pp. 9236-9242.

Graham et al, Journal of General Virology, "Characteristics of a Human Cell Line Transformed by DNA From Human Adenovirus Type 5", 1977, vol. 36, pp. 59-72.

Gregoriadis et al., S.T.P. Pharma Sciences, "Polysialylated Proteins: An Approach to Improve Enzyme Stability and Half-Life in the Blood Circulation", 1999, vol. 9, No. 1, pp. 61-66.

Higuchi et al., Genomics, "Characterization of Mutations in the Factor VIII Gene by Direct Sequencing of Amplified Genomic DNA", 1990, vol. 6, No. 1, pp. 65-71.

Jain S et al, BBA—General Subjects, Elsevier Science Publishers, NL, "Polysialylated Insulin: Synthesis, Characterization and Biological Activity In Vivo", 2003, vol. 1622, No. 1, pp. 42-49.

Jennings and Lugowski, Journal of Immunology, "Immunochemistry of Groups A, B, and C Meningococcal Polysaccharide-Tetanus Toxoid Conjugates", 1981, vol. 127, No. 3, pp. 1011-1018.

Julenius, K. et al., Bioinformatics for Glycobiology and Glycomics:, "Prediction of Glycosylation Sites in Proteins", 2009, pp. 163-185.

Karin Julenius et al., Glycobiology, "Prediction, Conservation Analysis, and Structural Characterization of Mammalian Mucin-Type O-Glycosylation Sites", 2004, vol. 15, No. 2, pp. 153-164.

Kiely et al., Journal of Biological Chemistry, "Studies on the Attachement of Carbohydrate to Ovalbumin Nascent Chains in Hen Oviduct", 1976, vol. 251, No. 18, pp. 5490-5495.

Kojima et al., FEBS Letters, "A Developmentally Regulated Member of the Sialyltransferase Family (ST8SIA II, STX) Is a Polysialic Acid Synthase", 1995, vol. 373, No. 2, pp. 119-122.

"Kunou M. et al., Biomacromolecules., "Synthesis of Sulfated Colominic Acids and Their Nteraction With Fibroblast Growth Factors", 2000, vol. 1, No. 3, pp. 451-458".

"Nakayama et al., Proceedings of the National Academy of Sciences of the USA, "Expression Cloning of a Human Polysialyltransferase That Forms the Polysialylated Neural Cell Adhesion Molecule Present in Embryonic Brain", 1995, vol. 92, No. 15, pp. 7031-7035".

P. J. Lenting et al., Haemophilia, "Factor VIII and Von Willebrand Factor—Too Sweet for Own Good", 2010, vol. 16, No. 5, pp. 194-199.

Saenko E L et al, Haemophilia, "Strategles Towards a Longer Acting Factor VIII", 2006, vol. 12, No. 3, pp. 42-51.

"Scheidegger et al., Journal of Biological Chemistry, "A Human STX CDNA Confers Polysialic Acid Expression in Mammalian Cells", 1995, vol. 270, No. 39, pp. 22685-22688".

Thim L, et al., Haemophilia, "Purification and Characterization of a New Recombinant Factor VIII(N8)", 2010, vol. 16, No. 2, pp. 349-359.

Urlaub G. et al, Somatic Cell and Molecular Genetics, "Effect of Gamma Rays at the Dihydrofolate Reductase Locus: Deletions and Inversions", 1986, vol. 12, No. 6, pp. 555-566.

Urlaub et al, Proceedings of the National Academy of Sciences of the USA, "Isolation of Chinese Hamster Cell Mutants Deficient in Dihydrofolate Reductase Activity", 1980, vol. 77, No. 7, pp. 4216-4220.

"Urlaub, Gail et al., Cell, "Deletion of the Diploid Dihydrofolate Reductase Locus From Cultured Mammalian Cells", 1983, vol. 33, No. 2, pp. 405-412".

Veronese et al, Journal of Bioactive and Compatible Polymers, "Branched and Linear Poly(Ethylene Glycol): Influence of the Polymer Structure on Enzymological, Pharmacokinetic, and Immunological Properties of Protein Conjugates", 1997, vol. 12, No. 3, pp. 196-207.

Veronese et al., Advanced Drug Delivery Reviews, "Introduction and Overview of Peptide and Protein Pegylation", 2002, vol. 54, pp. 453-456.

Waechter et al, Proceedings of the National Academy of Sciences of the USA, "Effect of Methylation on Expression of Microinjected Genes", 1982, vol. 79, pp. 1106-1110.

Willis et al., Glycobiology, "Characterization of the ¿ -2,8-Polysialyltransferase From Neisseria Meningitidis With Synthetic Acceptors, and the Development of a Self-Priming Polysialyltransferase Fusion Enzyme", 2008, vol. 18, No. 2, pp. 177-186.

Haack et al., "Analysis of Expression Kinetics and Activity of a New B-Domain Truncated and Full-Lenth FVIII Protein in Three Different Cell Lines," Ann Hematol, 1999, vol. 78, pp. 111-116.

Nakayama et al., "Expression Cloning of a Human Polysialyltransferase That Forms the Polysialylated Neural Cell Adhesion Molecule Present in Embryonic Brain," PNAS, 1995, vol. 92, No. 15, pp. 7031-7035.

Harduin-Lepers A et al. Biochemistry. "The Human Sialyltransferase Family" 2001. vol. 83(8) pp. 727-737.

Habegger et al., "The Metabolic Action of Glucagon Revisited," Naturel Reviews Endocrinology, vol. 6, pp. 689-697 (2010).

Nielsen et al., "Effect of Environmental Factors on the Kinetics," Biochemistry, vol. 40(20), pp. 6036-6046 (2001).

LeVine III, Harry, "Quantification of B-Sheet Amyloid Fibril," Methods in Enzymology, vol. 309, pp. 274-284 (1999).

Naiki et al., "Fluorometric Determination of Amyloid Fibril in . . . " Analytical Biochemistry, vol. 177(2), pp. 244-249 (1989).

Remington's Pharmaceutical Sciences: The Sciences (1995).

Berge et al., Pharmaceutical Salts, Journal of Pharmaceutical Salts, vol. 66(1), pp. 1-19 (1977).

(56) References Cited

OTHER PUBLICATIONS

Beaven et al., "Formations and Structure of Gels and Fibrils From . . . " European Journal of Biochemistry, vol. 11(1), pp. 37-42 (1969).
Schade & Eaton, "Modulation of the Catabolic Activity of Glucagon," Acta Diabetologica, vol. 14, pp. 62-72 (1977).
John Wilding. BMJ. "Science, Medecine and the Future Obesity Treatment." 1997. vol. 315. pp. 997-1000.
Bray et al. Nature. "Medicinal Strategies in the Treatment of Obesity." 2000. vol. 404. pp. 672-677.
Habegger et al. Natural Reviews of Endocrinology. "The Metabolic Actions of Glucagon Revisited." 2010. vol. 6. pp. 689-697.
Nielsen et al. Biochemistry. "Effect of Environmental Factors on the Kinetics of Insulin Fibril Formation:¿ Elucidation of the Molecular Mechanism." 2001. vol. 40(20). pp. 6036-6046.
LeVine III, Harry. Methods in Enzymology. "Quantification of B-Sheet Amyloid Fibril Structures With Thioflavin T." 1999. vol. 309. pp. 274-284.
Naiki et al. Analytical Biochemistry. "Fluorometric Determination of Amyloid Fibrils In Vitro Using the Fluorescent Dye, Thioflavine T." 1989. vol. 177(2). pp. 244-249.
Remington's Pharmaceutical Sciences: The Science and Practice of Pharmacy, 19th Edition. 1995.
Berge et al. Journal of Pharmceutical Sciences. "Pharmaceutical Salts." 1977. vol. 66(1). pp. 1-19.
Beaven et al. European Journal of Biochemistry. "Formation and Structure of Gels and Fibrils From Glucagon." 1969. vol. 11(1). pp. 37-42.
Schade & Eaton. Acta Diabetologica. "Modulation of the Catabolic Activity of Glucagon by Endogenous Insulin Secretion in Obese Man." 1977. vol. 14. pp. 62-72.
Moran TH, Gut peptides in the control of food intake, International Journal of Obesity, 2009, vol. 33, pp. S7-S10.
Dakin C. L. et al., Oxyntomodulin Inhibits Food Intake in the Rat, Endocrinology, 2001, vol. 142, No. 10, pp. 4244-4250.
Sherwin R. S. et al., Hyperglucagonemia and blood glucose regulation in normal, obese and diabetic subjects, The New England Journal of Medicine, 1976, vol. 294, No. 9, pp. 455-461.
Cho Min Y. et al., Targeting the glucagon receptor family for diabetes and obesity therapy, Pharmacology & Therapeutics, 2012, vol. 135, No. 3, pp. 247-278.
Dan Donnelly, The structure and function of the glucagon-like peptide-1 receptor and its ligands, British Journal of Pharmacology, 2012, vol. 166, No. 1, pp. 27-41.
Hongxiang H. et al., Structure and function studies of glucagon-like peptide-1 (GLP-1): the designing of a novel pharmacological agent for the treatment of diabetes, Diabetes/Metabolism Research and Reviews, Wiley, London, GB, 2005, vol. 21, No. 4, pp. 313-331.

GLUCAGON ANALOGUES

CROSS REFERENCE TO RELATED APPLICATIONS

This application is a continuation application Ser. No. 13/937,674, filed Jul. 9, 2013, which is a continuation of application Ser. No. 13/624,387, filed Sep. 21, 2012 (U.S. Pat. No. 8,541,368, Sep. 24, 2013) which claims priority to European Patent Application 11182476.9, filed Sep. 23, 2011, and this Application further claims priority under 35 U.S.C. §119 to U.S. Provisional Patent Application 61/539,148, filed Sep. 26, 2011, which are hereby incorporated by reference in their entirety as if fully set forth herein.

TECHNICAL FIELD

The present invention relates to novel glucagon peptide analogues, to the use of said peptides in therapy, to methods of treatment comprising administration of said peptides to patients, and to the use of said peptides in the manufacture of medicaments.

INCORPORATION BY REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Feb. 5, 2015. The Sequence Listing is made up of 3,457 bytes and the information contained in the attached "SeqList_8417 US01" is identical to the information in the specification as originally filed. No new matter is added.

BACKGROUND OF THE INVENTION

The precise control of blood glucose levels is of vital importance to humans as well as other mammals. It is well established that the two hormones insulin and glucagon are important for maintenance of correct blood glucose levels. While insulin acts in the liver and peripheral tissues by reducing blood glucose levels via increased peripheral uptake of glucose and reduced glucose output from the liver, glucagon acts mainly on the pancreas and liver, by increasing blood glucose levels via up-regulation of gluconeogenesis and glycogenolysis. Glucagon has also been reported to increase lipolysis, to induce ketosis and to reduce plasma triglyceride levels in plasma [Schade and Eaton, *Acta Diabetologica*, 1977, 14, 62].

Glucagon is an important part of the defence mechanism against hypoglycaemia and administration of a low dose of glucagon may prevent insulin-induced hypoglycaemia or improve the ability to recover from hypoglycaemia. Glucagon agonism has also been shown to exert effects on lipid metabolim, energy expenditure and food intake [Habegger et al. Nature Reviews Endocrinology 2010, 6, 689-697].

A large number of people suffering from diabetes, in particular Type 2 diabetes, are over-weight or obese. Obesity represents a high risk factor in serious and even fatal common diseases and for most diabetics it is highly desirable that their treatment does not cause weight gain.

Several patent applications disclosing different glucagon-based analogues and GLP-1/glucagon receptor co-agonists are known in the art, such as e.g. patents WO2008/086086, WO2008/101017, WO2007/056362, WO2008/152403 and WO96/29342. Other glucagon analogs disclosed are PEGylated (e.g. WO2007/056362) or acylated in specific positions of native human glucagon (e.g. WO96/29342). Glucagon peptides for prevention of hypoglycaemia have been disclosed, as e.g. in U.S. Pat. No. 7,314,859.

Glucagon is of limited potential use in pharmaceuticals due to fast clearance from circulation with a half life of approximately 5 min. A high clearance of a therapeutic agent is inconvenient in cases where it is desired to maintain a high blood level thereof over a prolonged period of time, since repeated administrations will then be necessary. In some cases it is possible to influence the release profile of peptides by applying suitable pharmaceutical compositions, but this approach has various shortcomings and is not generally applicable.

Glucagon is currently available as a freeze-dried formulation, with a short duration of action, restricted to less than an hour in spite of a glucagon level that peaks at levels far higher than endogenous glucagon levels. There is therefore a need for chemically modified glucagon compounds in order to be delivered at continuous levels, so that longer biological half-life is achieved, i.e. modified glucagon peptides with a protracted profile of action.

The physical as well as the chemical stability of glucagon is poor when dissolved in an aqueous solution. Solutions of glucagon form gels and fibrils within hours or days, depending on purity of the peptide, salt concentration, pH and temperature (Beaven et al. European J. Biochem. 1969, 11, 37-42). Glucagon contains several labile amino acids or amino acid sequences that may give rise to deamidation, cleavage, aspartimide formation and isomerisation. In addition the solubility of human glucagon is very poor in the pH range from 3.5-9.5.

SUMMARY OF THE INVENTION

The present invention relates to the use of said peptides in therapy, to methods of treatment comprising administration of said peptides to patients, and to the use of said peptides in the manufacture of medicaments for use in the treatment of diabetes, obesity and related diseases and conditions.

The present inventors have surprisingly found that one or more substitutions in amino acid positions 3, 15 and/or 16 of glucagon peptide and attachment in position 24 of said glucagon peptide of a substituent comprising three or more negative charged moieties, wherein one of the said negatively charged moieties is distal of a lipohilic moiety, leads to glucagon agonists with improved stability.

The present invention provides novel modified glucagon peptides with improved pharmacokinetic properties and with improved physical and chemical stability at neutral pH.

In a first embodiment (Embodiment 1), the present invention relates to a glucagon peptide comprising:

SEQ ID NO: 1, wherein $X_{24}$ represents Lys, wherein at least one of the following substitutions is present: $X_3$ is His, $X_{15}$ is Glu or $X_{16}$ is Ala, Ile, Phe, Arg, Thr, Val, Leu, Glu, Trp or Tyr and up to six additional amino acid substitutions in said glucagon peptide and a substituent comprising a lipophilic moiety and three or more negatively charged moieties, wherein one of the said negatively charged moieties is distal of said lipophilic moiety and where the substituent is attached at the side chain nitrogen of Lys in position 24, or a pharmaceutically acceptable salt, amide, acid or prodrug thereof.

In another embodiment, the present invention also provides ester forms of the glucagon peptide.

The present invention further relates to the use of the compounds of the present invention in therapy, to pharmaceutical compositions comprising compounds of the invention and the use of the compounds of the invention in the manufacture of medicaments.

DESCRIPTION OF THE INVENTION

Figure 1:
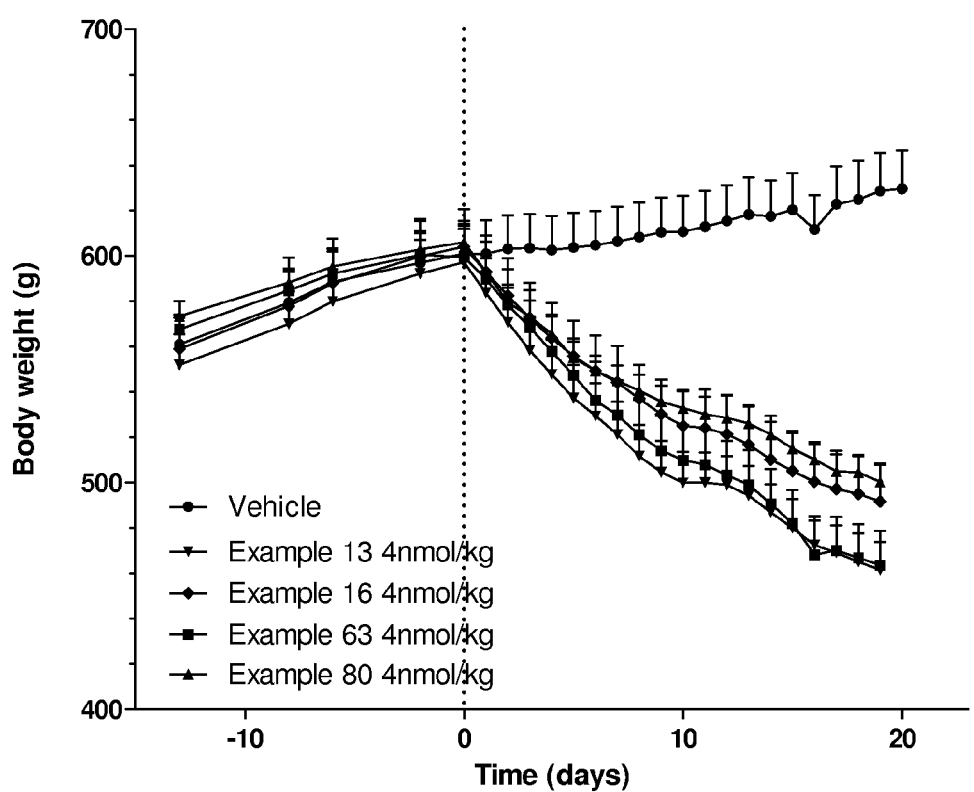
FIG. 1 shows effect of glucagon analogues on body weight in DIO rats. DIO rats were administered a daily subcutaneous dose (4 nmol/kg) of a glucagon analogue for three weeks and body weight was measured daily. All four glucagon analogues reduced body weight over time.

The peptides of the present invention provide novel modified glucagon peptides with a protracted profile of action in addition to providing such modified glucagon peptides in stable pharmaceutical compositions at physiological pH. The present invention relates to novel glucagon analogues with improved solubility, improved physical stability toward gel and fibril formation, improved chemical stability and with increased half life.

The inventors surprisingly found that the compounds of the present invention show improved physical stability toward gel and fibril formation, improved chemical stability and increased half life, while also showing improved aqueous solubility at neutral pH or slightly basic pH.

In one embodiment, the present invention relates to a glucagon peptide, wherein $X_{16}$ is Ile, Phe, Arg, Val, Leu, Glu, Trp or Tyr.

Among further embodiments of the present invention are the following:
2. The glucagon peptide according to embodiment 1, wherein said glucagon peptide comprises zero, one, two, three, four, five or six additional amino acid residues substitutions in said glucagon peptide.
3. The glucagon peptide according to embodiment 1, wherein said glucagon peptide comprises zero additional amino acid residues substitutions in said glucagon peptide.
4. The glucagon peptide according to embodiment 1, wherein said glucagon peptide comprises one additional amino acid residues substitutions in said glucagon peptide.
5. The glucagon peptide according to embodiment 1, wherein said glucagon peptide comprises two additional amino acid residues substitutions in said glucagon peptide.
6. The glucagon peptide according to embodiment 1, wherein said glucagon peptide comprises three additional amino acid residues substitutions in said glucagon peptide.
7. The glucagon peptide according to embodiment 1, wherein said glucagon peptide comprises four additional amino acid residues substitutions in said glucagon peptide.
8. The glucagon peptide according to embodiment 1, wherein said glucagon peptide comprises five additional amino acid residues substitutions in said glucagon peptide.
9. The glucagon peptide according to embodiment 1, wherein said glucagon peptide comprises six additional amino acid residues substitutions in said glucagon peptide.
10. The glucagon peptide according to any one of embodiments 1-2 and 4-9, wherein said additional amino acid substitutions can be in the following amino acid positions of said glucagon peptide: $X_9$, $X_{10}$, $X_{12}$, $X_{17}$, $X_{20}$, $X_{21}$, $X_{27}$, $X_{28}$, $X_{29}$ and/or $X_{30}$.
11. The glucagon peptide according to embodiment 10, wherein said additional amino acid substitutions can be in the following amino acid positions of said glucagon peptide: $X_{10}$, $X_{12}$, $X_{17}$, $X_{20}$, $X_{21}$, $X_{27}$, $X_{28}$ and/or $X_{29}$.
12. The glucagon peptide according to embodiment 11, wherein said additional amino acid substitutions can be in the following amino acid positions of said glucagon peptide: $X_{12}$, $X_{17}$, $X_{20}$, $X_{21}$, $X_{27}$, and/or $X_{28}$.
13. The glucagon peptide according to embodiment 12, wherein said additional amino acid substitutions can be in positions $X_{10}$, $X_{12}$, $X_{27}$ and/or $X_{28}$ of said glucagon peptide.
14. The glucagon peptide according to embodiment 13, wherein said additional amino acid substitutions can be in positions $X_{12}$, $X_{27}$ and/or $X_{28}$ of said glucagon peptide.
15. The glucagon peptide according to embodiment 11, wherein said additional amino acid substitutions can be in positions $X_{10}$, $X_{12}$, $X_{27}$ and/or $X_{29}$ of said glucagon peptide.
16. The glucagon peptide according to embodiment 15, wherein said additional amino acid substitutions can be in positions $X_{12}$, $X_{27}$ and/or $X_{29}$ of said glucagon peptide.
17. The glucagon peptide according to any one of embodiments 10-16, wherein said additional amino acid substitutions may be selected from the following positions of said glucagon peptide:
$X_9$ represents Glu;
$X_{10}$ represents Val;
$X_{12}$ represents Arg;
$X_{17}$ represents Lys;
$X_{20}$ represents Lys;
$X_{21}$ represents Glu;
$X_{27}$ represents Met(O), Val, Leu, Ile, Ala or Glu;
$X_{28}$ represents Ser, Thr, Ala, Gln, Val, Leu, Ile, Arg, Lys, His, Asp, Gly or Glu;
$X_{29}$ represents Ser, Gln, Ala, Val, Leu, Ile, Pro, Arg, Lys, His, Asp or Glu and)
$X_{30}$ is absent or represents Pro.
18. The glucagon peptide according to embodiment 17, wherein said additional amino acid substitutions may be selected from the following positions of said glucagon peptide: $X_{12}$ is Arg, $X_{17}$ is Lys, $X_{20}$ is Lys, $X_{21}$ is Glu, $X_{27}$ is Leu, $X_{28}$ is Ser, Ile or Thr.
19. The glucagon peptide according to embodiment 17, wherein said additional amino acid substitutions may be selected from the following positions of said glucagon peptide: $X_{10}$ is Val, $X_{21}$ is Glu, $X_{27}$ is Leu, $X_{28}$ is Ser.
20. The glucagon peptide according to embodiment 17, wherein $X_9$ represents Glu.
21. The glucagon peptide according to embodiment 19, wherein $X_{10}$ represents Val.
22. The glucagon peptide according to embodiment 18, wherein $X_{12}$ represents Arg.
23. The glucagon peptide according to any one of the previous embodiments, wherein $X_{16}$ represents Ala.
24. The glucagon peptide according to any one of the previous embodiments, wherein $X_{16}$ represents Ile.
25. The glucagon peptide according to any one of the previous embodiments, wherein $X_{16}$ represents Phe.
26. The glucagon peptide according to any one of the previous embodiments, wherein $X_{16}$ represents Arg.
27. The glucagon peptide according to any one of the previous embodiments, wherein $X_{16}$ represents Thr.

28. The glucagon peptide according to any one of the previous embodiments, wherein $X_{16}$ represents Val.
29. The glucagon peptide according to any one of the previous embodiments, wherein $X_{16}$ represents Leu.
30. The glucagon peptide according to any one of the previous embodiments, wherein $X_{16}$ represents Glu.
31. The glucagon peptide according to any one of the previous embodiments, wherein $X_{16}$ represents Trp.
32. The glucagon peptide according to any one of the previous embodiments, wherein $X_{16}$ represents Tyr.
33. The glucagon peptide according to any one of embodiments 23-32, wherein $X_{17}$ represents Lys.
34. The glucagon peptide according to embodiment 33, wherein $X_{20}$ represents Lys.
35. The glucagon peptide according to embodiment 34, wherein $X_{21}$ represents Glu.
36. The glucagon peptide according to embodiment 35, wherein $X_{27}$ represents Met(O), Met(O2), Val, Leu, Ile, Ala or Glu.
37. The glucagon peptide according to embodiment 36, wherein $X_{27}$ represents Leu or Glu.
38. The glucagon peptide according to embodiment 36, wherein $X_{27}$ represents Leu.
39. The glucagon peptide according to embodiment 36, wherein $X_{27}$ represents Glu.
40. The glucagon peptide according to any one of embodiments 33-39, wherein $X_{28}$ represents Ser, Thr, Ala, Gln, Val, Leu, Ile, Arg, Lys, His, Asp, Gly or Glu.
41. The glucagon peptide according to embodiment 40, wherein $X_{28}$ represents Ser, Thr, Gly or Ile.
42. The glucagon peptide according to embodiment 40, wherein $X_{28}$ represents Ser, Thr or Ile.
43. The glucagon peptide according to embodiment 40, wherein $X_{28}$ represents Ser.
44. The glucagon peptide according to embodiment 40, wherein $X_{28}$ represents Thr.
45. The glucagon peptide according to embodiment 40, wherein $X_{28}$ represents Gly.
46. The glucagon peptide according to embodiment 40, wherein $X_{28}$ represents Ile.
47. The glucagon peptide according to any one of embodiments 40-46, wherein $X_{29}$ represents Ser, Gln, Ala, Val, Leu, Ile, Pro, Arg, Lys, His, Asp or Glu.
48. The glucagon peptide according to embodiment 47, wherein $X_{29}$ represents Val, Leu or Ile.
49. The glucagon peptide according to any one of embodiments 47-48, wherein $X_{29}$ represents Val.
50. The glucagon peptide according to any one of embodiments 47-48, wherein $X_{29}$ represents Leu.
51. The glucagon peptide according to any one of embodiments 47-48, wherein $X_{29}$ represents Ile.
52. The glucagon peptide according to any one of embodiments 47-51, wherein $X_{30}$ is absent or represents Pro.
53. The glucagon peptide according to embodiment 52, wherein $X_{30}$ is absent.
54. The glucagon peptide according to any one of the previous embodiments, wherein said substituent has the formula II:

$$Z_1-Z_2-Z_3-Z_4 \qquad [II]$$

wherein, $Z_1$ represents a structure according to one of the formulas IIa or IIb;

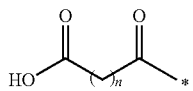

IIa

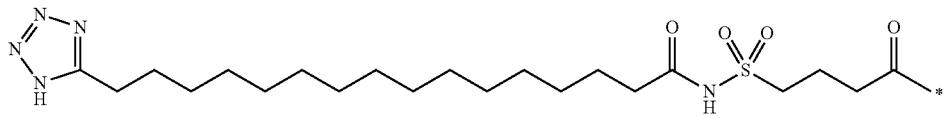

IIb wherein n in formula IIa is 6-20,
the symbol * in formula IIa and IIb represents the attachment point to the nitrogen in $Z_2$;
if $Z_2$ is absent, $Z_1$ is attached to the nitrogen on $Z_3$ at symbol * and if $Z_2$ and $Z_3$ are absent $Z_1$ is attached to the nitrogen on $Z_4$ at symbol *
$Z_2$ is absent or represents a structure according to one of the formulas IId, IIe, IIf, IIg, IIh, IIi, IIj or IIk;

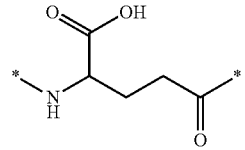

IId

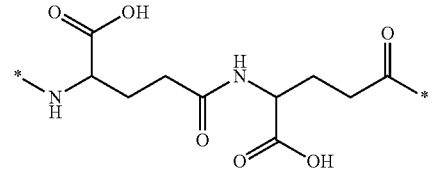

IIe

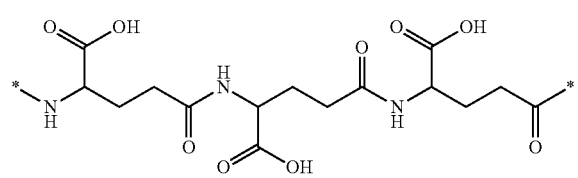
IIf

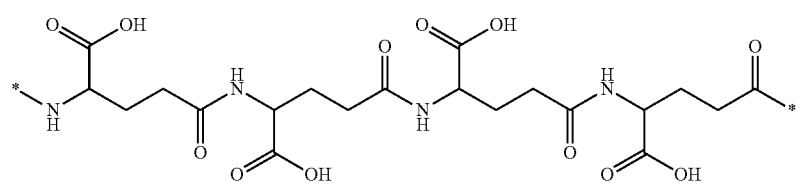
IIg

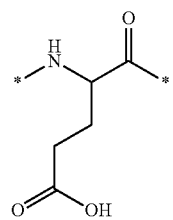
IIh

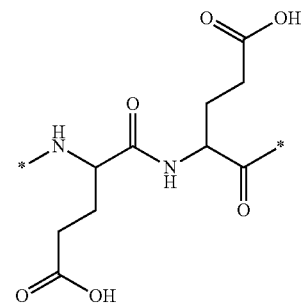
IIi

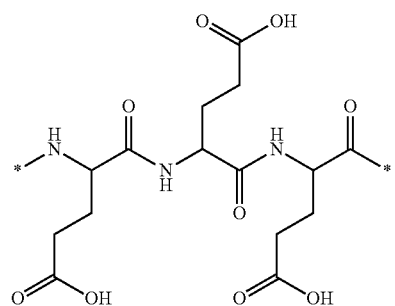
IIj

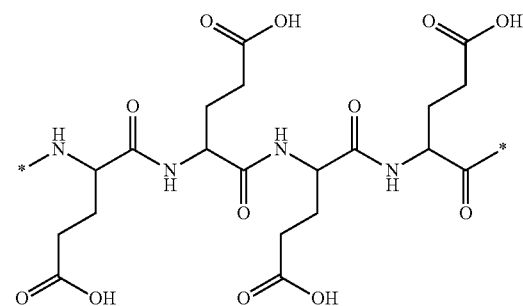
IIk wherein each amino acid moiety independently has the stereochemistry L or D;
wherein $Z_2$ is connected via the carbon atom denoted * to the nitrogen of $Z_3$ denoted *;
if $Z_3$ is absent, $Z_2$ is connected via the carbon atom denoted * to the nitrogen of $Z_4$ denoted * and if $Z_3$ and $Z_4$ are absent $Z_2$, is connected via the carbon denoted * to the epsilon nitrogen of Lys in position 24 of the glucagon peptide;
$Z_3$ is absent or represents a structure according to one of the formulas IIm, IIn, IIo or IIp;

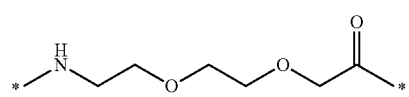
IIm

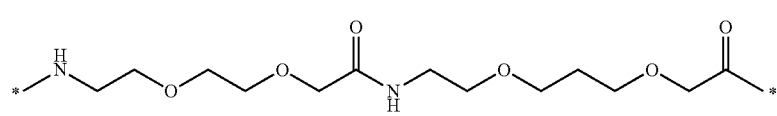
IIn

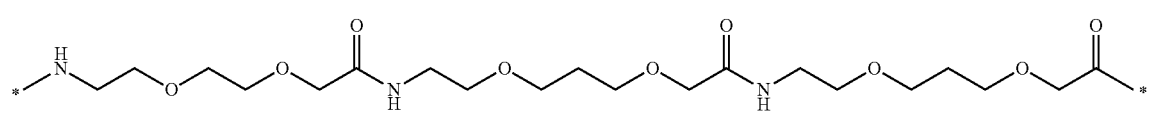
IIo

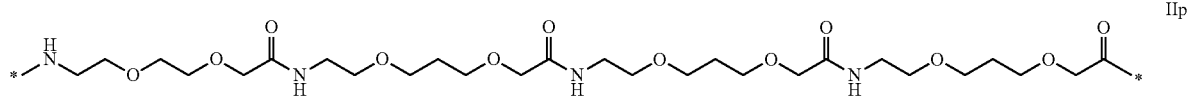

$Z_3$ is connected via the carbon of $Z_3$ with symbol* to the nitrogen of $Z_4$ with symbol*, if $Z_4$ is absent $Z_3$ is connected via the carbon with symbol* to the epsilon nitrogen of Lys in position 24 of the glucagon peptide;

$Z_4$ is absent or represents a structure according to one of the formulas IId, IIe, IIf, IIg, IIh, IIi, IIj or IIk; wherein each amino acid moiety is independently either L or D, wherein $Z_4$ is connected via the carbon with symbol* to the epsilon nitrogen of Lys in position 24 of the glucagon peptide, with the proviso that either $Z_2$ or $Z_4$ or both $Z_2$ and $Z_4$ are present in said substituent.

55. The glucagon peptide according to any one of the previous embodiments, wherein said substituent has the formula II:

$$Z_1-Z_2-Z_3-Z_4-\qquad [II]$$

wherein, $Z_1$ represents a structure according to one of the formulas IIa or IIb;

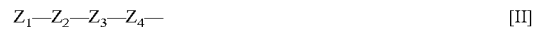

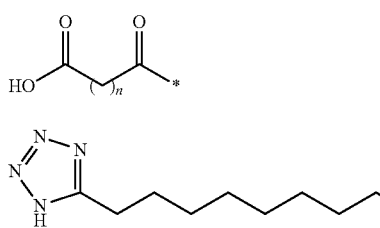

wherein n in formula IIa is 6-20, $Z_2$ is absent or represents a structure according to one of the formulas IId, IIe, IIf, IIg, IIh, IIi, IIj or IIk;

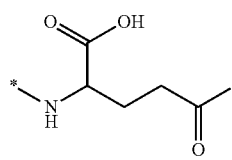

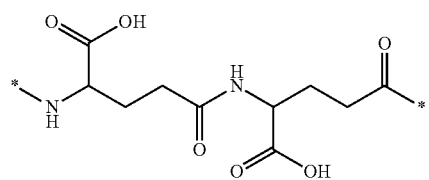

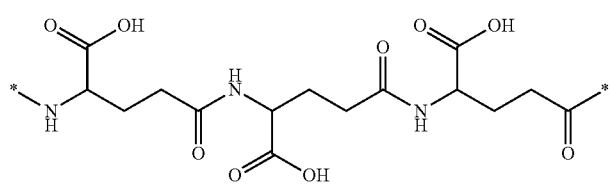

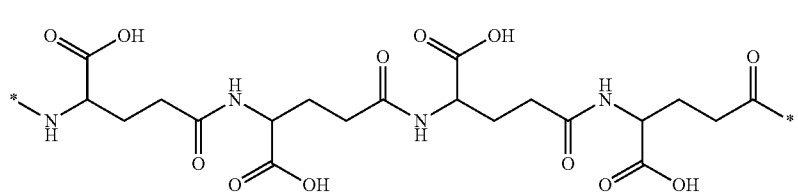

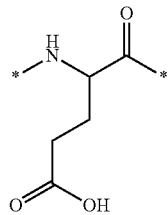
IIh

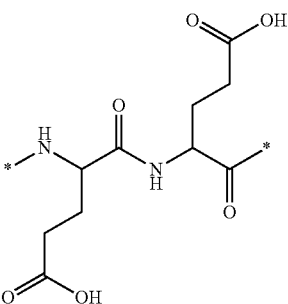
IIi

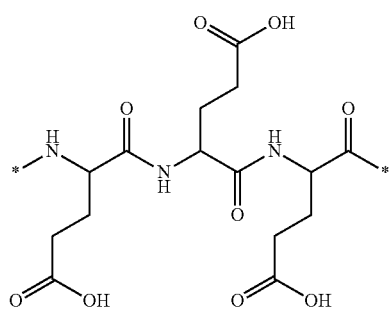
IIj

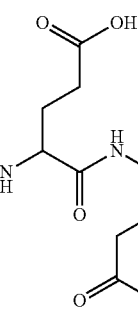
IIk wherein each amino acid moiety independently has the stereochemistry L or D.

$Z_3$ is absent or represents a structure according to one of the formulas IIm, IIn, IIo or IIp;

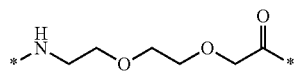
IIm

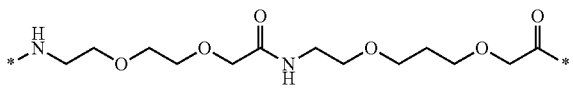
IIn

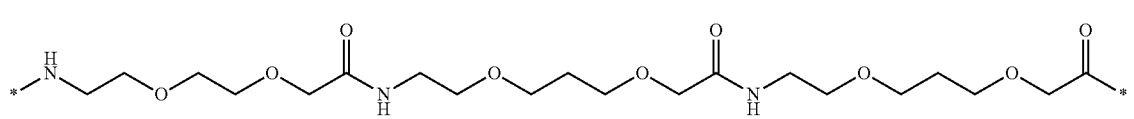
IIo

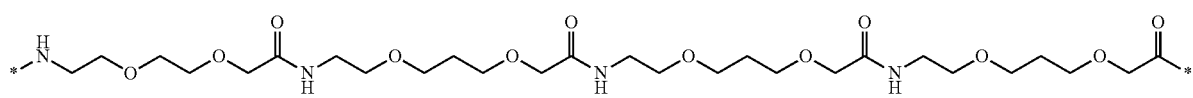
IIp $Z_4$ is absent or represents a structure according to one of the formulas IId, IIe, IIf, IIg, IIh, IIi, IIj or IIk;

wherein each amino acid moiety independently has the stereochemistry L or D.

56. The glucagon peptide according to any one of the previous embodiments, wherein the structures of formulas IId-IIk have the stereochemistry L.

57. The glucagon peptide according to any one of the previous embodiments, wherein the structures of formulas IId-IIk have the stereochemistry D.

58. The glucagon peptide according to any of the previous embodiments, wherein $Z_2$ of said substituent of formula II is absent when $Z_4$ is present.

59. The glucagon peptide according to any of the previous embodiments, wherein $Z_4$ of said substituent of formula II is absent when $Z_2$ is present.

60. The glucagon peptide according to any of the previous embodiments, wherein said substituent represents a structure according to one of the formulas IIIa, IIIb, IIIc, IIId, IIIe, IIIf, IIIg, IIIh, IIIi, IIIj, IIIk, IIIl, IIIm, IIIn, IIIo, IIIp, IIIq, IIIr, IIIs, IIIt, IIIu, IIIv, IIIw, IIIx or IIIy:

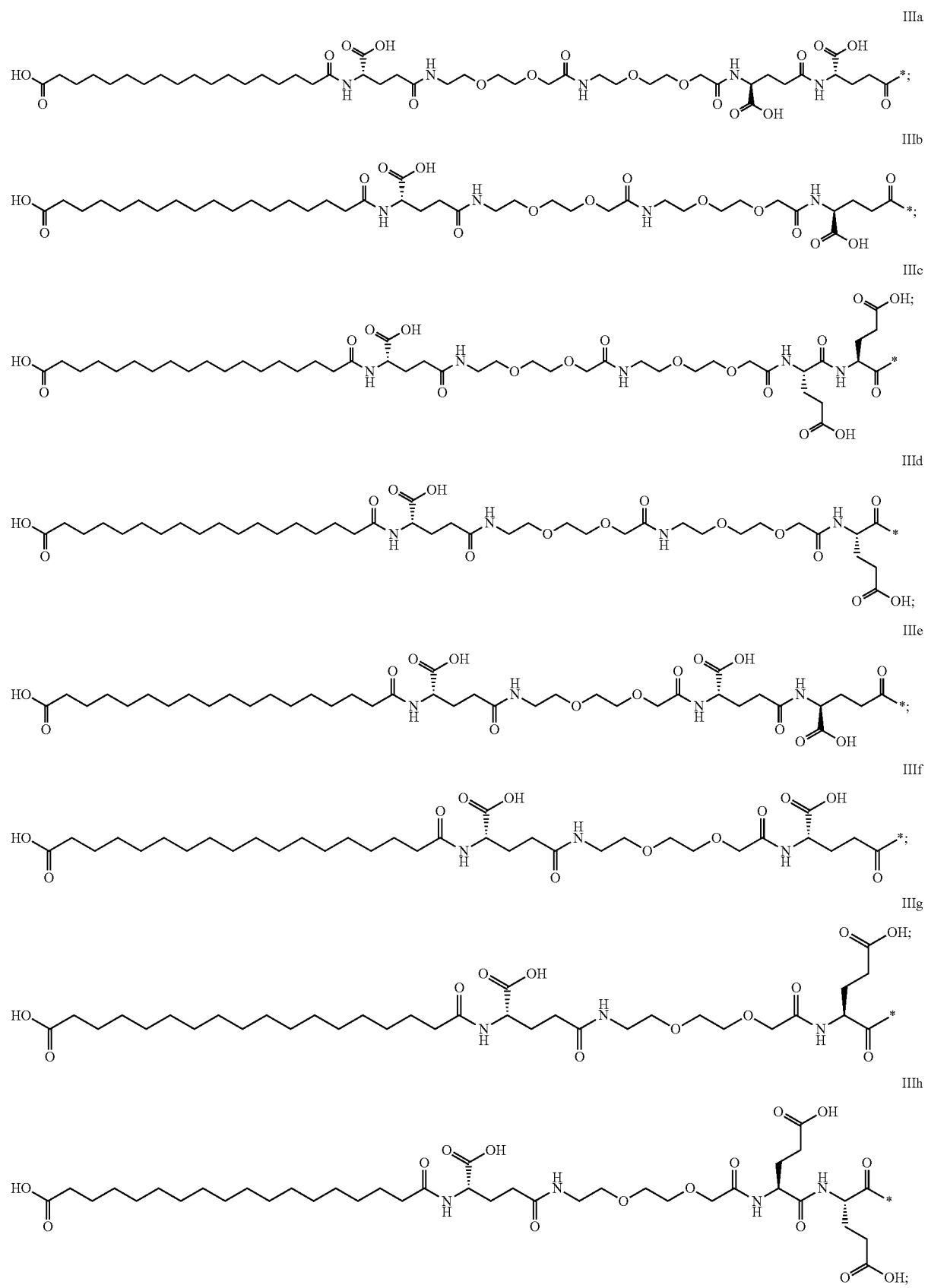

-continued
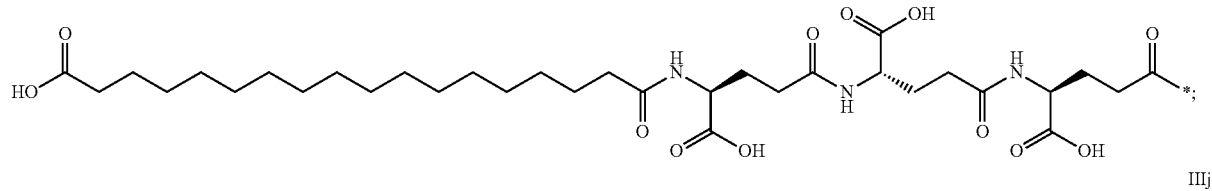
IIIi
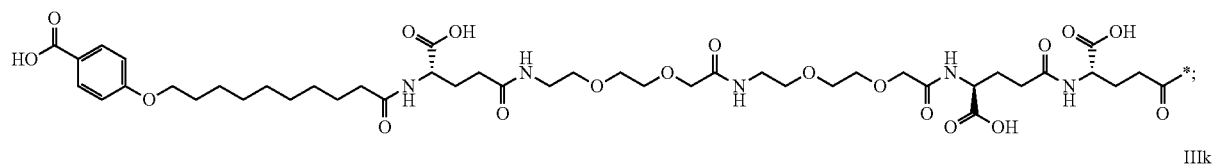
IIIj
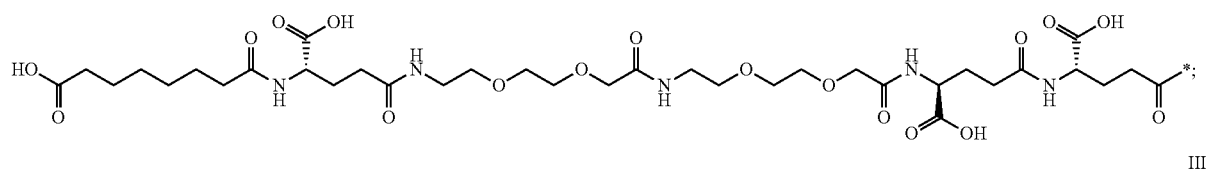
IIIk
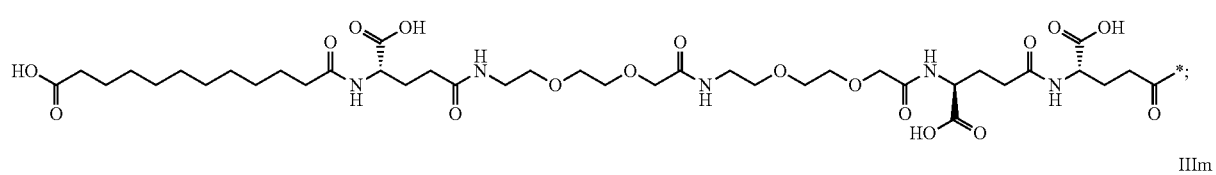
IIIl
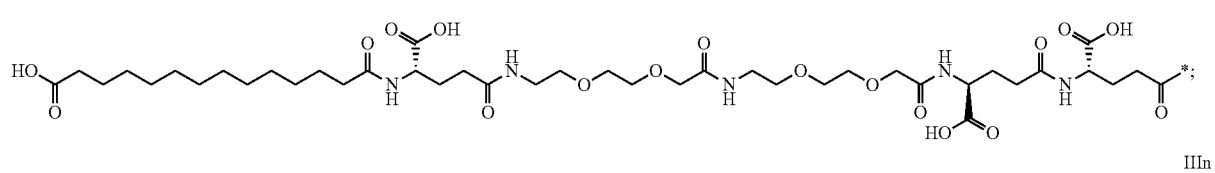
IIIm
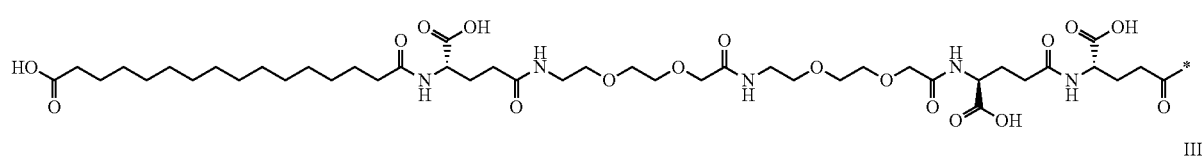
IIIn
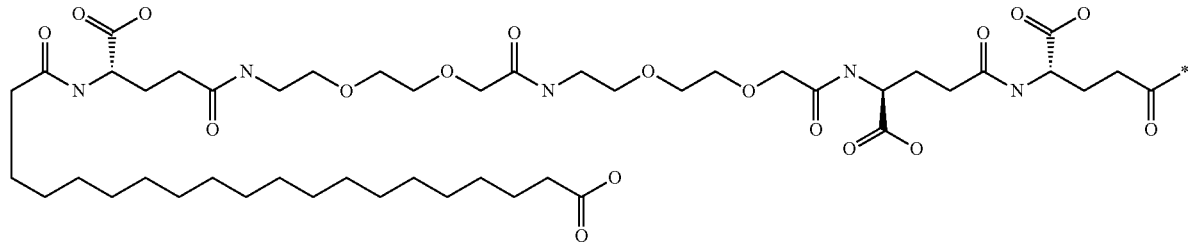
IIIo
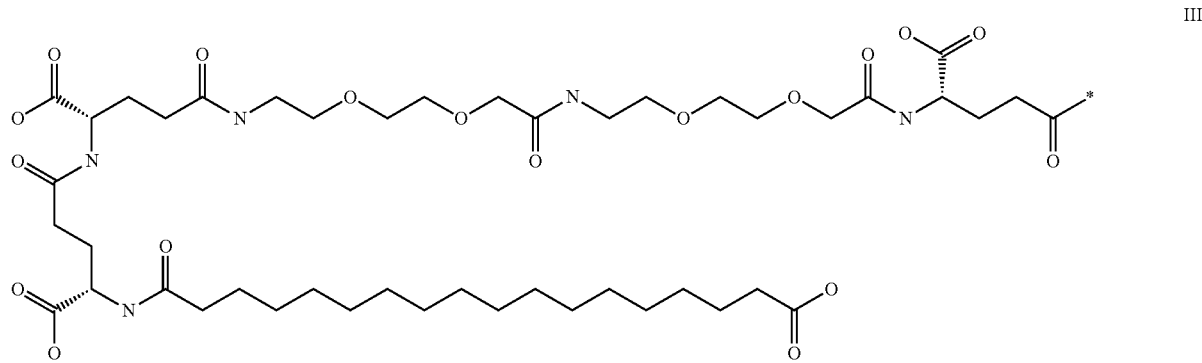
IIIp

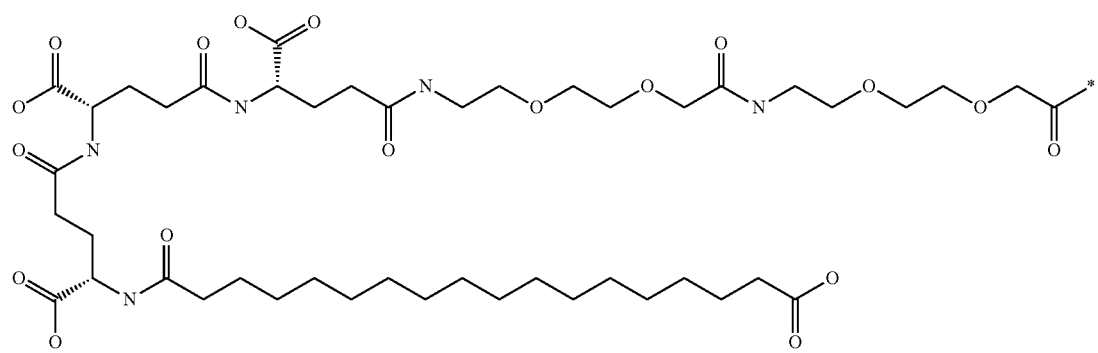
IIIq
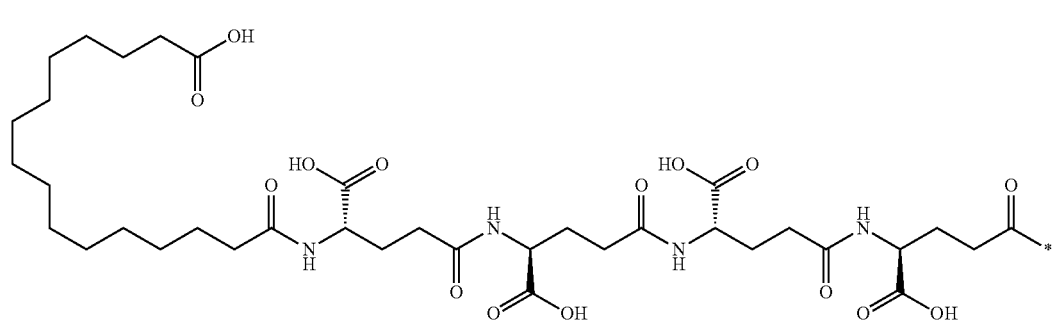
IIIr
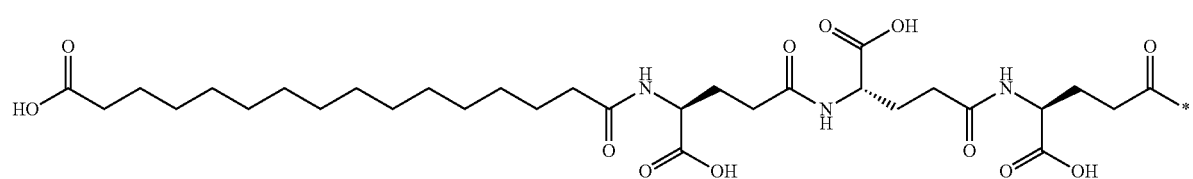
IIIs
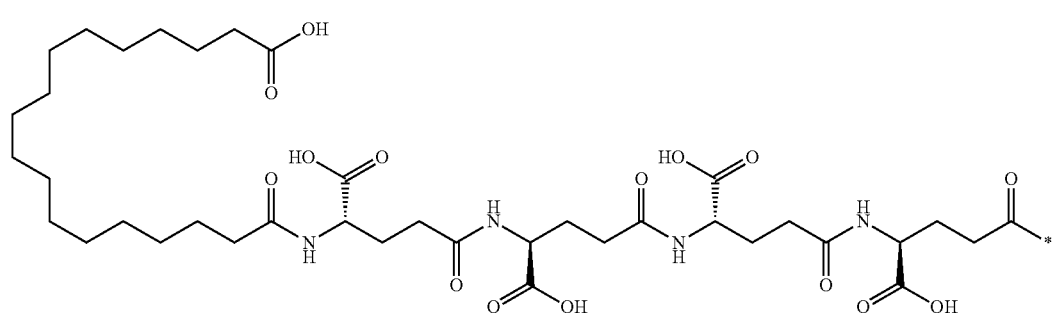
IIIt
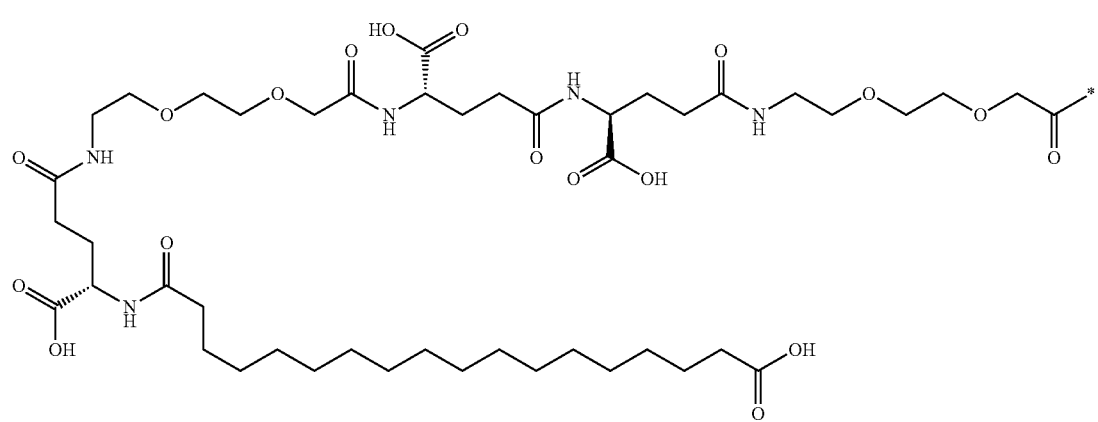
IIIu

-continued
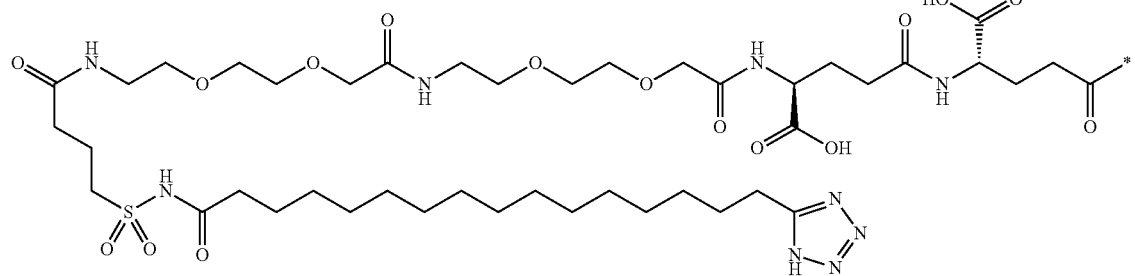
IIIv
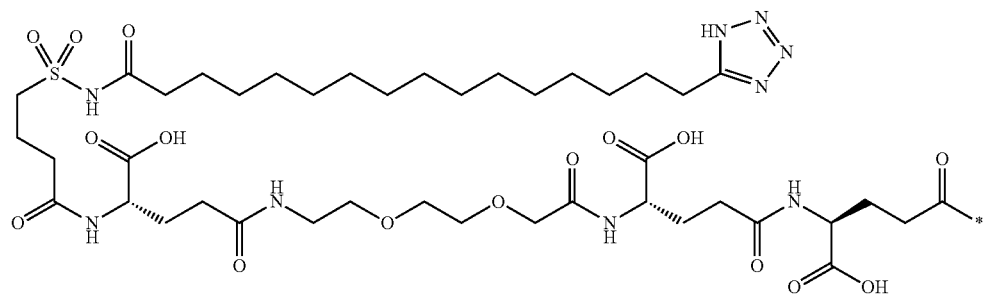
IIIw
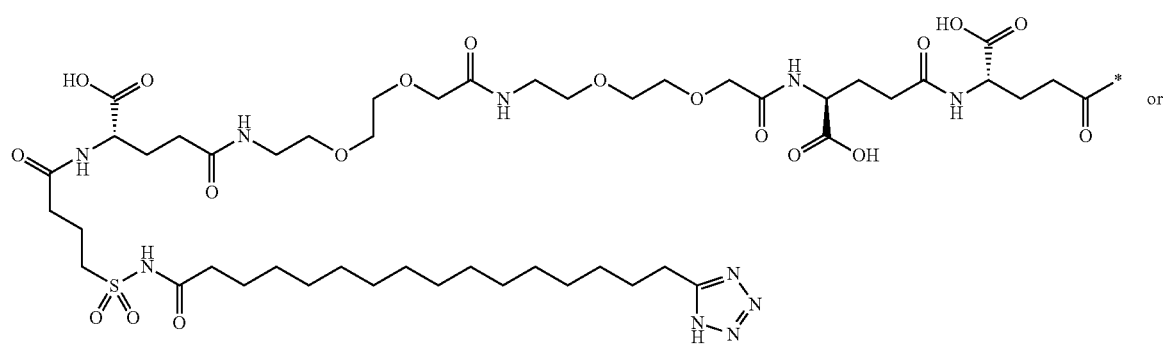
IIIx or
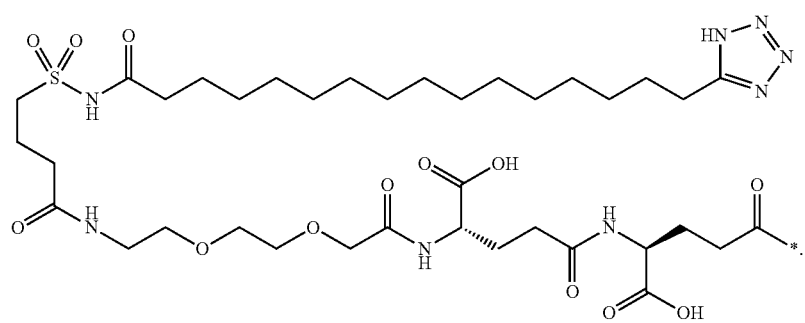
IIIy
61. The glucagon peptide according to any of the previous embodiments, wherein said substituent represents a structure according to one of the formulas IIIa, IIIb, IIIi, IIIn, IIIp, IIIr, IIIs, IIIt, IIIu, IIIy, IIIw, IIIx or IIIy:
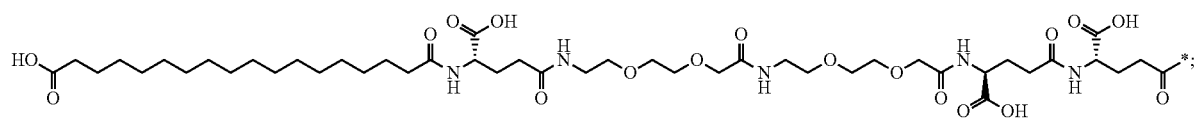
IIIa -continued
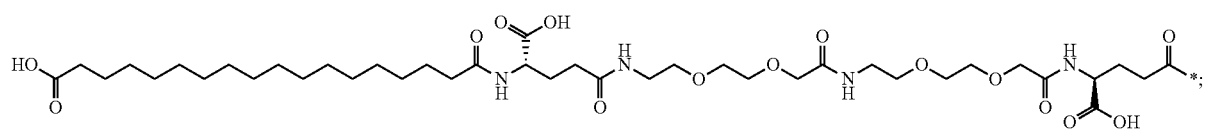
IIIb
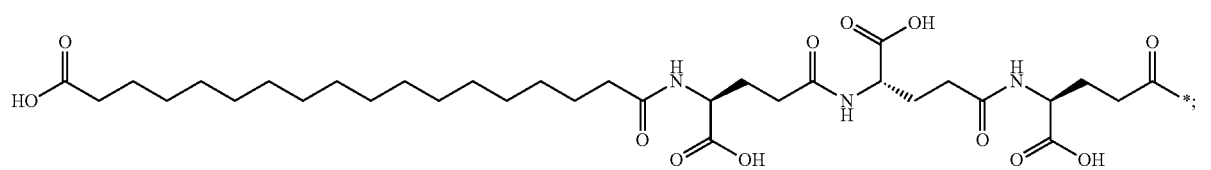
IIIi
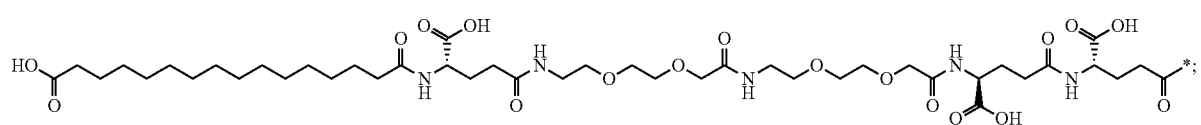
IIIn
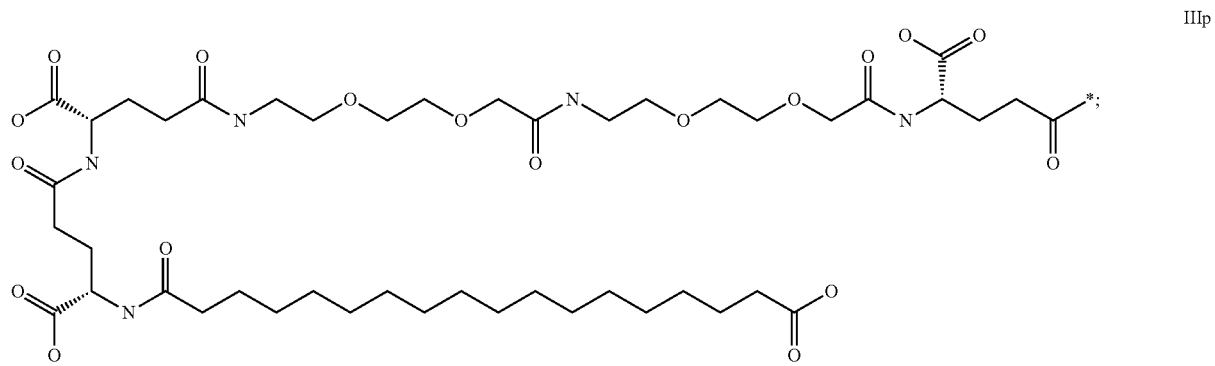
IIIp
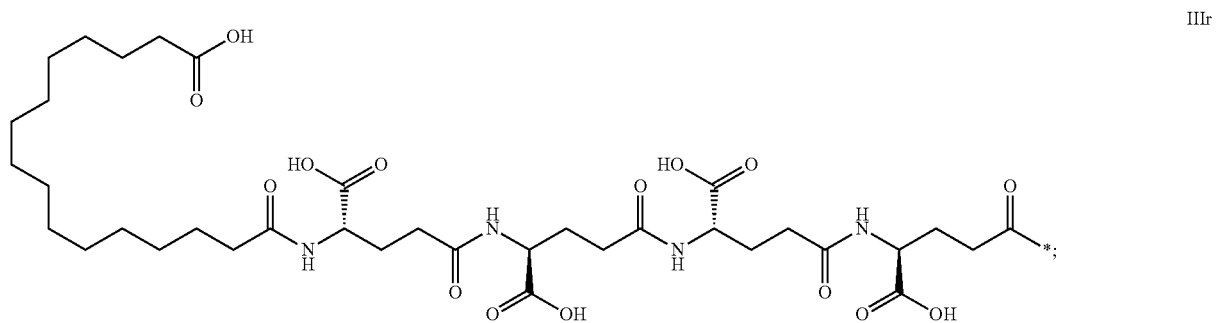
IIIr
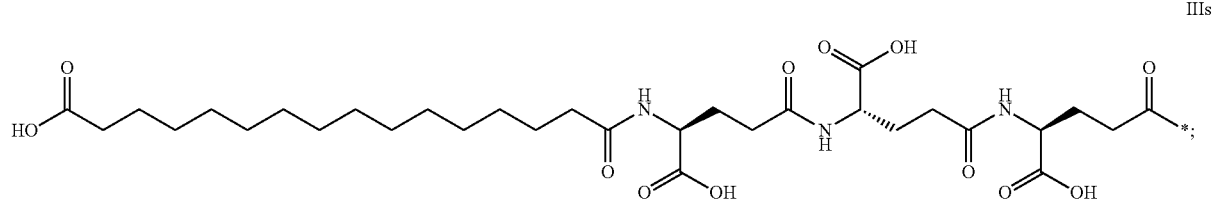
IIIs -continued
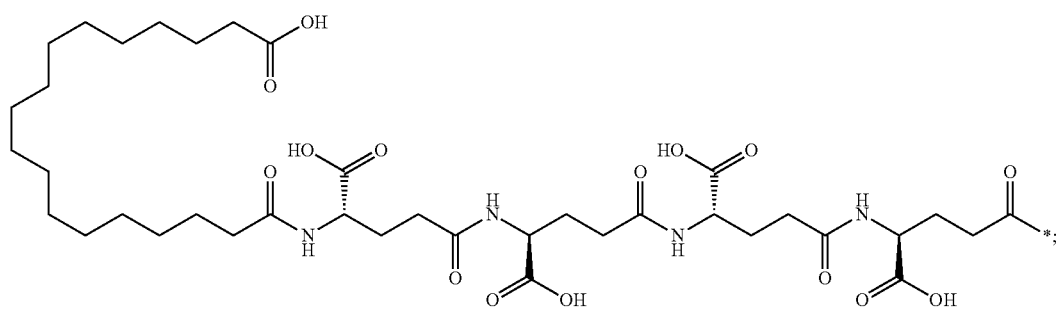
IIIt
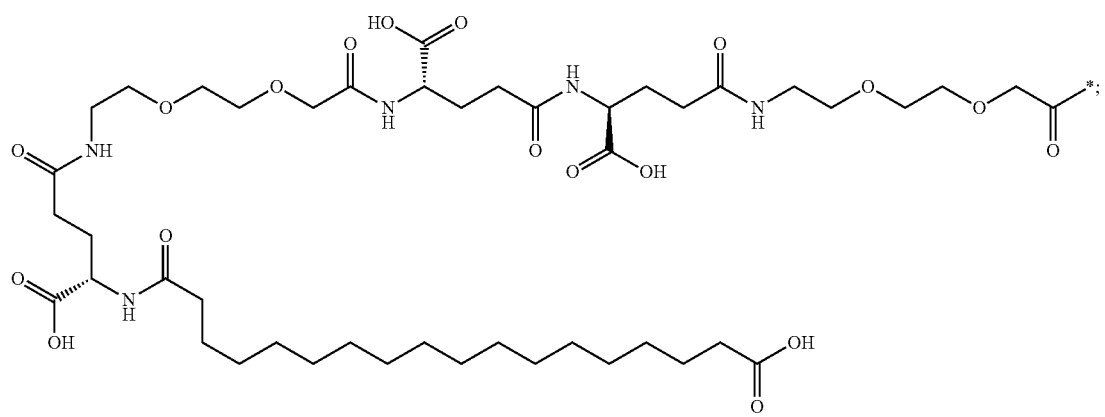
IIIu
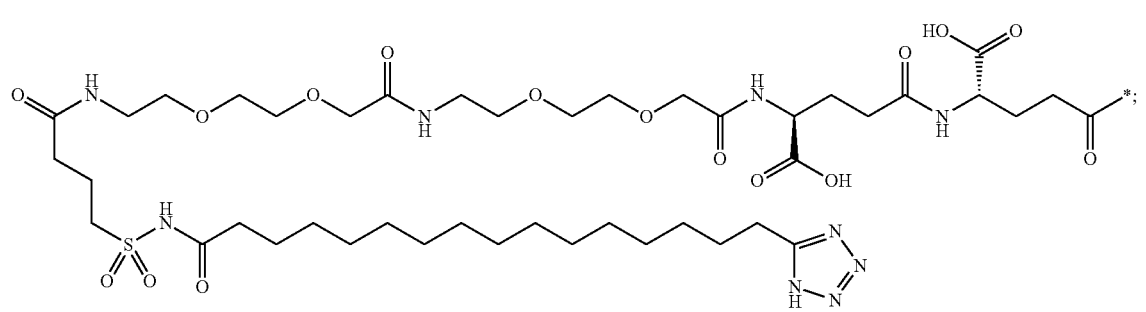
IIIv
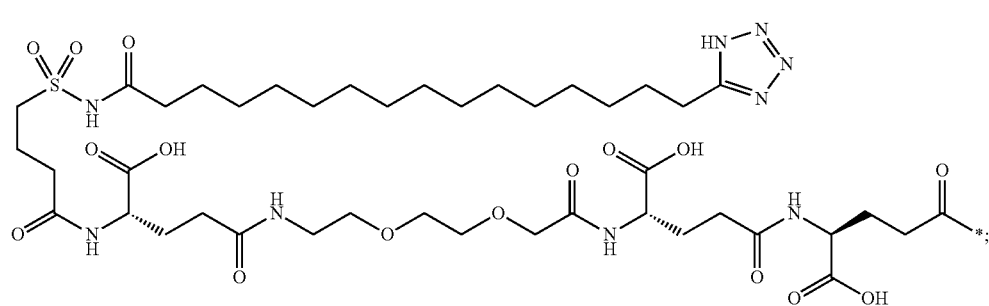
IIIw
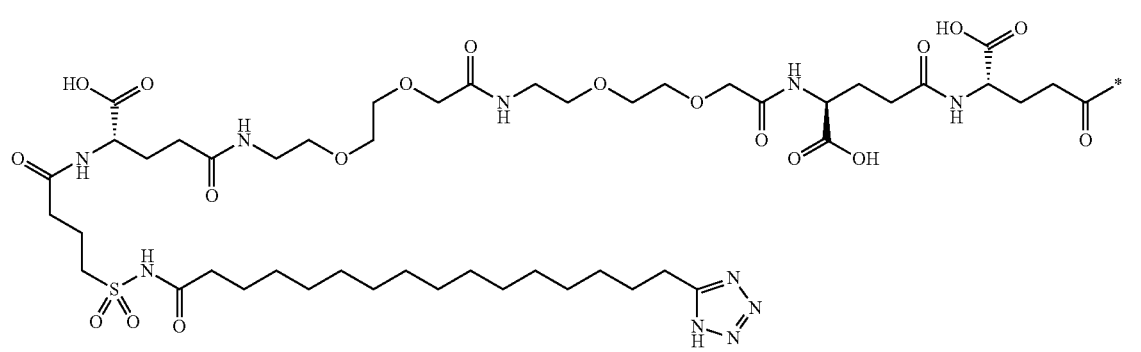
IIIx or

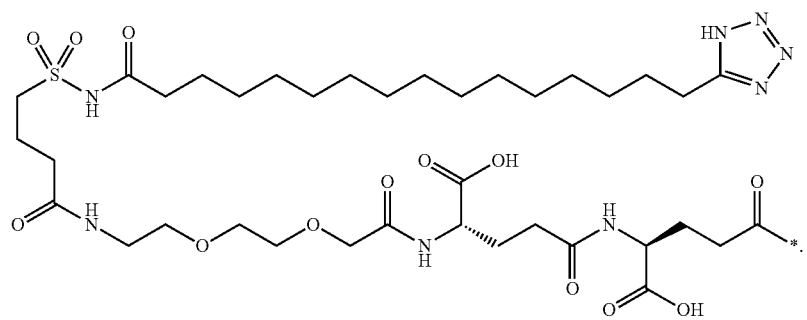

62. The glucagon peptide according to any of the previous embodiments, wherein said substituent represents a structure according to one of the formulas IIIa, IIIp or IIIt:

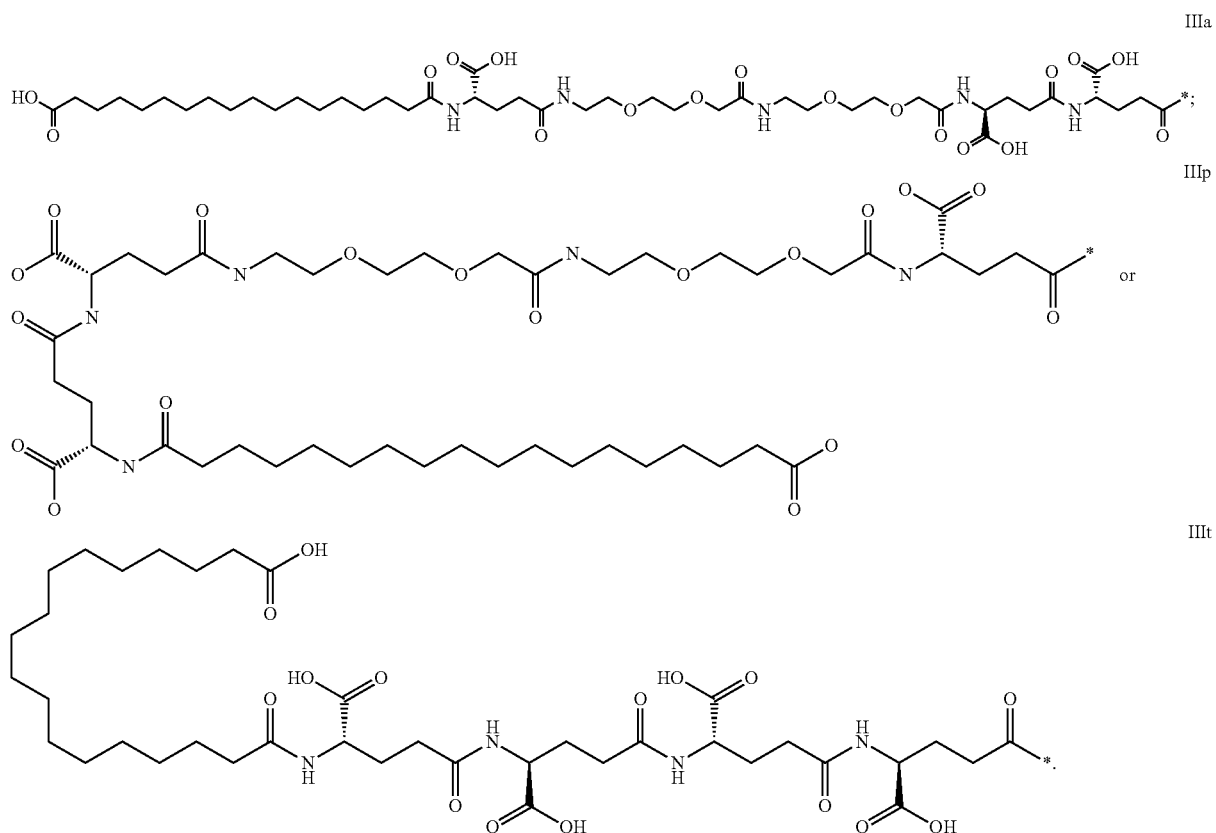

63. The glucagon peptide according to any of the previous embodiments, wherein $Z_4$ of said substituent is absent.
64. The glucagon peptide according to any of the previous embodiments, wherein $Z_3$ and $Z_4$ of said substituent are absent.
65. The glucagon peptide according to any of embodiments 1-62, wherein $Z_2$ and $Z_4$ of said substituent are independently represented by negatively charged moieties such as γGlu, Glu and/or Asp.
66. The glucagon peptide according to embodiment 65, wherein $Z_2$ and $Z_4$ of said substituent are independently represented by up to ten of said negatively charged moieties.
67. The glucagon peptide according to embodiment 66, wherein $Z_2$ and $Z_4$ of said substituent are independently represented by three of said negatively charged moieties.
68. The glucagon peptide according to embodiment 66, wherein $Z_2$ and $Z_4$ of said substituent are independently represented by four of said negatively charged moieties.
69. The glucagon peptide according to embodiment 66, wherein $Z_2$ and $Z_4$ of said substituent are independently represented by five of said negatively charged moieties.
70. The glucagon peptide according to any of embodiments 1-62 and 65-69, wherein $Z_2$ and $Z_4$ of said substituent are independently represented by Glu and/or γGlu moieties.

71. The glucagon peptide according to embodiment 70, wherein $Z_2$ and $Z_4$ of said substituent are independently represented by γGlu, γGlu-Glu, γGlu-Glu-Glu, γGlu-Glu-Glu-Glu, γGlu-Glu-Glu-Glu-Glu.
72. The glucagon peptide according to any of embodiments 1-62 and 65-69, wherein $Z_2$ and $Z_4$ of said substituent are independently represented by Glu and/or Asp moieties.
73. The glucagon peptide according to embodiment 72, wherein $Z_2$ and $Z_4$ of said substituent are independently represented by γGlu and/or Asp moieties.
74. The glucagon peptide according to any one of embodiments 72-73, wherein $Z_2$ and $Z_4$ of said substituent are independently represented by Asp moieties.
75. The glucagon peptide according to embodiment 74, wherein $Z_2$ and $Z_4$ of said substituent are independently represented by Asp, Asp-Asp, Asp-Asp-Asp or Asp-Asp-Asp-Asp.
76. The glucagon peptide according to any of embodiments 70 or 72, wherein $Z_2$ and $Z_4$ of said substituent are independently represented by Glu moieties.
77. The glucagon peptide according to embodiment 76, wherein $Z_2$ and $Z_4$ of said substituent are independently represented by Glu, Glu-Glu, Glu-Glu-Glu, Glu-Glu-Glu-Glu, Glu-Glu-Glu-Glu-Glu.
78. The glucagon peptide according to any of embodiments 70 or 73, wherein $Z_2$ and $Z_4$ of said substituent are independently represented by γGlu moieties.
79. The glucagon peptide according to embodiment 78, wherein $Z_2$ and $Z_4$ of said substituent are independently represented by γGlu, γGlu-γGlu, γGlu-γGlu-γGlu, γGlu-γGlu-γGlu-γGlu, γGlu-γGlu-γGlu-γGlu-γGlu.
80. The glucagon peptide according to any of the previous embodiments, wherein said substituent comprises a straight chain alkyl group or a branched alkyl group.
81. The glucagon peptide according to any of the previous embodiments, wherein $Z_1$ represents a structure according to formula IIa and n in formula IIa is amounting from 12 to 18.
82. The glucagon peptide according to any of the previous embodiments, wherein $Z_1$ represents 19-carboxynonadecanoyl, 17-carboxyheptadecanoyl, 15-carboxypentadecanoyl, 13-carboxytridecanoyl or 4-[16-(1H-tetrazol-5-yl)hexadecanoylsulfamoyl]butanoyl.
83. The glucagon peptide according to any of the previous embodiments, wherein $Z_1$ represents 19-carboxynonadecanoyl, 17-carboxyheptadecanoyl, 15-carboxypentadecanoyl or 13-carboxytridecanoyl.
84. The glucagon peptide according to any of the previous embodiments, wherein $Z_1$ represents 4-[16-(1H-tetrazol-5-yl)hexadecanoylsulfamoyl]butanoyl.
85. The glucagon peptide according to any of the previous embodiments, wherein $Z_1$ represents 19-carboxynonadecanoyl.
86. The glucagon peptide according to any of the previous embodiments, wherein $Z_1$ represents 17-carboxyheptadecanoyl.
87. The glucagon peptide according to any of the previous embodiments, wherein $Z_1$ represents 15-carboxypentadecanoyl.
88. The glucagon peptide according to any of the previous embodiments, wherein $Z_1$ represents 13-carboxytridecanoyl.
89. The glucagon peptide according to any of the previous embodiments, wherein said substituent binds non-covalently to albumin.
90. The glucagon peptide according to any of the previous embodiments, wherein said substituent is negatively charged at physiological pH.

The present invention relates to novel glucagon analogues with improved solubility, improved physical stability toward gel and fibril formation, improved chemical stability and with increased half life.

The inventors surprisingly found that the compounds of the present invention, show improved aqueous solubility at neutral pH or slightly basic pH. The solubility of different pH values can be measured as described in Assay IX. Furthermore, the present inventors have also surprisingly found that the glucagon analogues of the present invention have improved stability towards formation of gels and fibrils in aqueous solutions. The so-called physical stability of the compounds of the present invention may be measured by a method as described in Assay II. The glucagon analogues of the present invention have improved chemical stability i.e. the chemical degradation of the analogues are reduced. The chemical stability of the analogues can me measured as described in Assay X.

The inventors have found that the compounds of the present invention show improved pharmacokinetic properties, i.e., they have prolonged half-life in vivo. The half-life can be determined in a pharmacokinetic study in species such as rats (Assay VIII) or in pigs (Assay XI). Furthermore, the compounds of the present invention show a significant reduction in body weight with s.c. administration. The reduction in body weight can be measured in DIO mice as described in Assay XII.

Protracted effect of the compounds of the present invention means that the period of time in which they exert a biological activity is prolonged.

A better control of blood glucose levels in Type 1 and 2 diabetes may be achieved by co-administration of glucagon with known antidiabetic agents such as insulin, GLP-1 agonists and GIP agonists.

In one embodiment, the glucagon analogues of this invention can be co-formulated with GLP-1 analogues or insulin analogues, forming stable pharmaceutical compositions.

Combination of insulin and glucagon therapy may be advantageous compared to insulin-only therapy. Normally, in a postprandial situation when blood glucose levels become low the first hormonal response is reduction in the production of insulin. When blood glucose drop further the second line response is production of glucagon—resulting in increased glucose output from the liver. When diabetics receive an exogenous dose of insulin that is too high the natural response of raised glucagon is prevented by the presence of exogenous insulin, since insulin has an inhibiting effect on glucagon production. Consequently, slight overdosing of insulin may cause hypoglycaemia. Presently, many diabetic patients tend to prefer to use a little less insulin than optimal in fear of hypoglycaemic episodes which may be life-threatening.

The fact that the compounds of the present invention are soluble at neutral pH, may allow a co-formulation with insulin and allow for more stable blood glucose levels and a reduced number of hypoglycaemic episodes, as well as a reduced risk of diabetes related complications.

Further embodiments of the present invention are the following:
91. The glucagon peptide according to any one of the previous embodiments, wherein said glucagon peptide comprises C-terminal extensions of one amino acid residue.

92. The glucagon peptide according to any one the previous embodiments, wherein the glucagon peptide is a C-terminal amide or a C-terminal carboxylic acid.
93. The glucagon peptide according to any one of the previous embodiments, wherein said glucagon peptide is a C-terminal amide.
94. The glucagon peptide according to any one of the previous embodiments, wherein said glucagon peptide is a C-terminal carboxylic acid.
95. The glucagon peptide according to any one of the previous embodiments, wherein said glucagon peptide is selected from glucagon (1-29), glucagon (1-29)-amide, or an analogue thereof.
96. The glucagon peptide according to any one of the previous embodiments, selected from the group consisting of: Chem.1; Chem.2; Chem.3; Chem.4; Chem.5; Chem.6; Chem.7; Chem.8; Chem.9; Chem.10; Chem.11; Chem.12; Chem.13; Chem.14; Chem.15; Chem.16; Chem.17; Chem.18; Chem.19; Chem.20; Chem.21; Chem.22; Chem.23; Chem.24; Chem.25; Chem.26; Chem.27; Chem.28; Chem.29; Chem.30; Chem.31; Chem.32; Chem.33; Chem.34; Chem.35; Chem.36; Chem.37; Chem.38; Chem.39; Chem.40; Chem.41; Chem.42; Chem.43; Chem.44; Chem.45; Chem.46; Chem.47; Chem.48; Chem.49; Chem.50; Chem.51; Chem.52; Chem.53; Chem.54; Chem.55; Chem.56; Chem.57; Chem.58; Chem.59; Chem.60; Chem.61; Chem.62; Chem.63; Chem.64; Chem.65; Chem.66; Chem.67; Chem.68; Chem.69; Chem.70; Chem.71; Chem.72; Chem.73; Chem.74; Chem.75; Chem.76; Chem.77; Chem.78; Chem.79; Chem.80; Chem.81; Chem.82; Chem.83; Chem.84; Chem.85; Chem.86; Chem.87; Chem.88; Chem.89; Chem.90; Chem.91; Chem.92; Chem.93; Chem.94; Chem.95; Chem.96 and Chem.97.

Further embodiments of the present invention relate to administration of the compounds of the present invention with antidiabetic agents or anti-obesity agents:

97. The glucagon peptide according to any one of the previous embodiments, in combination with a glucagon-like peptide 1 (GLP-1) compound.
98. The glucagon peptide according to any one of the previous embodiments, in combination with an insulinic compound.
99. The glucagon peptide according to any one of the previous embodiments, in combination with exendin-4.
100. The glucagon peptide according to any one of the previous embodiments, which is in a dual chamber, depository and/or micro-encapsulation formulation.
101. The glucagon peptide according to any one of the previous embodiments, in combination with a glucagon-like peptide 1 (GLP-1) compound, for the preparation of a medicament for the treatment of diabetes and/or obesity.
102. The glucagon peptide according to any one of the previous embodiments, in combination with an insulinic compound, for the preparation of a medicament for the treatment of diabetes and/or obesity.
103. The glucagon peptide according to any one of the previous embodiments, in combination with exendin-4, for the preparation of a medicament for the treatment of diabetes and/or obesity.
104. The glucagon peptide according to any one of embodiments 97-103, wherein the GLP-1 compound and the insulinic compound are respresented by formulae G1-G4 and G5 respectively:

N-epsilon26-((S)-4-Carboxy-4-hexadecanoylamino-butyryl)[Arg34]GLP-1-(7-37):

(compound G1)

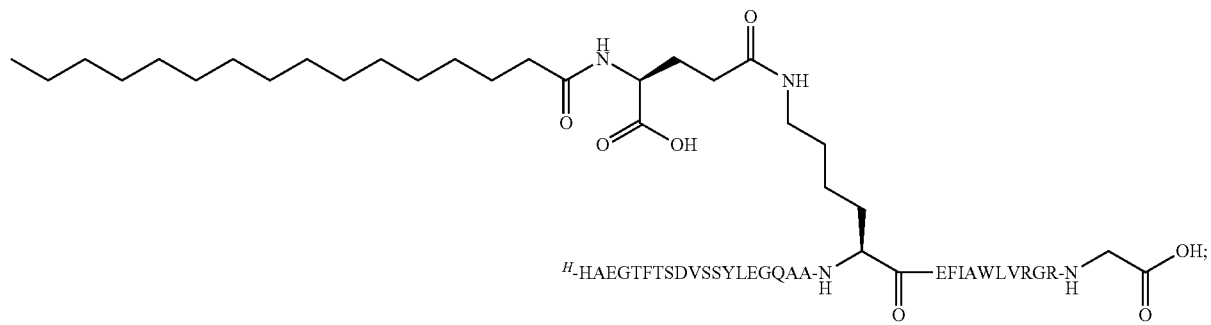

N-epsilon37-[2-(2-{2-[2-(2-{2-[(S)-4-Carboxy-4-({trans-4-[(19-carboxynonadecanoylamino)methyl] cyclohexanecarbonyl}amino)butyrylamino] ethoxy}ethoxy) acetylamino]ethoxy}ethoxy)acetyl] [DesaminoHis7,Glu22,Arg26,Arg34,Lys37]GLP-1-(7-37):

(compound G2)

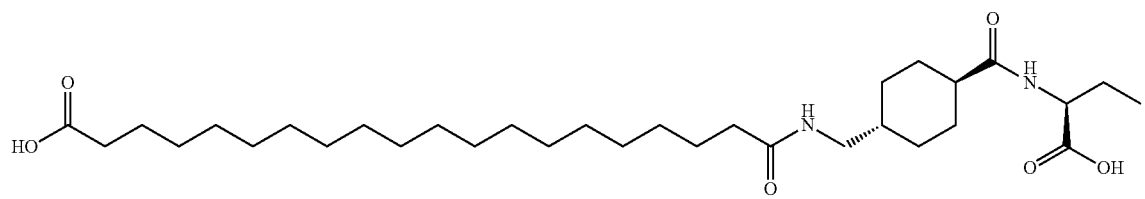

-continued
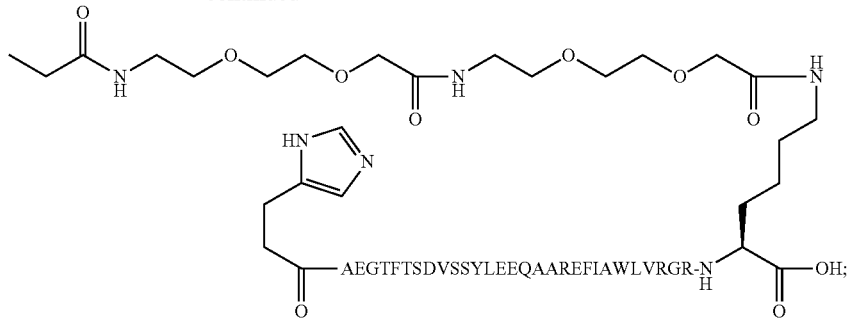
N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):
(compound G3)
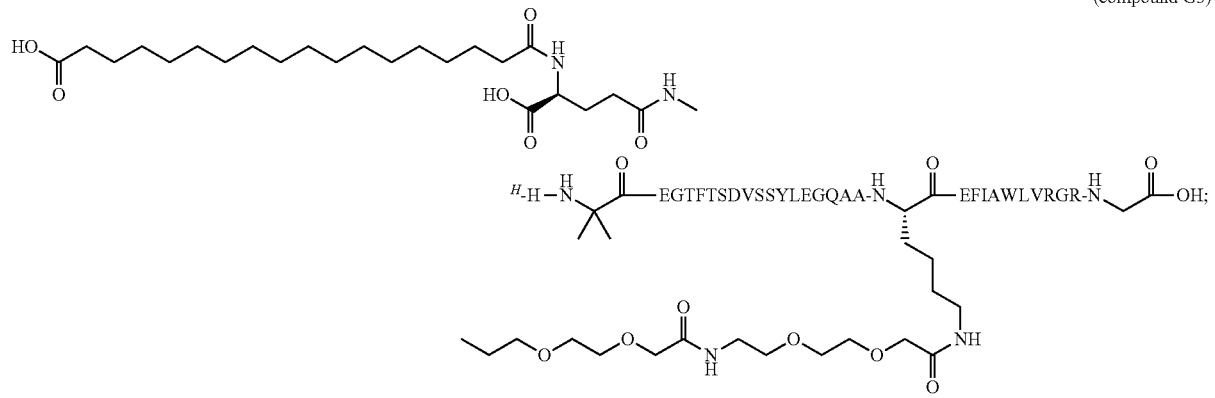
N-epsilon37-[2-(2-{2-[2-(2-{2-[(S)-4-carboxy-4-(15-carboxy-pentadecanoylamino)butyrylamino]-ethoxyl}-ethoxy)-acetylamino]-ethoxyl}-ethoxy)-acetyl][Aib8,22,35,Lys37]GLP-1-(7-37):
(compound G4)
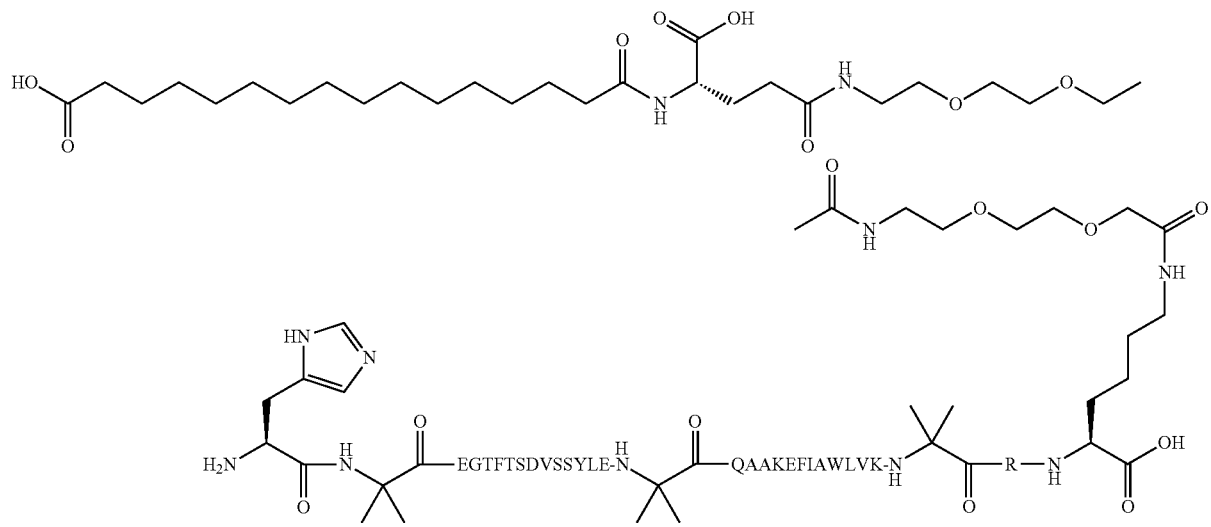

and
NεB29-hexadecandiyol-γ-Glu-(desB30) human insulin

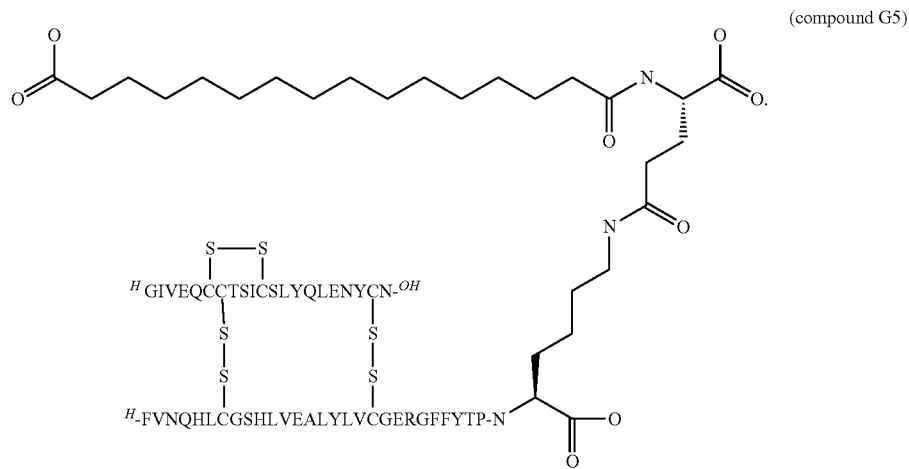
(compound G5)

105. The glucagon peptide according to embodiment 104, wherein the GLP-1 compound is represented by formula G1:
N-epsilon26-((S)-4-Carboxy-4-hexadecanoylamino-butyryl)[Arg34]GLP-1-(7-37):

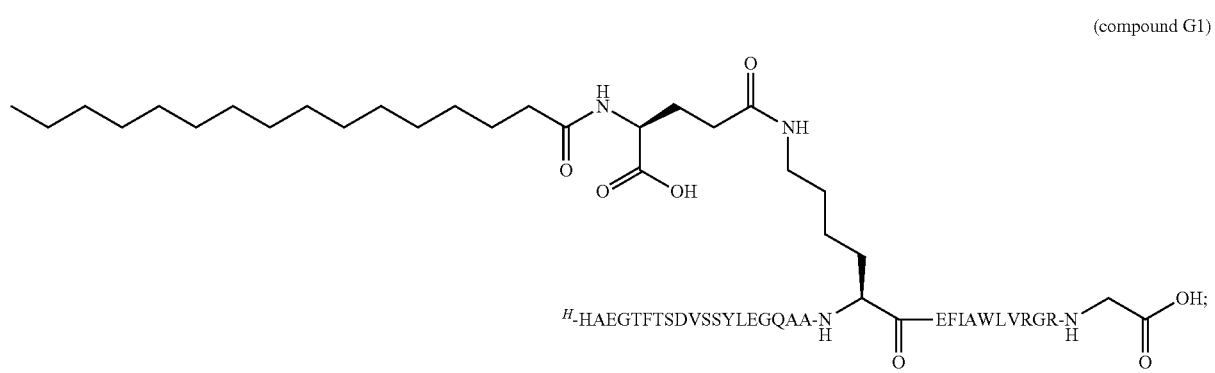
(compound G1)

106. The glucagon peptide according to embodiment 104, wherein the GLP-1 compound is represented by formula G2:
N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxyl}ethoxy) acetylamino]ethoxyl}ethoxy)acetyl][DesaminoHis7,Glu22,Arg26,Arg34,Lys37]GLP-1-(7-37):

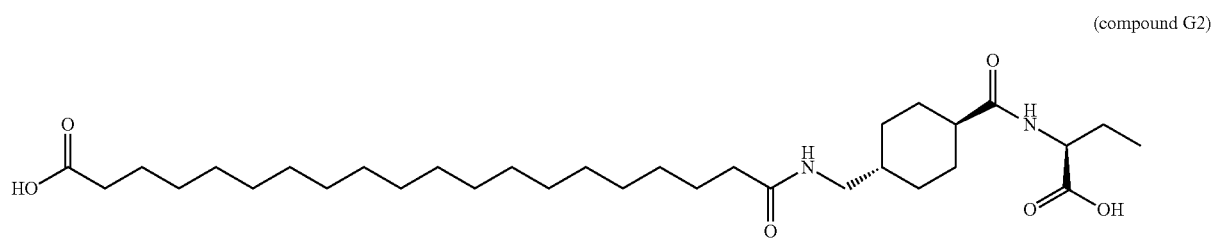
(compound G2)

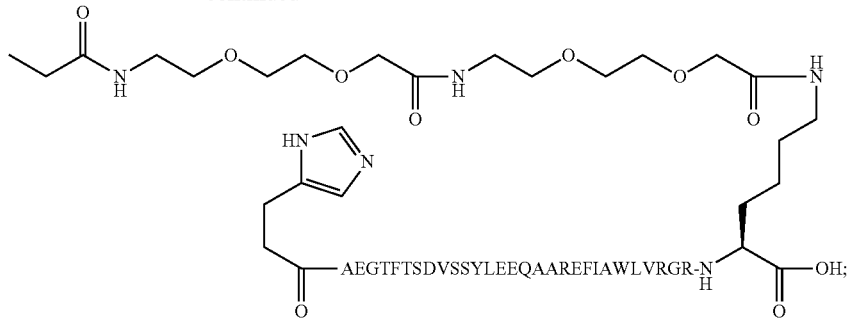

107. The glucagon peptide according to embodiment 104, wherein the GLP-1 compound is represented by formula G3:

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

(compound G3)

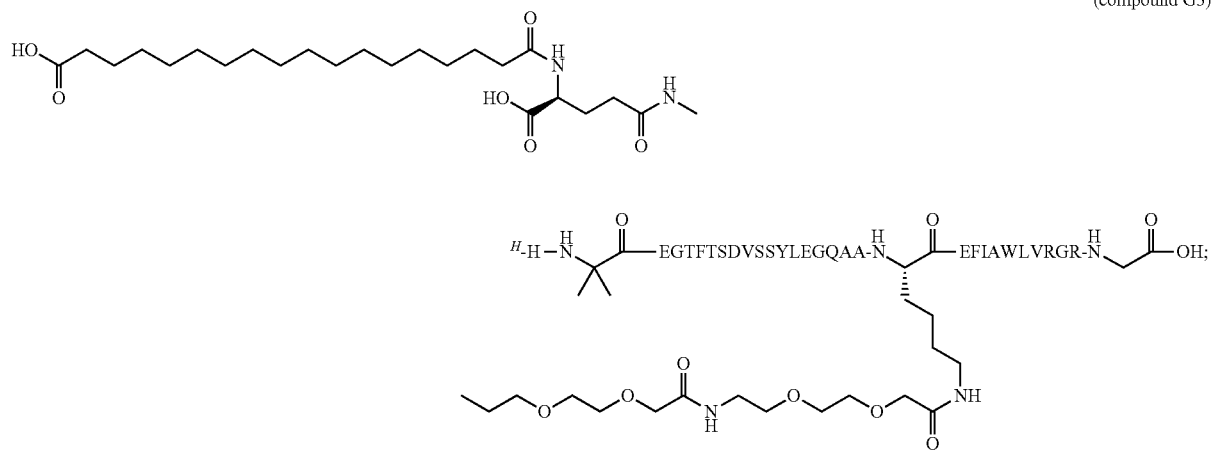

108. The glucagon peptide according to embodiment 104, wherein the GLP-1 compound is represented by formula G4:

N-epsilon37-[2-(2-{2-[2-(2-{2-[(S)-4-carboxy-4-(15-carboxy-pentadecanoylamino)butyrylamino]-ethoxyl}-ethoxy)-acetylamino]-ethoxyl}-ethoxy)-acetyl][Aib8,22,35,Lys37]GLP-1-(7-37):

(compound G4)

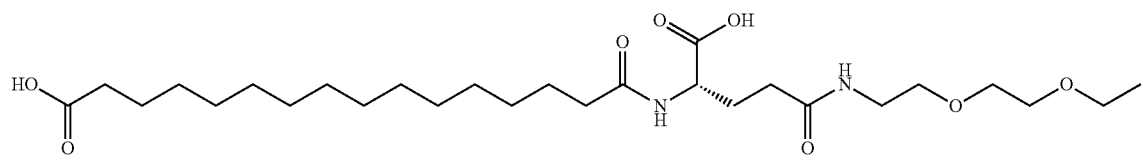

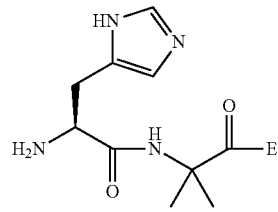
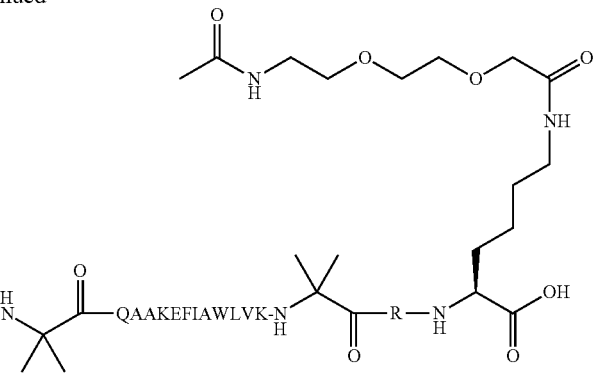

109. The glucagon peptide according to embodiment 104, wherein the insulinic compound is represented by formula G5:
NϵB29-hexadecandiyol-γ-Glu-(desB30) human insulin

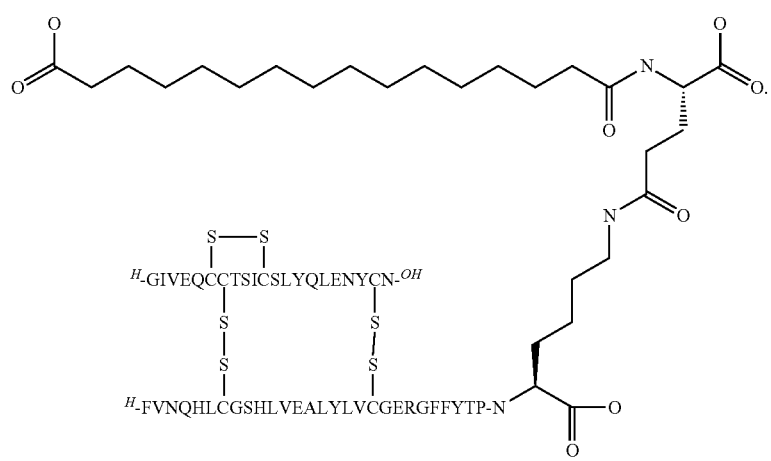

(compound G5)

110. The glucagon peptide according to any one of embodiments 97-104, wherein said glucagon peptide is selected from the group consisting of Chem.1-Chem. 97 and is in combination with a GLP-1 compound selected from the group: G1-G4.
111. The glucagon peptide according to any one of embodiments 97-104, wherein said glucagon peptide is selected from the group consisting of Chem.1-Chem. 97 and is in combination with an insulinic compound such as G5.
112. The glucagon peptide according to any one of embodiments 97-104, wherein said glucagon peptide is selected from the group consisting of Chem.1-Chem. 97 and is in combination with exendin-4.

GLP-1 is an incretin hormone produced by the endocrine cells of the intestine following ingestion of food. GLP-1 is a regulator of glucose metabolism, and the secretion of insulin from the beta cells of the islets of Langerhans in the pancreas. GLP-1 also causes insulin secretion in the diabetic state. The half-life in vivo of GLP-1 itself is, however, very short, thus, ways of prolonging the half-life of GLP-1 in vivo has attracted much attention.

WO 98/08871 discloses protracted GLP-1 analogues and derivatives based on human GLP-1(7-37) which have an extended half-life, including liraglutide, a GLP-1 derivative for once daily administration developed by Novo Nordisk NS marketed for the treatment of type 2 diabetes.

Exenatide is a commercial incretin mimetic for the treatment of diabetes mellitus type 2 which is manufactured and marketed by Amylin Pharmaceuticals and Eli Lilly & Co. Exenatide is based on exendin-4, a hormone found in the saliva of the Gila monster. It displays biological properties similar to human GLP-1. U.S. Pat. No. 5,424,286 relates i.a. to a method of stimulating insulin release in a mammal by administration of exendin-4 (SEQ ID NO: 3).

The term "GLP-1 compound" as used herein refers to human GLP-1(7-37), exendin-4 as well as analogues, fusion peptides, and derivatives thereof, which maintain GLP-1 activity.

As regards position numbering in GLP-1 compounds: for the present purposes any amino acid substitution, deletion, and/or addition is indicated relative to the sequences of GLP-1(7-37) (SEQ ID NO: 2) and/or exendin-4. However, the numbering of the amino acid residues in the sequence listing always starts with no. 1, whereas for the present purpose we want, following the established practice in the art, to start with amino acid residue no. 7 and assign number 7 to it in the case of GLP-1(7-37). Therefore, generally, any reference herein to a position number of the GLP-1(7-37) sequence is to the sequence starting with His at position 7 and ending with Gly at position 37.

GLP-1 compounds may be prepared as known in the art.
GLP-1 activity may be determined using any method known in the art, e.g. the assay (II) herein (stimulation of cAMP formation in a cell line expressing the human GLP-1 receptor).

Furthermore, the GLP-1 compound is a compound which may:

i) comprise at least one of the following: DesaminoHis7, Aib8, Aib22, Arg26, Aib35, and/or Lys37;

ii) be a GLP-1 derivative comprising an albumin binding moiety which comprises at least one, preferably at least two, more preferably two, free carboxylic acid groups; or a pharmaceutically acceptable salt thereof;

iii) be a GLP-1 derivative comprising an albumin binding moiety that comprises an acyl radical of a dicarboxylic acid, preferably comprising a total of from 12 to 24 carbon atoms, such as C12, C14, C16, C18, C20, C22, or C24, most preferably C16, C18, or C20; wherein preferably a) the acyl radical is attached to the epsilon amino group of a lysine residue of the GLP-1 peptide via a linker; b) the linker comprises at least one OEG radical, and/or at least one 4-Aminomethyl-cyclohexanecarboxylic acid radical, and, optionally, additionally at least one Glu; and/or iv) be selected from the group consisting of compounds N-epsilon26-((S)-4-Carboxy-4-hexadecanoylamino-butyryl)[Arg34]GLP-1-(7-37):

(compound G1)

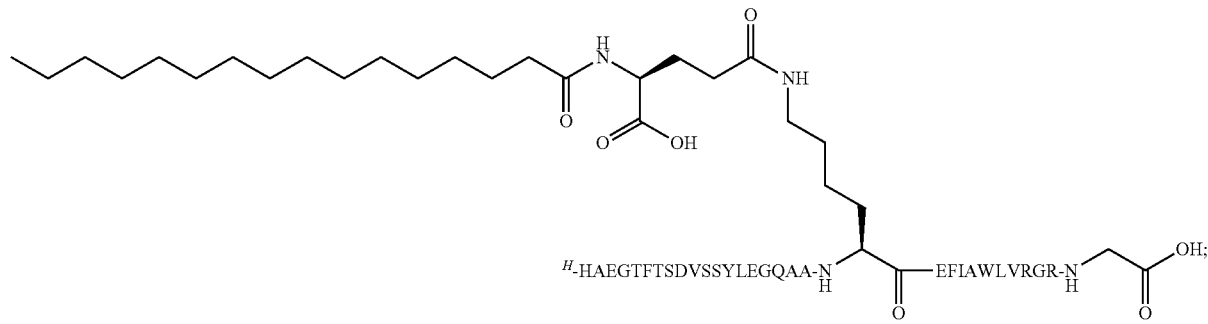

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxyl}ethoxy) acetylamino]ethoxy}ethoxy)acetyl][DesaminoHis7,Glu22,Arg26,Arg34,Lys37]GLP-1-(7-37):

(compound G2)

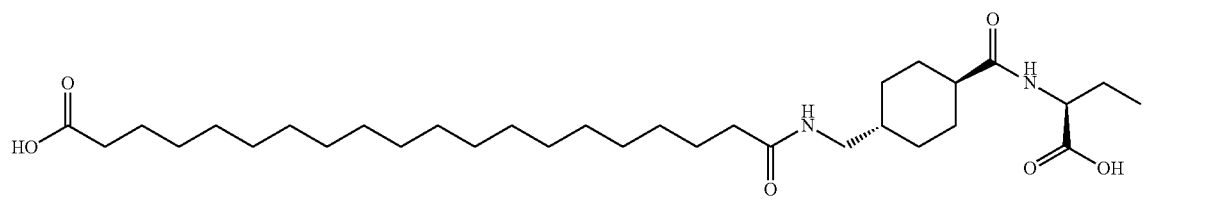

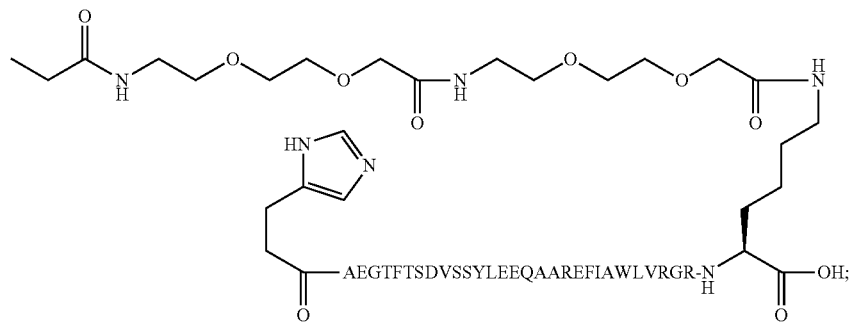

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

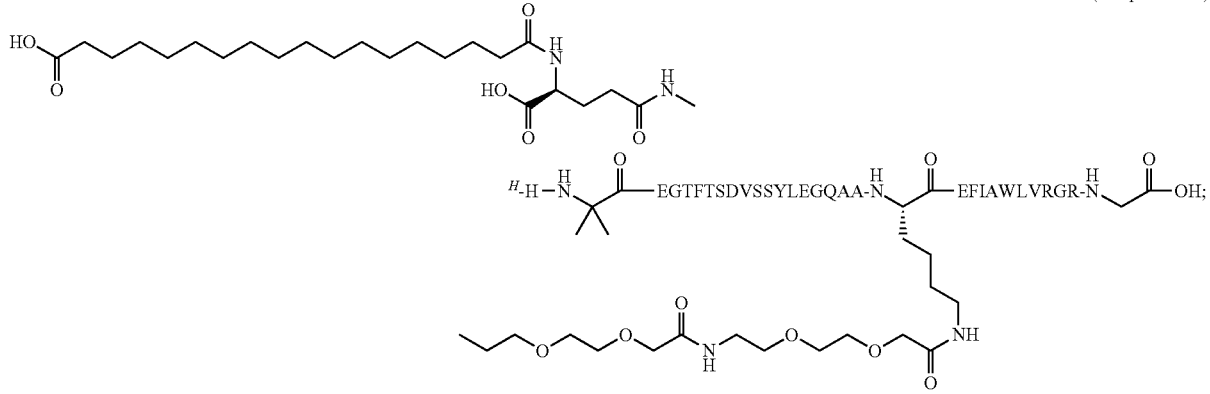

N-epsilon37-[2-(2-{2-[2-(2-{2-[(S)-4-carboxy-4-(15-carboxy-pentadecanoylamino)butyrylamino]-ethoxyl}-ethoxy)-acetylamino]-ethoxyl}-ethoxy)-acetyl][Aib8,22,35,Lys37]GLP-1-(7-37):

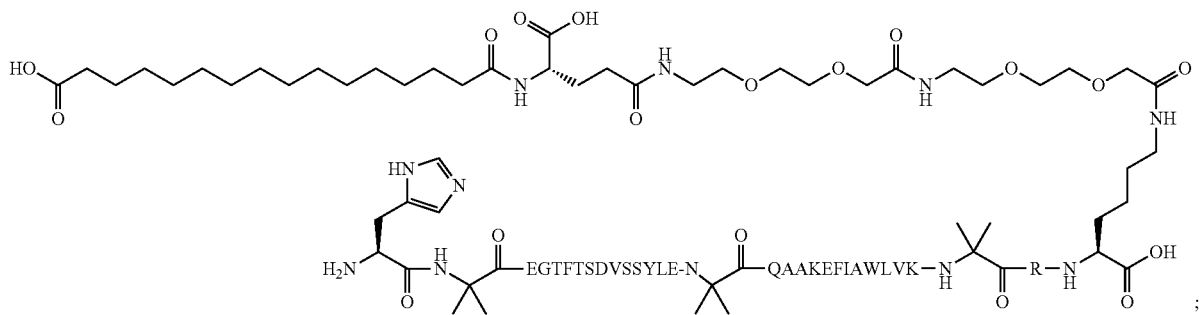

and their pharmaceutically acceptable salts, amides, alkyls, or esters.

An "insulin" according to the invention is herein to be understood as human insulin, an insulin analogue or an insulin derivative.

The insulinic compound is a compound which may for example, be represented by:

NεB29-hexadecandiyol-γ-Glu-(desB30) human insulin (compound G5)

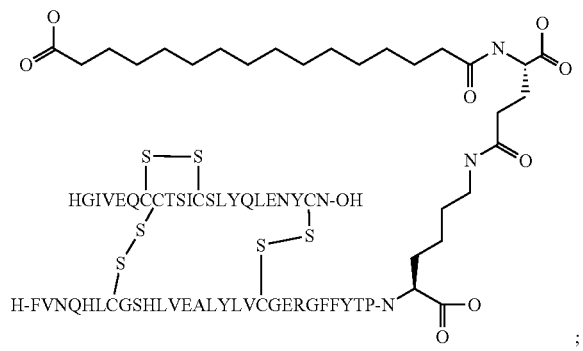

The compounds of the present invention and anti-obesity or anti-diabetic agents as defined in the present specification, may be administered simultaneously or sequentially. The factors may be supplied in single-dosage form wherein the (compound G3)

(compound G4)

single-dosage form contains both compounds, or in the form of a kit-of-parts comprising a preparation of a compound of the present invention as a first unit dosage form and a preparation of a anti-obesity or anti-diabetic agents as a second unit dosage form. Whenever a first or second or third, etc., unit dose is mentioned throughout this specification this does not indicate the preferred order of administration, but is merely done for convenience purposes.

By "simultaneous" dosing of a preparation of a compound of the present invention and a preparation of anti-obesity or anti-diabetic agents is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

As already indicated, in all of the therapeutic methods or indications disclosed above, a compound of the present invention may be administered alone. However, it may also be administered in combination with one or more additional therapeutically active agents, substances or compounds, either sequentially or concomitantly.

A typical dosage of a compound of the invention when employed in a method according to the present invention is in the range of from about 0.0001 to about 100 mg/kg body weight per day, preferably from about 0.001 to about 10 mg/kg body weight, more preferably from about 0.001 to about 5 mg/kg body weight per day, e.g. from about 0.001 to about 10 mg/kg body weight per day or from about 0.001 to about 5 mg/kg body weight per day administered in one or more doses, such as from 1 to 3 doses. The exact dosage will depend upon the frequency and mode of administration, the sex, age, weight and general condition of the subject treated, the nature and severity of the condition treated, any concomitant diseases to be treated and other factors evident to those skilled in the art.

Compounds of the invention comprise compounds that are believed to be well-suited to administration with longer intervals than, for example, once daily, thus, appropriately formulated compounds of the invention may be suitable for, e.g., twice-weekly or once-weekly administration by a suitable route of administration, such as one of the routes disclosed herein.

As described above, compounds of the present invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from, or associated with, diabetes.

Suitable antidiabetic agents include insulin, insulin derivatives or analogues, GLP-1 (glucagon like peptide-1) derivatives or analogues or other GLP-1 analogues such as liraglutide (Victoza, Novo Nordisk NS), exenatide (Byetta, Eli Lilly/Amylin), taspoglutide (Roche), albiglutide (Syncria, GlaxoSmithKline), amylin, amylin analogues (e.g. Symlin™/Pramlintide) as well as orally active hypoglycemic agents.

The compounds of the present invention have higher glucagon receptor selectivity in relation to previously disclosed peptides in the art. The peptides of the present invention also have prolonged in vivo half-life. The compounds of the present invention can be a soluble glucagon receptor agonist, for example with solubility of at least 0.1 mmol/l, 0.2 mmol/l, at least 0.5 mmol/l, at least 2 mmol/l, at least 4 mmol/l, at least 8 mmol/l, at least 10 mmol/l, or at least 15 mmol/I.

In the present context, if not stated otherwise, the terms "soluble", "solubility", "soluble in aquous solution", "aqueous solubility", "water soluble", "water-soluble", "water solubility" and "water-solubility", refer to the solubility of a compound in water or in an aqueous salt or aqueous buffer solution, for example a 10 mM phosphate solution, or in an aqueous solution containing other compounds, but no organic solvents.

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is used to describe analogues. Formulae of peptide analogs and derivatives thereof are drawn using standard single letter or three letter abbreviations for amino acids used according to IUPAC-IUB nomenclature.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like.

All amino acids for which the optical isomer is not stated is to be understood to mean the L-isomer.

The term "glucagon peptide" as used herein means glucagon peptide, glucagon compound, compound according to the present invention, compound of the present invention, compound of formula I, a glucagon analogue, a glucagon derivative or a derivative of a glucagon analogue human glucagon, human glucagon(1-29), glucagon(1-30), glucagon (1-31), glucagon(1-32) as well as analogues, fusion peptides, and derivatives thereof, which maintain glucagon activity.

As regards position numbering in glucagon compounds: for the present purposes any amino acid substitution, deletion, and/or addition is indicated relative to the sequences of native human glucagon (1-29) (SEQ ID NO: 1). Human glucagon amino acids positions 1-29 are herein to be the same as amino acid positions $X_1$ to $X_{29}$. The human glucagon (1-29) sequence is His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1).

Glucagon(1-30) means human glucagon with an extension of one amino acid in the C-terminal (SEQ ID NO: 5), glucagon(1-31) means human glucagon with an extension of two amino acid in the C-terminal (SEQ ID NO: 6) and glucagon(1-32) means human glucagon with an extension of three amino acid in the C-terminal (SEQ ID NO. 7).

The term "distal" as used herein, means most remote (terminal) from the point of attachment.

The term "negative charged moiety" as used herein, means a negatively chargeable chemical moiety such as, but not limited to a carboxylic acid, sulphonic acid or a tetrazole moiety.

The term "lipophilic moiety" as used herein, means an aliphatic or cyclic hydrocarbon moiety with more than 6 and less than 30 carbon atoms, wherein said hydrocarbon moiety may contain additional substituents.

The term "substituent" as used herein, means a chemical moiety or group replacing a hydrogen.

The term "1H-tetrazol-5-yl" as used herein as a part of chemical names is intended to indicate both 1H-tetrazol-5-yl and 2H-tetrazol-5-yl.

Further embodiments of the present invention relate to:
113. The glucagon peptide according to any of the previous embodiments, wherein said glucagon peptide is a DPPIV protected compound.
114. The glucagon peptide according to any of the previous embodiments, wherein said glucagon peptide is DPPIV stabilised.
115. The glucagon peptide according to any of the previous embodiments, wherein said glucagon peptide is an agonist of the glucagon receptor.
116. The glucagon peptide according to any of the previous embodiments, wherein said glucagon peptide is an agonist of the glucagon receptor, with an $EC_{50}<1$ nM.

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. glucagon, GLP-1, GLP-2, oxyntomodulin etc. Thus, a considerable effort is being made to develop analogues and derivatives of the polypeptides susceptible to DPP-IV mediated hydrolysis in order to reduce the rate of degradation by DPP-IV.

Furthermore, the compounds of the present invention may be stabilized against DPP-IV cleavage in an albumin free assay as described in Assay VII.

In the present context, the term "agonist" is intended to indicate a substance (ligand) that activates the receptor type in question.

In the present context, the term "antagonist" is intended to indicate a substance (ligand) that blocks, neutralizes or counteracts the effect of an agonist.

The term "glucagon agonist" as used herein refers to any glucagon peptide which fully or partially activates the human glucagon receptor. In a preferred embodiment, the "glucagon agonist" is any glucagon peptide that activates the glucagon receptor, preferably with an affinity a potency ($EC_{50}$) below 1 µM, e.g., below 100 nM or below 1 nM, as measured by Assay I.

In the present context, the term "pharmaceutically acceptable salt" is intended to indicate a salt which is not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric and nitric acids, and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene-salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. (1977) 66, 2, which is incorporated herein by reference. Examples of relevant metal salts include lithium, sodium, potassium and magnesium salts, and the like. Examples of alkylated ammonium salts include methylammonium, dimethylammonium, trimethylammonium, ethylammonium, hydroxyethylammonium, diethylammonium, butylammonium and tetramethylammonium salts, and the like.

As use herein, the term "therapeutically effective amount" of a compound refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the subject. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition, or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

The term "albumin binding residue" as used herein means a residue which binds non-covalently to human serum albumin. The albumin binding residue attached to the therapeutic polypeptide typically has an affinity below 10 µM to human serum albumin and preferably below 1 µM. A range of albumin binding residues are known among linear and branched lipohophillic moieties containing 4-40 carbon atoms.

Other embodiments of the present relates to pharmaceutical compositions:

117. A pharmaceutical composition comprising a glucagon peptide according to any one of embodiments 1-116.

118. The pharmaceutical composition according to embodiment 117, further comprising one or more additional therapeutically active compounds or substances.

119. The pharmaceutical composition according to any one of embodiments 117-118, further comprising a GLP-1 compound.

120. The pharmaceutical composition according to embodiment 119, wherein the GLP-1 compound is selected from the group consisting of:

N-epsilon26-((S)-4-Carboxy-4-hexadecanoylamino-butyryl)[Arg34]GLP-1-(7-37):

(compound G1)

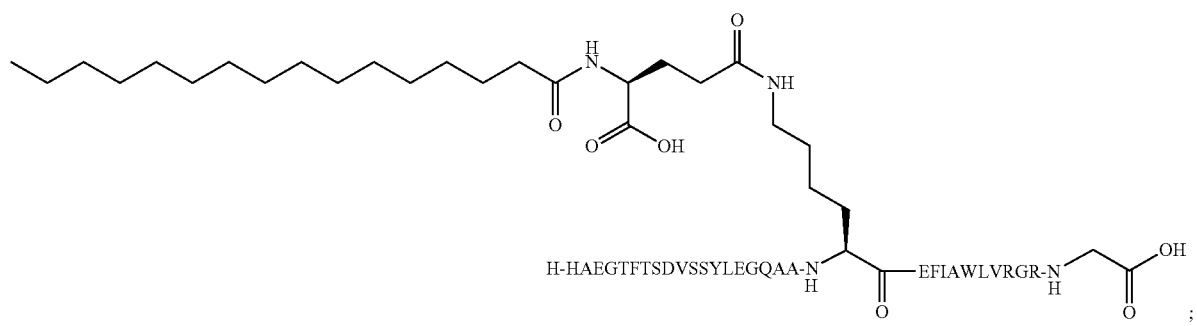

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy) acetylamino]ethoxy}ethoxy)acetyl][DesaminoHis7,Glu22,Arg26,Arg34,Lys37]GLP-1-(7-37):

(compound G2)

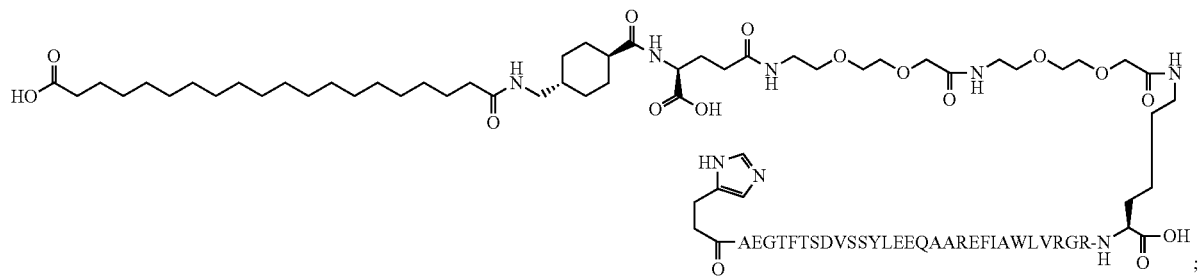

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

(compound G3)

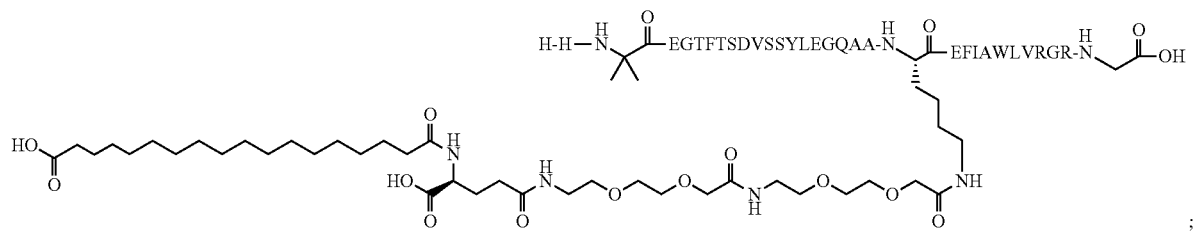

N-epsilon37-[2-(2-{2-[2-(2-{2-[(S)-4-carboxy-4-(15-carboxy-pentadecanoylamino)butyrylamino]-ethoxyl}-ethoxy)-acetylamino]-ethoxyl}-ethoxy)-acetyl][Aib8,22,35,Lys37]GLP-1-(7-37):

(compound G4)

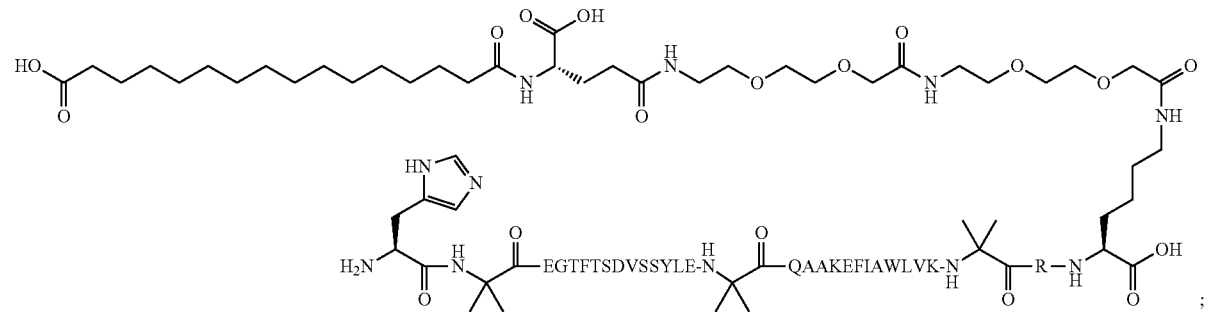

and their pharmaceutically acceptable salts, amides, alkyls, or esters.
121. The pharmaceutical composition according to any one of embodiments 117-118, further comprising an insulinic compound.
122. The pharmaceutical composition according to embodiment 121, wherein the insulin compound is:
NεB29-hexadecandiyol-γ-Glu-(desB30) human insulin (compound G5)

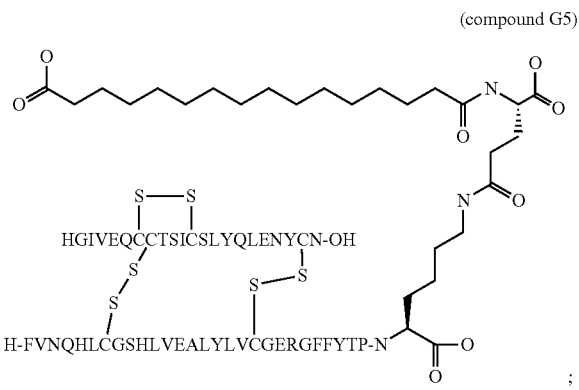

123. The pharmaceutical composition according to any one of embodiments 105-110, in unit dosage form comprising from about 0.01 mg to about 1000 mg, such as from about 0.1 mg to about 500 mg, from about 0.5 mg to about 5 mg, e.g. from about 0.5 mg to about 200 mg, of a glucagon peptide according to any of embodiments 1-116.
124. The pharmaceutical composition according to any one of embodiments 117-123, which is suited for parenteral administration.
125. The glucagon peptide according to any one of embodiments 1-116, for use in therapy.

Further embodiments of the present invention relate to the following:
126. The glucagon peptide according to any of embodiments 1-116, optionally in combination with one or more additional therapeutically active compounds, for use in treatment or prevention of hyperglycemia, type 2 diabetes, impaired glucose tolerance, type 1 diabetes and obesity.
127. The glucagon peptide according to any of embodiments 1-116, optionally in combination with one or more additional therapeutically active compounds, for use in delaying or preventing disease progression in type 2 diabetes.
128. The glucagon peptide according to any of embodiments 1-116, optionally in combination with one or more additional therapeutically active compounds, for use treating obesity or preventing overweight.
129. The glucagon peptide according to any of embodiments 1-116, optionally in combination with one or more additional therapeutically active compounds, for use in for decreasing food intake.
130. The glucagon peptide according to any of embodiments 1-116, optionally in combination with one or more additional therapeutically active compounds, for use in increasing energy expenditure.
131. The glucagon peptide according to any of embodiments 1-116, optionally in combination with one or more additional therapeutically active compounds, for use in reducing body weight.
132. The glucagon peptide according to any of embodiments 1-116, optionally in combination with one or more additional therapeutically active compounds, for use in delaying the progression from impaired glucose tolerance (IGT) to type 2 diabetes.
133. The glucagon peptide according to any of embodiments 1-116, optionally in combination with one or more additional therapeutically active compounds, for use in delaying the progression from type 2 diabetes to insulin-requiring diabetes.
134. The glucagon peptide according to any of embodiments 1-116, optionally in combination with one or more additional therapeutically active compounds, for use regulating appetite.
135. The glucagon peptide according to any of embodiments 1-116, optionally in combination with one or more additional therapeutically active compounds, for use inducing satiety.
136. The glucagon peptide according to any of embodiments 1-116, optionally in combination with one or more additional therapeutically active compounds, for use in preventing weight regain after successful weight loss.
137. The glucagon peptide according to any of embodiments 1-116, optionally in combination with one or more additional therapeutically active compounds, for use in treating a disease or state related to overweight or obesity.
138. The glucagon peptide according to any of embodiments 1-116, optionally in combination with one or more additional therapeutically active compounds, for use in treating bulimia.
139. The glucagon peptide according to any of embodiments 1-116, optionally in combination with one or more additional therapeutically active compounds, for use in treating binge-eating.
140. The glucagon peptide according to any of embodiments 1-116, optionally in combination with one or more additional therapeutically active compounds, for use in treating atherosclerosis.
141. The glucagon peptide according to any of embodiments 1-116, optionally in combination with one or more additional therapeutically active compounds, for use in treating hypertension.
142. The glucagon peptide according to any of embodiments 1-116, optionally in combination with one or more additional therapeutically active compounds, for use in treating type 2 diabetes.
143. The glucagon peptide according to any of embodiments 1-116, optionally in combination with one or more additional therapeutically active compounds, for use in treating impaired glucose tolerance.
144. The glucagon peptide according to any of embodiments 1-116, optionally in combination with one or more additional therapeutically active compounds, for use in treating dyslipidemia.
145. The glucagon peptide according to any of embodiments 1-116, optionally in combination with one or more additional therapeutically active compounds, for use in treating coronary heart disease.
146. The glucagon peptide according to any of embodiments 1-116, optionally in combination with one or more additional therapeutically active compounds, for use in treating hepatic steatosis.
147. The glucagon peptide according to any of embodiments 1-116, optionally in combination with one or more additional therapeutically active compounds, for use in treating hepatic steatosis.

148. The glucagon peptide according to any of embodiments 1-116, optionally in combination with one or more additional therapeutically active compounds, for use in treating beta-blocker poisoning.
149. The glucagon peptide according to any of embodiments 1-116, optionally in combination with one or more additional therapeutically active compounds, for use in inhibition of the motility of the gastrointestinal tract, useful in connection with investigations of the gastrointestinal tract using techniques such as x-ray, CT- and NMR-scanning.
150. The glucagon peptide according to any of embodiments 1-116, optionally in combination with one or more additional therapeutically active compounds, for use in treatment or prevention of hypoglycaemia.
151. The glucagon peptide according to any of embodiments 1-116, optionally in combination with one or more additional therapeutically active compounds, for use in treatment or prevention of insulin induced hypoglycaemia.
152. The glucagon peptide according to any of embodiments 1-116, optionally in combination with one or more additional therapeutically active compounds, for use in treatment or prevention of reactive hypoglycaemia.
153. The glucagon peptide according to any of embodiments 1-116, optionally in combination with one or more additional therapeutically active compounds, for use in treatment or prevention of diabetic hypoglycaemia.
154. The glucagon peptide according to any of embodiments 1-116, optionally in combination with one or more additional therapeutically active compounds, for use in treatment or prevention of non-diabetic hypoglycaemia.
155. The glucagon peptide according to any of embodiments 1-116, optionally in combination with one or more additional therapeutically active compounds, for use in treatment or prevention of fasting hypoglycaemia.
156. The glucagon peptide according to any of embodiments 1-116, optionally in combination with one or more additional therapeutically active compounds, for use in treatment or prevention of drug-induced hypoglycaemia.
157. The glucagon peptide according to any of embodiments 1-116, optionally in combination with one or more additional therapeutically active compounds, for use in treatment or prevention of gastric by-pass induced hypoglycaemia.
158. The glucagon peptide according to any of embodiments 1-116, optionally in combination with one or more additional therapeutically active compounds, for use in treatment or prevention of hypoglycemia in pregnancy.
159. The glucagon peptide according to any of embodiments 1-116, optionally in combination with one or more additional therapeutically active compounds, for use in treatment or prevention of alcohol-induced hypoglycaemia.
160. The glucagon peptide according to any of embodiments 1-116, optionally in combination with one or more additional therapeutically active compounds, for use in treatment or prevention of insulinoma.
161. The glucagon peptide according to any of embodiments 1-116, optionally in combination with one or more additional therapeutically active compounds, for use in treatment or prevention of Von Girkes disease.

Further embodiments of the present invention relate to the following methods:
162. A method for treating or preventing hypoglycemia, type 2 diabetes, impaired glucose tolerance, type 1 diabetes and obesity, comprising administering to a patient in need thereof, an effective amount of a glucagon peptide according to any of embodiments 1-116, optionally in combination with one or more additional therapeutically active compounds.
163. A method for delaying or preventing disease progression in type 2 diabetes, comprising administering to a patient in need thereof, an effective amount of a glucagon peptide according to any of embodiments 1-116, optionally in combination with one or more additional therapeutically active compounds.
164. A method for treating obesity or preventing overweight, comprising administering to a patient in need thereof, an effective amount of a glucagon peptide according to any of embodiments 1-116, optionally in combination with one or more additional therapeutically active compounds.
165. A method for decreasing food intake, comprising administering to a patient in need thereof, an effective amount of a glucagon peptide according to any of embodiments 1-116, optionally in combination with one or more additional therapeutically active compounds.
166. A method for use in increasing energy expenditure, comprising administering to a patient in need thereof, an effective amount of a glucagon peptide according to any of embodiments 1-116, optionally in combination with one or more additional therapeutically active compounds.
167. A method for use in reducing body weight, comprising administering to a patient in need thereof, an effective amount of a glucagon peptide according to any of embodiments 1-116, optionally in combination with one or more additional therapeutically active compounds.
168. A method for use in delaying the progression from impaired glucose tolerance (IGT) to type 2 diabetes, comprising administering to a patient in need thereof, an effective amount of a glucagon peptide according to any of embodiments 1-116, optionally in combination with one or more additional therapeutically active compounds.
169. A method for use in delaying the progression from type 2 diabetes to insulin-requiring diabetes, comprising administering to a patient in need thereof, an effective amount of a glucagon peptide according to any of embodiments 1-116, optionally in combination with one or more additional therapeutically active compounds.
170. A method for use in regulating appetite, comprising administering to a patient in need thereof, an effective amount of a glucagon peptide according to any of embodiments 1-116, optionally in combination with one or more additional therapeutically active compounds.
171. A method for use in inducing satiety, comprising administering to a patient in need thereof, an effective amount of a glucagon peptide according to any of embodiments 1-116, optionally in combination with one or more additional therapeutically active compounds.
172. A method for use in preventing weight regain after successful weight loss, comprising administering to a patient in need thereof, an effective amount of a glucagon peptide according to any of embodiments 1-116, optionally in combination with one or more additional therapeutically active compounds.
173. A method for use in treating a disease or state related to overweight or obesity, comprising administering to a patient in need thereof, an effective amount of a glucagon peptide according to any of embodiments 1-116, optionally in combination with one or more additional therapeutically active compounds.
174. A method for use in treating bulimia, comprising administering to a patient in need thereof, an effective amount of a glucagon peptide according to any of embodiments 1-116, optionally in combination with one or more additional therapeutically active compounds.
175. A method for use in treating binge-eating, comprising administering to a patient in need thereof, an effective amount of a glucagon peptide according to any of embodiments 1-116, optionally in combination with one or more additional therapeutically active compounds.
176. A method for use in treating atherosclerosis, comprising administering to a patient in need thereof, an effective amount of a glucagon peptide according to any of embodiments 1-116, optionally in combination with one or more additional therapeutically active compounds.
177. A method for use in treating hypertension, comprising administering to a patient in need thereof, an effective amount of a glucagon peptide according to any of embodiments 1-116, optionally in combination with one or more additional therapeutically active compounds.
178. A method for use in treating type 2 diabetes, comprising administering to a patient in need thereof, an effective amount of a glucagon peptide according to any of embodiments 1-116, optionally in combination with one or more additional therapeutically active compounds.
179. A method for use in treating impaired glucose tolerance, comprising administering to a patient in need thereof, an effective amount of a glucagon peptide according to any of embodiments 1-116, optionally in combination with one or more additional therapeutically active compounds.
180. A method for use in treating dyslipidemia, comprising administering to a patient in need thereof, an effective amount of a glucagon peptide according to any of embodiments 1-116, optionally in combination with one or more additional therapeutically active compounds.
181. A method for use in treating coronary heart disease, comprising administering to a patient in need thereof, an effective amount of a glucagon peptide according to any of embodiments 1-116, optionally in combination with one or more additional therapeutically active compounds.
182. A method for use in treating hepatic steatosis, comprising administering to a patient in need thereof, an effective amount of a glucagon peptide according to any of embodiments 1-116, optionally in combination with one or more additional therapeutically active compounds.
183. A method for use in treating beta-blocker poisoning, comprising administering to a patient in need thereof, an effective amount of a glucagon peptide according to any of embodiments 1-116, optionally in combination with one or more additional therapeutically active compounds.
184. A method for use in inhibition of the motility of the gastrointestinal tract, useful in connection with investigations of the gastrointestinal tract using techniques such as x-ray, CT- and NMR-scanning, comprising administering to a patient in need thereof, an effective amount of a glucagon peptide according to any of embodiments 1-116, optionally in combination with one or more additional therapeutically active compounds.
185. A method for use in treatment or prevention of hypoglycaemia, comprising administering to a patient in need thereof, an effective amount of a glucagon peptide according to any of embodiments 1-116, optionally in combination with one or more additional therapeutically active compounds.
186. A method for use in treatment or prevention of insulin induced hypoglycaemia, comprising administering to a patient in need thereof, an effective amount of a glucagon peptide according to any of embodiments 1-116, optionally in combination with one or more additional therapeutically active compounds.
187. A method for use in treatment or prevention of reactive hypoglycaemia, comprising administering to a patient in need thereof, an effective amount of a glucagon peptide according to any of embodiments 1-116, optionally in combination with one or more additional therapeutically active compounds.
188. A method for use in treatment or prevention of diabetic hypoglycaemia, comprising administering to a patient in need thereof, an effective amount of a glucagon peptide according to any of embodiments 1-116, optionally in combination with one or more additional therapeutically active compounds.
189. A method for use in treatment or prevention of non-diabetic hypoglycaemia, comprising administering to a patient in need thereof, an effective amount of a glucagon peptide according to any of embodiments 1-116, optionally in combination with one or more additional therapeutically active compounds.
190. A method for use in treatment or prevention of fasting hypoglycaemia, comprising administering to a patient in need thereof, an effective amount of a glucagon peptide according to any of embodiments 1-116, optionally in combination with one or more additional therapeutically active compounds.
191. A method for use in treatment or prevention of drug-induced hypoglycaemia, comprising administering to a patient in need thereof, an effective amount of a glucagon peptide according to any of embodiments 1-116, optionally in combination with one or more additional therapeutically active compounds.
192. A method for use in treatment or prevention of gastric by-pass induced hypoglycaemia, comprising administering to a patient in need thereof, an effective amount of a glucagon peptide according to any of embodiments 1-116, optionally in combination with one or more additional therapeutically active compounds.
193. A method for use in treatment or prevention of hypoglycemia in pregnancy, comprising administering to a patient in need thereof, an effective amount of a glucagon peptide according to any of embodiments 1-116, optionally in combination with one or more additional therapeutically active compounds.
194. A method for use in treatment or prevention of alcohol-induced hypoglycaemia, comprising administering to a patient in need thereof, an effective amount of a glucagon peptide according to any of embodiments 1-116, optionally in combination with one or more additional therapeutically active compounds.
195. A method for use in treatment or prevention of insulinoma, comprising administering to a patient in need thereof, an effective amount of a glucagon peptide according to any of embodiments 1-116, optionally in combination with one or more additional therapeutically active compounds.
196. A method for use in treatment or prevention of Von Girkes disease, comprising administering to a patient in need thereof, an effective amount of a glucagon peptide according to any of embodiments 1-116, optionally in combination with one or more additional therapeutically active compounds.

Further embodiments of the present invention relate to the following uses:
197. Use of a glucagon peptide according to any one of the embodiments 1-116, for the preparation of a medicament.

198. Use of a glucagon peptide according to any one of embodiments 1-116, for the preparation of a medicament for the treatment or prevention of hyperglycemia, type 2 diabetes, impaired glucose tolerance, type 1 diabetes and obesity.

199. Use of a glucagon peptide according to any one of the embodiments 1-116, for the preparation of a medicament for delaying or preventing disease progression in type 2 diabetes, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge-eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as x-ray, CT- and NMR-scanning.

200. Use of a glucagon peptide according to any one of the embodiments 1-116, for the preparation of a medicament for reatment or prevention of hypoglycemia, insulin induced hypoglycemia, reactive hypoglycemia, diabetic hypoglycemia, non-diabetic hypoglycemia, fasting hypoglycemia, drug-induced hypoglycemia, gastric by-pass induced hypoglycemia, hypoglycemia in pregnancy, alcohol induced hypoglycemia, insulinoma and Von Girkes disease.

Further embodiments of the present invention relate to the following:

201. A glucagon peptide according to any of the previous embodiments, wherein said glucagon peptide has more than 70% recovery in the ThT fibrillation assay.
202. A glucagon peptide according to any of the previous embodiments, wherein said glucagon peptide has more than 90% recovery in the ThT fibrillation assay.
203. A glucagon peptide according to any of the previous embodiments, wherein said glucagon peptide has about 100% recovery in the ThT fibrillation assay.
204. A glucagon peptide according to any of the previous embodiments, wherein said glucagon peptide has more than 7 hours lag time in the ThT fibrillation assay.
205. A glucagon peptide according to any of the previous embodiments, wherein said glucagon peptide has more than 20 hours lag time in the ThT fibrillation assay.
206. A glucagon peptide according to any of the previous embodiments, wherein said glucagon peptide has 45 hours lag time or more in the ThT fibrillation assay.
207. A glucagon peptide according to any of the previous embodiments, wherein said glucagon peptide has less than 14% degradation in the chemical stability assay.
208. A glucagon peptide according to any of the previous embodiments, wherein said glucagon peptide has less than 13% degradation in the chemical stability assay.
209. A glucagon peptide according to any of the previous embodiments, wherein said glucagon peptide has less than 12% degradation in the chemical stability assay.
210. A glucagon peptide according to any of the previous embodiments, wherein said glucagon peptide has less than 10% degradation in the chemical stability assay.
211. A glucagon peptide according to any of the previous embodiments, wherein said glucagon peptide has less than 9% degradation in the chemical stability assay.
212. A glucagon peptide according to any of the previous embodiments, wherein said glucagon peptide has less than 7% degradation in the chemical stability assay.
213. A glucagon peptide according to any of the previous embodiments, wherein said glucagon peptide has less than 5% degradation in the chemical stability assay.
214. A glucagon peptide according to any of the previous embodiments, wherein said glucagon peptide has less than 3% degradation in the chemical stability assay.
215. A glucagon peptide according to any of the previous embodiments, wherein said glucagon peptide is 30 times more selective for glucagon receptor than for GLP-1 receptor.
216. A glucagon peptide according to any of the previous embodiments, wherein said glucagon peptide is 50 times more selective for glucagon receptor than for GLP-1 receptor.
217. A glucagon peptide according to any of the previous embodiments, wherein said glucagon peptide is 100 times more selective for glucagon receptor than for GLP-1 receptor.
218. A glucagon peptide according to any of the previous embodiments, wherein said glucagon peptide is 250 times more selective for glucagon receptor than for GLP-1 receptor.
219. A glucagon peptide according to any of the previous embodiments, wherein said glucagon peptide is 500 times more selective for glucagon receptor than for GLP-1 receptor.
220. A glucagon peptide according to any of the previous embodiments, wherein said glucagon peptide is 1000 times more selective for glucagon receptor than for GLP-1 receptor.

The selectivity between the GLP-1 and the glucagon receptor can be measured as the ratio between $EC_{50}$ values or $IC_{50}$ values on the two receptors. Assays (I) and (III) can be used to measure the activity on the glucagon and GLP-1 receptors, respectively.

In the case of administration of a glucagon peptide of the invention, optionally in combination with one or more additional therapeutically active compounds or substances as disclosed above, for a purpose related to treatment or prevention of obesity or overweight, i.e. related to reduction or prevention of excess adiposity, it may be of relevance to employ such administration in combination with surgical intervention for the purpose of achieving weight loss or preventing weight gain, e.g. in combination with bariatric surgical intervention. Examples of frequently used bariatric surgical techniques include, but are not limited to, the following: vertical banded gastroplasty (also known as "stomach stapling"), wherein a part of the stomach is stapled to create a smaller pre-stomach pouch which serves as a new stomach; gastric banding, e.g. using an adjustable gastric band system (such as the Swedish Adjustable Gastric Band (SAGB), the LAP-BAND™ or the MIDband™), wherein a small pre-stomach pouch which is to serve as a new stomach is created using an elastomeric (e.g. silicone) band which can be adjusted in size by the patient; and gastric bypass surgery, e.g. "Roux-en-Y" bypass wherein a small stomach pouch is created using a stapler device and is connected to the distal small intestine, the upper part of the small intestine being reattached in a Y-shaped configuration.

The administration of a glucagon peptide of the invention (optionally in combination with one or more additional therapeutically active compounds or substances as disclosed above) may take place for a period prior to carrying out the bariatric surgical intervention in question and/or for a period of time subsequent thereto. In many cases it may be preferable to begin administration of a compound of the invention after bariatric surgical intervention has taken place.

The term "obesity" implies an excess of adipose tissue. When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity. In this context, obesity is best viewed as any degree of excess adipose tissue that imparts a health risk. The distinction between normal and obese individuals can only be approximated, but the health risk imparted by obesity is probably a continuum with increasing adipose tissue. However, in the context of the present invention, individuals with a body mass index (BMI=body weight in kilograms divided by the square of the height in meters) above 25 are to be regarded as obese.

The amino acid abbreviations used in the present context have the following meanings:

| Ado | ![structure] |
|---|---|
| Aib | 2-Aminoisobutyric acid |
| Ala | Alanine |
| Asn | Asparagine |
| Asp | Aspartic acid |
| Arg | Arginine |
| Cit | Citrulline |
| Cys | Cysteine |
| Gln | Glutamine |
| Glu | Glutamic acid |
| γ-Glu | ![structure] α-nitrogen and γ-carboxy group form the amide bonds to the two neighboring residues |
| Gly | Glycine |
| His | Histidine |
| Hyp | 4-hydroxyproline |
| Ile | Isoleucine |
| Leu | Leucine |
| Lys | Lysine |
| Met | Methionine |
| Met(O) | ![structure] |
| Orn | Ornithine |
| Phe | Phenylalanine |
| Pro | Proline |
| Ser | Serine |
| Thr | Threonine |
| Tyr | Tyrosine |

-continued

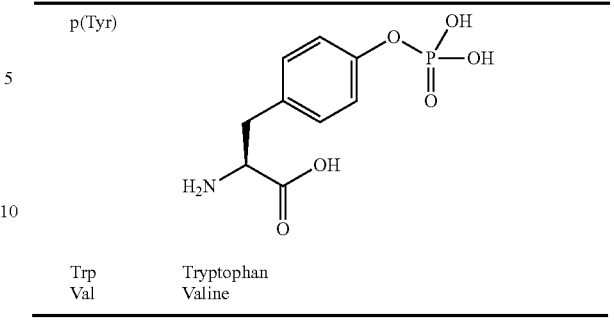

| p(Tyr) | |
| Trp | Tryptophan |
| Val | Valine |

Amino acid abbreviations beginning with D-followed by a three letter code, such as D-Ser, D-His and so on, refer to the D-enantiomer of the corresponding amino acid, for example D-serine, D-histidine and so on.

Pharmaceutical Compositions

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

The pharmaceutical compositions may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

The pharmaceutical formulation may comprise a glucagon peptide in a concentration from [0.01] mg/mL to [50] mg/mL. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a dried formulation (e.g. freeze-dried or spray-dried) ready for use without any prior dissolution.

The buffer may be selected from the group consisting of acetate, carbonate, citrate, glycylglycine, histidine, glycine, phosphate, hydrogen phosphate, and tris(hydroxynnethyl)aminomethan (TRIS), bicine, tricine, succinate, aspartic acid, asparagine or mixtures thereof.

In a further embodiment of the invention the formulation further comprises a pharmaceutically acceptable preservative. In a further embodiment of the invention the preservative is selected from the group consisting of phenol, m-cresol, methyl p-hydroxybenzoate, propyl p-hydroxybenzoate, 2-phenoxyethanol, benzyl alcohol, chlorobutanol, chlorocresol, benzethonium chloride, or mixtures thereof. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. The isotonic agent may be selected from the group consisting of a salt (e.g. sodium chloride), a sugar such as mono-, di-, or polysaccharides, or water-soluble glucans, including for example fructose, glucose, mannose, lactose, sucrose, trehalose, dextran, or sugar alcohol such as, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Sugar alcohol includes, for example, mannitol, sorbitol, inositol, galactitol, dulcitol, xylitol, and arabitol.

The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, EGTA, and mixtures thereof.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

The pharmaceutical compositions of the invention may further comprise an amount of an amino acid base sufficient to decrease aggregate formation by the polypeptide or protein during storage of the composition. By "amino acid base" is intended an amino acid or a combination of amino acids, where any given amino acid is present either in its free base form or in its salt form. The amino acids may be arginine, lysine, aspartic acid, and glutamic acid, aminoguanidine, ornithine and N-monoethyl L-arginine, ethionine and buthionine and S-methyl-L cysteine.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

In a further embodiment of the invention the formulation further comprises a surfactant. Typical surfactants (with examples of trade names given in brackets [ ]) are polyoxyethylene sorbitan fatty acid esters such as polyoxyethylene (20) sorbitan monolaurate [Tween 20], polyoxyethylene (20) sorbitan monopalmitate [Tween 40] or polyoxyethylene (20) sorbitan monooleate [Tween 80], poloxamers such as polyoxypropylene-polyoxyethylene block copolymer [Pluronic F68/poloxamer 188], polyethylene glycol octylphenyl ether [Triton X-100] or polyoxyethyleneglycol dodecyl ether [Brij 35]. The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases or an activated enzyme such as FVIIa in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine).

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins for example albumin, gels for example, thermogelling systems, for example block co-polymeric systems well known to those skilled in the art, micelles, liposomes, microparticles, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the glucagon peptide in the form of a nasal or pulmonal spray. As a still further option, the pharmaceutical compositions containing the glucagon peptide of the invention can also be adapted to transdermal administration, e.g.

by needle-free injection or from a patch, optionally an iontophoretic patch, or transmucosal, e.g. buccal, administration.

Pharmaceutical formulations for oral application of therapeutic proteins and polypeptides can include encapsulation of the active compound into nanoparticles, microparticles or other kinds of multiparticulate dosage forms. A further option is the use of permeation enhancers such as surface active compounds, cell penetrating peptides, mucoadhesive drug delivery systems, chelating agents and others. A still further option can be the addition of protease inhibitors. Another option is the use of lipid based drug delivery systems such as SEDDS, SMEDDS SNEDDS (Self Emulsifying, Self Micro-Emulsifying or Self Nano-Emulsifying drug delivery systems). Above mentioned drug delivery systems can be formulated into a tablet or filled into a suitable hard or soft capsule which can be coated to release the active compound in a controlled manner or at a preferred intestinal segment.

The present invention also contemplates the following embodiments:

221. A glucagon peptide comprising:
SEQ ID NO: 1, wherein $X_{24}$ represents Lys and wherein at least one of the following substitutions are present:
$X_3$ is His, $X_{15}$ is Glu and/or $X_{16}$ is Ala, Ile, Phe, Arg, Thr, Val, Leu, Glu, Trp or Tyr and up to six additional amino acid substitutions in said glucagon peptide and
a substituent comprising three or more negatively charged moieties, wherein one of the said negatively charged moieties is distal of a lipophilic moiety and where the substituent is attached at the side chain nitrogen of Lys in position 24,
or a pharmaceutically acceptable salt, amide, acid or prodrug thereof.

222. The glucagon peptide according to embodiment 221, wherein said amino acid substitutions may be selected from the following positions of said glucagon peptide:
$X_{12}$ is Arg
$X_{17}$ is Lys
$X_{20}$ is Lys
$X_{21}$ is Glu
$X_{27}$ is Leu
$X_{28}$ is Ser, Ile or Thr 223. The glucagon peptide according to any of embodiments 221-222, wherein said substituent has the formula II:

$$Z_1-Z_2-Z_3-Z_4 \quad [II]$$

wherein, $Z_1$ represents a structure according to one of the formulas IIa, IIb or IIc;

IIa

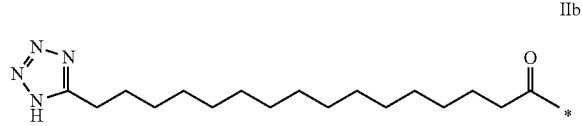

IIb

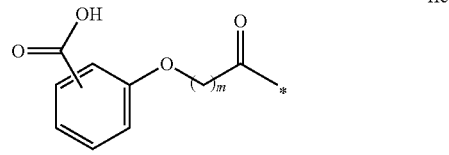

IIc wherein n in formula IIa is 6-20,
m in formula IIc is 5-11
the COOH group in formula IIc can be attached to position 2, 3 or 4 on the phenyl ring, the symbol * in formula IIa, IIb and IIc represents the attachment point to the nitrogen in $Z_2$;
if $Z_2$ is absent, $Z_1$ is attached to the nitrogen on $Z_3$ at symbol * and if $Z_2$ and $Z_3$ are absent $Z_1$ is attached to the nitrogen on $Z_4$ at symbol *
$Z_2$ is absent or represents a structure according to one of the formulas IId, IIe, IIf, IIg, IIh, IIj or IIk;

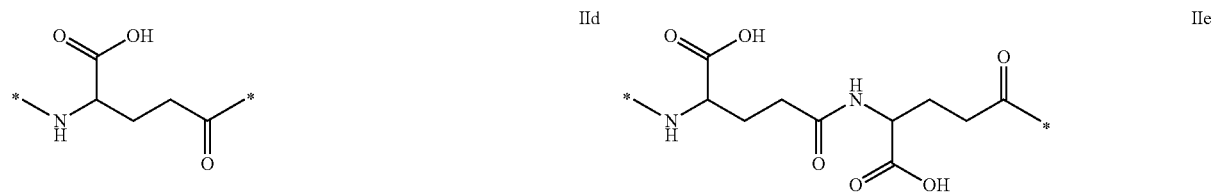

IId / IIe

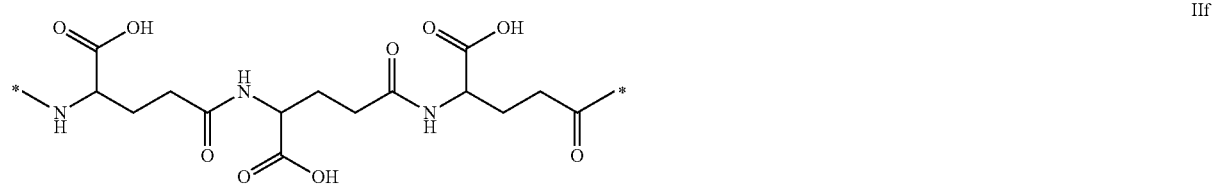

IIf

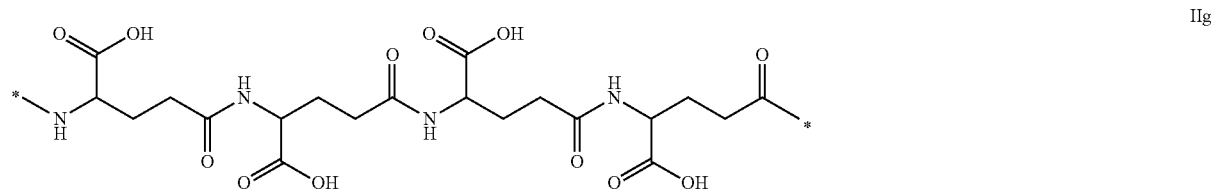

IIg

-continued

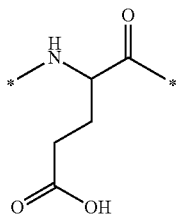
IIh

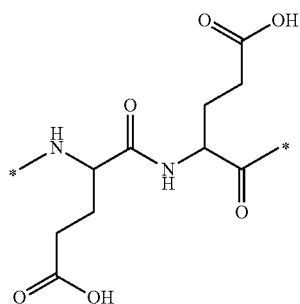
IIi

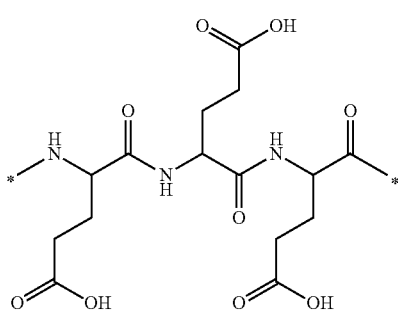
IIj

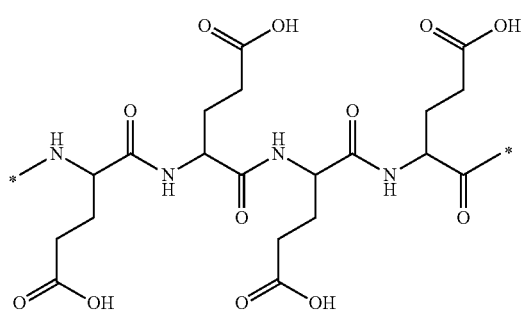
IIk wherein each amino acid moiety independently has the stereochemistry L or D;

wherein $Z_2$ is connected via the carbon atom denoted * to the nitrogen of $Z_3$ denoted *;

if $Z_3$ is absent, $Z_2$ is connected via the carbon atom denoted * to the nitrogen of $Z_4$ denoted * and if $Z_3$ and $Z_4$ are absent $Z_2$, is connected via the carbon denoted * to the epsilon nitrogen of a lysine or the delta nitrogen of an ornithine of the glucagon peptide.

$Z_3$ is absent or represents a structure according to one of the formulas IIm, IIn, IIo or IIp;

$Z_3$ is connected vi the carbon of $Z_3$ with symbol* to the nitrogen of $Z_4$ with symbol*, if $Z_4$ is absent $Z_3$ is connected via the carbon with symbol* to the epsilon nitrogen of a lysine or the delta nitrogen of an ornithine of the glucagon peptide $Z_4$ is absent or represents a structure according to one of the formulas IId, IIe, IIf, IIg, IIh, IIj or IIk; wherein each amino acid moiety is independently either L or D, wherein $Z_4$ is connected via the carbon with symbol* to the epsilon nitrogen of a lysine or the delta nitrogen of an ornithine of the glucagon peptide.

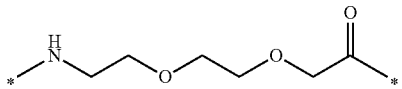
IIm

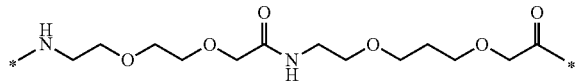
IIn

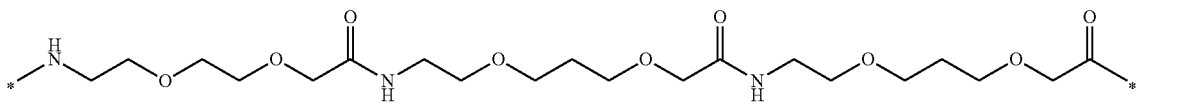
IIo

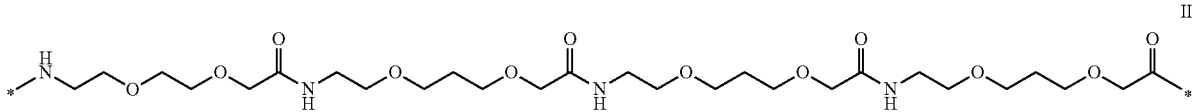
IIp

224. The glucagon peptide according to any of embodiments 221-223, wherein said substituent represents a structure according to one of the formulas IIIa, IIIb, IIIc, IIId, IIIe, IIIf, IIIg, IIIh, IIIi, IIIj, IIIk, IIIl, IIIm, IIIn, IIIo, IIIp, IIIq or IIIr:
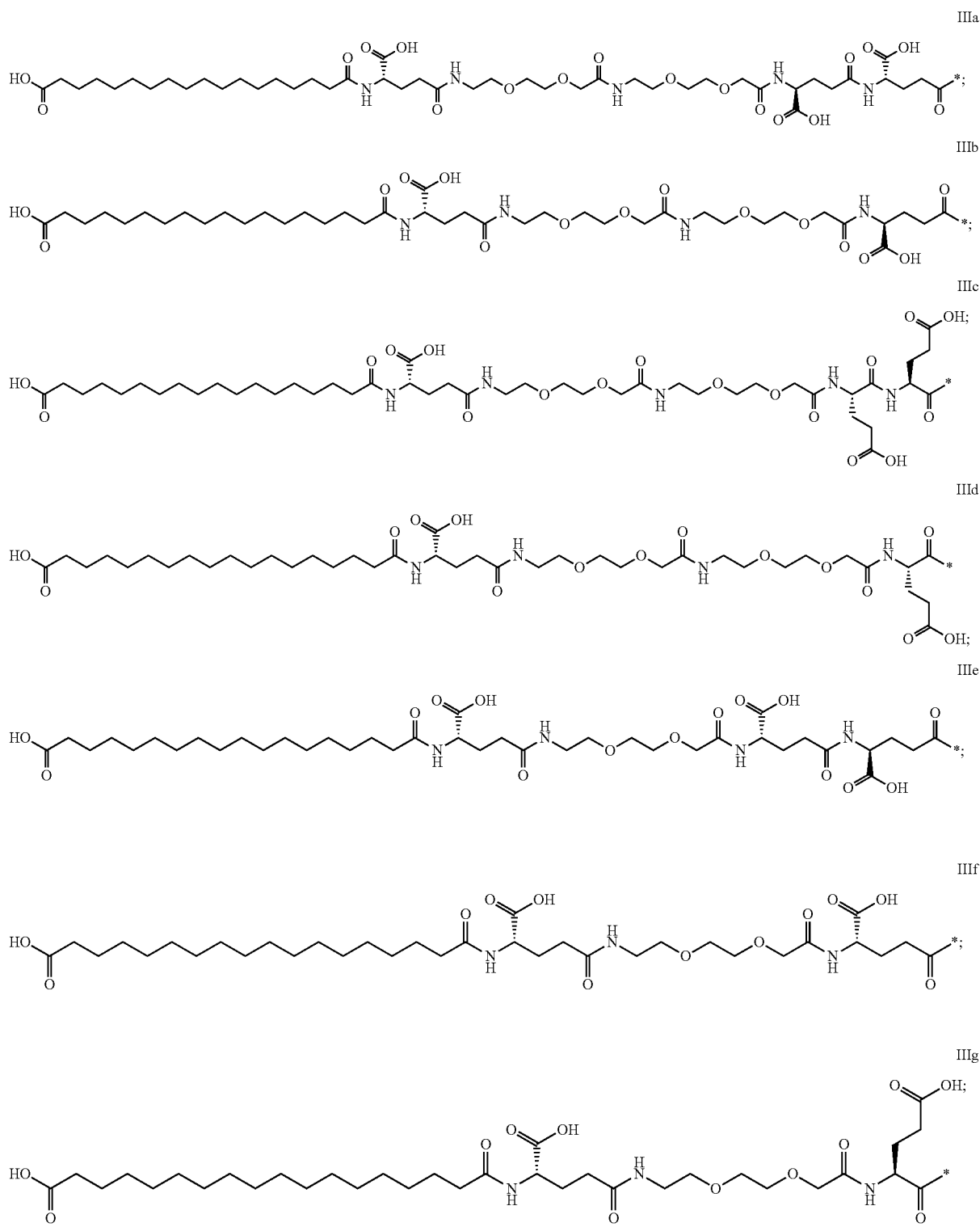

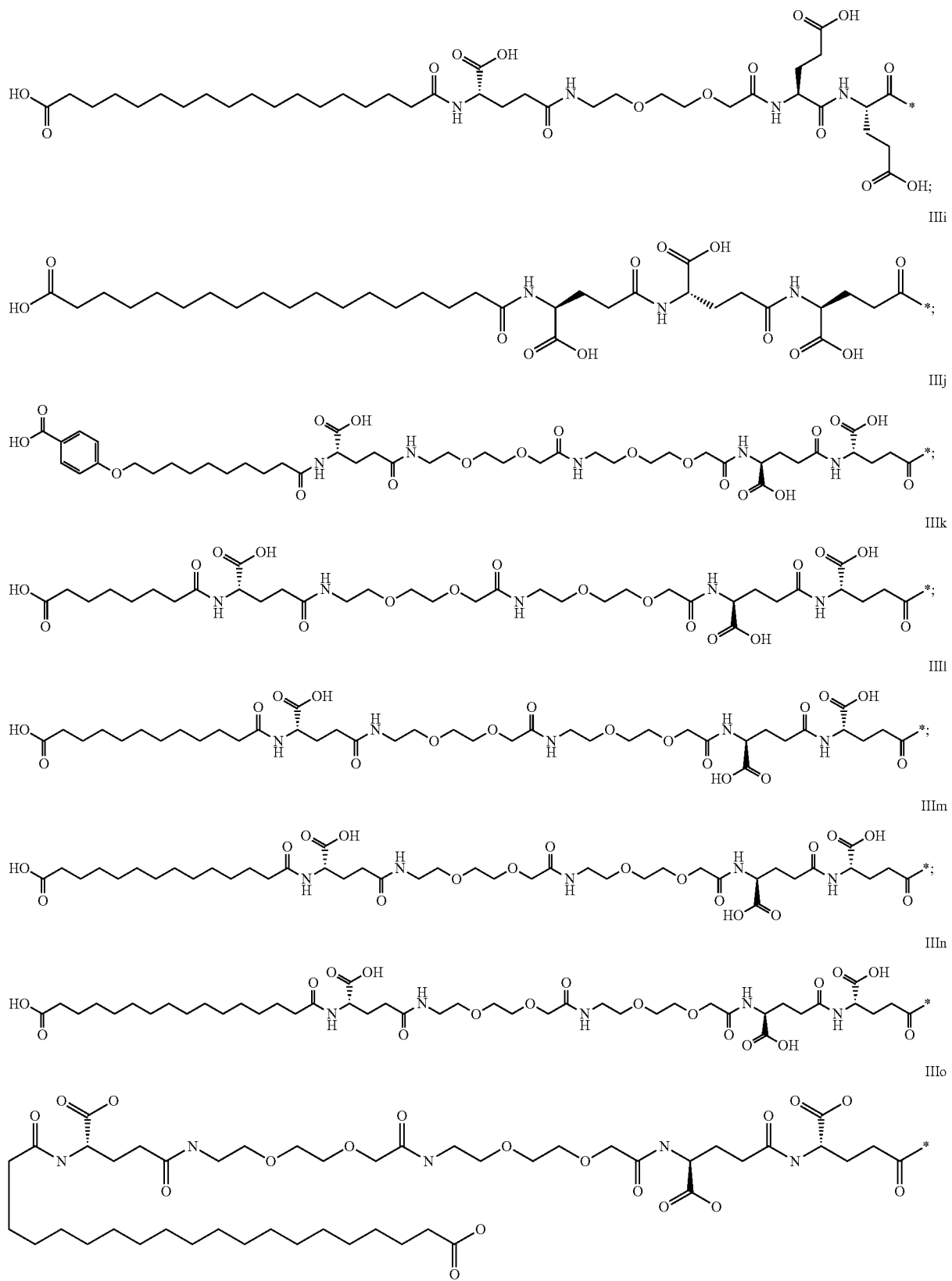

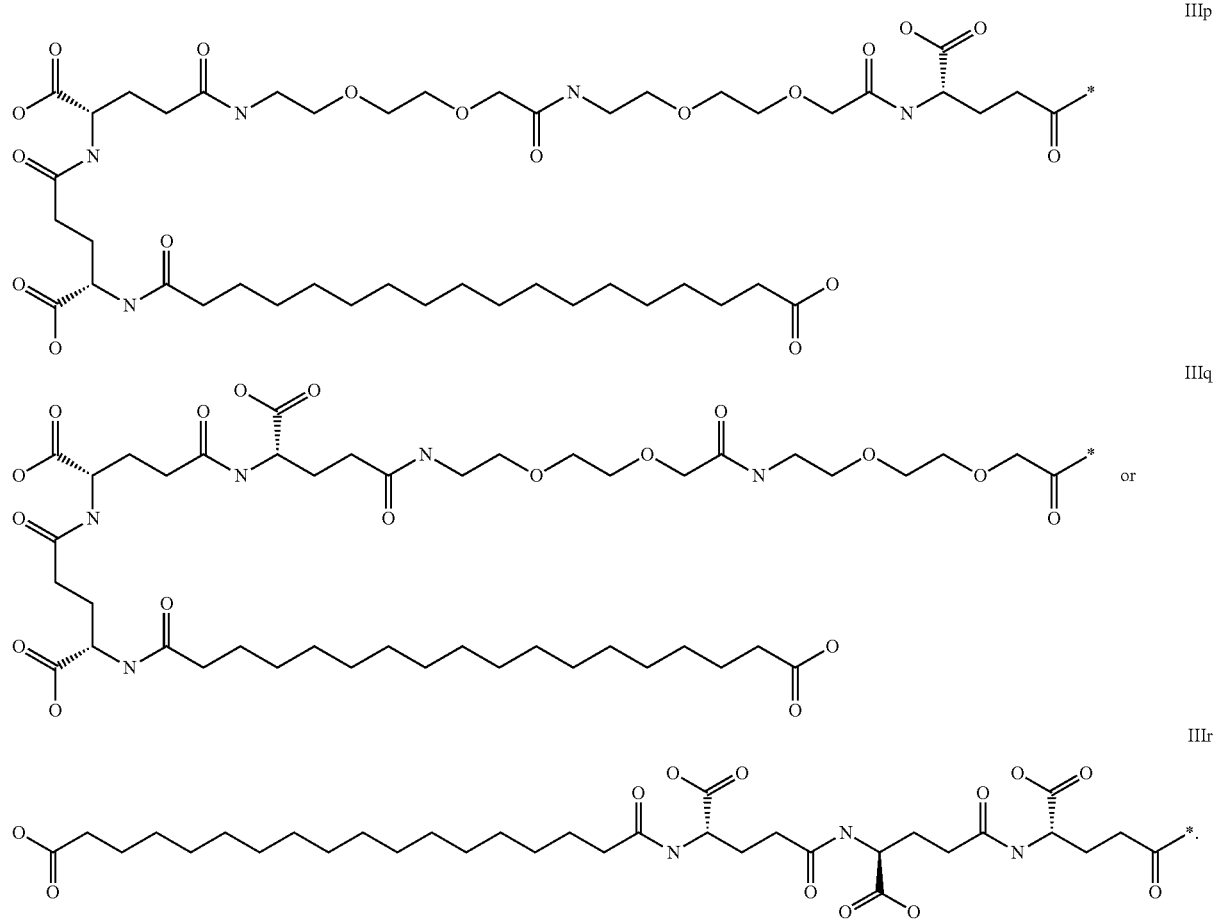

225. The glucagon peptide according to any of embodiments 221-224, selected from the group consisting of: Chem.1, Chem.2, Chem.3, Chem.4, Chem.5, Chem.6, Chem.7, Chem.8, Chem.9, Chem.10, Chem.11, Chem.12, Chem.13, Chem.14, Chem.15, Chem.16, Chem.17, Chem.18, Chem.19, Chem.20, Chem.21, Chem.22, Chem.23, Chem.24, Chem.25, Chem.26, Chem.27, Chem.28 and Chem.29.

226. A pharmaceutical composition comprising a glucagon peptide according to any one of to any of embodiments 221-225.

227. The pharmaceutical composition according to embodiment 226, further comprising one or more additional therapeutically active compounds or substances.

228. The pharmaceutical composition according to any one of embodiment 226-227, further comprising a GLP-1 compound.

229. The pharmaceutical composition according to any one of embodiments 226-228, further comprising an insulinic compound.

230. The pharmaceutical composition according to any one of embodiments 226-229, which is suited for parenteral administration.

231. A glucagon peptide according to any one of embodiments 221-225, for use in therapy.

232. Use of a glucagon peptide according to any one of embodiments 221-225, for the preparation of a medicament.

233. Use of a glucagon peptide according to any one of embodiments 221-225, for the preparation of a medicament for the treatment or prevention of hyperglycemia, type 2 diabetes, impaired glucose tolerance, type 1 diabetes and obesity.

234. Use of a glucagon peptide according to any one of embodiments 221-225, for the preparation of a medicament for delaying or preventing disease progression in type 2 diabetes, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge-eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as x-ray, CT- and NMR-scanning.

235. Use of a glucagon peptide according to any one of embodiments 221-225, for the preparation of a medicament for treatment or prevention of hypoglycemia, insulin induced hypoglycemia, reactive hypoglycemia, diabetic hypoglycemia, non-diabetic hypoglycemia, fasting hypoglycemia, drug-induced hypoglycemia, gastric by-pass induced hypoglycemia, hypoglycemia in pregnancy, alcohol induced hypoglycemia, insulinoma and Von Girkes disease.

EXAMPLES

List of Abbreviations

BOC: tert-Butyl oxycarbonyl
DCM: Dichloromethane
DIC: Diisopropylcarbodiimide
Fmoc: 9-fluorenylmethyloxycarbonyl
HOAt: 1-hydroxy-7-azabenzotriazole
HPLC: High Performance Liquid Chromatography
LCMS: Liquid Chromatography Mass Spectroscopy
MeCN: Acetonitrile
Mtt: 4-Methyltrityl
NMP: N-methyl pyrrolidone
Oxyma Pure: Cyano-hydroxyimino-acetic acid ethyl ester
RP: Reverse Phase
RP-HPLC: Reverse Phase High Performance Liquid Chromatography
RT: Room Temperature
Rt: Retention time
SPPS: Solid Phase Peptide Synthesis
TFA: Trifluoroacetic acid
TIPS: Triisopropylsilane
UPLC: Ultra Performance Liquid Chromatography
General Methods This section relates to methods for synthesising resin bound peptide (SPPS methods, including methods for de-protection of amino acids, methods for cleaving the peptide from the resin, and for its purification), as well as methods for detecting and characterising the resulting peptide (LCMS and UPLC methods).
SPPS General Methods The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH supplied from e.g. Anaspec, Bachem, Iris Biotech, or NovabioChem. SPPS were performed using Fmoc based chemistry on a Prelude Solid Phase Peptide Synthesizer from Protein Technologies (Tucson, Ariz. 85714 U.S.A.). A suitable resin for the preparation of C-terminal carboxylic acids is a pre-loaded, low-load Wang resin available from NovabioChem (e.g. low load fmoc-Thr(tBu)-Wang resin, LL, 0.27 mmol/g). The N-terminal alpha amino group was protected with Boc.

Fmoc-deprotection was achieved with 20% piperidine in NMP for 2×3 min. The coupling chemistry was either DIC/HOAt/collidine or DIC/Oxyma Pure/collidine. Amino acid/HOAt or amino acid/Oxyma Pure solutions (0.3 M/0.3 M in NMP at a molar excess of 3-10 fold) were added to the resin followed by the same molar equivalent of DIC (3 M in NMP) followed by collidine (3 M in NMP). For example, the following amounts of 0.3 M amino acid/HOAt solution were used per coupling for the following scale reactions: Scale/ml, 0.05 mmol/1.5 mL, 0.10 mmol/3.0 mL, 0.25 mmol/7.5 mL. Coupling time was either 2×30 min or 1×240 min.

The Mtt group was removed by washing the resin with HFIP/DCM (75:25) (2×2 min), washed with DCM and suspending the resin in HFIP/DCM (75:25)(2×20 min) and subsequently washed in sequence with Piperidine/NMP (20: 80), DCM(1×), NMP(1×), DCM(1×), NMP(1×).

The introduction of a substituent on the 8-nitrogen of a lysine was achived using a Lysine protected with Mtt (Fmoc-Lys(Mtt)-OH). Likewise when the side-chain was present on an ornithine sidechain the delta aminogroup of the ornithine to be acylated was protected with Mtt (e.g. Fmoc-Orn(Mtt)-OH. Alternatively the ε-nitrogen of a lysine could be protected with an ivDde group (Fmoc-Lys(ivDde)-OH). The delta amino group of an ornitine could likewise be protected with an ivDde group (Fmoc-Orn(ivDde)-OH). The incorporation of gamma-Glu moieties in the side-chain were achieved by coupling with the amino acid Fmoc-Glu-OtBu. Introduction of each moiety in the side-chain was achieved using prolonged coupling time (1×6 hours) followed by capping with acetic anhydride or alternatively acetic acid/ DIC/HOAt/collidine. Acetylation of the terminal nitrogen on the substituent was achieved using acetic anhydride (10 eq.) and collidine (20 eq.) in NMP.
Attachment of the Substituent The albumin binding moiety can be introduced in a stepwise procedure by the Prelude peptide synthesizer as described above using suitably protected building blocks, with the modification that the amino acids and fatty acid derivatives including Fmoc-Ado-OH, Fmoc-Glu-OtBu, and octadecanedioic acid mono-tert-butyl ester (or the analogous C8, C10, C12-, C14- C16-, C20-diacid mono tert-butyl esters) were coupled for 6 hrs in each step. After each coupling step, unreacted peptide intermediate was capped using acetic acid anhydride and collidine in excess (>10 eq.). Compounds containing a 4-[16-(1H-tetrazol-5-yl)hexade-canoylsulfannoyl]butanoyl moiety are prepared in a similar manner by using the building block 4-(N-(16-(tetrazol-5-yl) hexadecanoyl)sulfannoyl)butyric acid (available by the synthetic procedure described in WO 2007/009894).
Cleavage from the Resin After synthesis the resin was washed with DCM, and the peptide was cleaved from the resin by a 2-3 hour treatment with TFA/TIS/water (95/2.5/2.5) followed by precipitation with diethylether. The precipitate was washed with diethylether.
Purification and Quantification The crude peptide is dissolved in a suitable mixture of water and MeCN such as water/MeCN (4:1) and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or UPLC. Fractions containing the pure target peptide are mixed and concentrated under reduced pressure. The resulting solution is analyzed (HPLC, LCMS) and the product is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.
Methods for Detection and Characterization
LCMS Methods
Method: LCMS_2

A Perkin Elmer Sciex API 3000 mass spectrometer was used to identify the mass of the sample after elution from a Perkin Elmer Series 200 HPLC system. Eluents: A: 0.05% Trifluoro acetic acid in water; B: 0.05% Trifluoro acetic acid in acetonitrile. Column: Waters Xterra MS C-18×3 mm id 5 µm. Gradient: 5%-90% B over 7.5 min at 1.5 ml/min.
Method: LCMS 4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.
Method: LCMS_13

Method LCMS_13 was performed on a Waters Acquity UPLC SQD 2000 system consisting of a UPLC system with PDA UV detector and single quadrupol mass detector with electrospray ionisation. Eluents: A: 0.1% Trifluoroacetic acid in water; B: 0.1% Trifluoroacetic acid in acetonitrile. Column: Waters Acquity UPLC BEH C18, 100 Å, 1.7 µm, 2.1 mm×100 mm. Gradient: Linear 10%-90% B over 3 min, flow 0.3 ml/min, total run time 4 min. MS scanning range: 500-2000 amu.
Method: LCMSAP A Micromass Quatro micro API mass spectrometer was used to identify the mass of the sample after elution from a HPLC system composed of Waters2525 binary gradient modul, Waters2767 sample manager, Waters 2996 Photodiode Array Detector and Waters 2420 ELS Detector. Eluents: A: 0.1% Trifluoro acetic acid in water; B: 0.1% Trifluoro acetic acid in acetonitrile. Column: Phenomenex Synergi MAXRP, 4 um, 75×4.6 mm. Gradient: 5%-95% B over 7 min at 1.0 ml/min.
UPLC Methods
Method 04_A3_1

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 90% H2O, 10% CH3CN, 0.25 M ammonium bicarbonate
B: 70% CH3CN, 30% H2O The following linear gradient was used: 75% A, 25% B to 45% A, 55% B over 16 minutes at a flow-rate of 0.35 ml/min.
Method 04_A4_1

UPLC (method 04_A4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 90% H2O, 10% CH3CN, 0.25 M ammonium bicarbonate
B: 70% CH3CN, 30% H2O The following linear gradient was used: 65% A, 35% B to 25% A, 65% B over 16 minutes at a flow-rate of 0.35 ml/min.
Method: 04_A2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 90% H2O, 10% CH3CN, 0.25 M ammonium bicarbonate; B: 70% CH3CN, 30% H2O. The following linear gradient was used: 90% A, 10% B to 60% A, 40% B over 16 minutes at a flow-rate of 0.40 ml/min.
Method: 04_A6_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% H2O, 20%, pH 7.3; B: 80% CH3CN, 20% H2O. The following linear gradient was used: 95% A, 5% B to 10% A, 90% B over 16 minutes at a flow-rate of 0.35 ml/min.
Method: 04_A7_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% H2O, 20%, pH 7.3; B: 80% CH3CN, 20% H2O. The following linear gradient was used: 95% A, 5% B to 40% A, 60% B over 16 minutes at a flow-rate of 0.40 ml/min.
Method: 04_A9_1

The RP-analysis was performed using a Waters UPLC system fitted with a dual band detector. UV detections at 214 nm and 254 nm were collected using an ACQUITY UPLC BEH Shield RP18, C18, 1.7 um, 2.1 mm×150 mm column, 60° C. The UPLC system was connected to two eluent reservoirs containing: A: 200 mM Na2SO4+20 mM Na2HPO4+20 mM NaH2PO4 in 90% $H_2O$/10% CH3CN, pH 7.2; B: 70% $CH_3CN$, 30% $H_2O$. The following step gradient was used: 90% A, 10% B to 80% A, 20% B over 3 minutes, 80% A, 20% B to 50% A, 50% B over 17 minutes at a flow-rate of 0.40 ml/min.
Method 05_B5_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 0.2 M Na2SO4, 0.04 M H3PO4, 10% CH3CN (pH 3.5)
B: 70% CH3CN, 30% H2O The following linear gradient was used: 60% A, 40% B to 30% A, 70% B over 8 minutes at a flow-rate of 0.35 ml/min.
Method: 05_B7_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M Na2SO4, 0.04 M H3PO4, 10% CH3CN (pH 3.5); B: 70% CH3CN, 30% H2O. The following linear gradient was used: 80% A, 20% B to 40% A, 60% B over 8 minutes at a flow-rate of 0.40 ml/min.
Method: 05_B8_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M Na2SO4, 0.04 M H3PO4, 10% CH3CN (pH 3.5); B: 70% CH3CN, 30% H2O. The following linear gradient was used: 50% A, 50% B to 20% A, 80% B over 8 minutes at a flow-rate of 0.40 ml/min.

Method: 05_B9_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M Na2SO4, 0.04 M H3PO4, 10% CH3CN (pH 3.5); B: 70% CH3CN, 30% H2O. The following linear gradient was used: 70% A, 30% B to 20% A, 80% B over 8 minutes at a flow-rate of 0.40 ml/min.

Method: 05_B10_1

The RP-analyses was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M Na2SO4, 0.04 M H3PO4, 10% CH3CN (pH 3.5); B: 70% CH3CN, 30% H2O. The following linear gradient was used: 40% A, 60% B to 20% A, 80% B over 8 minutes at a flow-rate of 0.40 ml/min.

Method: 07_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing: A: 99.95% H2O, 0.05% TFA; B: 99.95% CH3CN, 0.05% TFA. The following linear gradient was used: 95% A, 5% B to 5% A, 95% B over 16 minutes at a flow-rate of 0.40 ml/min.

Method: 09_B2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% H2O, 0.05% TFA; B: 99.95% CH3CN, 0.05% TFA. The following linear gradient was used: 95% A, 5% B to 40% A, 60% B over 16 minutes at a flow-rate of 0.40 ml/min.

Method: 09_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% H2O, 0.05% TFA; B: 99.95% CH3CN, 0.05% TFA. The following linear gradient was used: 95% A, 5% B to 5% A, 95% B over 16 minutes at a flow-rate of 0.40 ml/min.

Method 08_B2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 99.95% H2O, 0.05% TFA
B: 99.95% CH3CN, 0.05% TFA The following linear gradient was used: 95% A, 5% B to 40% A, 60% B over 16 minutes at a flow-rate of 0.40 ml/min.

Method 08_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 99.95% H2O, 0.05% TFA
B: 99.95% CH3CN, 0.05% TFA The following linear gradient was used: 95% A, 5% B to 5% A, 95% B over 16 minutes at a flow-rate of 0.40 ml/min.

Method 10_B4_2

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 50° C.

The UPLC system was connected to two eluent reservoirs containing:
A: 99.95% H2O, 0.05% TFA
B: 99.95% CH3CN, 0.05% TFA The following linear gradient was used: 95% A, 5% B to 5% A, 95% B over 12 minutes at a flow-rate of 0.40 ml/min.

Method 10_B5_2

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 50° C.

The UPLC system was connected to two eluent reservoirs containing:
A: 70% MeCN, 30% Water
B: 0.2M Na2SO4, 0.04 M H3PO4, 10% MeCN, pH 2.25

The following linear gradient was used: 40% A in 1 min, 40->70% A in 7 min at a flow-rate of 0.40 ml/min.

Method: 10_B14_1

The RP-analyses was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% H2O, 0.05% TFA; B: 99.95% CH3CN, 0.05% TFA. The following linear gradient was used: 70% A, 30% B to 40% A, 60% B over 12 minutes at a flow-rate of 0.40 ml/min.

Method: AP_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 30° C.

The UPLC system was connected to two eluent reservoirs containing: A: 99.95% H2O, 0.05% TFA; B: 99.95% CH3CN, 0.05% TFA. The following linear gradient was used: 95% A, 5% B to 5% A, 95% B over 16 minutes at a flow-rate of 0.30 ml/min.

Example 1

$N^{\epsilon 24}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Glu$^{15}$,Lys$^{24}$,Leu$^{27}$,Ser$^{28}$]-Glucagon Chem. 1

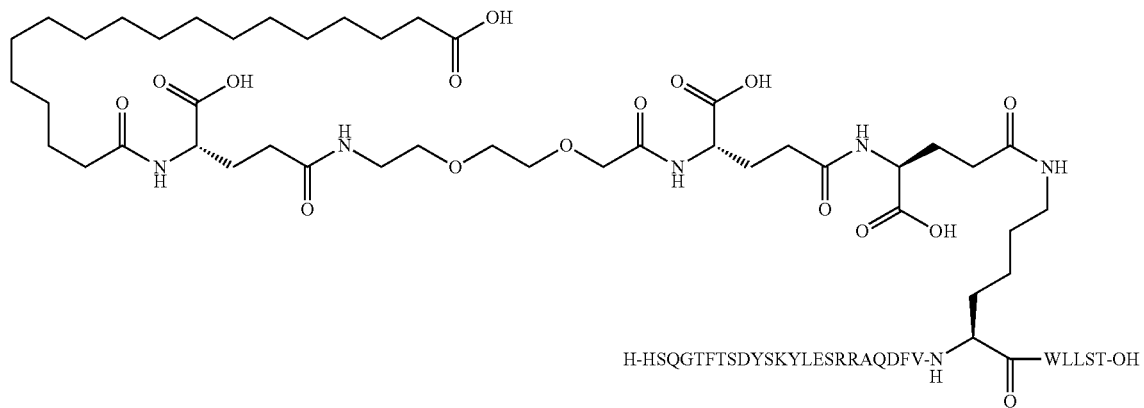

UPLC Method: 04_A9_1: Rt=12.84 min
UPLC Method: 09_B4_1: Rt=8.61 min
LCMS Method: LCMS_4: Rt=3.7 min, m/3=1427; m/4=1071; m/5=857

Example 2

$N^{\epsilon 24}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[His$^3$,Lys$^{24}$,Leu$^{27}$,Ser$^{28}$]-Glucagon Chem. 2

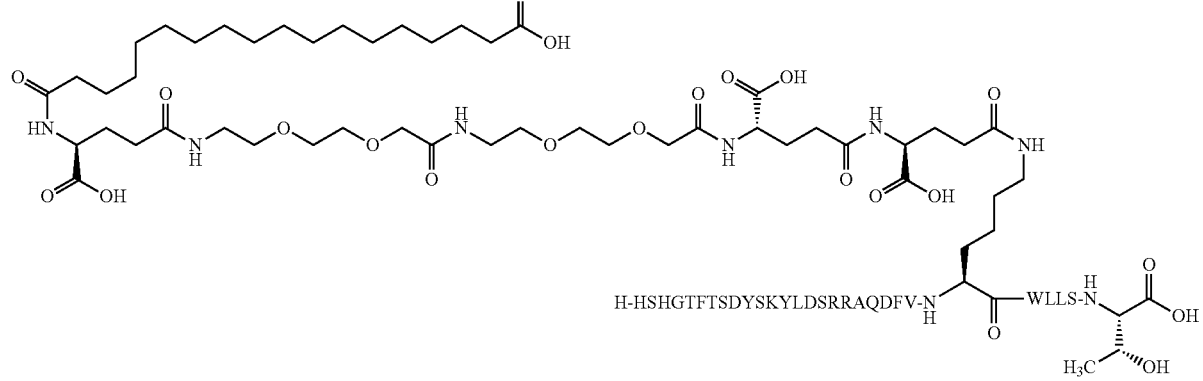

UPLC Method: 05_B9_1: Rt=8.4
LCMS Method: LCMS_4: Rt=2.8 min, m/4=1106

Example 3

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[His$^3$,Lys$^{20}$,Lys$^{24}$,Leu$^{27}$,Ser$^{28}$]-Glucagon

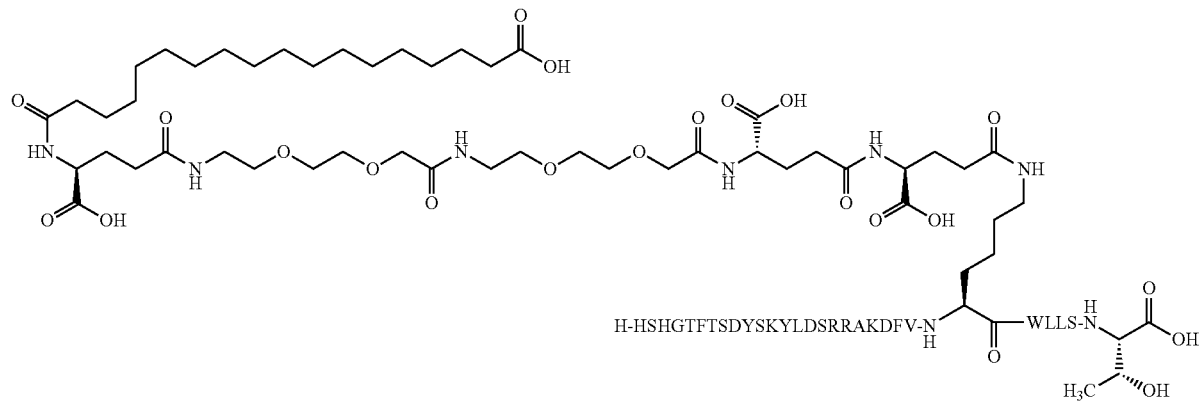

Chem. 3

UPLC Method: 04_A9_1: Rt=13.1 min
UPLC Method: 09_B4_1: Rt=8.0 min
LCMS Method: LCMS_4: RT=2.8 min, m/3=1474; m/4=1106; m/5=885

Example 4

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[His$^3$,Glu$^{16}$,Lys$^{20}$,Lys$^{24}$,Leu$^{27}$,Ser$^{28}$]-Glucagon

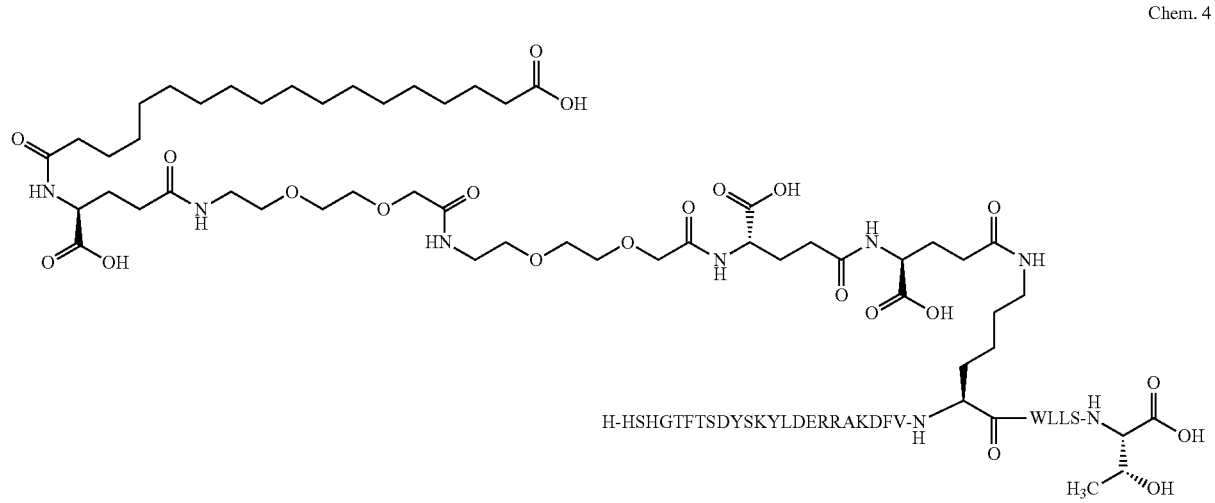

Chem. 4

UPLC Method: 04_A9_1: Rt=12.0 min
UPLC Method: 09_B4_1: Rt=8.0 min
LCMS Method: LSMS_4: RT=2.8 min, m/3=1488; m/4=1117; m/5=893

Example 5

$N^{\epsilon 24}$-[(4S)-4-carboxy-4-[[(4S)-4-carboxy-4-[[2-[2-[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[His³,Lys²⁴,Leu²⁷]-Glucagon

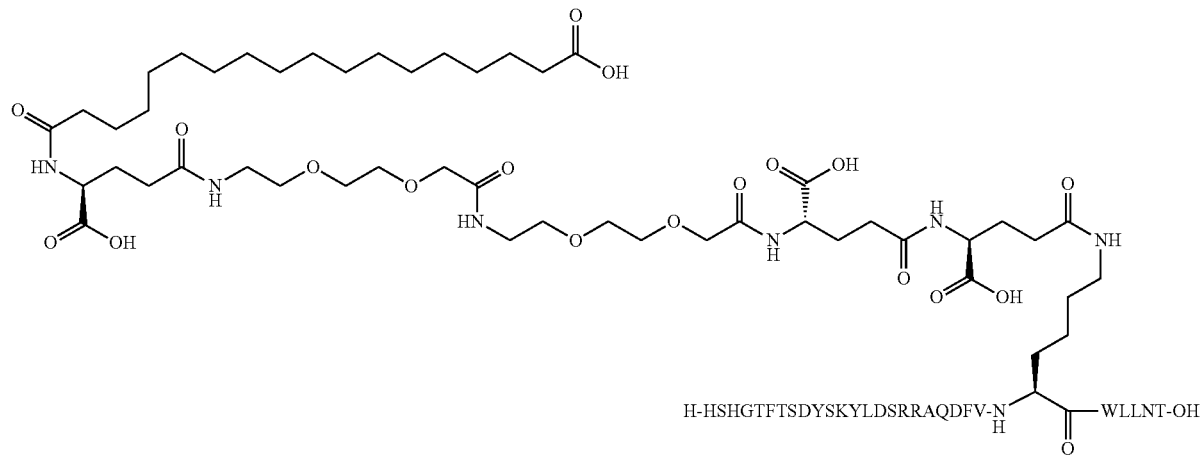

Chem. 5

UPLC Method: 09_B4 Rt=8.29 min
UPLC Method: Rt=7.66 min
LCMS: Method: LCMS_4 Rt=2.85; m/Z=4452; M/3: 1483, M/4: 1113

Example 6

$N^{\epsilon 24}$-[(4S)-4-carboxy-4-[[(4S)-4-carboxy-4-[[2-[2-[2-[[(4S)-4-carboxy-4-(17-carboxyheptadecanoyl-lamino)butanoyl]amino]ethoxy]ethoxy]acetyl]amino]butanoyl]amino]butanoyl]-[His³,Lys¹⁷,Glu²¹,Lys²⁴,Leu²⁷,Ser²⁸]-Glucagon

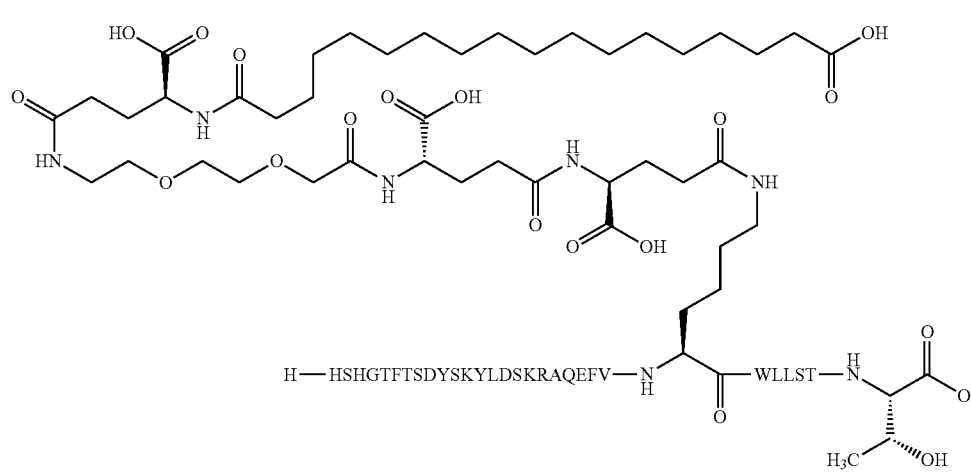

Chem. 6

UPLC Method: 04_A9_1; Rt=12.2 min
UPLC Method: 09_B4_1; Rt=8.2 min
LCMS Method: LCMS_4; RT=2.1 min; m/3=1421; m/4=1066; m/5=853

Example 7

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Val$^{16}$,Lys$^{24}$,Leu$^{27}$]-Glucagon

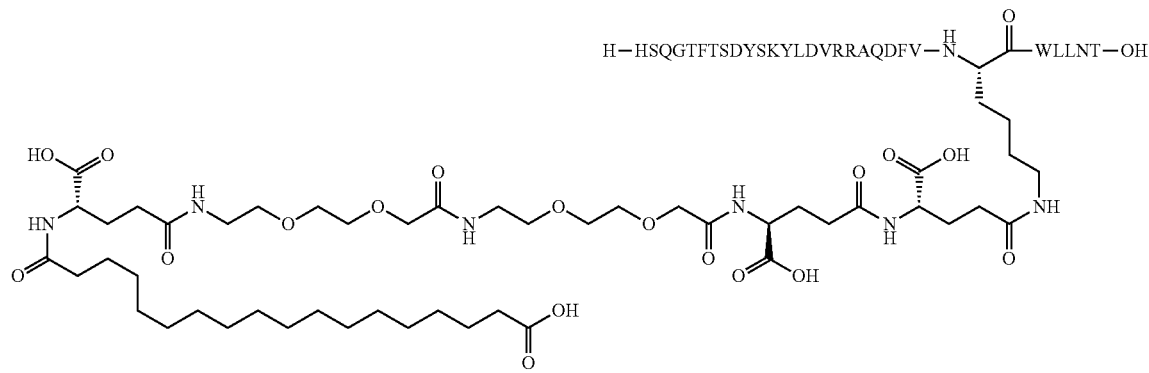

Chem. 7

UPLC Method: 09_B2_1: Rt=13.1 min
UPLC Method: 09_B4_1: Rt=8.6 min
UPLC Method: 04_A9_1: Rt=12.9 min
LCMS Method: LCMS_4: Rt=2.2 min, m/3=1485; m/4=1114; m/5=891

Example 8

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Ile$^{16}$,Lys$^{24}$,Leu$^{27}$]-Glucagon

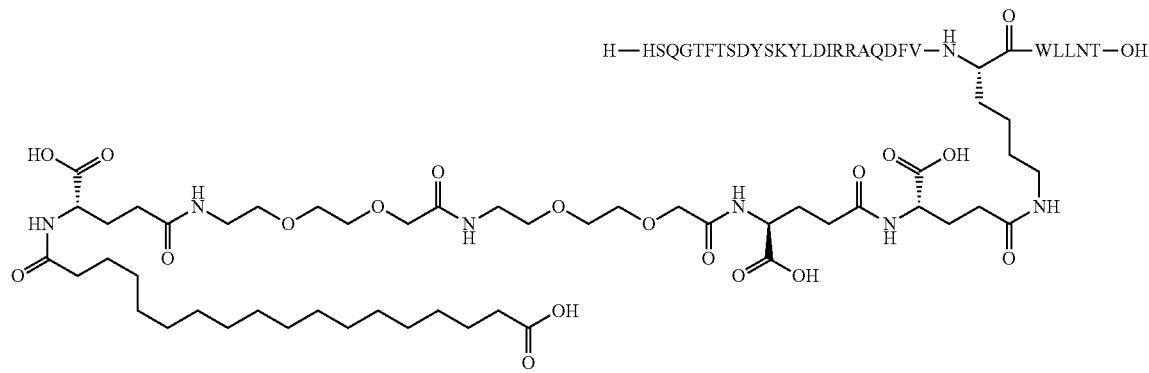

Chem. 8

UPLC Method: 09_B2_1: Rt=13.2 min
UPLC Method: 09_B4_1: Rt=8.7 min
UPLC Method: 04_A9_1: Rt 13.6 min
LCMS Method: LCMS_4: Rt=2.2 min, m/3=1489; m/4=1117; m/5=894

Example 9

N^{ε24}-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[His³,Glu¹⁵,Thr¹⁶,Lys²⁴,Leu²⁷]-Glucagon

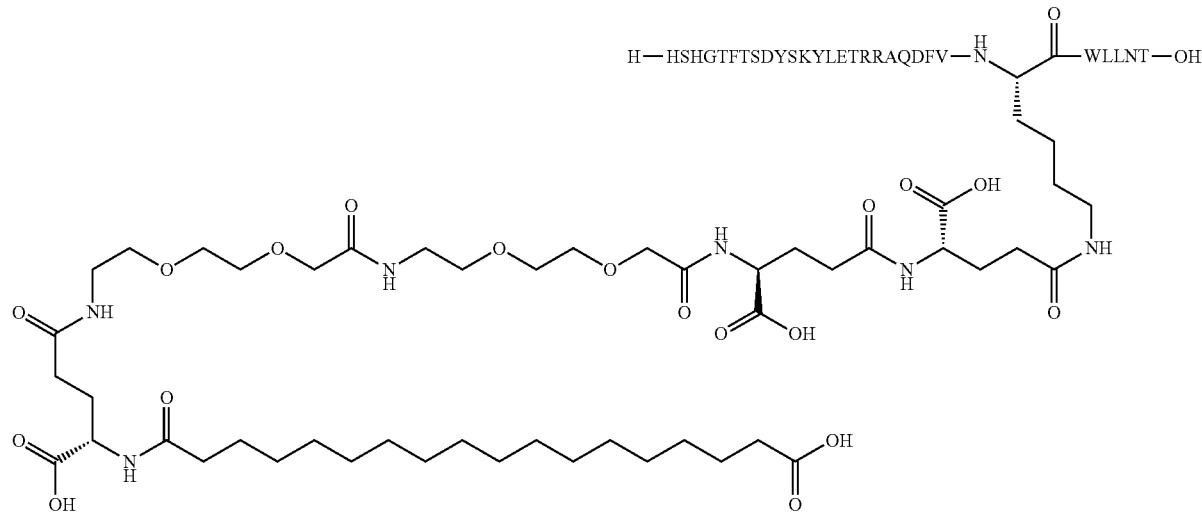

Chem. 9

UPLC Method: 09_B2_1: Rt=12.4 min
UPLC Method: 09_B4_1: Rt=8.2 min
UPLC Method: 04_A9_1: Rt=12.7 min
LCMS Method: LCMS_4: Rt=2.2 min, m/3=1493; m/4=1120; m/5=896

Example 10

N^{ε24}-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Arg¹²,Thr¹⁶,Lys²⁴,Leu²⁷]-Glucagon Chem. 10

UPLC Method: 09_B2_1: Rt=12.6 min
UPLC Method: 09_B4_1: Rt=8.3 min
UPLC Method: 04_A9_1: Rt=13.4 min
LCMS Method: LCMS_4: Rt=2.3 min, m/3=1495, m/4=1121; m/5=897

Chem. 11:

Example 11

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Ile$^{16}$,Lys$^{24}$,Leu$^{27}$,Ser$^{28}$]-Glucagon

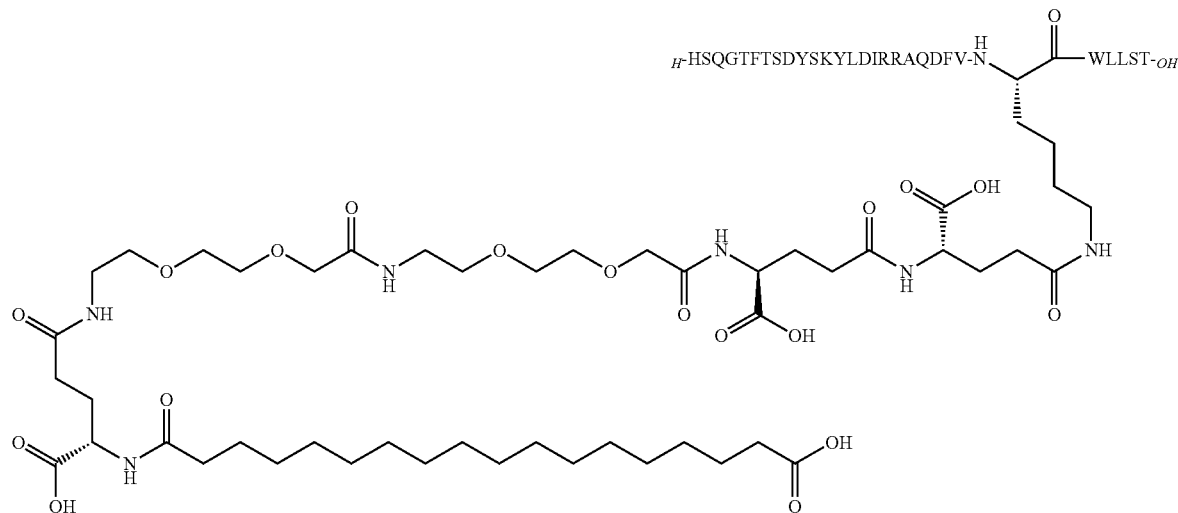

UPLC Method: 09_B2_1: Rt=13.1 min
UPLC Method: 09_B4_1: Rt=8.6 min
UPLC Method: 04_A9_1: Rt=15.0 min
LCMS Method: LCMS_4: Rt=2.3 min, m/3=1480; m/4=1110; m/5=889

Example 12

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Thr$^{16}$,Lys$^{24}$,Leu$^{27}$,Ser$^{28}$]-Glucagon Chem. 12

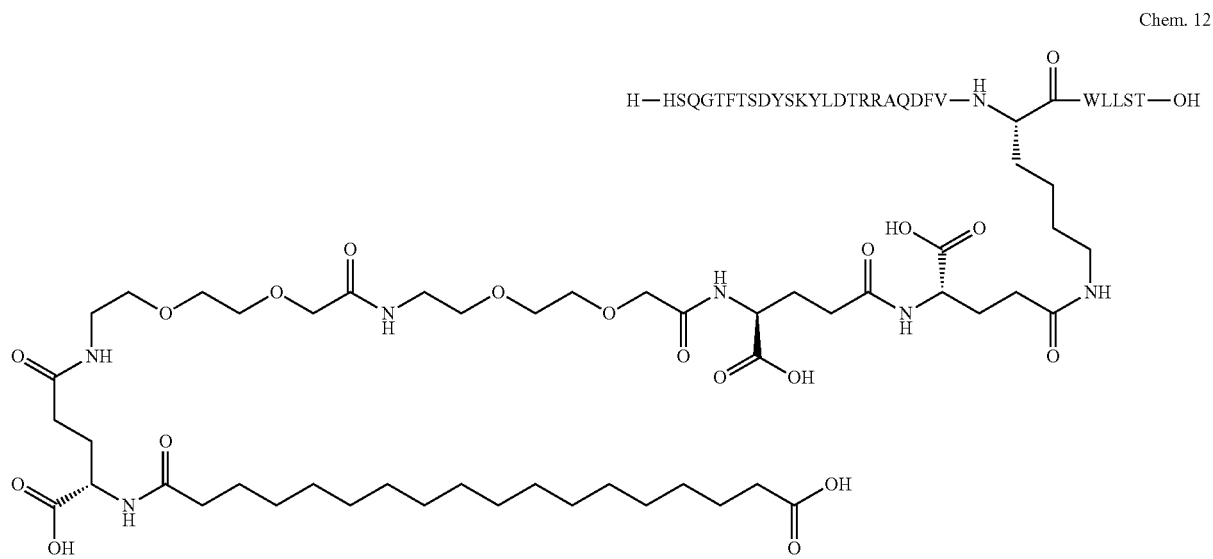

UPLC Method: 09_B2_1: Rt=12.7 min
UPLC Method: 09_B4_1: Rt=8.4 min
UPLC Method: 04_A9_1: Rt=12.9 min
LCMS Method: LCMS_4: Rt=2.2 min, m/3=1476; m/4=1107; m/5=886

Example 13

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Leu$^{16}$,Lys$^{24}$,Leu$^{27}$,Ser$^{25}$]-Glucagon

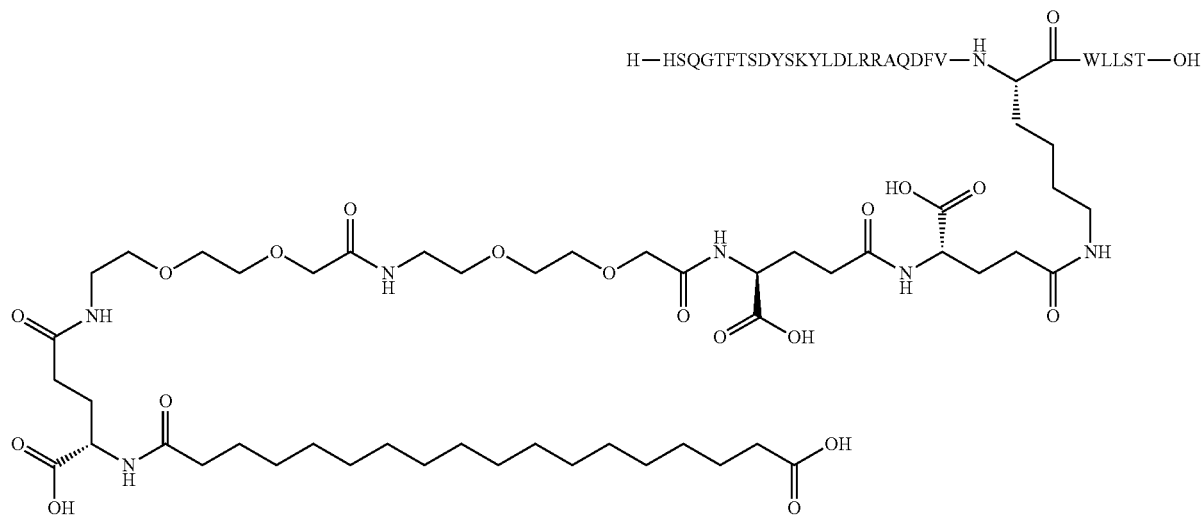

Chem. 13

UPLC Method: 09_B2_1: Rt=13.1 min
UPLC Method: 09_B4_1: Rt=8.6 min
UPLC Method: 04_A9_1: Rt=15.0 min
LCMS Method: LCMS_4: Rt=2.4 min, m/3=1480; m/4=1110; m/5=889

Example 14

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Glu$^{15}$,Lys$^{24}$,Leu$^{27}$,Ser$^{25}$]-Glucagon

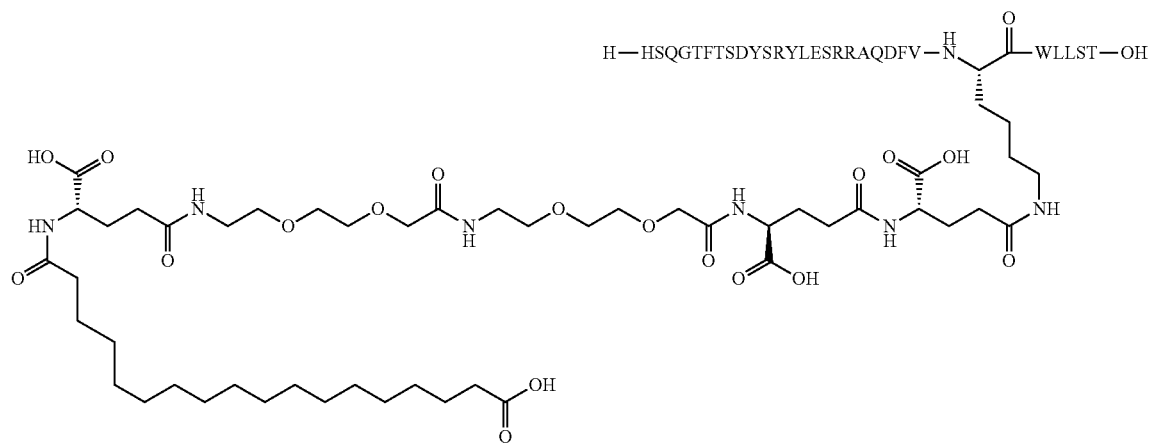

Chem. 14

UPLC Method: 09_B4_1: Rt=8.4 min
UPLC Method: 04_A6_1: Rt=5.9 min
UPLC Method: 04_A9_1: Rt=13.0 min
LCMS Method: LCMS_4: Rt=2.2 min, m/3=1486; m/4=1115; m/5=892

Example 15

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Ser$^{28}$]-Glucagon Chem. 15

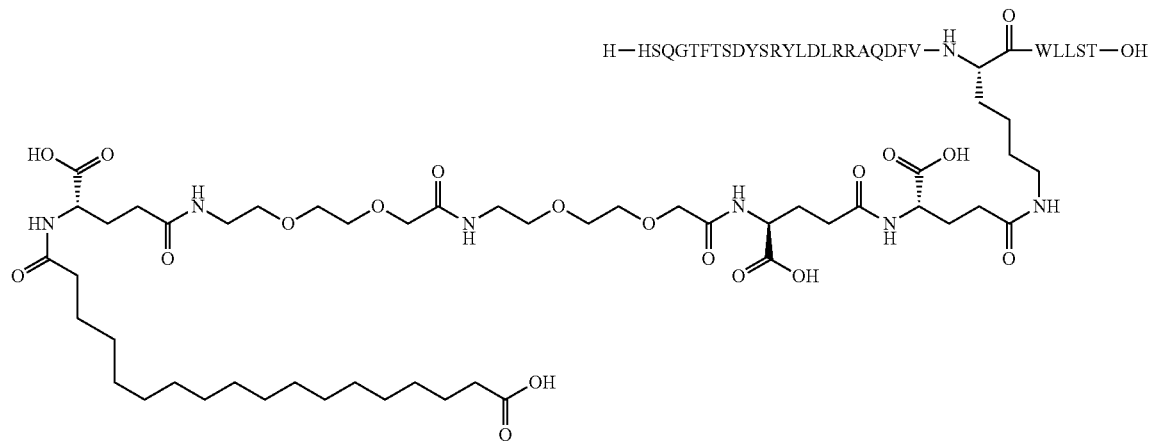

UPLC Method: 09_B4_1: Rt=8.7 min
UPLC Method: 04_A6_1: Rt=7.2 min
UPLC Method: 04_A9_1: Rt=16.0 min
LCMS Method: LCMS_4: Rt=2.4 min, m/3=1490; m/4=1117; m/5=894

Example 16

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Ala$^{16}$,Lys$^{24}$,Leu$^{27}$,Ser$^{28}$]-Glucagon Chem. 16

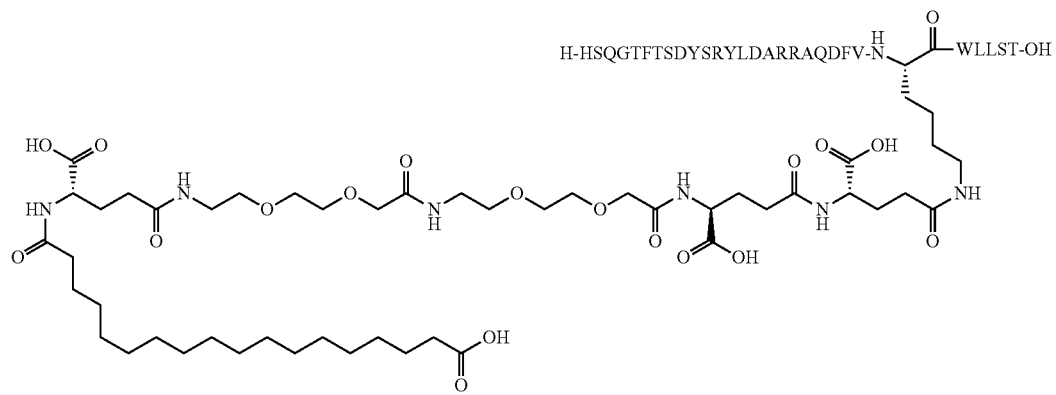

UPLC Method: 09_B2_1: Rt=12.7 min
UPLC Method: 09_B4_1: Rt=8.4 min
UPLC Method: 04_A9_1: Rt=14.0 min
LCMS Method: LCMS_4: Rt=2.4 min, m/3=1476; m/4=1107; m/5=886

Example 17

N$^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Phe$^{16}$,Lys$^{24}$,Leu$^{27}$,Ser$^{28}$]-Glucagon Chem. 17

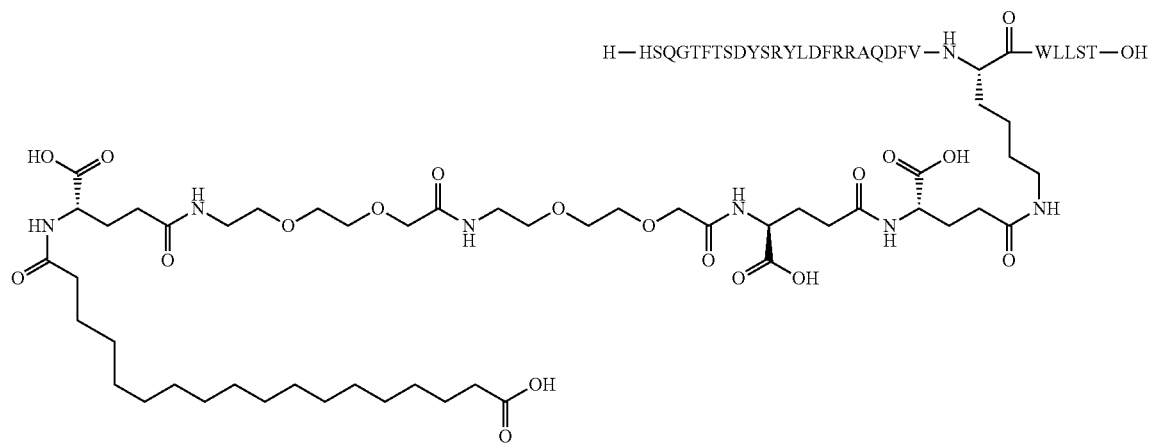

UPLC Method: 09_B2_1: Rt=13.1 min
UPLC Method: 09_B4_1: Rt=8.6 min
UPLC Method: 04_A9_1: Rt=15.9 min
LCMS Method: LCMS_4: Rt=2.5 min, m/3=1501; m/4=1126; m/5=901

Example 18

N$^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Ile$^{28}$]-Glucagon Chem. 18

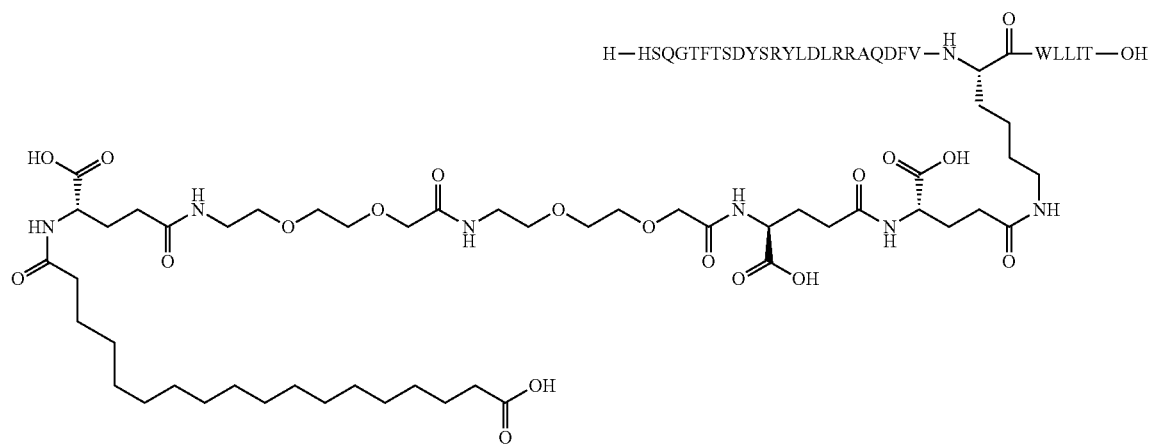

UPLC Method: 09_B2_1: Rt=13.0 min
UPLC Method: 09_B4_1: Rt=8.6 min
UPLC Method: 04_A9_1: Rt=15.4 min
LCMS Method: LCMS_4: Rt=2.4 min, m/3=1499; m/4=1124; m/5=899

Example 19

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Thr$^{28}$]-Glucagon

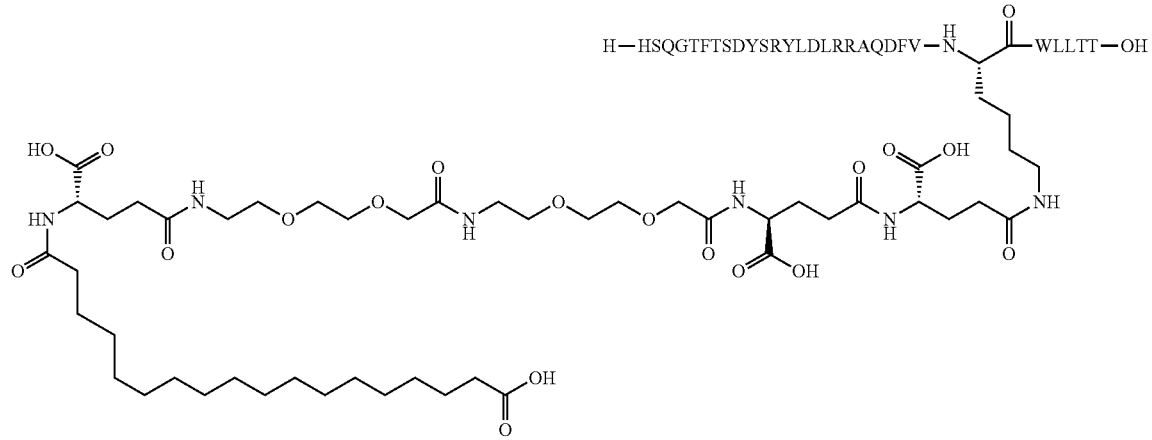

Chem. 19

UPLC Method: 09_B2_1: Rt=13.1 min
UPLC Method: 09_B4_1: Rt=8.6 min
UPLC Method: 04_A9_1: Rt=15.6 min
LCMS Method: LCMS_4: Rt=2.5 min, m/3=1494; m/4=1121; m/5=897

Example 20

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Arg$^{16}$,Lys$^{24}$,Leu$^{27}$,Ser$^{28}$]-Glucagon

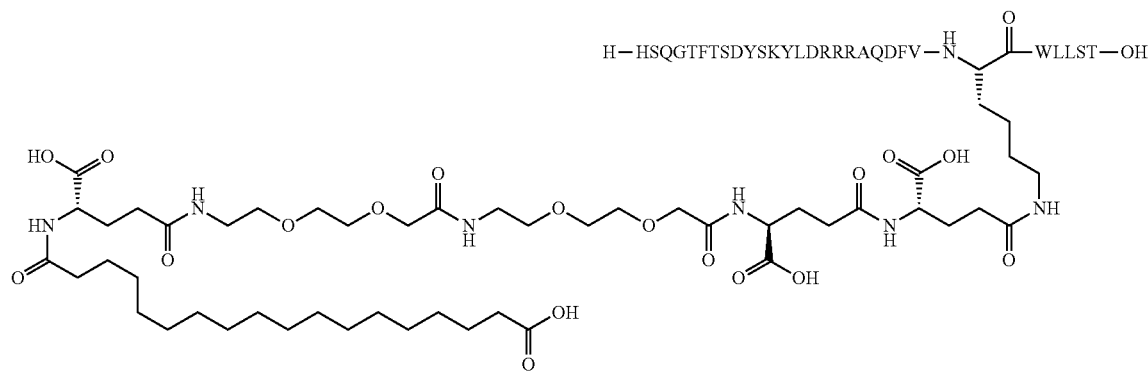

Chem. 20

UPLC Method: 09_B4_1: Rt=10.6 min;
UPLC Method: 04_A6_1: Rt=5.9 min;
LCMS Method: LCMS_4: Rt=2.1 min; m/3=1504; m/4=1128; m/5=903

Example 21

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Val$^{16}$,Lys$^{24}$,Leu$^{27}$,Ser$^{28}$]-Glucagon Chem. 21

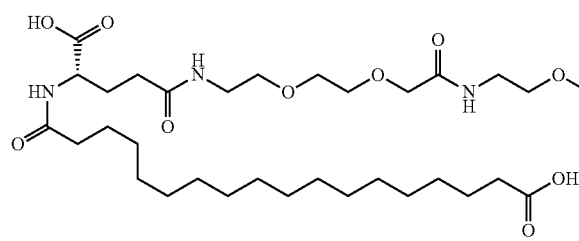

UPLC Method: 10_B4_1: Rt=8.5 min; UPLC Method: 04_A9_1: Rt=14.5 min; LCMS Method: LCMS_4: Rt=2.1 min; m/3=1485; m/4=1114; m/5=891

Example 22

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Thr$^{16}$,Lys$^{24}$,Leu$^{27}$,Ser$^{28}$]-Glucagon Chem. 22

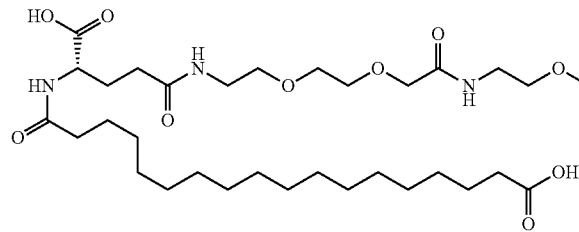

UPLC Method: 04_A9_1; Rt=13.1 min
UPLC Method: 10_B4_1; Rt=8.4 min
LC-MS Method: LCMS_4; RT=2.2; m/3=1485; m/4=1114; m/5=892

Example 23

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Ile$^{16}$,Lys$^{24}$,Leu$^{27}$,Ser$^{28}$]-Glucagon

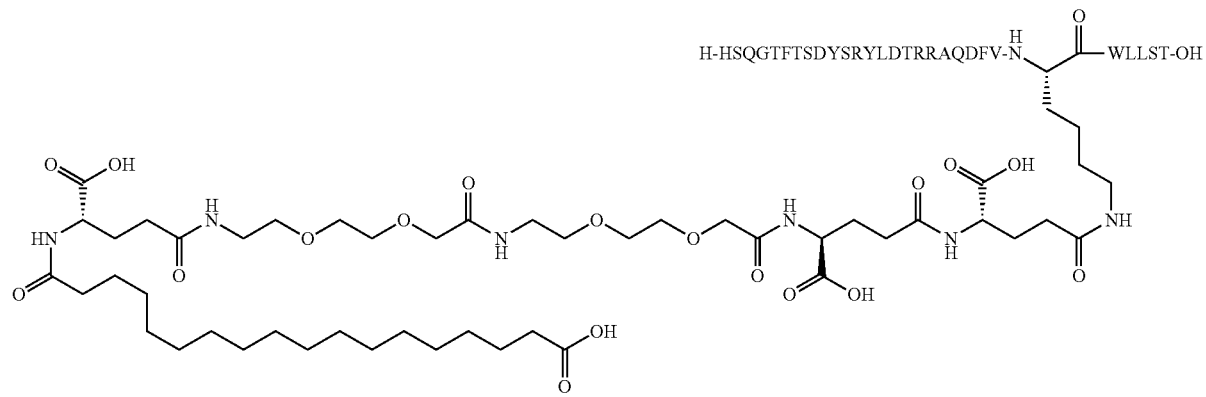

Chem. 22

UPLC Method: 10_B4_1: Rt=8.6 min;
UPLC Method: 04_A9_1: Rt=15.2 min;
LCMS Method: LCMS_4: Rt=2.1 min; m/3=1490; m/4=1118; m/5=894

Example 24

$N^{\epsilon 24}$-[(4S)-4-carboxy-4-[[(4S)-4-carboxy-4-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Ser$^{28}$]-Glucagon

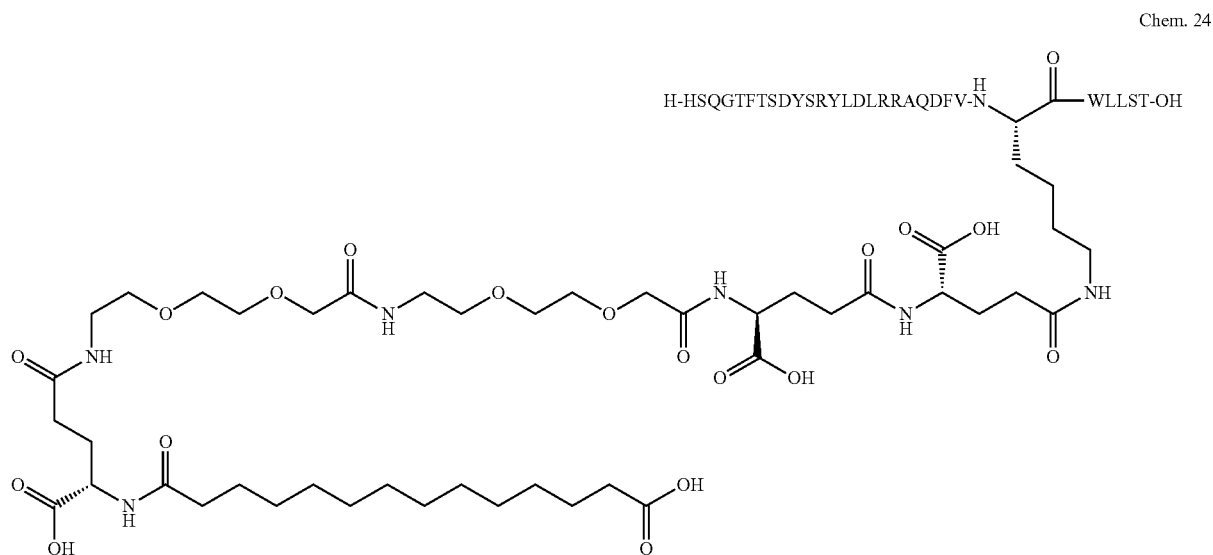

Chem. 24

UPLC Method: 09_B2_1: Rt=11.7 min
UPLC Method: 09_B4_1: Rt=7.7 min
UPLC Method: 04_A9_1: Rt=13.2 min
LCMS Method: LCMS_4: Rt=2.3 min, m/3=1471; m/4=1103; m/5=883

Example 25

$N^{\epsilon 24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Ser$^{28}$]-Glucagon Chem. 25

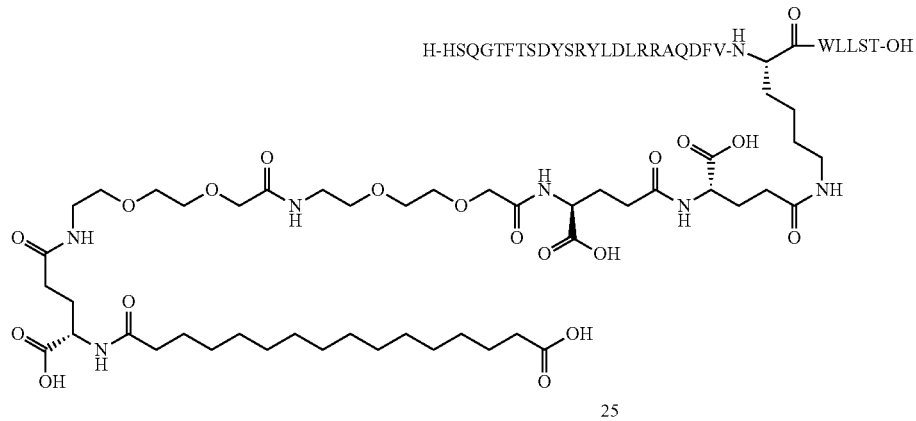

UPLC Method: 09_B2_1: Rt=12.4 min
UPLC Method: 09_B4_1: Rt=8.2 min
UPLC Method: 04_A9_1: Rt=14.0 min
LCMS Method: LCMS_4: Rt=2.3 min, m/3=1481; m/4=1110; m/5=889

Example 26

$N^{\epsilon 24}$-[(4S)-4-carboxy-4-[[(4S)-4-carboxy-4-[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]butanoyl]amino]butanoyl]-[Arg$^{12}$,Leu$^{16}$,Lys$^{24}$,Leu$^{27}$,Ser$^{28}$]-Glucagon Chem. 26

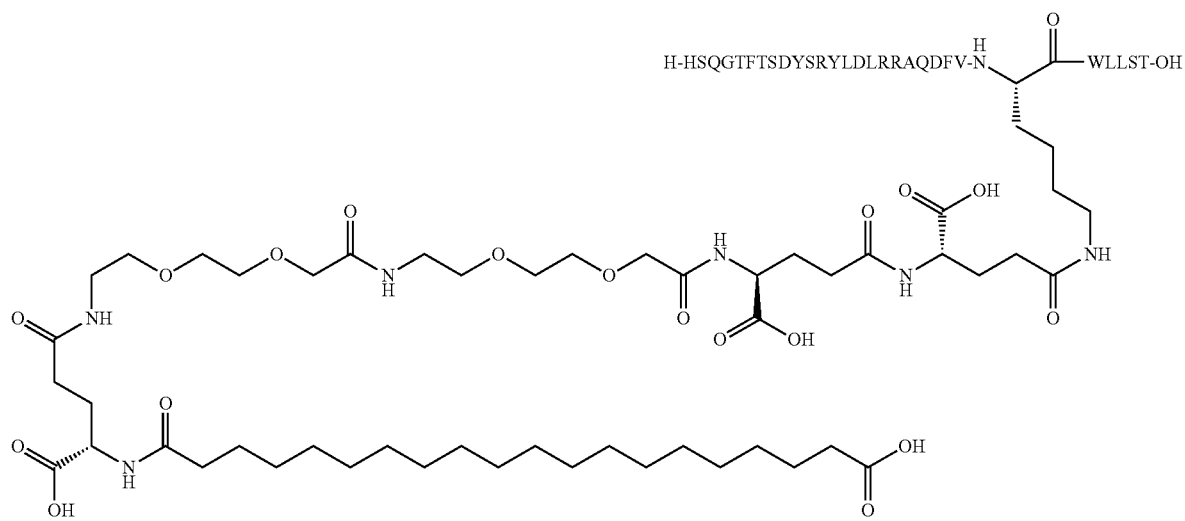

UPLC Method: 09_B2_1: Rt=14.0 min
UPLC Method: 09_B4_1: Rt=9.2 min
UPLC Method: 04_A9_1: Rt=16.6 min
LCMS Method: LCMS_4: Rt=2.5 min, m/3=1499; m/4=1124; m/5=900

Example 27

$N^{\epsilon 24}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Arg$^{12}$,Leu$^{16}$,Lys$^{24}$,Leu$^{27}$,Ser$^{28}$]-Glucagon

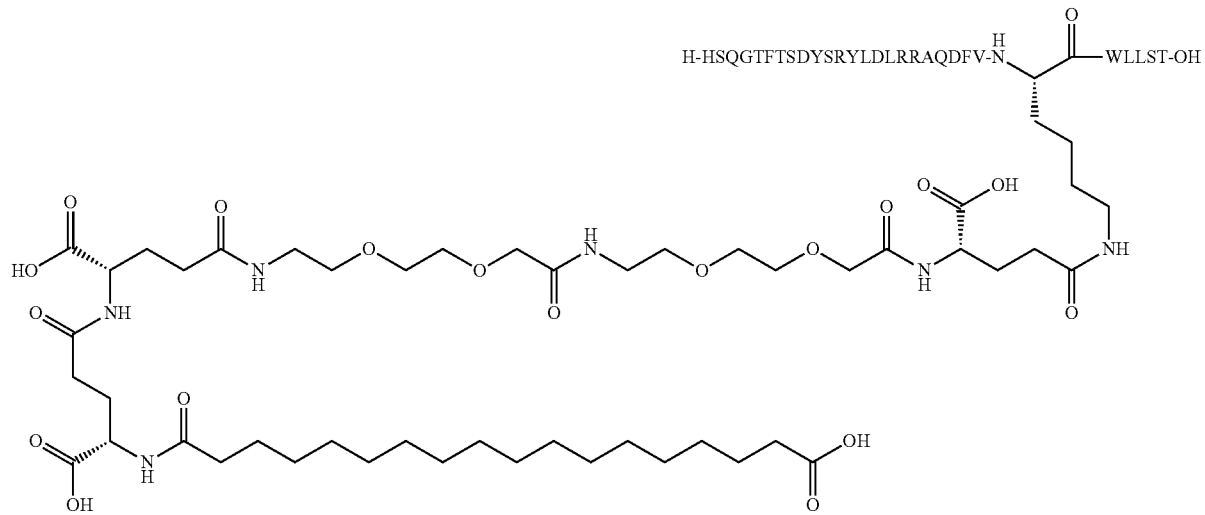

Chem. 27

UPLC Method: 09_B2_1: Rt=13.0 min
UPLC Method: 09_B4_1: Rt=8.6 min
UPLC Method: 04_A9_1: Rt=14.7 min
LCMS Method: LCMS_4: Rt=2.4 min, m/3=1489; m/4=1117; m/5=894

Example 28

$N^{\epsilon 24}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Arg$^{12}$,Leu$^{16}$,Lys$^{24}$,Leu$^{27}$,Ser$^{28}$]-Glucagon

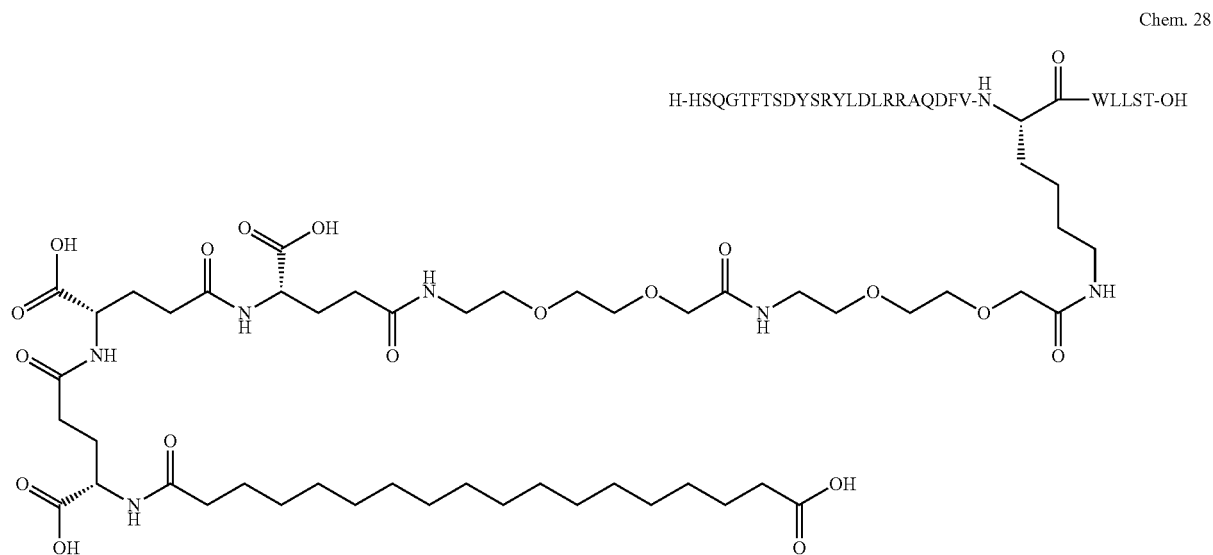

Chem. 28

UPLC Method: 09_B2_1: Rt=13.0 min
UPLC Method: 09_B4_1: Rt=8.5 min
UPLC Method: 04_A9_1: Rt=14.7 min
LCMS Method: LCMS_4: Rt=2.4 min, m/3=1489; m/4=1117; m/5=894

Example 29

$N^{\epsilon 24}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Arg$^{12}$, Leu$^{16}$,Lys$^{24}$,Leu$^{27}$,Ser$^{28}$]-Glucagon

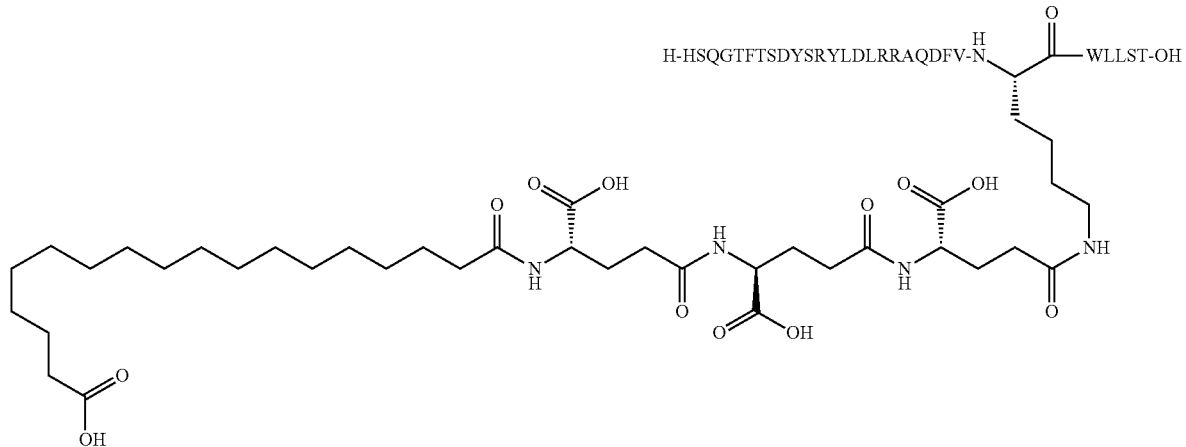

Chem. 29

UPLC Method: 09_B2_1: Rt=13.2 min
UPLC Method: 09_B4_1: Rt=8.7 min
UPLC Method: 04_A9_1: Rt=15.2
LCMS Method: LCMS_4: Rt=2.5 min, m/3=1392; m/4=1045; m/5=836

Example 30

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Val16,Lys24,Leu27,Ser28]-Glucagon

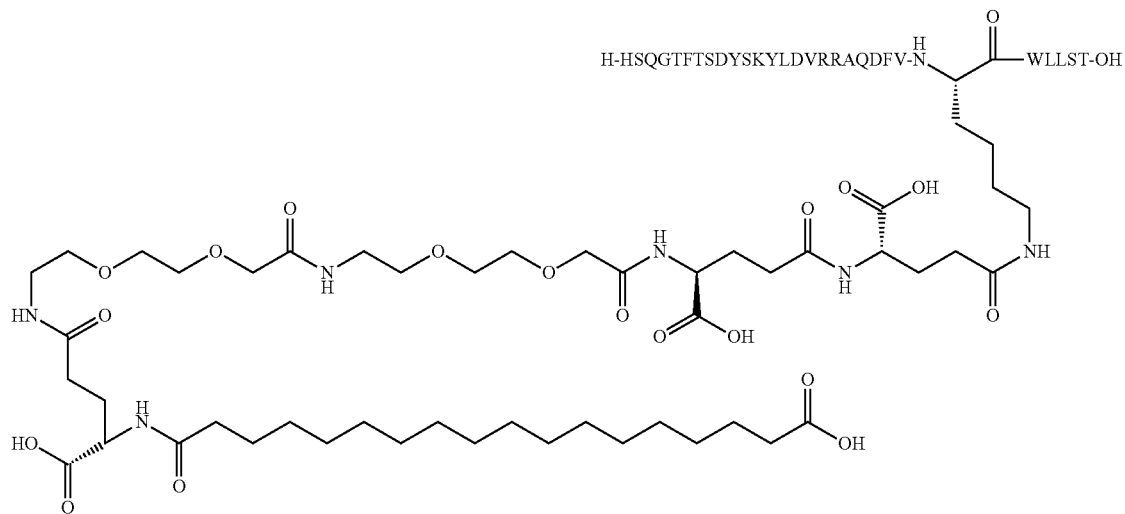

Chem. 30

UPLC Method: 10_B4_1; Rt=8.6 min
UPLC Method: 04_A6_1; Rt=7.3 min
LC-MS Method: LCMS_4; Rt=2.3, m/3=1475; m/4=1107; m/5=886

Example 31

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Thr16,Glu21,Lys24,Leu27,Ser28]-Glucagon

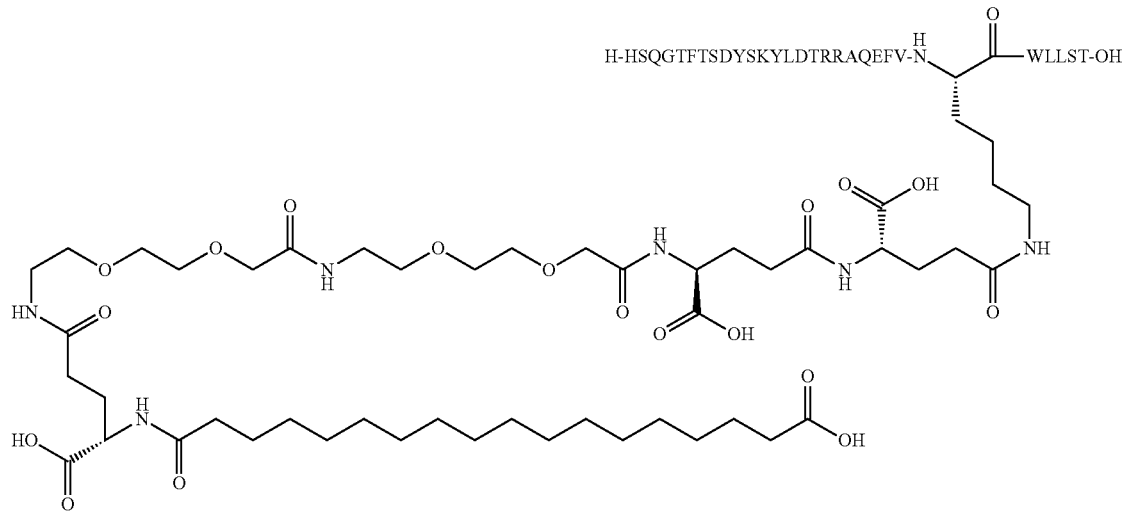

Chem. 31

UPLC Method: 10_B4_1; Rt=8.4 min
UPLC Method: 04_A9_1; Rt=13.3 min
LC-MS Method: LCMS_4; RT=2.2, m/3=1481; m/4=1111; m/5=889

Example 32

$N^{\epsilon24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Glu15,Lys24,Leu27,Ile29]-Glucagon

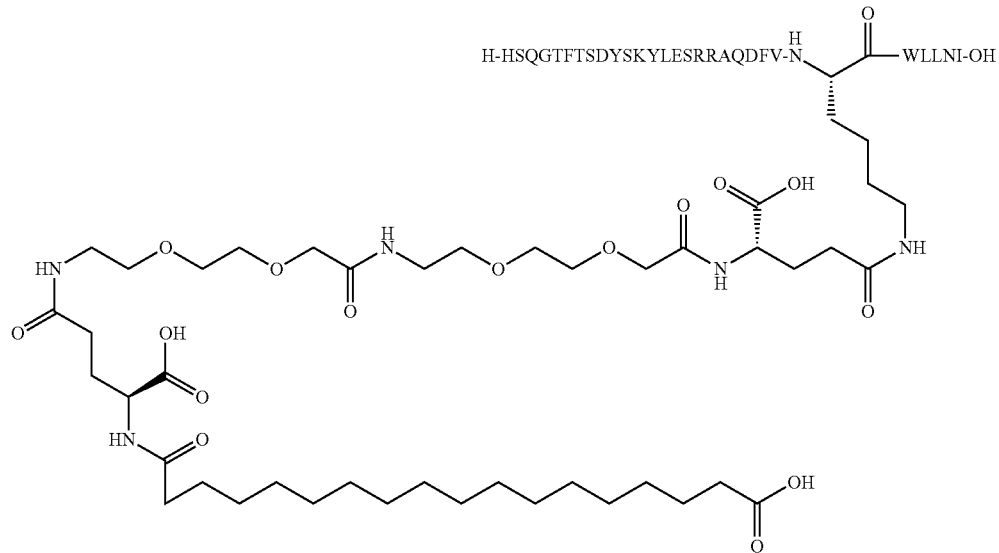

Chem. 32

UPLC Method: 10_B4_1; Rt=8.8 min
UPLC Method: 04_A9_1; Rt=13.5 min
LC-MS Method: LCMS_4; RT=2.4, m/3=1446; m/4=1085; m/5=868

Example 33

N$^{\epsilon 24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Glu15,Lys24,Leu27,Val29]-Glucagon

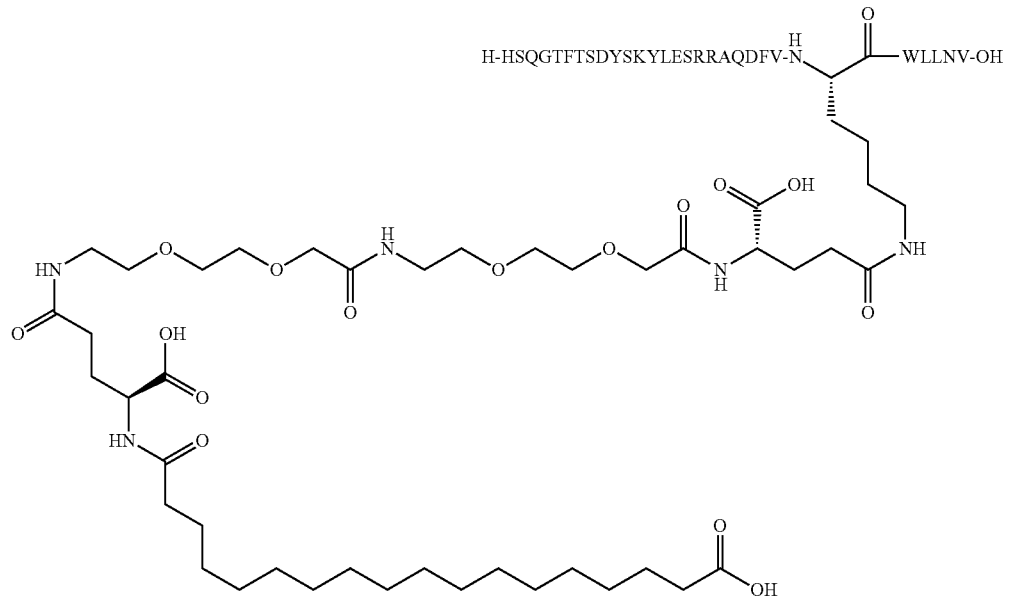

Chem. 33

UPLC Method: 10_B4_1; Rt=8.6 min
UPLC Method: 04_A9_1; Rt=12.9 min
LC-MS Method: LCMS_4; RT=2.4, m/3=1442; m/4=1081; m/5=865

Example 34

N$^{\epsilon 24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Glu15,Lys24,Leu27,Leu29]-Glucagon

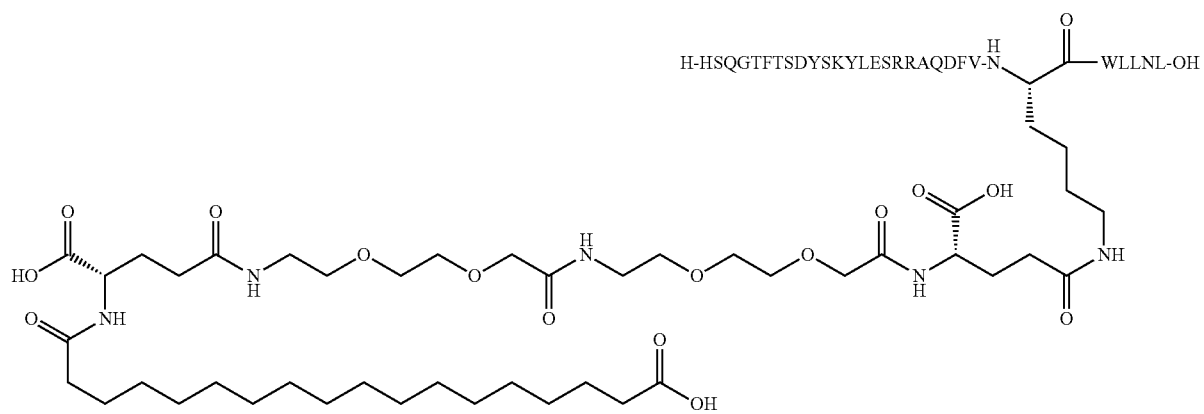

Chem. 34

UPLC Method: 10_B4_1; Rt=8.9 min
UPLC Method: 04_A9_1; Rt=13.8 min
LC-MS Method: LCMS_4; RT=2.5, m/3=1446; m/4=1085; m/5=868

Example 35

$N^{\epsilon24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Thr16,Lys24,Leu27,Ile29]-Glucagon

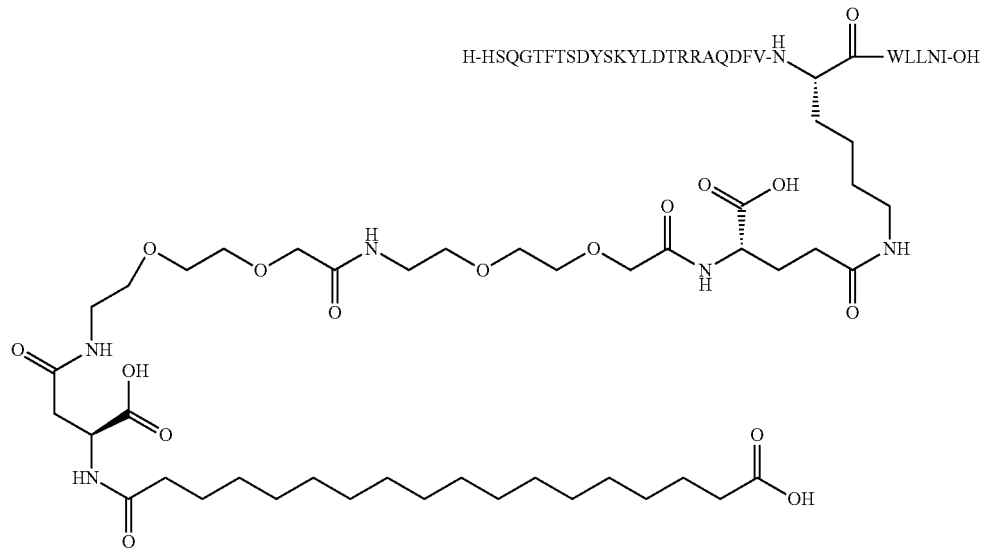

Chem. 35

UPLC Method: 09_B4_1; Rt=8.8 min
LC-MS Method: LCMS_4; Rt=2.4 min, m/3=1446; m/4=1085; m/5=868

Example 36

$N^{\epsilon24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Thr16,Glu21,Lys24,Leu27,Val29]-Glucagon

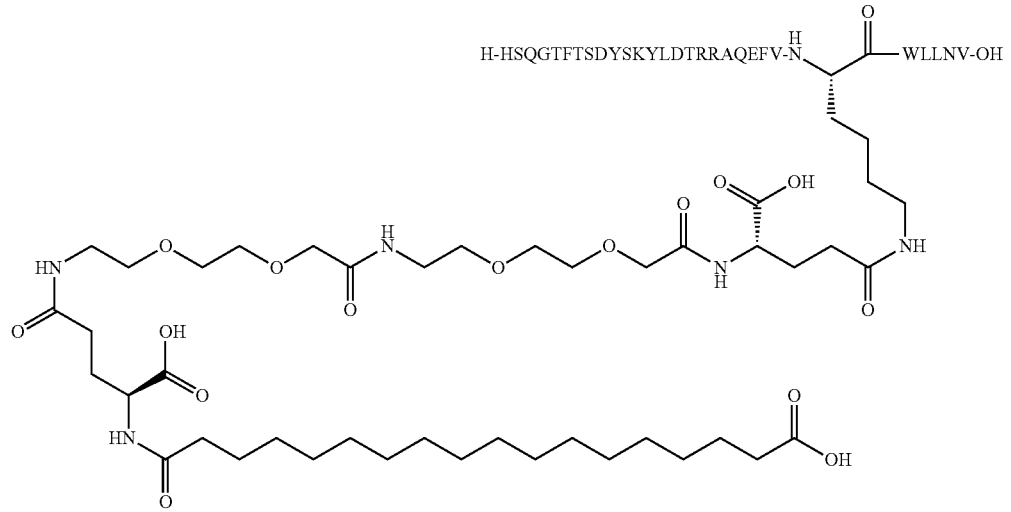

Chem. 36

UPLC Method: 09_B4_1; Rt=8.6 min
LC-MS Method: LCMS_4; Rt=2.3 min; m/4=1085; m/5=868

Example 37

$N^{\epsilon 24}$-[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]-[Thr16,Glu21,Lys24,Leu27,Leu29]-Glucagon Chem. 37

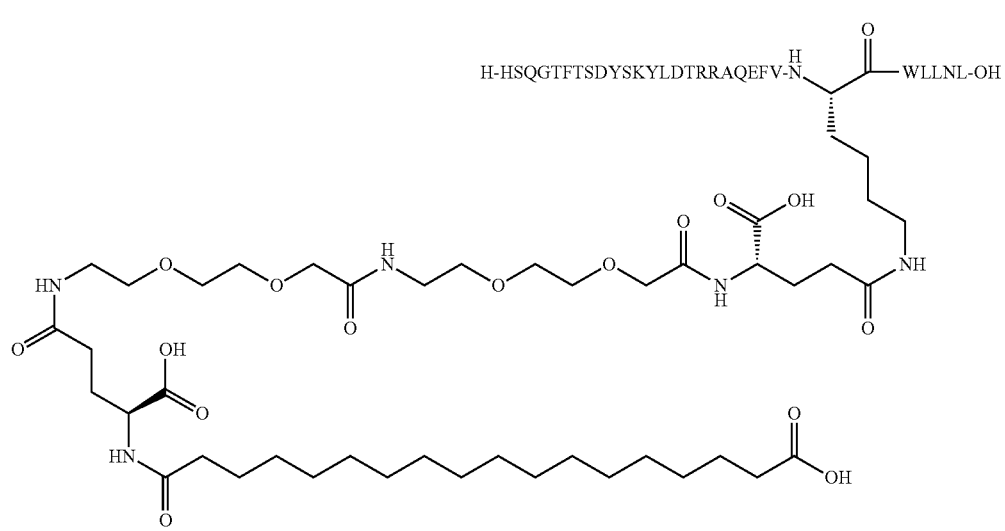

UPLC Method: 09_B4_1; Rt=8.9 min
LC-MS Method:LCMS_2: Rt=6.2 min; m/3=1451, m/4=1088

Example 38

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Val10,Thr16,Glu21,Lys24,Leu27,Ser28]-Glucagon Chem. 38

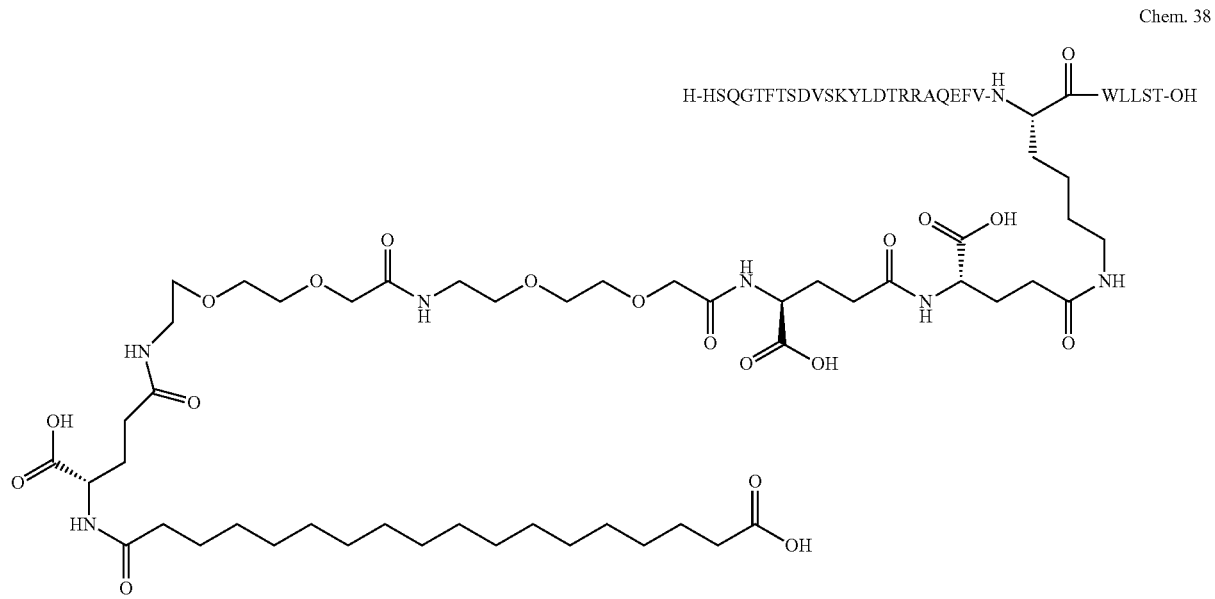

UPLC Method: 06_B4_1: Rt=8.4 min
LC-MS Method: LCMS_4: Rt=2.2 min, m/3=1494.1; m/4=1120.5; m/5=896.8

Example 39

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Thr16,Lys24,Leu27,Ser28]-Glucagon amide

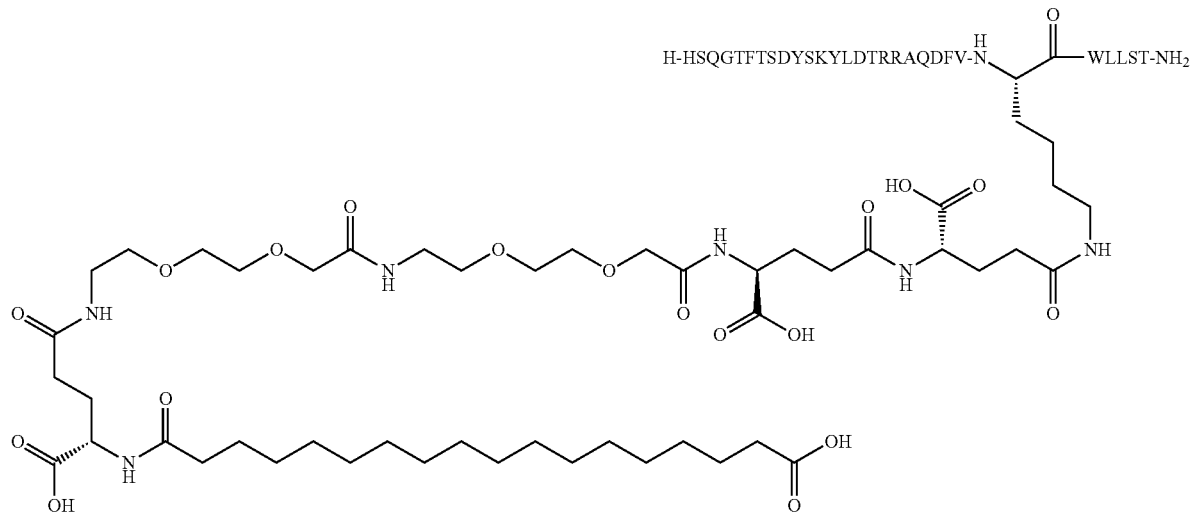

Chem. 39

UPLC Method: 08_B2_1: Rt=12.6 min
UPLC Method: 08_B4_1: Rt=8.3 min
UPLC Method: 04_A3_1: Rt=15.3 min
LCMS Method: LCMS_4: Rt=2.2 min, m/3=1476; m/4=1107; m/5=886

Example 40

$N^{\epsilon24}$-[2-[2-[2-[[(4S)-4-carboxy-4-[[(4S)-4-carboxy-4-[[2-[2-[2-[[(4S)-4-carboxy-4-(17-carboxyheptade-canoylamino)butanoyl]amino]ethoxy]ethoxy]acetyl]amino]butanoyl]amino]butanoyl]amino]ethoxy]ethoxy]acetyl]-[Thr16,Lys24,Leu27,Ser28]-Glucagon

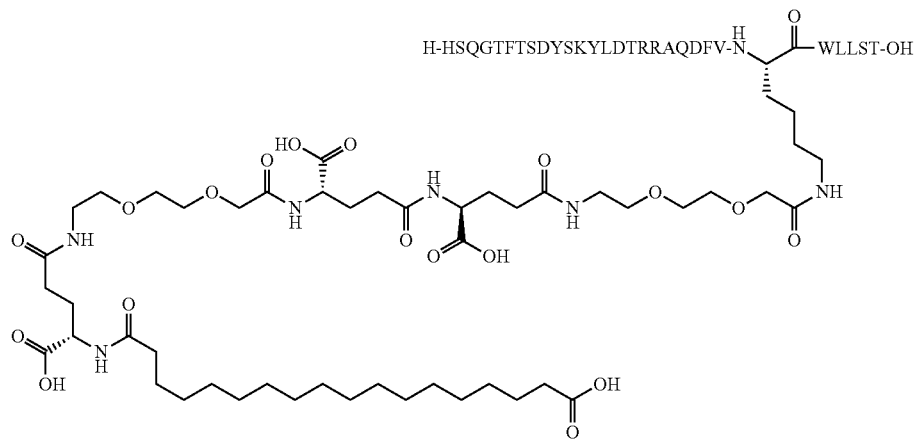

Chem. 40

UPLC Method: 08_B2_1: Rt=12.6 min
UPLC Method: 08_B4_1: Rt=8.3 min
UPLC Method: 04_A3_1: Rt=12.8 min
LCMS Method: LCMS_4: Rt=2.2 min, m/3=1476; m/4=1107; m/5=886

Example 41
$N^{\epsilon 24}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Glu16,Lys24,Leu27,Ser28]-Glucagon

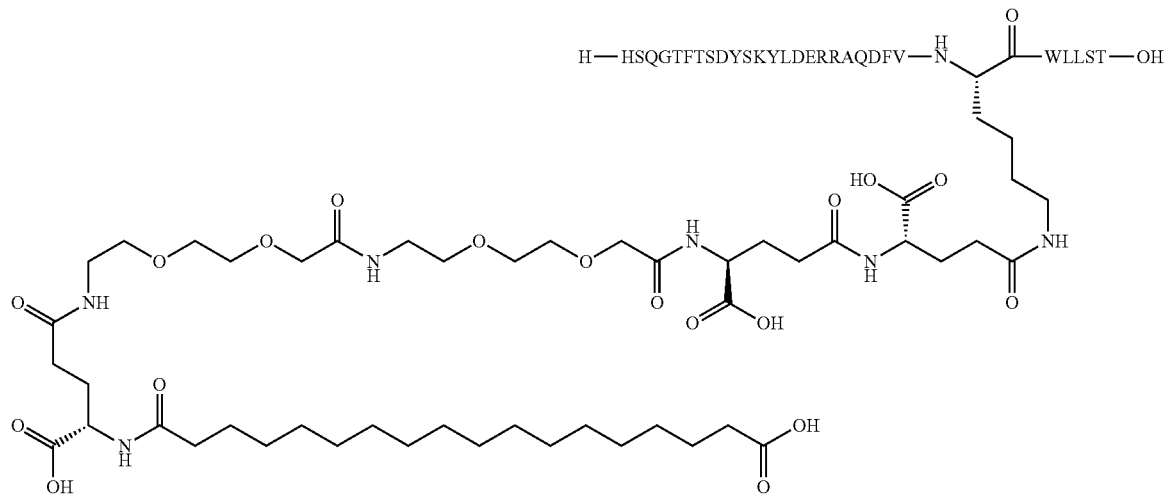

Chem. 41

UPLC Method: 08_B2_1: Rt=12.6 min
UPLC Method: 08_B4_1: Rt=8.3 min
UPLC Method: 04_A3_1: Rt=11.4 min
LCMS Method: LCMS_4: Rt=2.1 min, m/3=1485; m/4=1114; m/5=892

Example 42
$N^{\epsilon 24}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Glu16,Lys24,Leu27,Ser28]-Glucagon

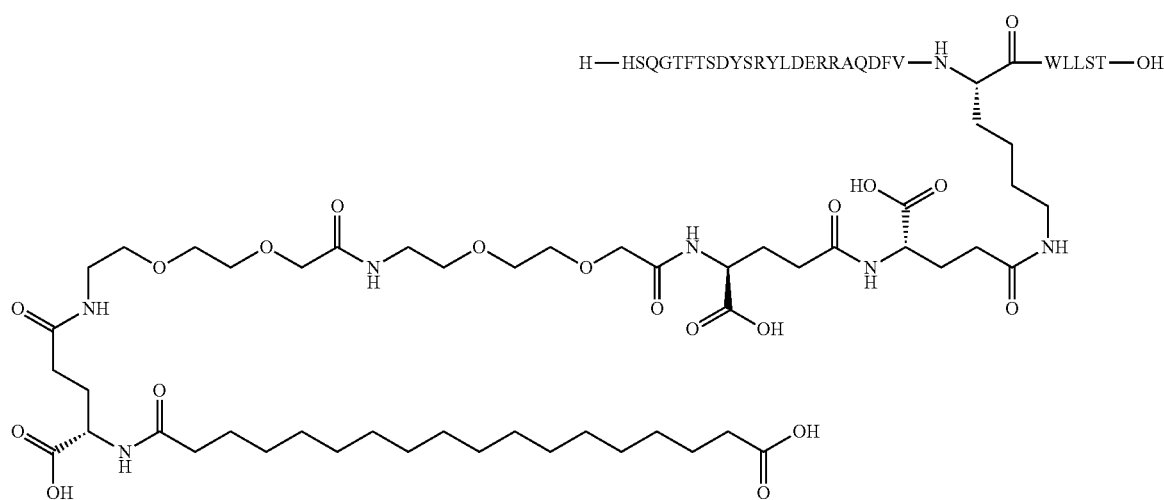

Chem. 42

UPLC Method: 08_B2_1: Rt=12.6 min
UPLC Method: 08_B4_1: Rt=8.3 min
UPLC Method: 04_A3_1: Rt=11.4 min
LCMS Method: LCMS_4: Rt=2.2 min, m/3=1495; m/4=1121; m/5=897

Example 43

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Ala16,Lys24,Leu27,Ser28]-Glucagon

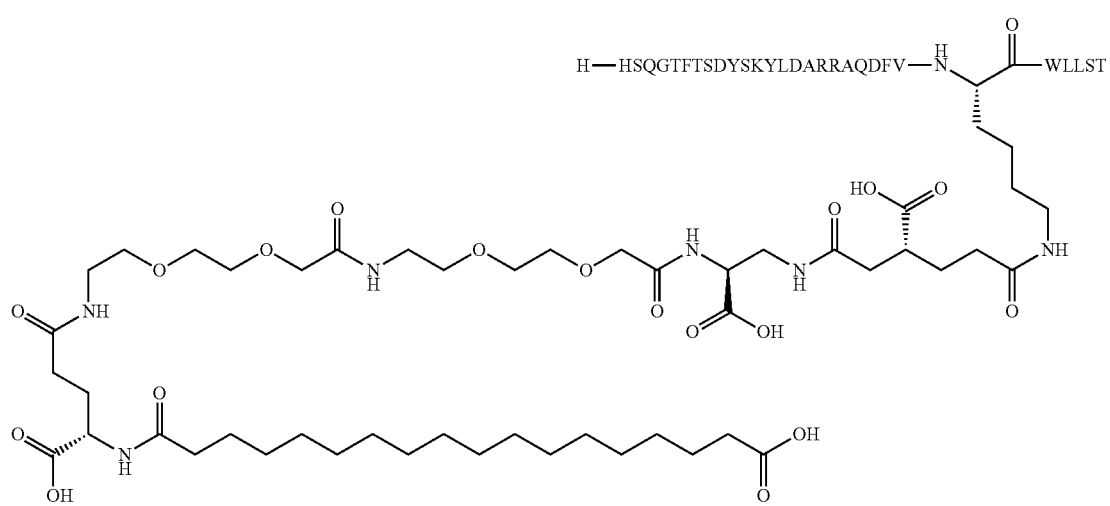

Chem. 43

UPLC Method: 08_B2_1: Rt=12.6 min
UPLC Method: 08_B4_1: Rt=8.4 min
UPLC Method: 04_A3_1: Rt=13.2 min
LCMS Method: LCMS_4: Rt=2.2 min, m/3=1466; m/4=1100; m/5=880

Example 44

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Arg12,Thr16,Lys24,Glu27,Ser28]-Glucagon

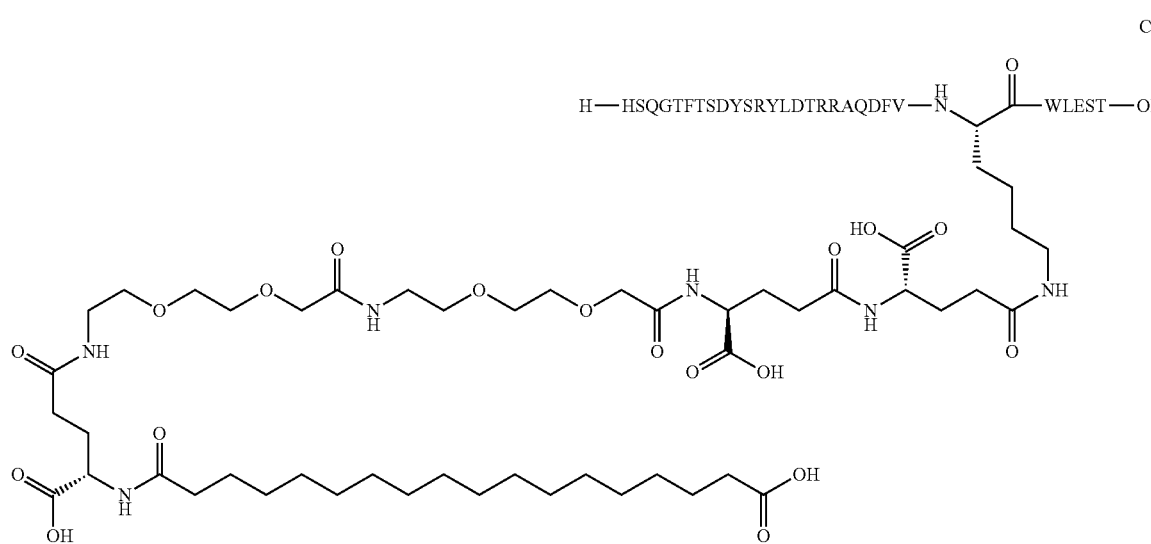

Chem. 44

UPLC Method: 08_B2_1: Rt=11.9 min
UPLC Method: 08_B4_1: Rt=7.9 min
UPLC Method: 04_A3_1: Rt=9.0 min
LCMS Method: LCMS_4: Rt=2.0 min, m/3=1491; m/4=1118; m/5=895

Example 45

$N^{\epsilon 24}$-[(4S)-4-carboxy-4-[[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]amino]butanoyl]-[Arg12,Leu16,Lys24,Leu27,Ser28]-Glucagon Chem. 45

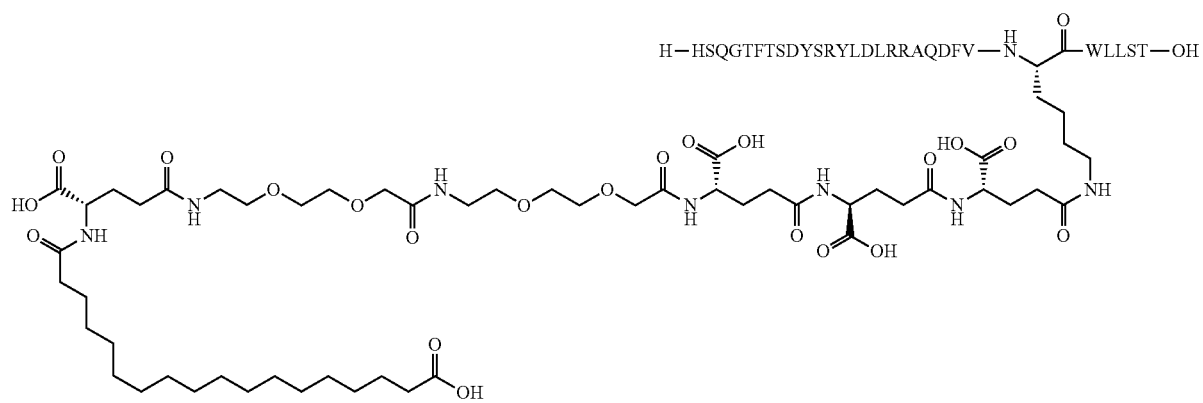

UPLC Method: 09_B2_1: Rt=14.0 min
LCMS Method: LCMS_4: Rt=2.4 min, m/3=1532; m/4=1149; m/5=920

Example 46

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Leu16,Glu21,Lys24,Leu27,Ser28]-Glucagon Chem. 46

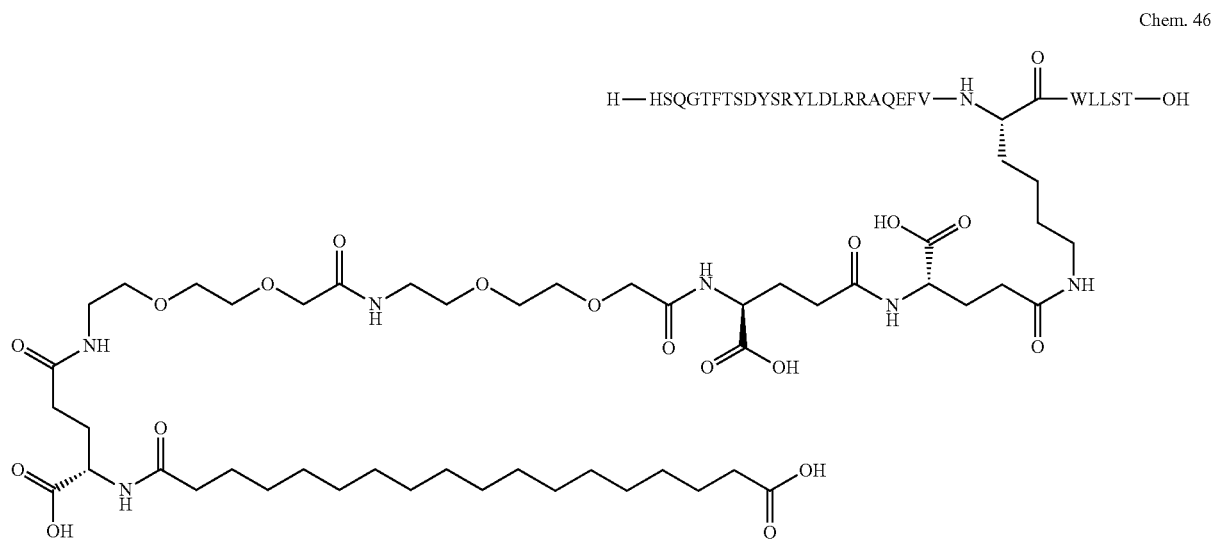

UPLC Method: 08_B2_1: Rt=13.9 min
UPLC Method: 08_B4_1: Rt=9.4 min
UPLC Method: 04_A3_1: Rt=15.8 min
LCMS Method: LCMS_4: Rt=2.3 min, m/3=1494; m/4=1121; m/5=897

Example 47

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Arg12,Leu16,Lys24,Glu27,Ser28]-Glucagon

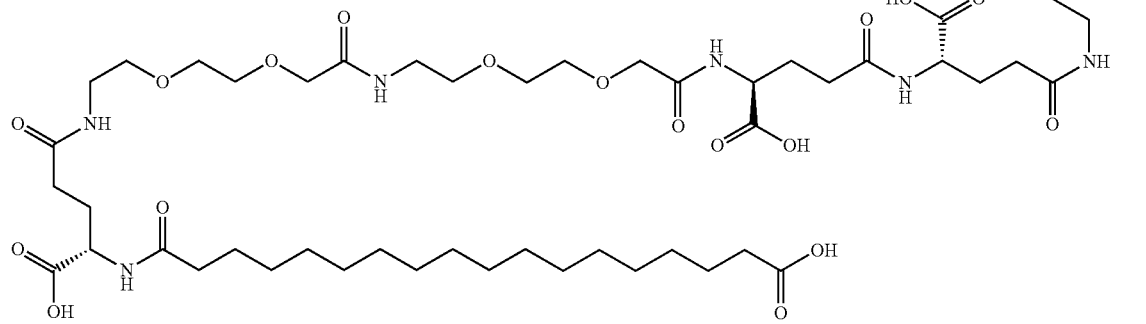

Chem. 47

UPLC Method: 08_B2_1: Rt=12.9 min
UPLC Method: 08_B4_1: Rt=8.8 min
UPLC Method: 04_A3_1: Rt=10.8 min
LCMS Method: LCMS_4: Rt=2.1 min, m/3=1495; m/4=1121; m/5=897

Example 48

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Arg12,Leu16,Lys24,Leu27,Gln28]-Glucagon

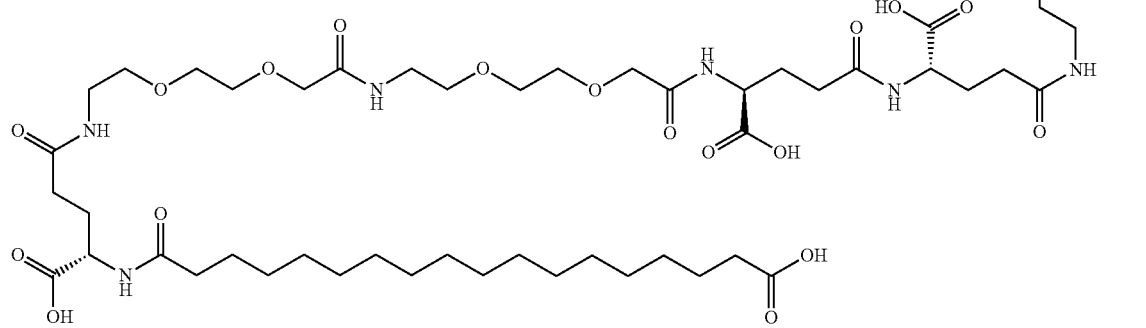

Chem. 48

UPLC Method: 08_B2_1: Rt=13.6 min
UPLC Method: 08_B4_1: Rt=9.2 min
UPLC Method: 04_A3_1: Rt=14.9 min
LCMS Method: LCMS_4: Rt=2.3 min, m/3=1503; m/4=1127; m/5=902

Example 49

N$^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Glu15,Glu21,Lys24,Leu27,Ser28]-Glucagon

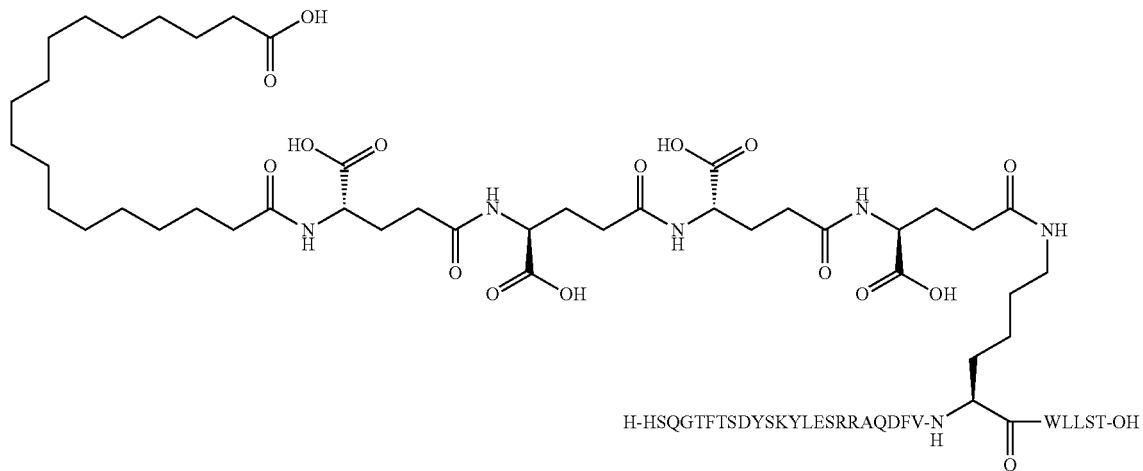

Chem. 49

UPLC Method: 08_B2_1: Rt=13.1 min
UPLC Method: 08_B4_1: Rt=8.9 min
UPLC Method: 04_A3_1: Rt=11.5 min
LCMS Method: LCMS_4: Rt=2.1 min, m/3=1427; m/4=1070; m/5=857

Example 50

N$^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Val10,Glu15,Glu21,Lys24,Leu27,Ser28]-Glucagon

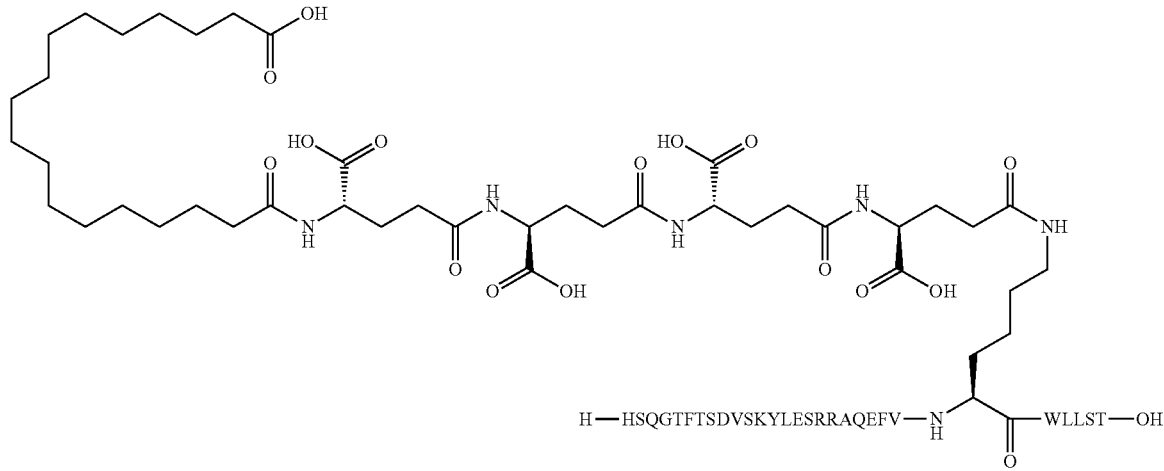

Chem. 50

UPLC Method: 08_B2_1: Rt=13.2 min
UPLC Method: 08_B4_1: Rt=9.0 min
UPLC Method: 04_A3_1: Rt=12.0 min
LCMS Method: LCMS_4: Rt=2.2 min, m/3=1406; m/4=1054; m/5=844

Example 51

N$^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Arg12,Glu15,Glu21,Lys24,Leu27,Ser28]-Glucagon Chem. 51

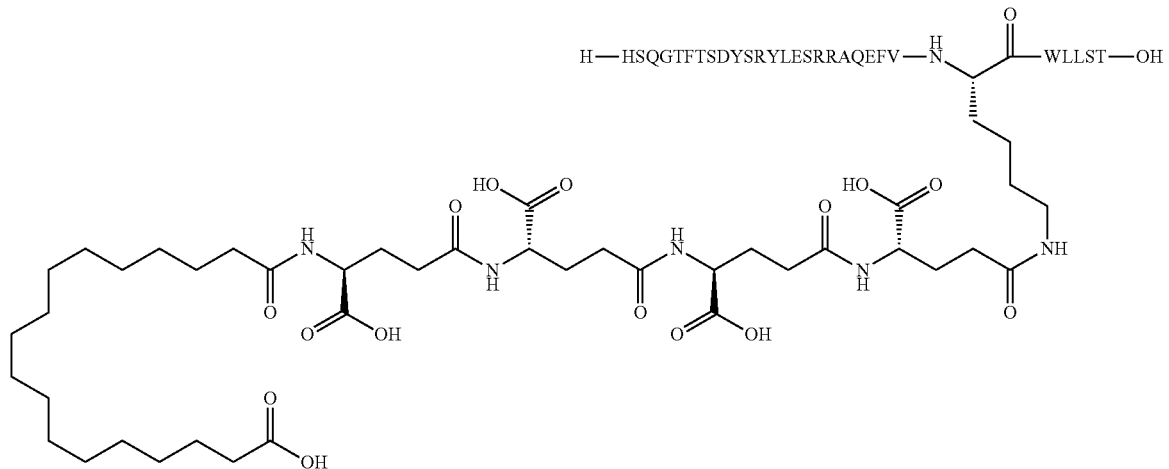

UPLC Method: 08_B2_1: Rt=13.2 min
UPLC Method: 08_B4_1: Rt=9.0 min
UPLC Method: 04_A3_1: Rt=12.0 min
LCMS Method: LCMS_4: Rt=2.2 min, m/3=1436; m/4=1077; m/5=862

Example 52

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Glu15,Glu21,Lys24,Leu27,Ser28]-Glucagon Chem. 52

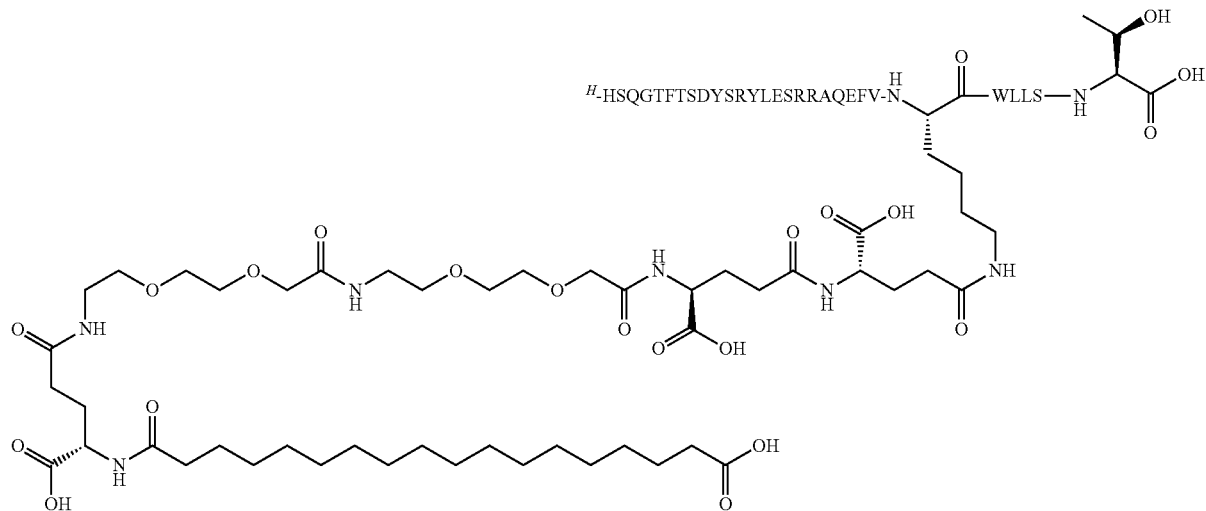

UPLC Method: 04_A9_1; Rt=12.2 min
UPLC Method: 10_B4_1; Rt=8.3 min
LC-MS Method: LCMS_4; RT=2.2, m/3=1490; m/4=1118; m/5=894

Example 53

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Arg12,Ile16,Glu21,Lys24,Glu27,Ser28]-Glucagon

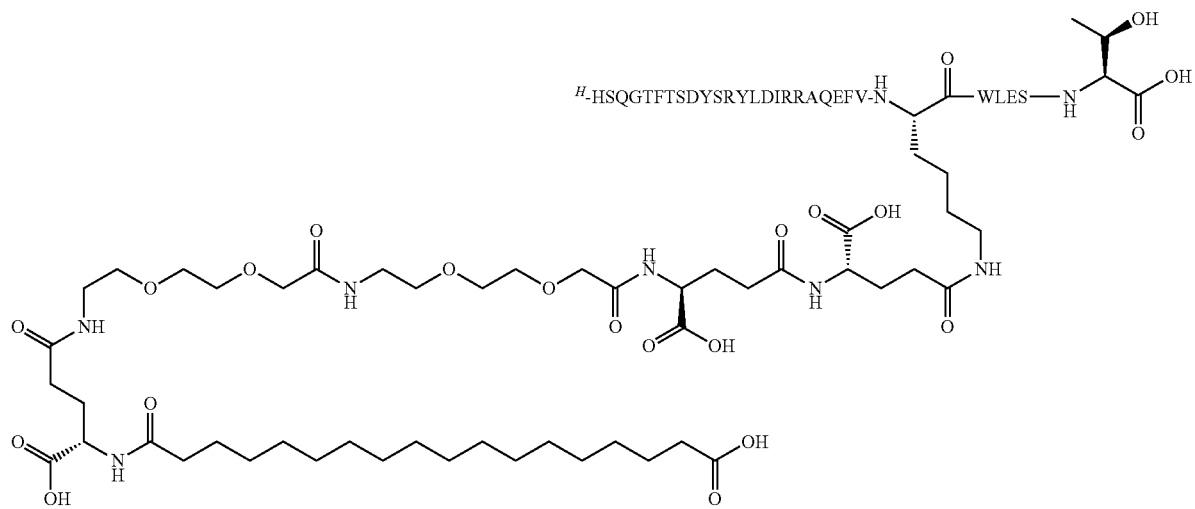

Chem. 53

UPLC Method: 04_A9_1; Rt=11.0 min
UPLC Method: 10_B4_1; Rt=8.0 min
LC-MS Method: LCMS_4; RT=2.2, m/3=1499, m/4=1125, m/5=900

Example 54

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Val10,Arg12,Glu15,Glu21,Lys24,Glu27,Ser28]-Glucagon

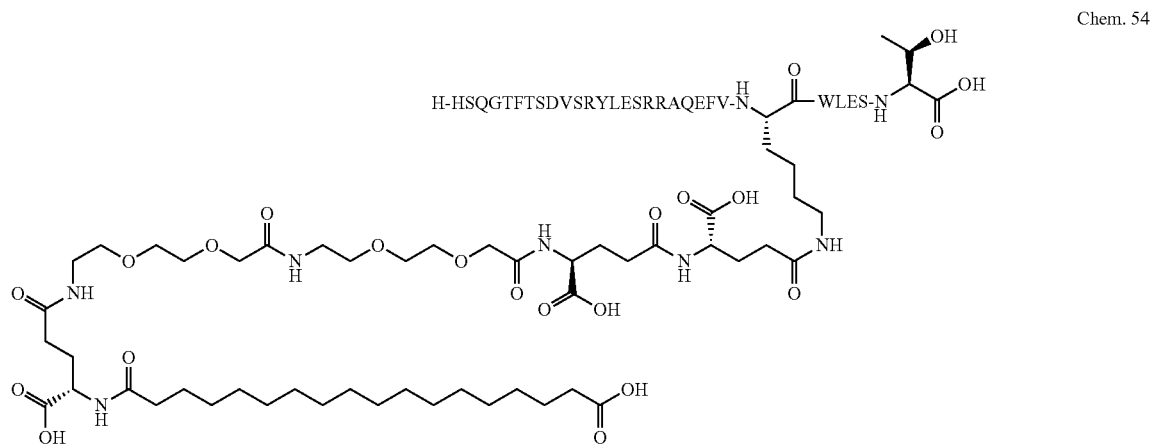

Chem. 54

UPLC Method: 04_A9_1; Rt=9.0 min
UPLC Method: 10_B4_1; Rt=8.1 min
LC-MS Method: LCMS_4; RT=2.2, m/3=1474; m/4=1106; m/5=885

Example 55

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Glu15,Glu21,Lys24,Glu27,Ser28]-Glucagon Chem. 55

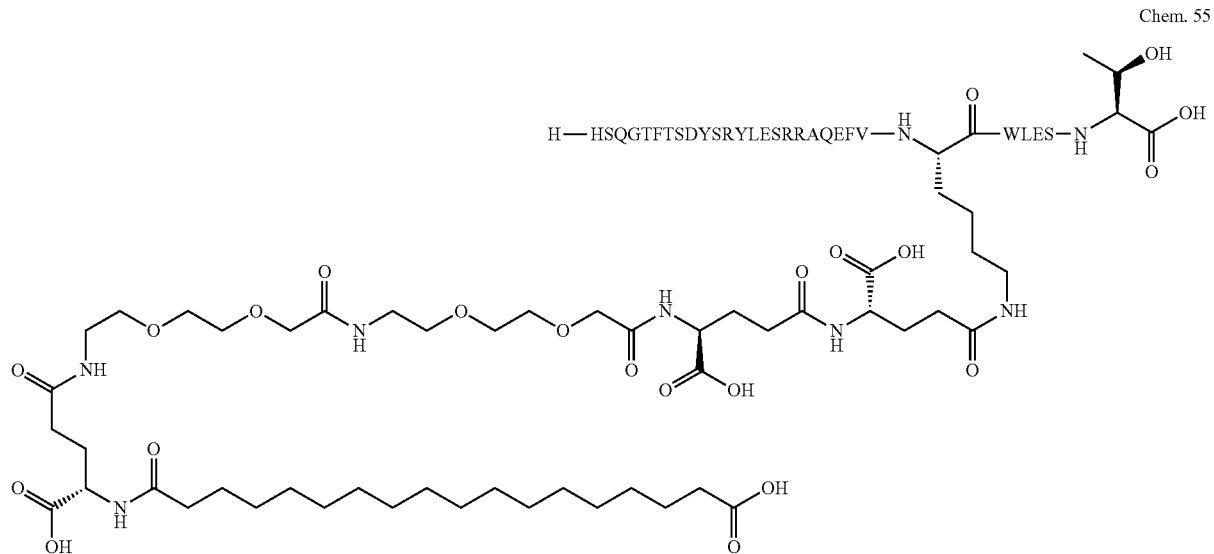

UPLC Method: 04_A9_1; Rt=8.8 min
UPLC Method: 10_B4_1; Rt=8.1 min
LC-MS Method: LCMS_4; RT=2.2; m/3=1495; m/4=1121; m/5=898

Example 56

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Ala16,Lys24,Leu27,Gln28]-Glucagon Chem. 56

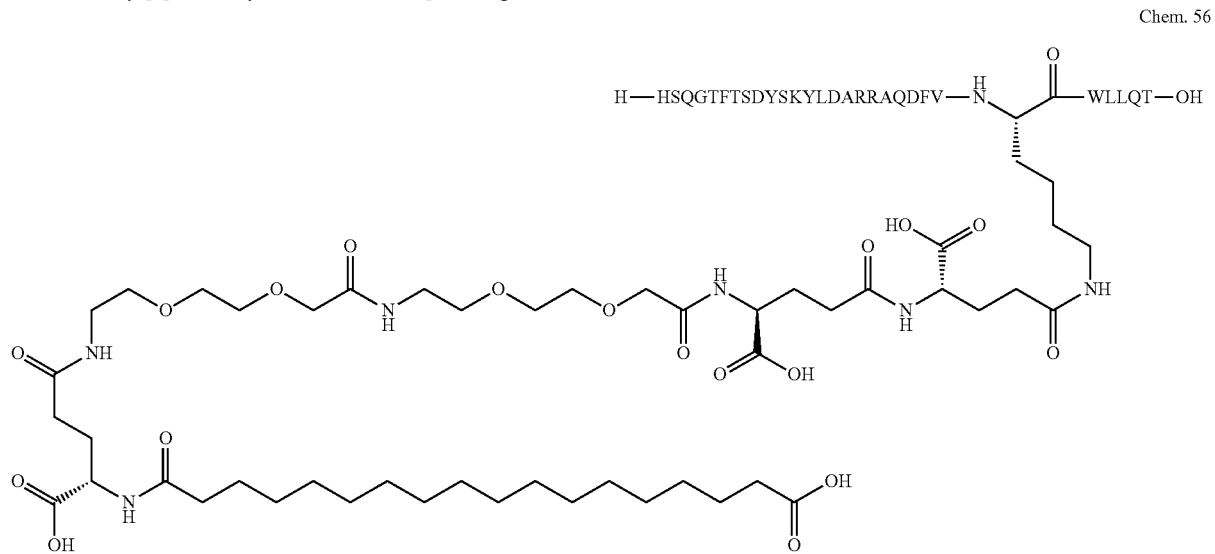

UPLC Method: 08_B2_1: Rt=13.3 min
UPLC Method: 08_B4_1: Rt=9.0 min
UPLC Method: 04_A3_1: Rt=13.5 min
LCMS Method: LCMS_4: Rt=2.3 min, m/3=1480; m/4=1110; m/5=888

Example 57

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Ala16,Lys24,Glu27,Ser28]-Glucagon

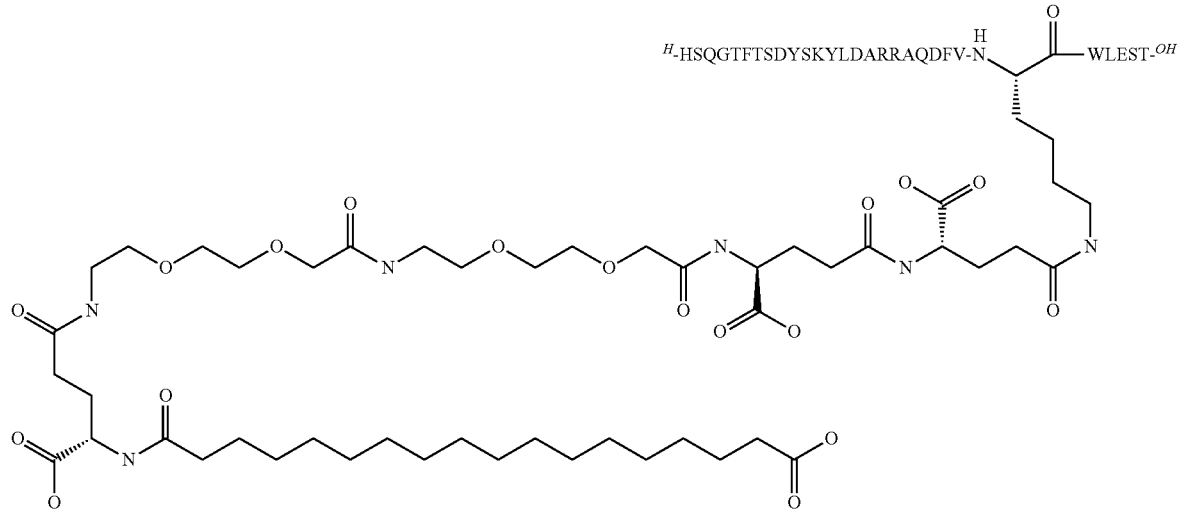

Chem. 57

UPLC Method: 08_B2_1: Rt=12.5 min
UPLC Method: 08_B4_1: Rt=8.6 min
UPLC Method: 04_A3_1: Rt=9.5 min
LCMS Method: LCMS_4: Rt=2.2 min, m/3=1471; m/4=1104; m/5=883

Example 58

$N^{\epsilon24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Glu15,Lys24,Leu27,Ser28]-Glucagon amide

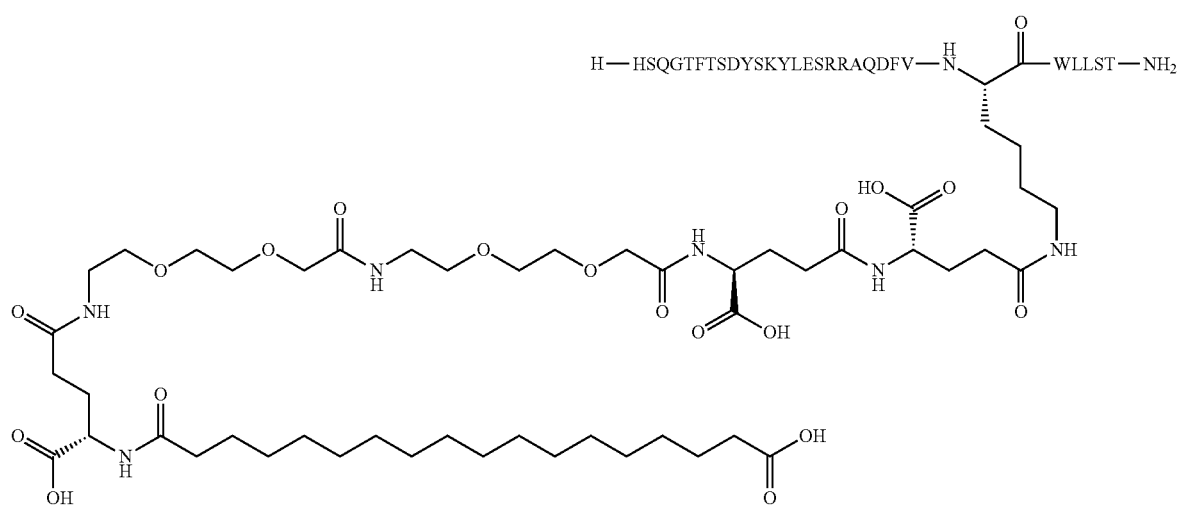

Chem. 58

UPLC Method: 08_B2_1: Rt=13.2 min
UPLC Method: 08_B4_1: Rt=9.0 min
UPLC Method: 04_A3_1: Rt=14.8 min
LCMS Method: LCMS_4: Rt=2.2 min, m/3=1476; m/4=1107; m/5=886

Example 59
$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Glu15,Lys24,Glu27,Ser28]-Glucagon

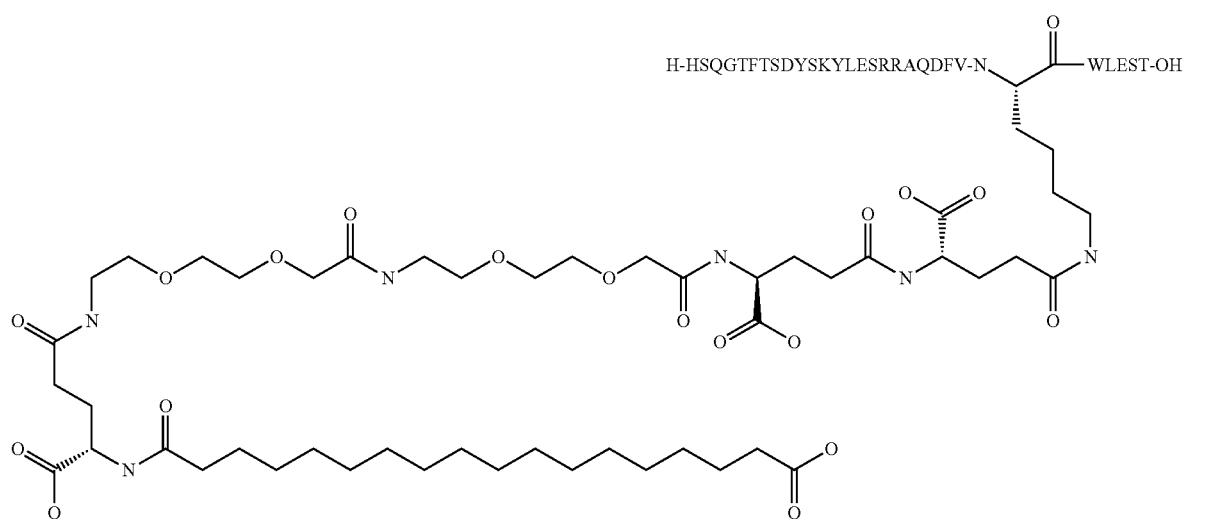

Chem. 59

UPLC Method: 08_B2_1: Rt=12.5 min
UPLC Method: 08_B4_1: Rt=8.5 min
UPLC Method: 04_A3_1: Rt=8.6 min
LCMS Method: LCMS_4: Rt=2.1 min, m/3=1481; m/4=1111; m/5=889

Example 60
$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Glu15,Lys24,Leu27,Gln28]-Glucagon

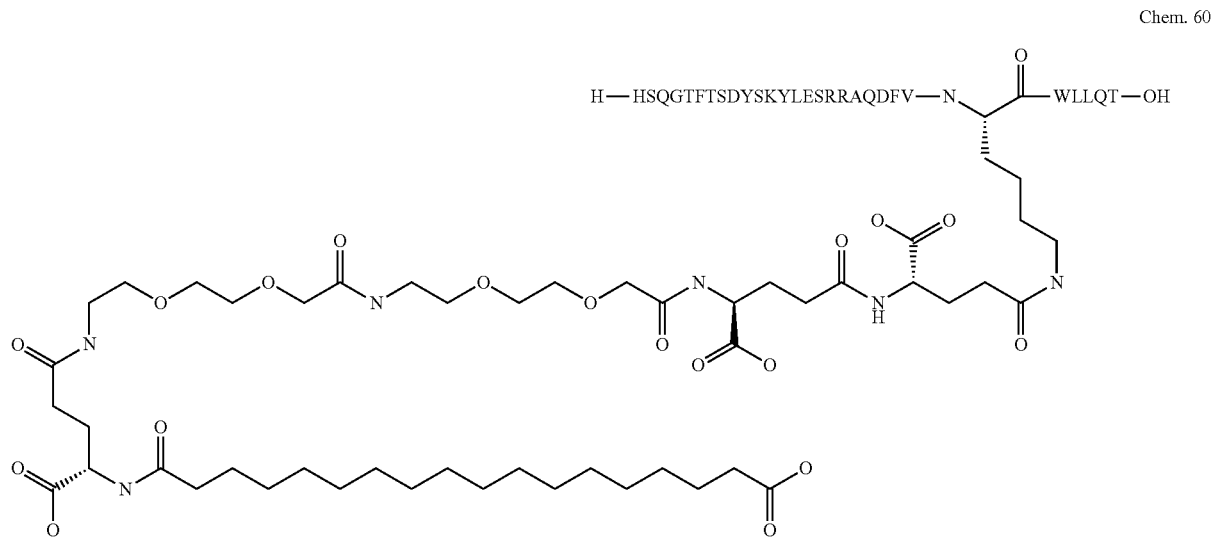

Chem. 60

UPLC Method: 08_B2_1: Rt=13.1 min
UPLC Method: 08_B4_1: Rt=8.9 min
UPLC Method: 04_A3_1: Rt=12.2 min
LCMS Method: LCMS_4: Rt=2.2 min, m/3=1489; m/4=1117; m/5=894

Example 61

$N^{\epsilon 24}$-[(4S)-4-carboxy-4-[[2-[2-[2-[[2-[2-[2-[[(4S)-4-carboxy-4-[[(4S)-4-carboxy-4-(17-carboxyheptade-canoylamino)butanoyl]amino]butanoyl]amino]ethoxy]ethoxy]acetyl]amino]ethoxy]ethoxy]acetyl]amino]butanoyl]-[Val10,Thr16,Glu21,Lys24,Leu27,Ser28]-Glucagon amide

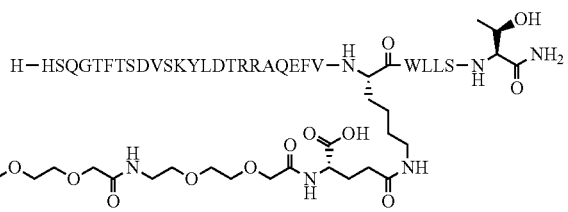

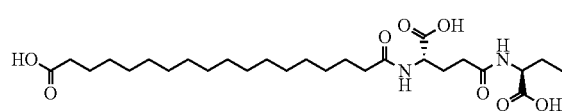

Chem. 61

UPLC Method: 04_A9_1; Rt=16.1 min
UPLC Method: 10_B4_1: Rt=9.6 min
LC-MS Method: LCMS_4; RT=2.5; m/3=1459; m/4=1094; m/5=875

Example 62

$N^{\epsilon 24}$-[2-[2-[2-[[2-[2-[2-[[(4S)-4-carboxy-4-[[(4S)-4-carboxy-4-[[(4S)-4-carboxy-4-(17-carboxyheptade-canoylamino)butanoyl]amino]butanoyl]amino]butanoyl]amino]ethoxy]ethoxy]acetyl]amino]ethoxy]ethoxy]acetyl]-[Val10,Thr16,Glu21,Lys24,Leu27,Ser28]-Glucagon

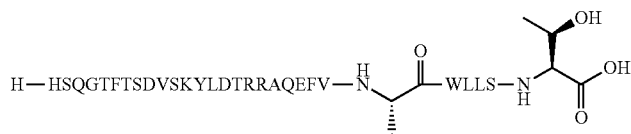

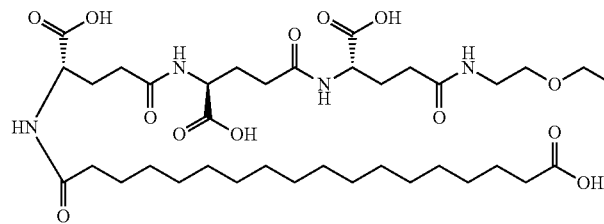

Chem. 62

UPLC Method: 05_B4_1: Rt=9.6 min
LC-MS Method: LCMS_4; Rt=2.5 min; m/3=1459; m/4=1095; m/5=876

Example 63

N^ε24-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Val10,Leu16,Glu21,Lys24,Leu27,Ser28]-Glucagon

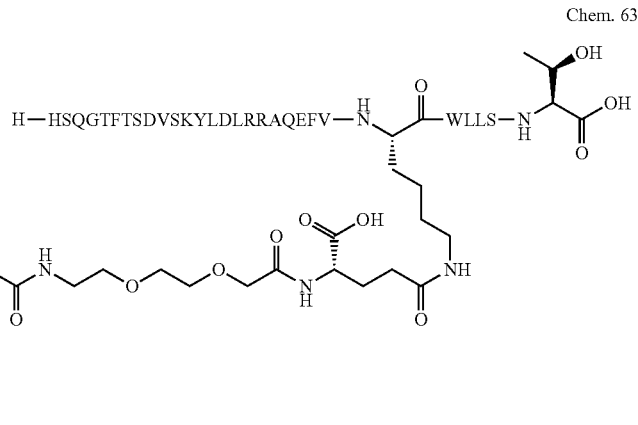

Chem. 63

UPLC Method: 05_B4_1: Rt=8.6 min
LC-MS Method: LCMS_4; Rt=2.6 m/3=1463; m/4=1098; m/5=878

Example 64

N^ε24-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Val10,Arg12,Thr16,Glu21,Lys24,Leu27,Ser28]-Glucagon

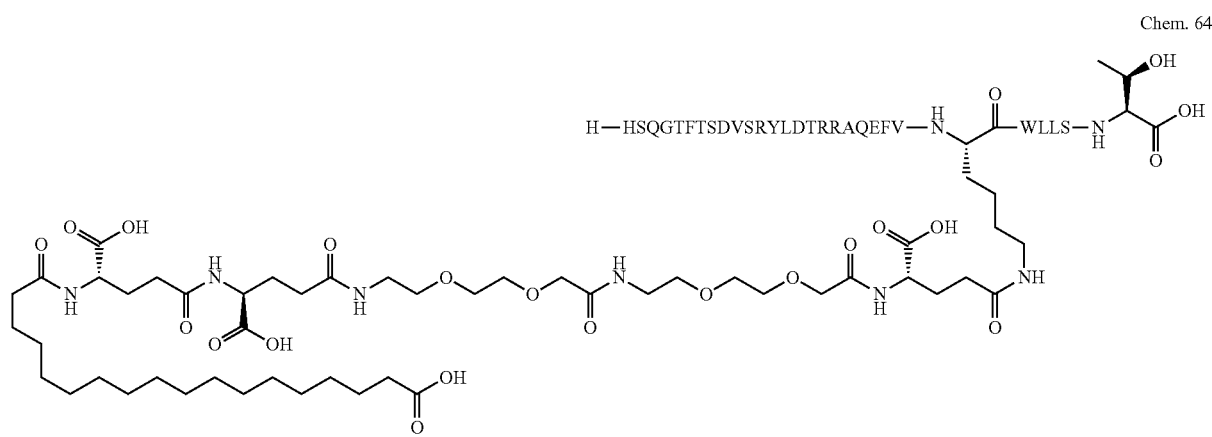

Chem. 64

UPLC Method: 05_B4_1: Rt=9.7 min
LC-MS Method: LCMS_4; RT=2.5 min; m/3=1468; m/4=1101; m/5=881

Example 65

N^ε24-[(4S)-4-carboxy-4-[[(4S)-4-carboxy-4-[[2-[2-[2-[[(4S)-4-carboxy-4-[4-[16-(1H-tetrazol-5-yl)hexadecanoylsulfarnoyl]butanoylamino]butanoyl]amino]ethoxy]ethoxy]acetyl]amino]butanoyl]amino]butanoyl]-[Glu15,Lys24,Leu27,Ser28]-Glucagon

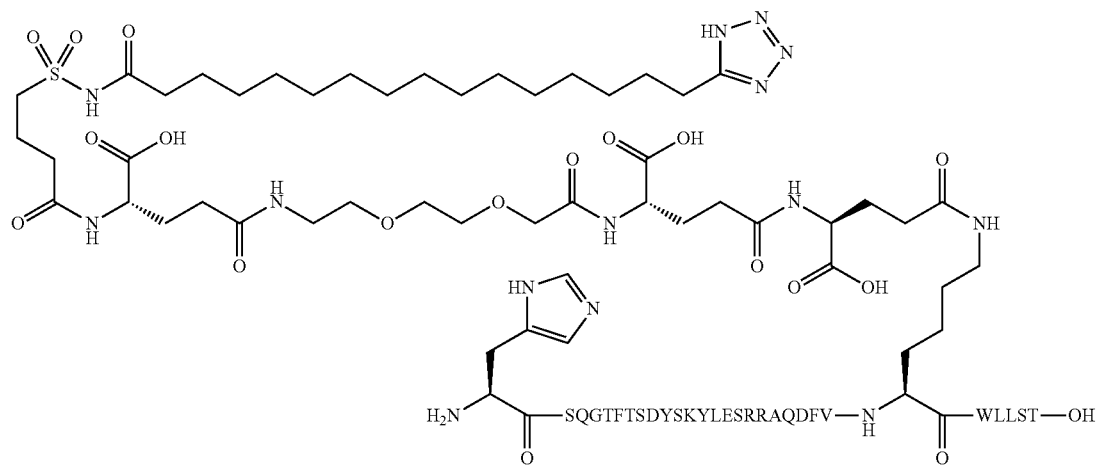

Chem. 65

UPLC Method: 04_A3_1: Rt=12.1 min
LCMS Method: LCMS_4: Rt=2.2 min, m/3=1481; m/4=1111

Example 66

N^ε24-[(4S)-4-carboxy-4-[[(4S)-4-carboxy-4-[[2-[2-[2-[4-[16-(1H-tetrazol-5-yl)hexadecanoylsulfarnoyl]butanoylamino]ethoxy]ethoxy]acetyl]amino]butanoyl]amino]butanoyl][Glu15,Lys24,Leu27,Ser28]-Glucagon

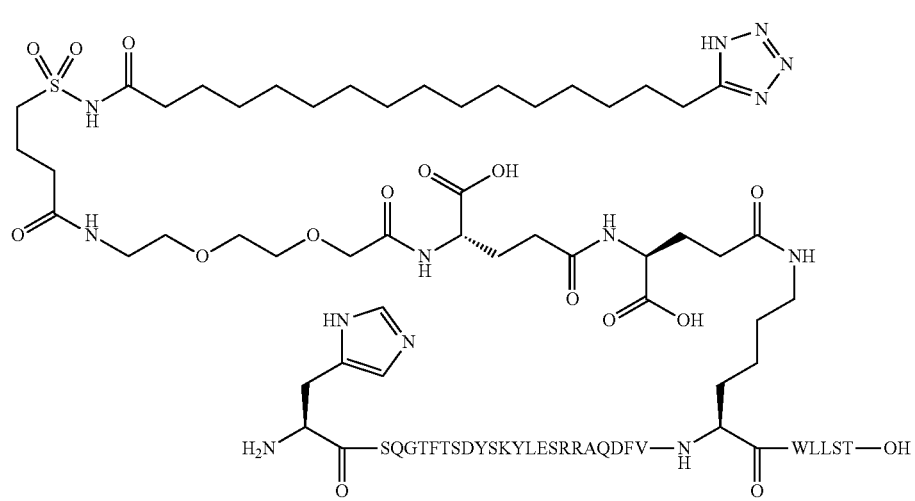

Chem. 66

UPLC Method: 04_A3_1: Rt=12.2 min
LCMS Method: LCMS_4: Rt=2.3 min, m/3=1437

Example 67

$N^{\epsilon 24}$-[(4S)-4-carboxy-4-[[(4S)-4-carboxy-4-[[2-[2-[2-[[2-[2-[2-[[(4S)-4-carboxy-4-[4-[16-(1H-tetrazol-5-yl)hexadecanoylsulfannoyl]butanoylamino]butanoyl]amino]ethoxy]ethoxy]acetyl]amino]ethoxy]ethoxy]acetyl]amino]butanoyl]amino]butanoyl]-[Arg12,Leu16,Lys24,Leu27,Ser28]-Glucagon

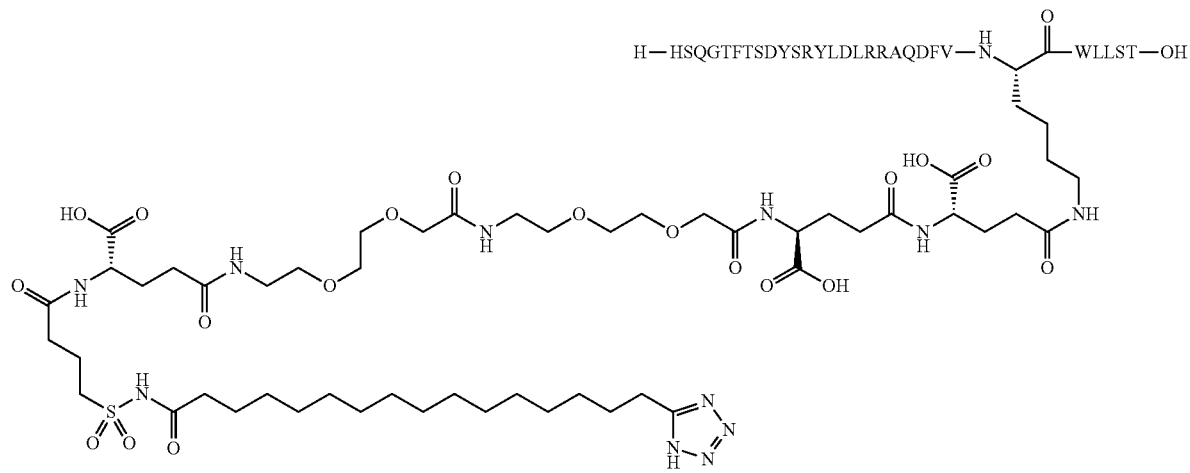

Chem. 67

UPLC Method: 04_A3_1: Rt=12.5 min
LCMS Method: LCMS_4: Rt=2.4 min, m/3=1542; m/4=1157

Example 68

$N^{\epsilon 24}$-[(4S)-4-carboxy-4-[[(4S)-4-carboxy-4-[[2-[2-[2-[[2-[2-[2-[4-[16-(1H-tetrazol-5-yl)hexadecanoyl-sulfannoyl]butanoylamino]ethoxy]ethoxy]acetyl]amino]ethoxy]ethoxy]acetyl]amino]butanoyl]amino]butanoyl]-[Arg12, Leu16, Lys24, Leu27,Ser28]-Glucagon

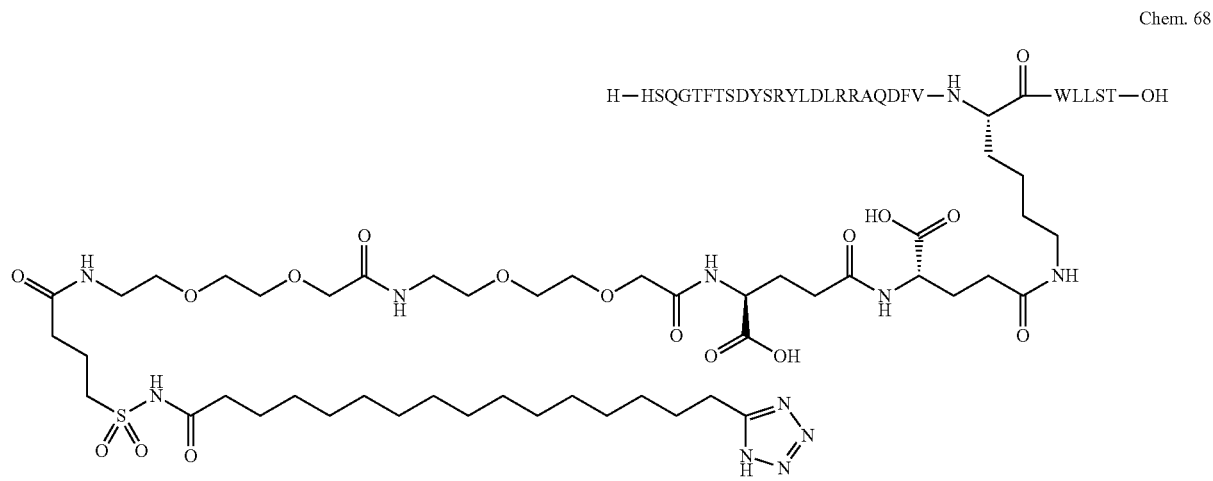

Chem. 68

UPLC Method: 04_A3_1: Rt=12.6 min
LCMS Method: LCMS_4: Rt=2.4 min, m/3=1499; m/4=1124

Example 69

N$^{\epsilon 24}$-[(4S)-4-carboxy-4-[[(4S)-4-carboxy-4-[[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Glu15,Lys24,Leu27,Ser28]-Glucagon

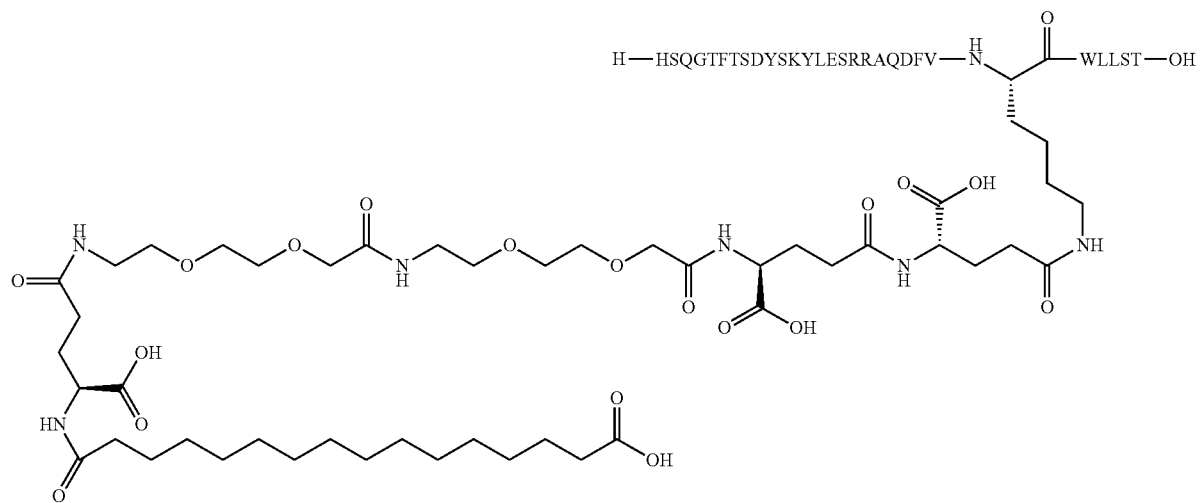

Chem. 69

UPLC Method: 04_A3_1: Rt=11.8 min
LCMS Method: LCMS_4: Rt=2.3 min, m/3=1467; m/4=1100

Example 70

N$^{\epsilon 24}$-[(4S)-4-carboxy-4-[[(4S)-4-carboxy-4-[[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Glu15,Lys24,Leu27,Ser28]-Glucagon

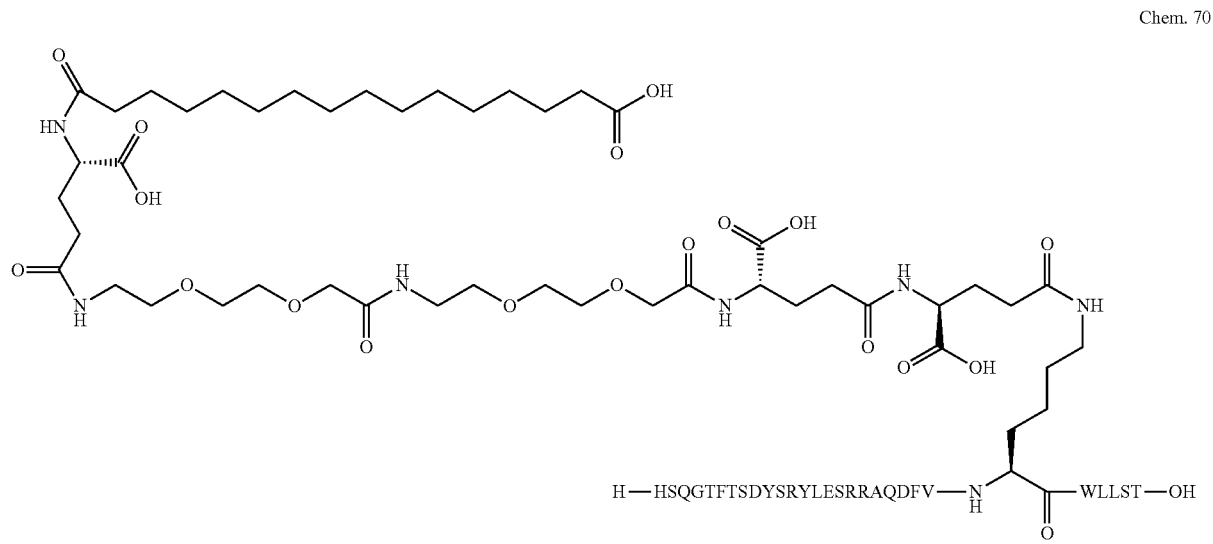

Chem. 70

UPLC Method: 04_A3_1: Rt=11.8 min
LCMS Method: LCMS_4: Rt=2.3 min, m/3=1476; m/4=1107

Example 71

$N^{\epsilon 24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Glu15,Glu21,Lys24,Leu27,Ser28]-Glucagon Chem. 71

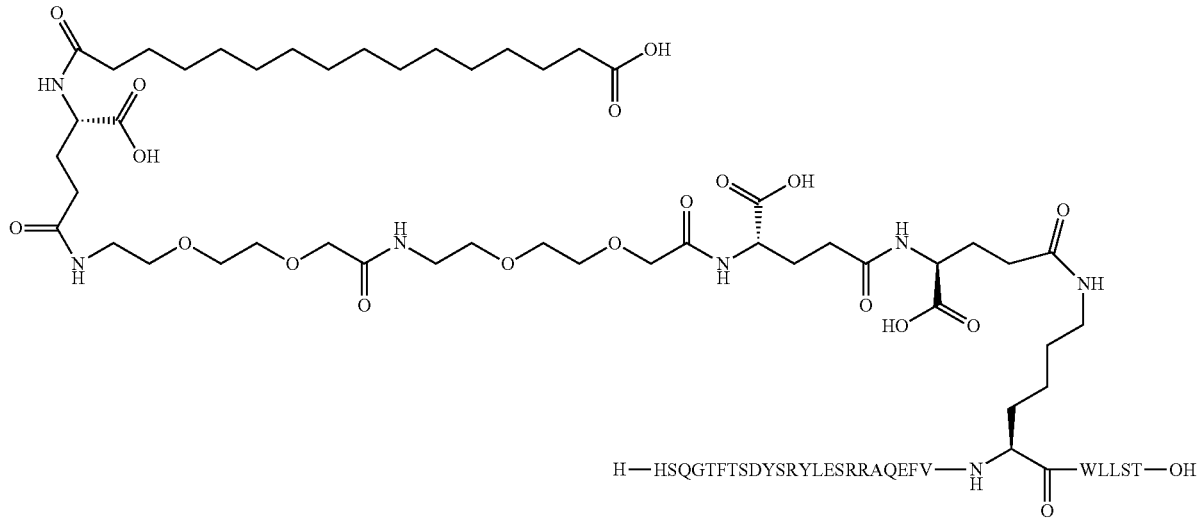

UPLC Method: 04_A3_1: Rt=11.7 min
LCMS Method: LCMS_4: Rt=2.2 min, m/3=1481

Example 72

$N^{\epsilon 24}$-[(4S)-4-carboxy-4-[[(4S)-4-carboxy-4-[[(4S)-4-carboxy-4-(15-carboxypentadecanoylamino)butanoyl]amino]butanoyl]amino]butanoyl]-[Arg12,Ala16,Lys24,Leu27,Ser28]-Glucagon Chem. 72

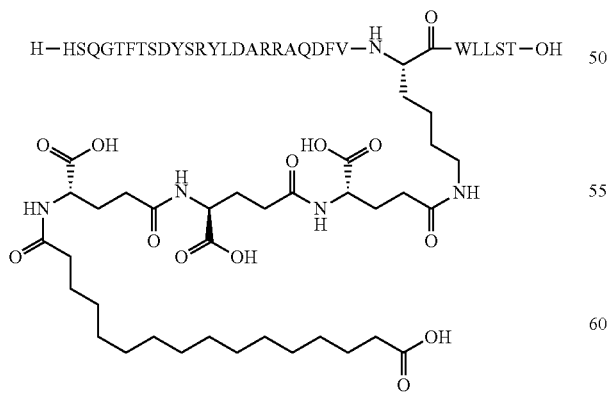

UPLC Method: 09_B4_1: Rt=7.9 min
LCMS Method: LCMS_13: Rt=2.2 min, m/3=1369; m/4=1027

Example 73

N$^{\epsilon 24}$-[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl]-[Arg12,Ala16,Lys24,Leu27,Ser28]-Glucagon

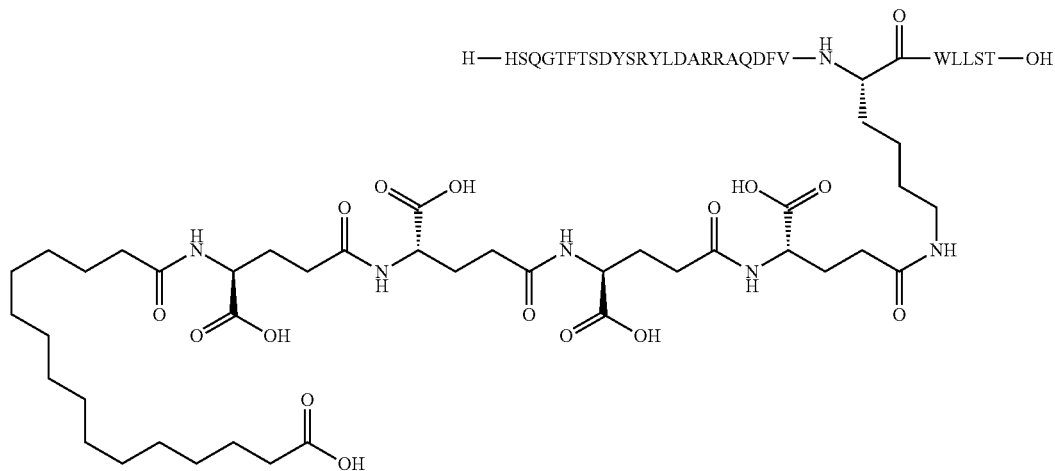

Chem. 73

UPLC Method: 09_B4_1: Rt=7.9 min
LCMS Method: LCMS_4: Rt=2.3 min, m/3=1412; m/4=1060; m/5=848

Example 74

N$^{\epsilon 24}$-[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl]-[Arg12,Leu16,Lys24,Leu27,Ser28]-Glucagon

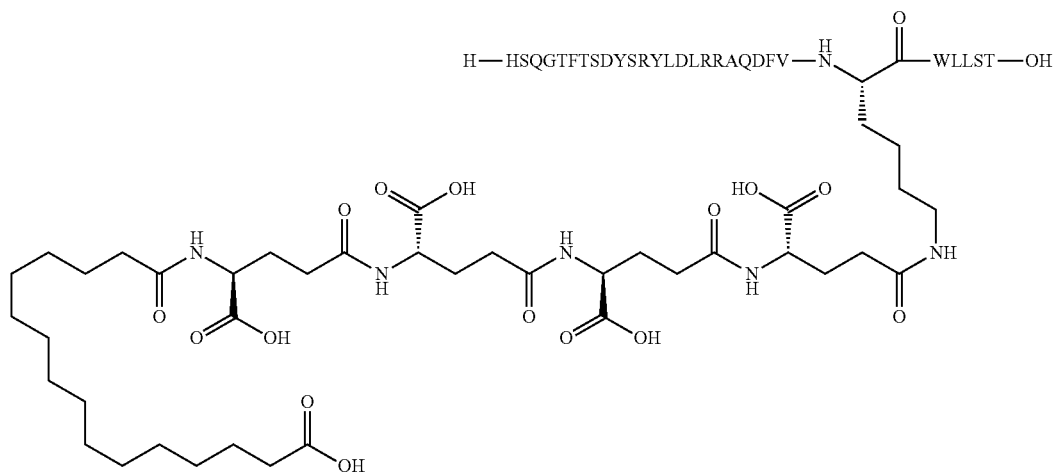

Chem. 74

UPLC Method: 09_B4_1: Rt=8.1 min
LCMS Method: LCMS 13: Rt=2.2 min, m/3=1426; m/4=1070

Example 75

$N^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Ile16,Lys24,Leu27,Ser28]-Glucagon amide Chem. 75

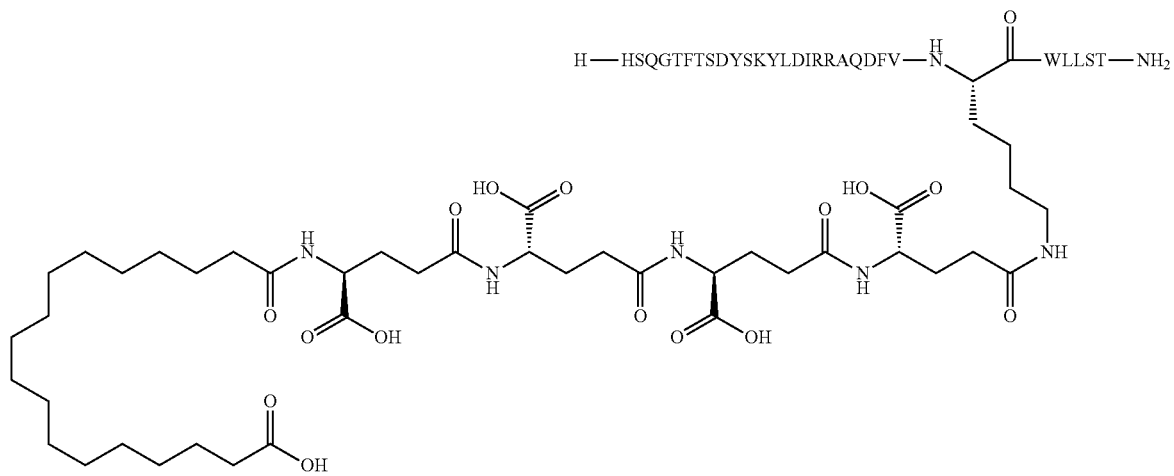

UPLC Method: 08_B2_1: Rt=13.0 min
UPLC Method: 08_B4_1: Rt=8.6 min
UPLC Method: 04_A3_1: Rt=15.2 min
LCMS Method: LCMS_4: Rt=2.3 min, m/3=1426; m/4=1070; m/5=856

Example 76

$N^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Val16,Lys24,Leu27,Ser28]-Glucagon amide Chem. 76

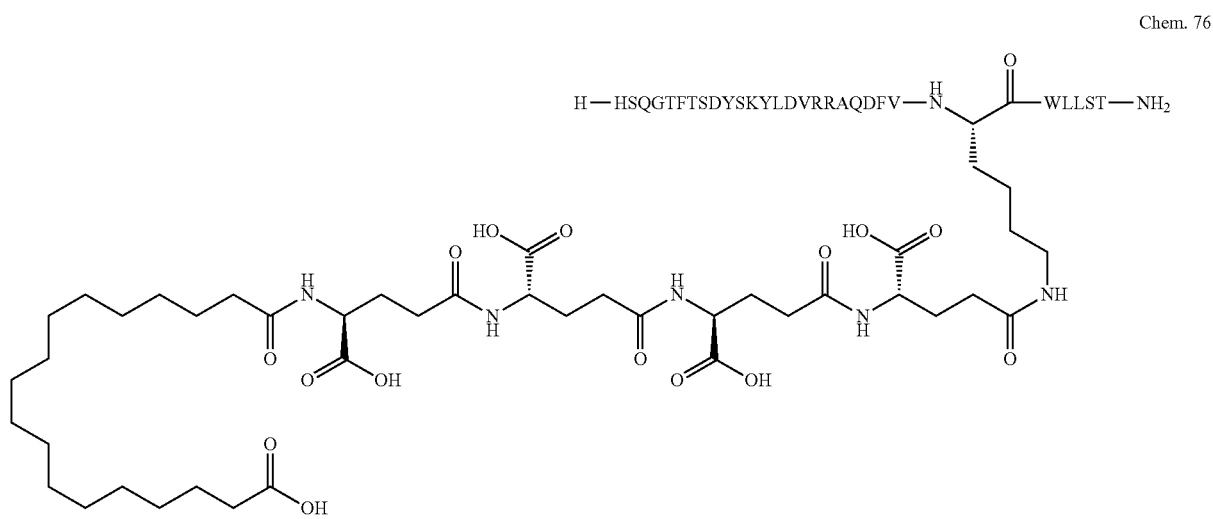

UPLC Method: 08_B2_1: Rt=12.9 min
UPLC Method: 08_B4_1: Rt=8.5 min
UPLC Method: 04_A3_1: Rt=14.6 min
LCMS Method: LCMS_4: Rt=2.3 min, m/3=1421; m/4=1066; m/5=853

Example 77

$N^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Leu16,Lys24,Leu27,Ser28]-Glucagon amide Chem. 77

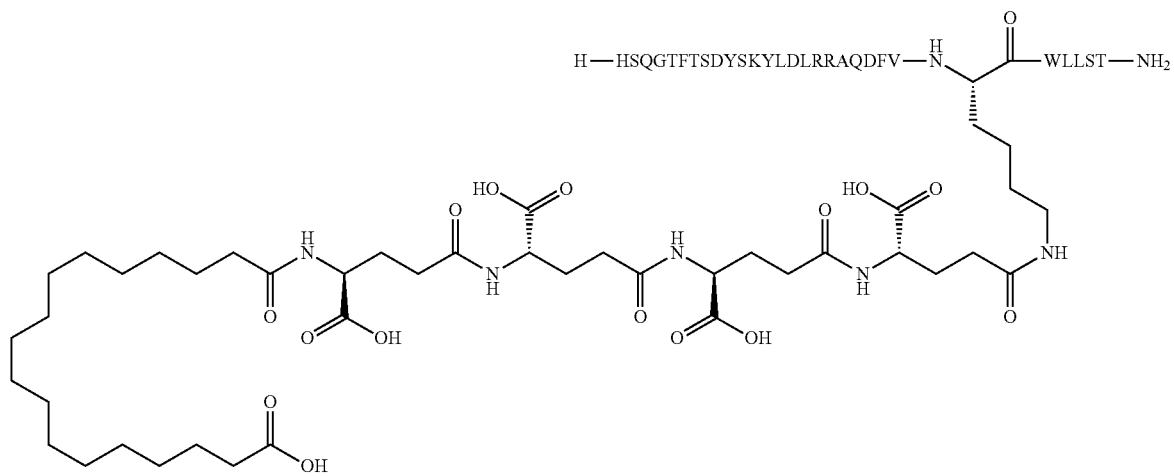

UPLC Method: 08_B2_1: Rt=13.0 min
UPLC Method: 08_B4_1: Rt=8.6 min
UPLC Method: 04_A3_1: Rt=15.2 min
LCMS Method: LCMS_4: Rt=2.3 min, m/3=1426; m/4=1070; m/5=856

Example 78

$N^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Val16,Lys24,Leu27,Ser28]-Glucagon Chem. 78

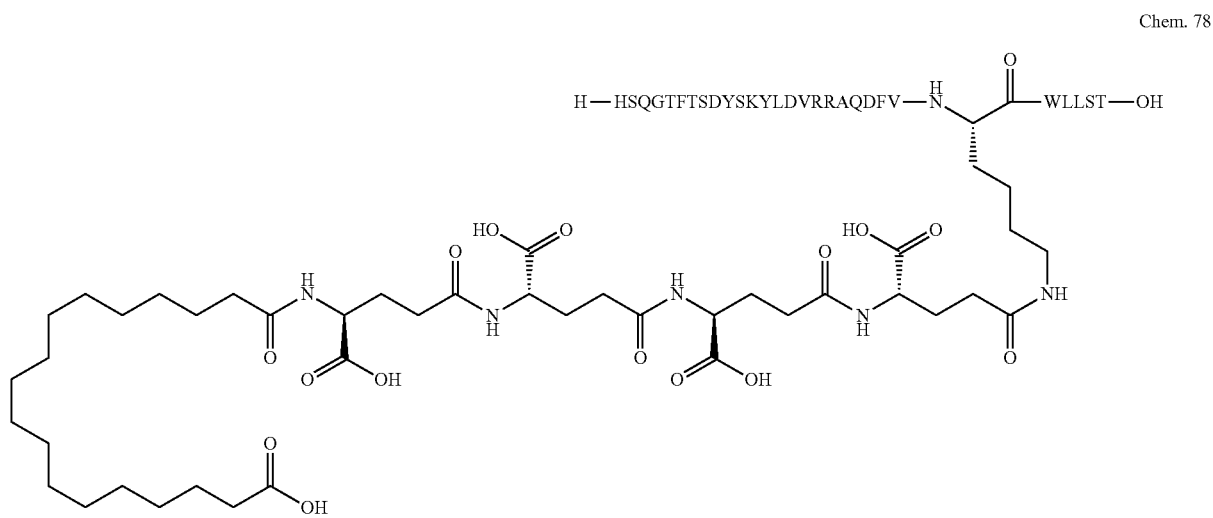

UPLC Method: 08_B2_1: Rt=12.9 min
UPLC Method: 08_B4_1: Rt=8.5 min
UPLC Method: 04_A3_1: Rt=12.4 min
LCMS Method: LCMS_4: Rt=2.3 min, m/3=1422; m/4=1066; m/5=853

Example 79

$N^{\epsilon24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Ile16,Lys24,Leu27,Ser28]-Glucagon

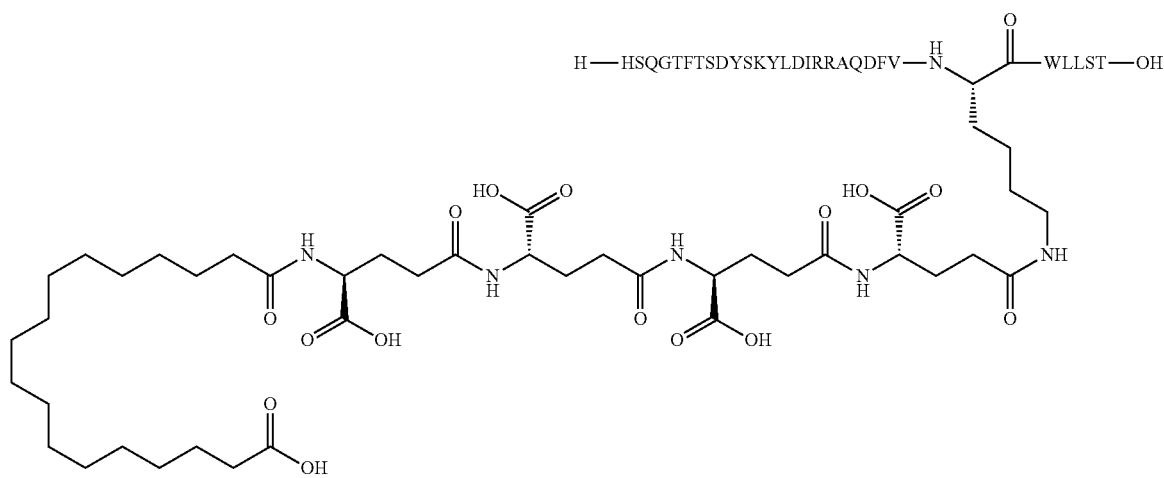

Chem. 79

UPLC Method: 08_B2_1: Rt=13.0 min
UPLC Method: 08_B4_1: Rt=8.6 min
UPLC Method: 04_A3_1: Rt=13.1 min
LCMS Method: LCMS_4: Rt=2.3 min, m/3=1426; m/4=1070; m/5=856

Example 80

$N^{\epsilon24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Leu16,Lys24,Leu27,Ser28]-Glucagon

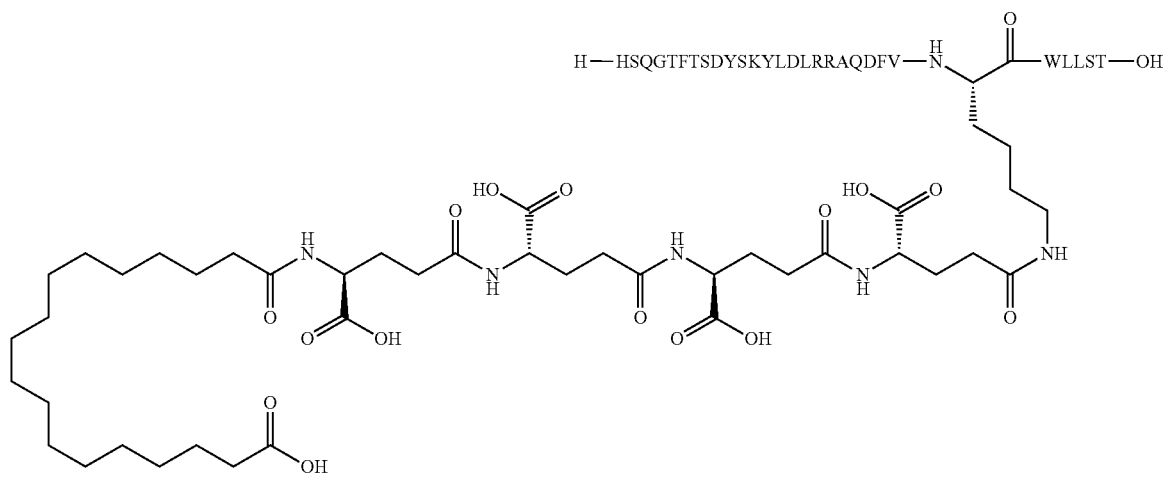

Chem. 80

UPLC Method: 08_B2_1: Rt=13.1 min
UPLC Method: 08_B4_1: Rt=8.6 min
UPLC Method: 04_A3_1: Rt=13.0 min
LCMS Method: LCMS_4: Rt=2.3 min, m/3=1426; m/4=1070; m/5=856

Example 81

$N^{\epsilon 24}$-[(4S)-4-carboxy-4-[[(4S)-4-carboxy-4-[[2-[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl]amino]butanoyl]amino]butanoyl]-[Thr16,Lys24,Leu27,Ser28]-Glucagon

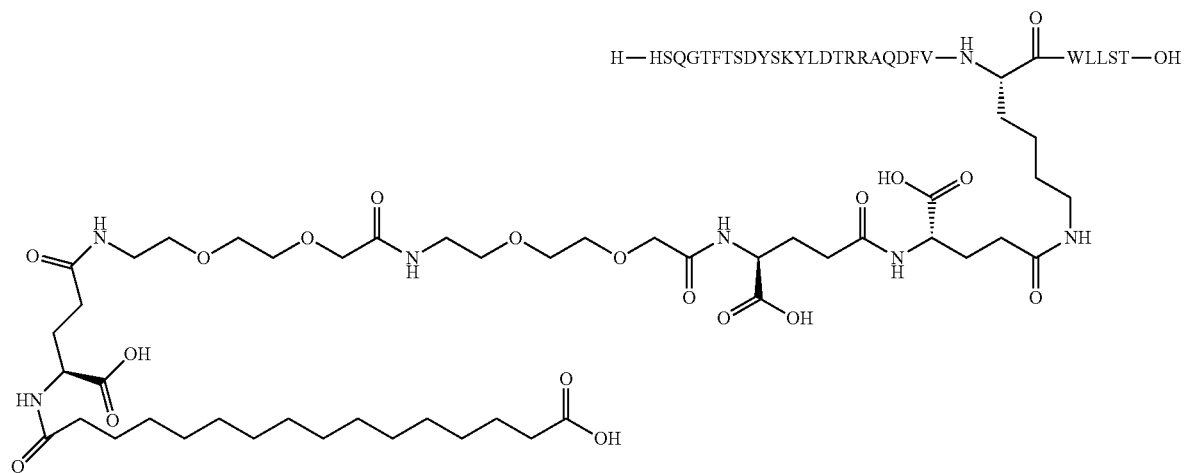

Chem. 81

UPLC Method: 04_A3_1: Rt=11.8 min
LCMS Method: LCMS_4: Rt=2.4 min, m/3=1466

Example 82

$N^{\epsilon 24}$-[(4S)-4-carboxy-4-[[(4S)-4-carboxy-4-[[2-[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl]amino]butanoyl]amino]butanoyl]-[Arg12,Thr16,Lys24,Leu27,Ser28]-Glucagon

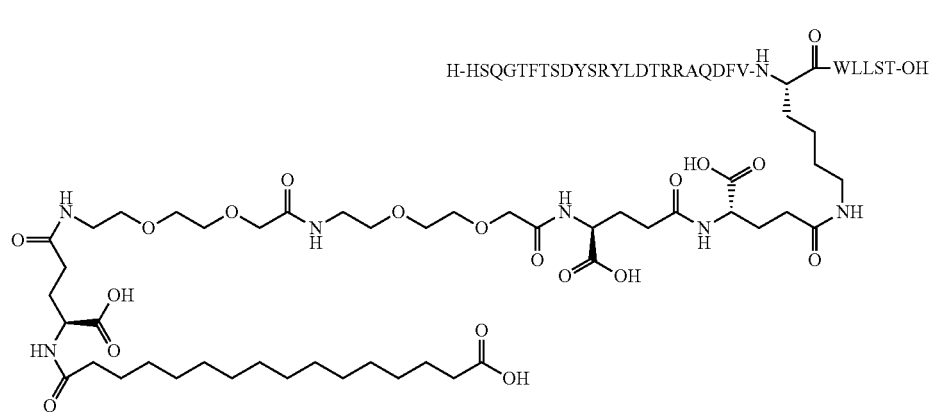

Chem. 48

UPLC Method: 04_A3_1: Rt=11.8 min
LCMS Method: LCMS_4: Rt=2.5 min, m/3=1476

Example 83

$N^{\epsilon24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Ala16,Lys24,Leu27,Ser28]-Glucagon

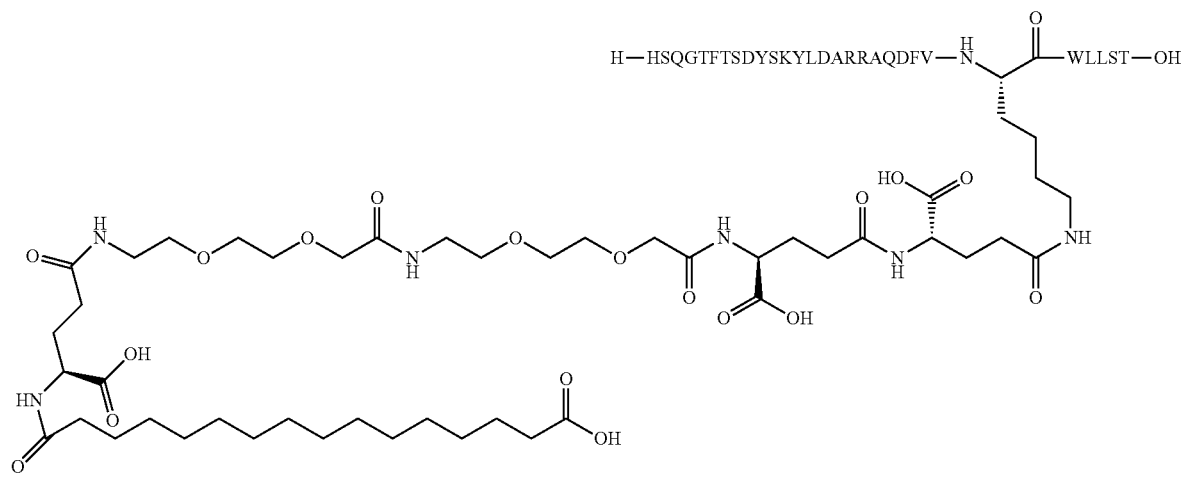

Chem. 83

UPLC Method: 04_A3_1: Rt=11.8 min
LCMS Method: LCMS_4: Rt=2.4 min, m/3=1457; m/4=1093

Example 84

$N^{\epsilon24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Ala16,Lys24,Leu27,Ser28]-Glucagon

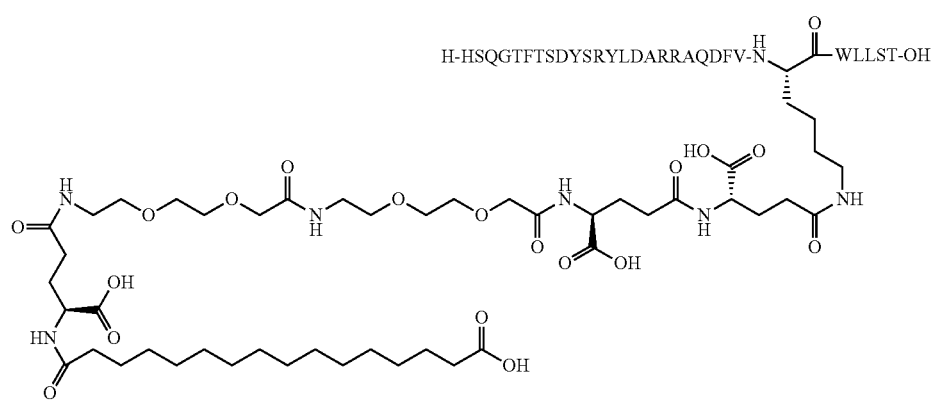

Chem. 84

UPLC Method: 04_A3_1: Rt=11.8 min
LCMS Method: LCMS_4: Rt=2.4 min, m/3=1466; m/4=1100

Example 85

N^{ε24}-[(4S)-4-carboxy-4-[[(4S)-4-carboxy-4-[[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl]amino]butanoyl]amino]butanoyl]-[Leu16,Lys24,Leu27,Ser28]-Glucagon Chem. 85

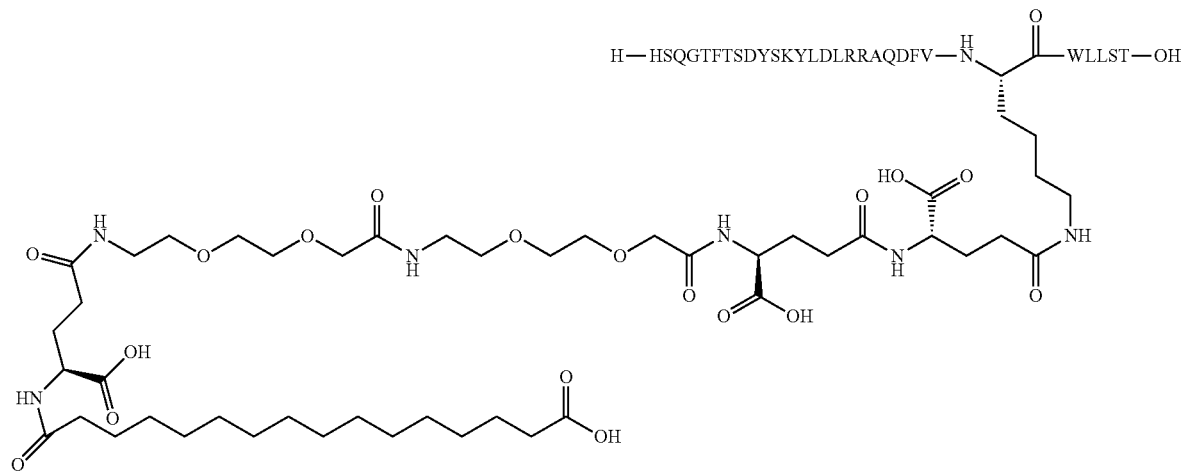

UPLC Method: 04_A3_1: Rt=12.2 min
LCMS Method: LCMS_4: Rt=2.4 min, m/3=1471; m/4=1103

Example 86

N^{ε24}-[(4S)-4-carboxy-4-[[(4S)-4-carboxy-4-[[(4S)-4-carboxy-4-[[(4S)-4-carboxy-4-(17-carboxyheptade-canoylamino)butanoyl]amino]butanoyl]amino]butanoyl]amino]butanoyl]-[Arg12,Leu16,Lys24,Leu27,Ser28]-Glucagon Chem. 86

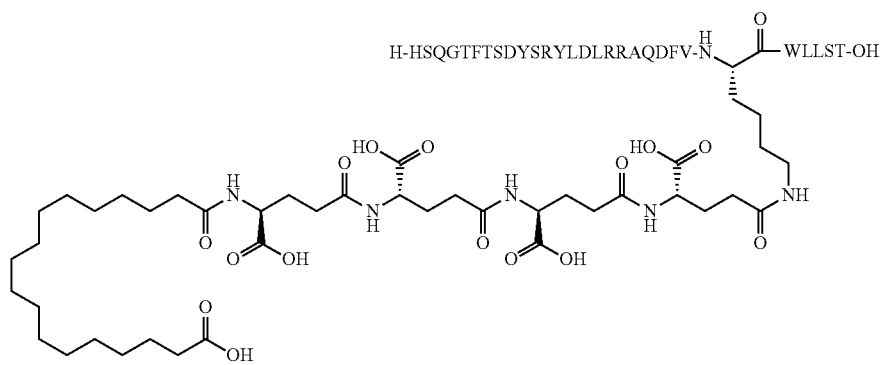

UPLC Method: 08_B2_1: Rt=13.0 min
UPLC Method: 08_B4_1: Rt=8.6 min
UPLC Method: 04_A3_1: Rt=15.4 min LCMS Method:
LCMS_4: Rt=2.6 min, m/3=1436; m/4=1077; m/5=862

Example 87
$N^{\epsilon 24}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Leu16,Lys24,Leu27,Ala28]-Glucagon
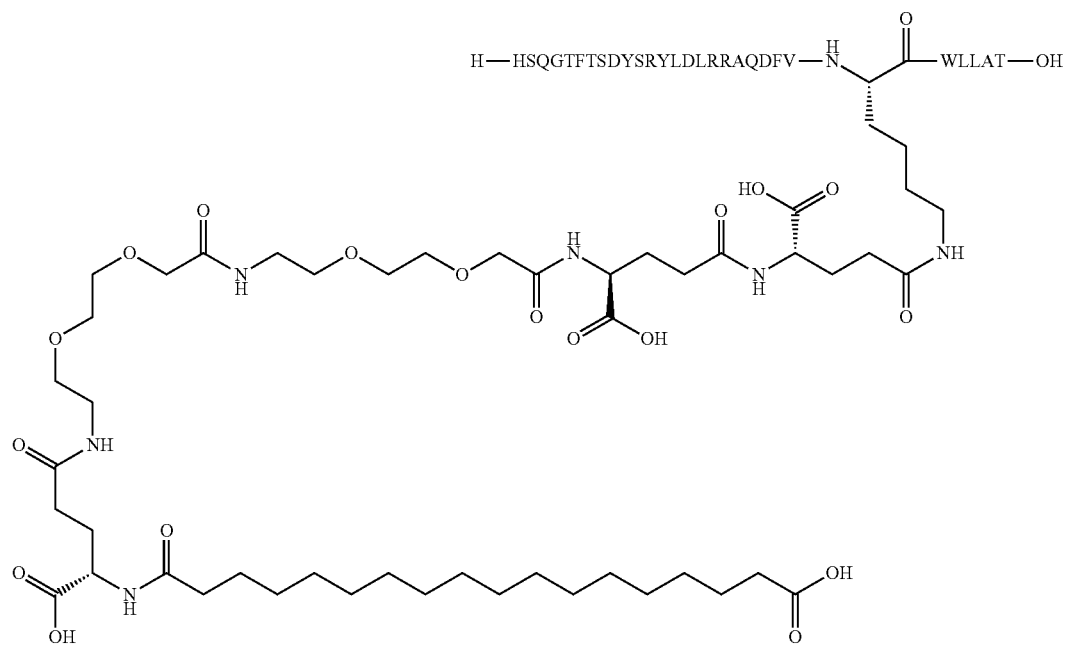
Chem. 87
UPLC Method: 08_B2_1: Rt=12.9 min
UPLC Method: 08_B4_1: Rt=8.5 min
UPLC Method: 04_A3_1: Rt=15.5 min
LCMS Method: LCMS_4: Rt=2.6 min, m/3=1484; m/4=1113; m/5=891

Example 88
$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg12,Leu16,Lys24,Leu27,Gly28]-Glucagon
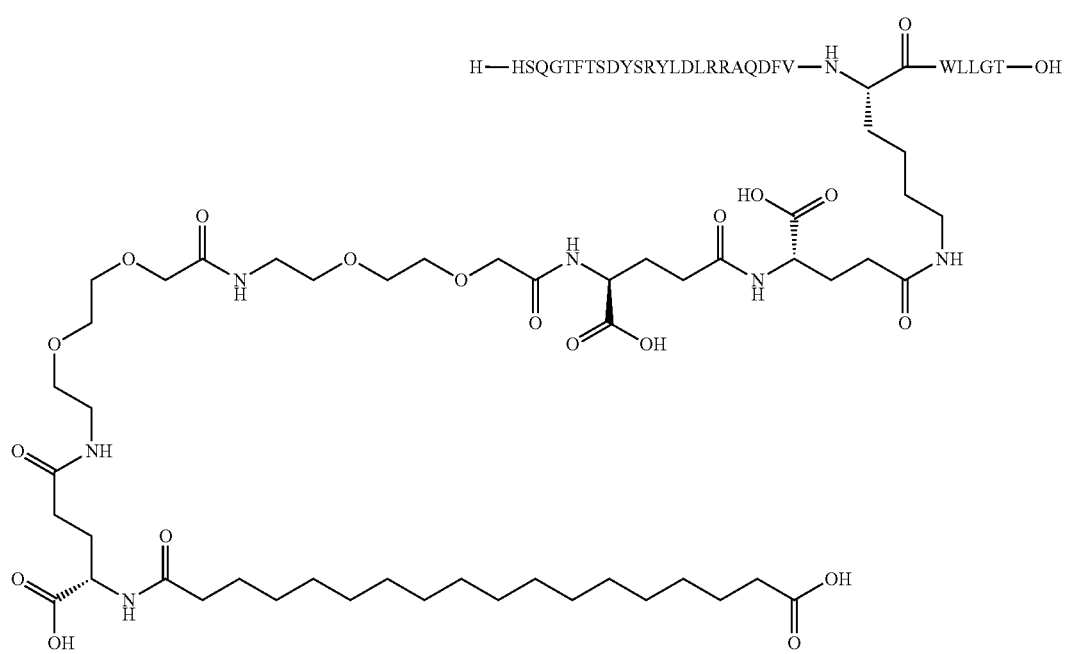
Chem. 88
UPLC Method: 08_B2_1: Rt=13.0 min
UPLC Method: 08_B4_1: Rt=8.6 min
UPLC Method: 04_A3_1: Rt=16.0 min
LCMS Method: LCMS_4: Rt=2.6 min, m/3=1479; m/4=1110; m/5=888

Example 89
$N^{\epsilon24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Leu16,Lys24,Leu27,Ala28]-Glucagon
Chem. 89
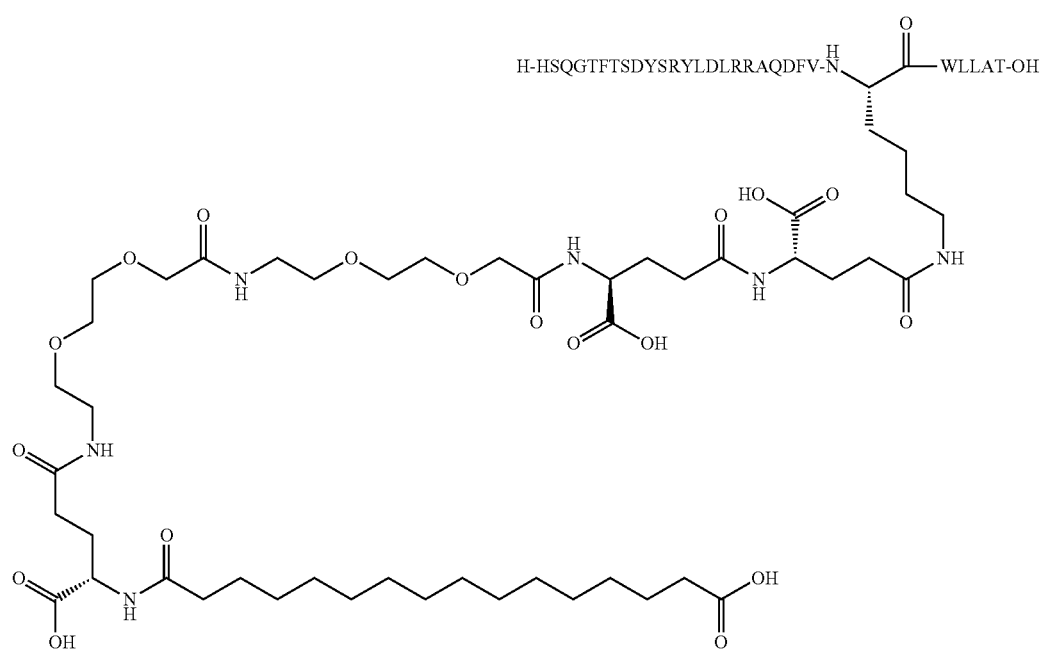
UPLC Method: 08_B2_1: Rt=12.2 min
UPLC Method: 08_B4_1: Rt=8.0 min
UPLC Method: 04_A3_1: Rt=14.4 min
LCMS Method: LCMS_4: Rt=2.5 min, m/3=1475; m/4=1106; m/5=885

Example 90

N^ε24-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Leu16,Lys24,Leu27,Gly28]-Glucagon Chem. 90

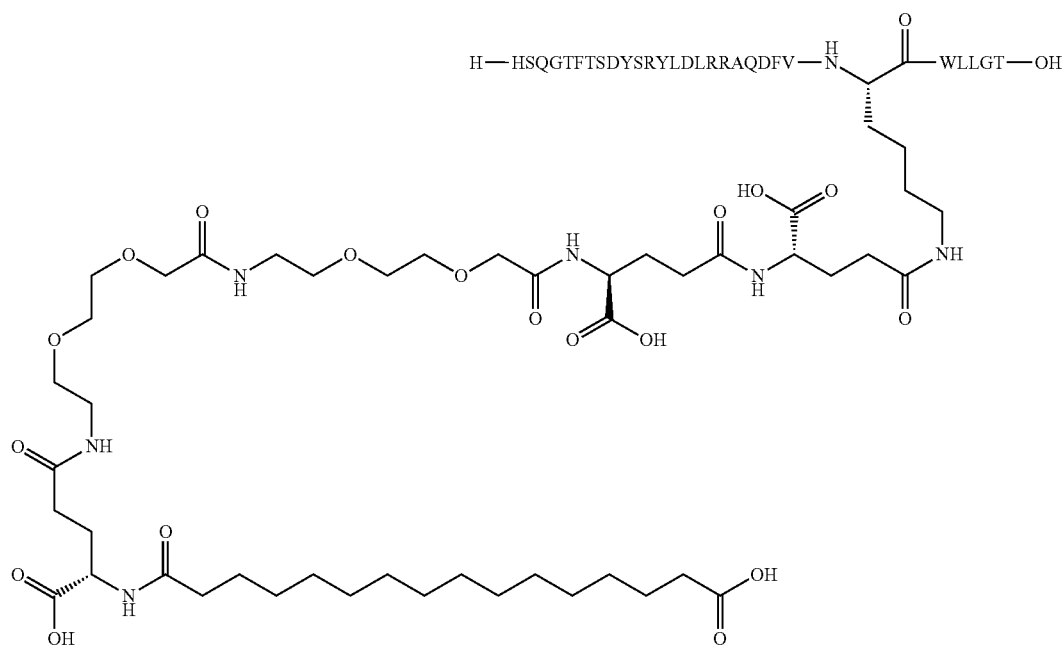

UPLC Method: 08_B2_1: Rt=12.3 min
UPLC Method: 08_B4_1: Rt=8.1 min
UPLC Method: 04_A3_1: Rt=14.9 min
LCMS Method: LCMS_4: Rt=2.5 min, m/3=1470; m/4=1103; m/5=882

Example 91

N^ε24-[(4S)-4-carboxy-4-[[(4S)-4-carboxy-4-[[(4S)-4-carboxy-4-(15-carboxypentadecanoylamino)butanoyl]amino]butanoyl]amino]butanoyl]-[Arg12,Leu16,Lys24,Leu27,Ser28]-Glucagon Chem. 91

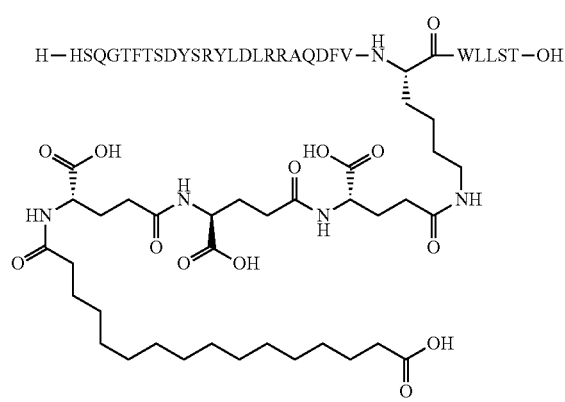

UPLC Method: 09_B4_1: Rt=8.2 min
LCMS Method: LCMS 13: Rt=2.2 min, m/3=1383; m/4=1038

Example 92

N^ε24-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Arg12,Ala16,Lys24,Leu27,Ser28]-Glucagon Chem. 92

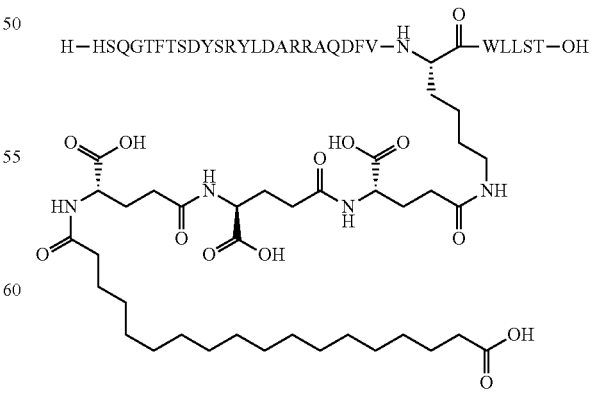

UPLC Method: 09_B4_1: Rt=8.5 min
LCMS Method: LCMS 13: Rt=2.3 min, m/3=1379; m/4=1034

Example 93

$N^{\epsilon24}$-[(4S)-4-carboxy-4-[[(4S)-4-carboxy-4-[[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl]amino]butanoyl]amino]butanoyl]-[Glu16,Lys24,Leu27,Ser28]-Glucagon

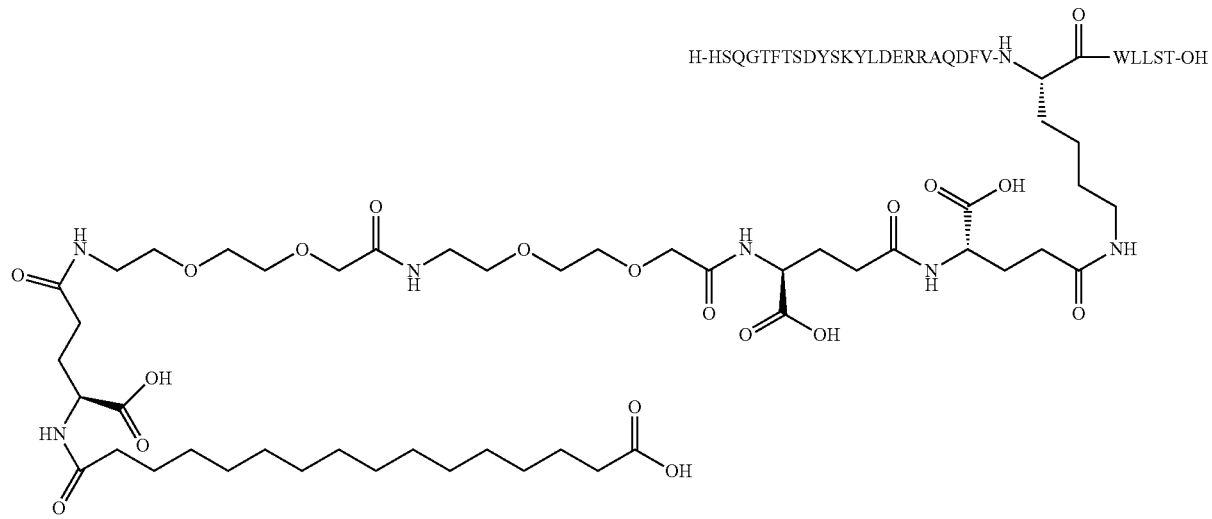

Chem. 93

UPLC Method: AP_B4_1: Rt=7.8 min
LCMS Method: LCMS_AP: Rt=5.1 min, m/3=1476; m/4=1107

Example 94

$N^{\epsilon24}$-[(4S)-4-carboxy-4-[[(4S)-4-carboxy-4-[[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl]amino]butanoyl]amino]butanoyl]-[Arg12,Glu16,Lys24,Leu27,Ser28]-Glucagon

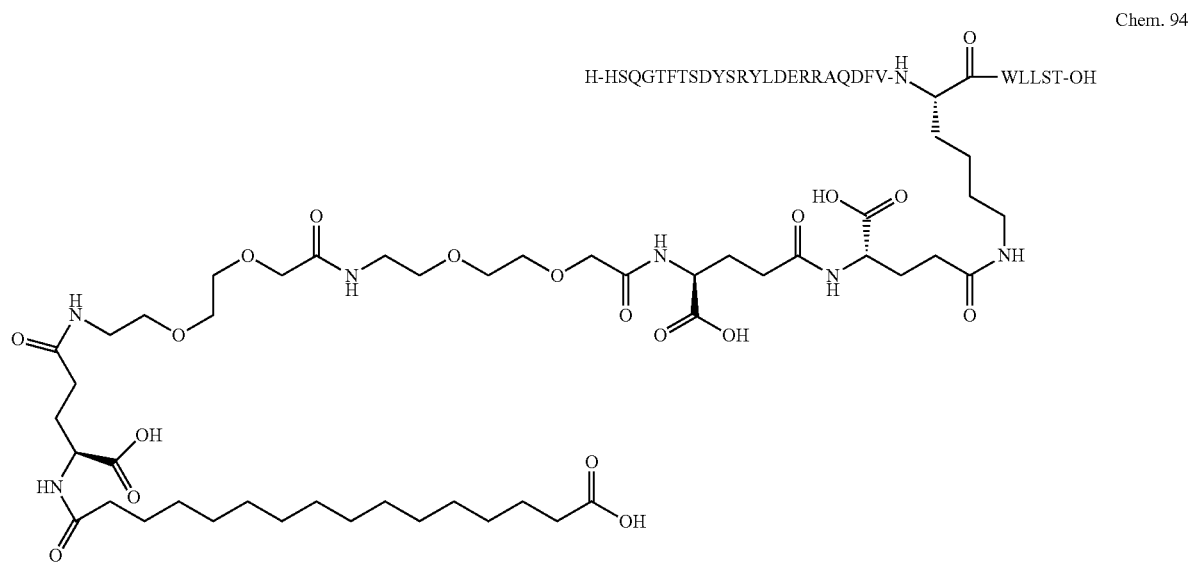

Chem. 94

UPLC Method: AP_B4_1: Rt=7.8 min
LCMS Method: LCMS_AP: Rt=5.3 min, m/3=1485; m/4=1116

Example 95

N^ε24-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Val16,Lys24,Leu27,Ser28]-Glucagon

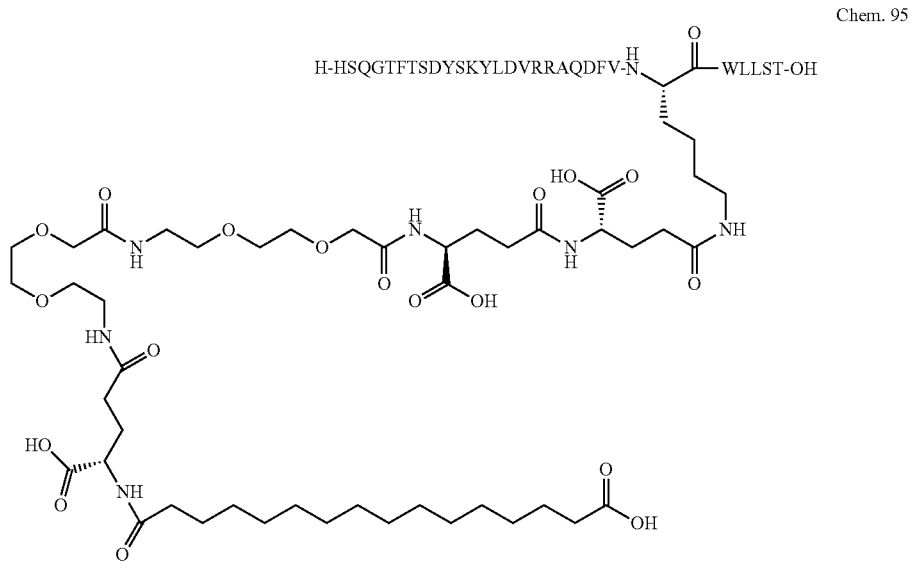

Chem. 95

UPLC Method: AP_B4_1: Rt=8.0 min
LCMS Method: LCMS_AP: Rt=5.2 min, m/3=1466; m/4=1100

Example 96

N^ε24-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Arg12,Ala16,Lys24,Leu27,Ser28]-Glucagon

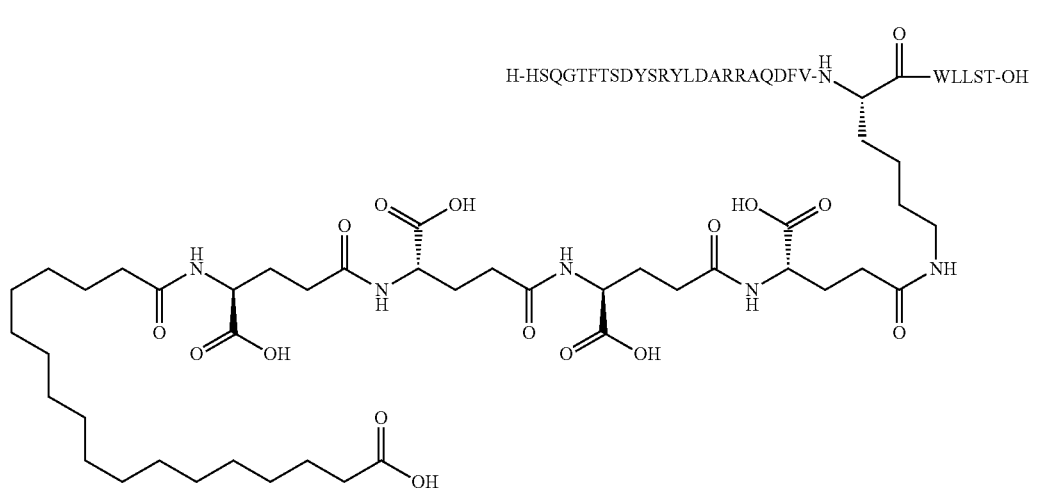

Chem. 96

UPLC Method: 09_B4_1: Rt=8.4 min
LCMS Method: LCMS 13: Rt=2.3 min, m/3=1422; m/4=1067

Example 97

$N^{\epsilon 24}$-[(4S)-4-carboxy-4-[[(4S)-4-carboxy-4-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]butanoyl]amino]butanoyl]-[Arg12,Val16,Lys24,Leu27,Ser28]-Glucagon

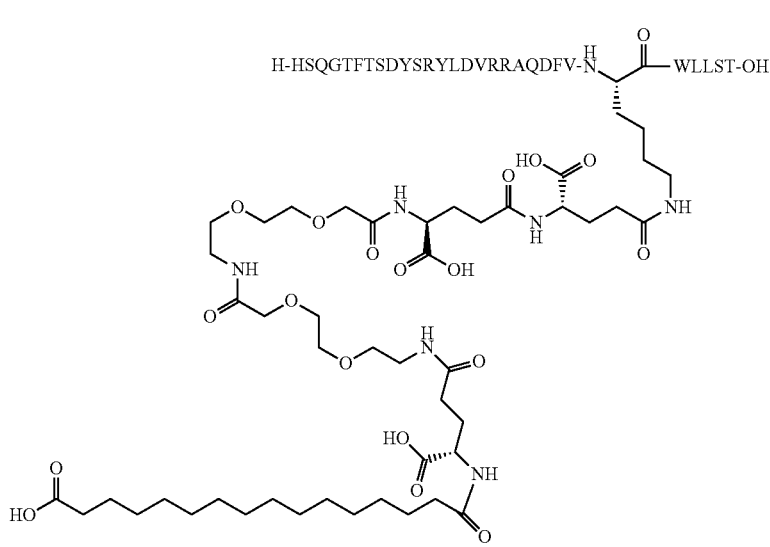

Chem. 97

UPLC Method: AP_B4_1: Rt=8.2 min
LCMS Method: LCMS_AP: Rt=5.2 min, m/3=1475; m/4=1106
Methods
Assay (I)
Glucagon Activity The glucagon receptor was cloned into HEK-293 cells having a membrane bound cAMP biosensor (ACTOne™). The cells (14000 per well) were incubated (37° C., 5% CO2) overnight in 384-well plates. Next day the cells were loaded with a calcium responsive dye that only distributed into the cytoplasm. Probenecid, an inhibitor of the organic anion transporter, was added to prevent the dye from leaving the cell. A PDE inhibitor was added to prevent formatted cAMP from being degraded. The plates were placed into a FLIP-RTETRA and the glucagon analogues were added. End point data were collected after 6 minutes. An increase in intracellular cAMP was proportional to an increased in calcium concentrations in the cytoplasm. When calcium was bound the dry a fluorescence signal was generated. EC50-values were calculated in Prism5.

Assay (II)
ThT Fibrillation Assays for the Assessment of Physical Stability of Peptide Formulations Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. BioChem. 177, 244-249; LeVine (1999) Methods. Enzymol. 309, 274-284].

The time course for fibril formation can be described by a sigmoidal curve with the following expression [Nielsen et al. (2001) BioChemistry 40, 6036-6046]:

$$F = f_i + m_i t + \frac{f_f + m_f t}{1 + e^{-[(t-t_0)/\tau]}} \qquad \text{Eq. (1)}$$

Figure 2:
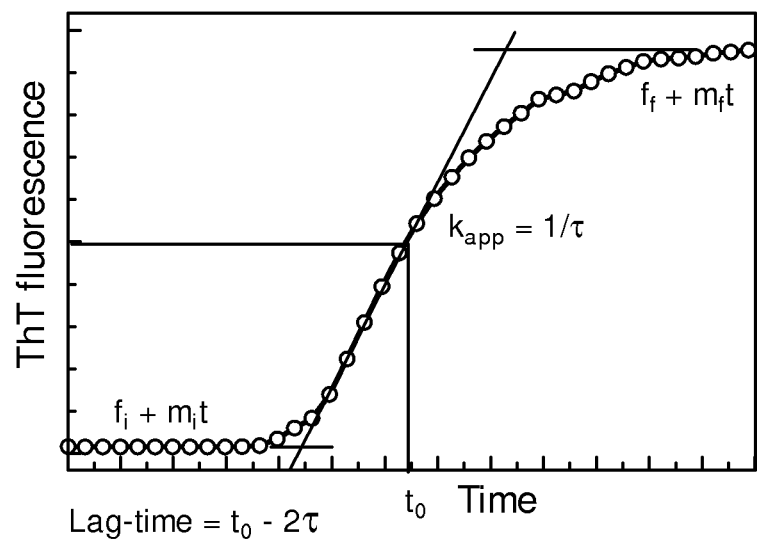
FIG. 2 depicts ThT fluorescence as a function of time t.

Here, F is the ThT fluorescence at the time t. The constant t0 is the time needed to reach 50% of maximum fluorescence, as depicted in FIG. 2. The two important parameters describing fibril formation are the lag-time calculated by t0−2τ and the apparent rate constant kapp 1/τ.

Formation of a partially folded intermediate of the peptide is suggested as a general initiating mechanism for fibrillation. Few of those intermediates nucleate to form a template onto which further intermediates may assembly and the fibrillation proCeeds. The lag-time corresponds to the interval in which the critical mass of nucleus is built up and the apparent rate constant is the rate with which the fibril itself is formed.

Samples were prepared freshly before each assay. Each sample composition is described in the legends. The pH of the sample was adjusted to the desired value using appropriate amounts of concentrated NaOH and HCl. Thioflavin T was added to the samples from a stock solution in H2O to a final concentration of 1 μM.

Sample aliquots of 200 μl were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation at given temperature, shaking and measurement of the ThT fluorescence emission were done in a Fluoroskan Ascent FL fluorescence platereader (Thermo Labsystems). The temperature was adjusted to the desired value, typically 30° C. or 37° C. The plate was either incubated without shaking (no external physical stress) or with orbital shaking adjusted to 960 rpm with an amplitude of 1 mm. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

After completion of the ThT assay the four or eight replica of each sample was pooled and centrifuged at 20000 rpm for 30 minutes at 18° C. The supernatant was filtered through a 0.22 μm filter and an aliquot was transferred to a HPLC vial.

The concentration of peptide in the initial sample and in the filtered supernatant was determined by reverse phase HPLC using an appropriate standard as reference. The percentage fraction the concentration of the filtered sample constituted of the initial sample concentration was reported as the recovery.

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, the lag time before fibrillation may be assessed by visual inspection of the curve identifying the time point at which ThT fluorescence increases significantly above the background level.

TABLE 1

In vitro data on receptor binding, ThT assay lag time and recovery at pH 7.5 and chemical stability at pH 8.15

| Compound | Assay(I) Glucagon [EC50] (nM) | ThT assay [Lagtime] (h) | ThT assay [Recovery] (%) | Chemical stability [Purity loss/ 14 days 37 C.] (%) |
|---|---|---|---|---|
| Example 1 | 0.28 | 45 | 100 | 7.6 |
| Example 2 | 0.129 | 45 | 100 | n.d. |
| Example 3 | 0.249 | 45 | 100 | n.d. |
| Example 4 | 0.237 | 45 | 96 | 7.5 |
| Example 5 | 0.105 | 45 | 100 | n.d. |
| Example 6 | 0.077 | 45 | 100 | n.d. |
| Example 7 | 0.081 | 29 | 100 | n.d. |
| Example 8 | 0.081 | 40 | 100 | n.d. |
| Example 9 | 0.036 | 45 | 98 | 10 |
| Example 10 | 0.031 | 45 | 96 | 10.3 |
| Example 11 | 0.084 | 4.3 | 21 | 6.2 |
| Example 12 | 0.075 | 45 | 100 | 7.0 |
| Example 13 | 0.136 | 45 | 100 | 5.1 |
| Example 14 | 0.748 | 45 | 100 | 8.6 |
| Example 15 | 0.255 | 23 | 96 | 5.3 |
| Example 16 | 0.158 | 45 | 100 | n.d. |
| Example 17 | 1.642 | 12 | 58 | 3.1 |
| Example 18 | 1.666 | 0 | 87 | n.d. |
| Example 19 | 0.754 | 8 | 88 | 4.3 |
| Example 20 | 0.355 | 45 | 100 | 10.4 |
| Example 21 | 1.324 | 6.3 | 9 | 2.9 |
| Example 22 | 0.297 | 45 | 97 | 8.8 |
| Example 23 | 1.038 | 10 | 11 | 3.1 |
| Example 24 | 0.006 | 26.9 | 81 | n.d. |
| Example 25 | 0.067 | 45 | 100 | n.d. |
| Example 26 | 1.070 | 8 | 57 | n.d. |
| Example 27 | 0.910 | 3 | 13 | n.d. |
| Example 28 | 0.100 | 2 | 12 | n.d. |
| Example 29 | 1.323 | 37 | 96 | 2.8 |
| Example 30 | 0.307 | 5.3 | 17 | n.d. |
| Example 31 | 0.072 | 45 | 100 | n.d. |
| Example 32 | 1.121 | 45 | 100 | n.d. |
| Example 33 | 0.920 | 45 | 100 | n.d. |
| Example 34 | 1.895 | 45 | 100 | n.d. |
| Example 35 | 0.413 | 45 | 100 | n.d. |
| Example 36 | 0.120 | 39 | 100 | n.d. |
| Example 37 | 0.183 | 44 | 100 | n.d. |
| Example 38 | 0.139 | 45 | 100 | 4.2 |
| Example 39 | 0.039 | 45 | 100 | 7.8 |
| Example 40 | 0.078 | 45 | 100 | 7.5 |
| Example 41 | 0.130 | 45 | 100 | 7.3 |
| Example 42 | 0.153 | 6 | 100 | 7.2 |
| Example 43 | 0.049 | 19 | 100 | 7.6 |
| Example 44 | 0.176 | 45 | 100 | 10.5 |
| Example 45 | 0.243 | 14 | 100 | 3.3 |
| Example 46 | 0.095 | 7 | 8 | n.d. |
| Example 47 | 0.136 | 12 | 69 | n.d. |
| Example 48 | 0.204 | 8.3 | 27 | n.d. |
| Example 49 | 0.169 | 45 | 100 | 6.8 |
| Example 50 | 0.118 | 45 | 100 | 4.8 |
| Example 51 | 0.148 | 45 | 100 | 5.7 |
| Example 52 | 0.289 | 45 | 100 | 6.3 |
| Example 53 | 0.099 | 3.7 | 83 | 2.5 |
| Example 54 | 1.629 | n.d. | n.d. | n.d. |
| Example 55 | 1.090 | n.d. | n.d. | n.d. |
| Example 56 | 0.192 | 45 | 100 | 8.1 |
| Example 57 | 0.070 | 3.3 | 65 | 7.9 |
| Example 58 | 0.134 | 8 | 100 | 7.3 |
| Example 59 | 0.682 | n.d. | n.d. | n.d. |
| Example 60 | 0.517 | n.d. | n.d. | n.d. |
| Example 61 | 0.156 | 45 | 100 | 6.2 |
| Example 62 | 0.080 | 45 | 89 | 5.6 |
| Example 63 | 0.088 | 45 | 100 | 4.1 |
| Example 64 | 0.176 | 45 | 100 | 5.1 |
| Example 65 | 0.362 | n.d. | n.d. | 7.8 |
| Example 66 | 0.395 | 10.3 | 74 | 8.3 |
| Example 67 | 0.231 | n.d. | n.d. | 7.4 |
| Example 68 | 0.357 | 13.7 | 26 | 5.6 |
| Example 69 | 0.071 | 45 | 96 | 8.2 |
| Example 70 | 0.140 | 21 | 88 | 7.6 |
| Example 71 | 0.072 | 45 | 95 | n.d. |
| Example 72 | 0.016 | 7 | 81 | 6.1 |
| Example 73 | 0.106 | 0 | 29 | n.d. |
| Example 74 | 0.109 | 0 | 5 | n.d. |
| Example 75 | 0.402 | 45 | 100 | 3.6 |
| Example 76 | 0.268 | 45 | 93 | 5.5 |
| Example 77 | 0.812 | 45 | 96 | 4.1 |
| Example 78 | 0.134 | 36.6 | 93 | 4.3 |
| Example 79 | 0.189 | 45 | 92 | 3.8 |
| Example 80 | 0.126 | 45 | 94 | 4.5 |
| Example 81 | 0.017 | 45 | 96 | n.d. |
| Example 82 | 0.025 | n.d. | n.d. | n.d. |
| Example 83 | 0.016 | 45 | 96 | 10.3 |
| Example 84 | 0.022 | 45 | 96 | 10.7 |
| Example 85 | 0.039 | 45 | 100 | 7.4 |
| Example 86 | 0.343 | 45 | 94 | 3.7 |

TABLE 1-continued

In vitro data on receptor binding, ThT assay lag time and recovery at pH 7.5 and chemical stability at pH 8.15

| Compound | Assay(I) Glucagon [EC50] (nM) | ThT assay [Lagtime] (h) | ThT assay [Recovery] (%) | Chemical stability [Purity loss/ 14 days 37 C.] (%) |
|---|---|---|---|---|
| Example 87 | 0.253 | 45 | 90 | 5.8 |
| Example 88 | 0.470 | 25.3 | 73 | 4.7 |
| Example 89 | 0.064 | 45 | 93 | 6.8 |
| Example 90 | 0.090 | 45 | 93 | 5.4 |
| Example 91 | 0.027 | 6.3 | 5 | n.d. |
| Example 92 | 0.066 | 13 | 53 | 6.5 |
| Example 93 | 0.017 | 45 | 100 | 14 |
| Example 94 | 0.029 | 45 | 100 | 8.8 |
| Example 95 | 0.009 | 45 | 34 | 5.1 |
| Example 96 | 0.062 | 45 | 100 | 4.5 |
| Example 97 | 0.026 | 1 | 3 | n.d. | n.d.: not determined

TABLE 2

Half-life of glucagon analogues in minipigs

| Example | iv PK minipig [T½] (h) |
|---|---|
| Example 13 | 76.4 |
| Example 15 | 77.4 |
| Example 16 | 86.6 |
| Example 24 | 4.1 |
| Example 25 | 59.6 |
| Example 38 | 83.0 |
| Example 63 | 63.7 |
| Example 80 | 60.9 |

Assay (III)
GLP-1 Activity

The GLP-1 receptor is cloned into HEK-293 cells having a membrane bound cAMP biosensor (ACTOne™). The cells (14000 per well) is incubated (37° C., 5% CO2) overnight in 384-well plates. Next day the cells are loaded with a calcium responsive dye that only distributed into the cytoplasm. Probenecid, an inhibitor of the organic anion transporter, is added to prevent the dye from leaving the cell. A PDE inhibitor is added to prevent formatted cAMP from being degraded. The plates are placed into a FLIPRTETRA and the glucagon analogues are added. End point data are collected after 6 minutes. An increase in intracellular cAMP is proportional to an increased in calcium concentrations in the cytoplasm. When calcium is bound the dry a fluorescence signal is generated. EC50-values are calculated in Prism5.

Assay (IV)
LOCI Assay

Samples are analyzed for peptide using Luminescence Oxygen Channeling Immunoassay (LOCI). The donor beads are coated with streptavidin, while acceptor beads are conjugated with a monoclonal antibody (1F120) specific for glucagon. The other glucagon-binding monoclonal antibody (2F7) is biotinylated. Three reactants are combined with the analyte and form a two-sited immuno-complex. Illumination of the complex released singlet oxygen atoms from the donor beads. They are channeled into the acceptor beads and triggered chemiluminescence which is measured in the EnVision plate reader. The amount of emitted light is proportional to the concentration of peptide.

One μL sample/calibrator/control is applied to the wells of 384-well LOCI plates followed by a 15 μL mixture of the antibody-coated acceptor beads (0.5 μg/well) and the biotinylated antibody. The plates are incubated for 1 h at 21-22° C. Then 30 μL the streptavidin-coated donor-beads (2 μg/well) are added to each well and incubated for 30 minutes at 21-22° C. The plates are red in an Envision plate reader at 21-22° C. with a filter having a bandwidth of 520-645 nm after excitation by a 680 nm laser. The total measurement time per well is 210 ms including a 70 ms excitation time.

Assay (V)
Body Weight Loss in Diet Induced Obese Rats

Sixtyfour high fat (Research Diet D12492) fed and eight low fat (Research Diet D12450B) fed Sprague Dawley rats from Taconic Europe are used for this study. The rats should weigh app. 970 g and 730 g, respectively before dosing. Rats should have ad libitum access to water and be housed individually to allow daily monitoring of food intake. Lights are turned off from 10 AM to 10 PM.

Rats are divided into groups of eight and dosed subcutaneously (sc) once daily with two test substances for 15 days, dose volume is 0.5 ml/kg. Before dosing is initiated rats are handled daily and trained for sc. dosing for 5 days.

At the 5$^{th}$ dosing day the doses of glucagon analogue are adjusted from 30 nmol/kg to 3 nmol/kg and from 300 nmol/kg to 30 nmol/kg due to the dramatic weight loss curve experienced in the rats.

At day 11 the rats are subjected to a blood glucose profiling. Rats are terminated either at day 15 or day 16, and blood is sampled for measurement of insulin and cholesterol.

Assay (VI)
Experimental Protocol for Efficacy Testing on Appetite with a Glucagon Derivative, Using an Ad Libitum Fed Rat Model Sprague Dawley (SD) rats from Taconic Europe, Denmark are used for the experiments. The rats have a body weight 200-250 g at the start of experiment. The rats arrive 14 days before start of experiment to allow acclimatization to experimental settings. During this period the animals are handled two times. After arrival rats are housed individually for one week in a reversed light/dark phase (meaning that lights are off during day time and on during night time) for two weeks. Since rats are normally active and eat their major part of their daily food intake during the dark period, rats are dosed in the morning right before lights are turned off. This set-up results in the lowest data variation and highst test sensitivity. The experiment is conducted in the rats' home cages and rats have free access to food and water throughout the acclimatization period and the experiment period. Each dose of derivative is tested in a group of 5 rats. A vehicle group of 6-7 rats is included in each set of testing. Rats are dosed once according to body weight with a 0.01-3 mg/kg solution administered subcutaneously (sc.). After dosing, the rats are returned to their home cages, where they have access to food and water. The food consumption is recorded individually continuously by on-line registration or manually every hour for 7 hours, and then after 24 h and again after 48 h. At the end of the experimental session, the animals are euthanised.

The individual data are recorded in Microsoft excel sheets. Outliers are excluded after applying the Grubbs statistical evaluation test for outliers. Data are reported as acumulated food intake as functions of time. Comparisons are made between vehicle group and test groups using Student's t-test or one-way ANOVA.

Assay (VII)
DPP-IV Stability Assay

10 μM of peptide is incubated with DPP-IV (2 μg/ml) in duplicate at 37° C. in a HEPES buffer to which 0.005%

Tween20 is added. In the experiment human GLP-1 is used as a positive control. Aliqouts of sample are taken at 3, 15, 30, 60, 120 and 240 min and three volumes of ethanol are added to stop the reaction. The samples are analysed by LC-MS for parent peptide. Data are plotted according to $1^{st}$ kinetics and the stability is reported as half-lives.

Assay (VIII)

PK Profile

Fifteen male rats (Sprague Dawley, 400 g, Taconic Europe) are divided into three groups of five rats. The rats are dosed at t=0 with either 15 nmol/kg IV, 30 nmol/kg SC, or 100 nmol/kg, respectively. The IV dosing is performed via the tail vein while the rats were shortly under isoflurane anaesthesia. Blood samples are obtained via the sublingual vein at times t=−15 min, 5 min (only IV dosed rats), 15 min, 30 min, 1 h, 1½ h, 2 h, 4 h, 6 h, 12 h, 24 h, 48 h and 72 h. Plasma samples are stored on freeze until analysed by Assay IV.

Assay (IX)

pH Dependent Solubility

The solubility of peptides and proteins depends on the pH of the solution. Often a protein or peptide precipitates at or close to its isoelectric point (pI), at which its net charge is zero. At low pH (i.e. lower than the pI) proteins and peptides are typically positively charged, at pH higher than the pI they are negatively charged.

It is advantageous for a therapeutic peptide if it is soluble in a sufficient concentration at a given pH, which is suitable for both formulating a stable drug product and for administrating the drug product to the patient e.g. by subcutaneous injection.

Solubility versus pH curves are measured as described: a formulation or a peptide solution in water is prepared and aliquots are adjusted to pH values in the desired range by adding HCl and NaOH. These samples are left equilibrating at room temperature for 2-4 days. Then the samples are centrifuged. A small aliquot of each sample is withdrawn for reverse HPLC analysis for determination of the concentration of the proteins in solution. The pH of each sample is measured after the centrifugation, and the concentration of each protein is depicted versus the measured pH.

Assay (X)

Chemical Stability Assessment

Chemical stability of glucagon analogues was investigated by RP-UPLC separation and UV detection. Lyophilized samples were dissolved in buffer (see below for detailed compositions) to a final concentration of 333 µM and a pH of 8.15, and were incubated for 14 days at 5° C. and 37° C. followed by RP-UPLC analysis. Purity was defined as the area percentage of the main peak in relation to the total area of all integrated peaks in each chromatogram. Purity loss after 14 days at 37° C. was determined as the difference in purity between the samples incubated at 5° C. and 37° C., divided by the purity of the sample after incubation for 14 days at 5° C.

RP-UPLC analysis was performed using a Waters BEH130 2.1 mm×150 mm, 1.7 µm column operated at 50° C. and a flow rate of 0.4 mL/min using a mobile phase system consisting of typically A: 50 mM Phosphate, 10 w/w % Acetonitrile pH 3 and B: 80 v/v Acetonitrile. UV-detection was performed at 215 nm. The typical gradient profile used for most of the samples is shown below.

| Time/min. | B |
|---|---|
| Injection | 20 |
| 30 | 50 |
| 31 | 99 |
| 32 | 99 |
| 34 | 20 |
| 35 | 20 |
| 40 | 20 |

For some individual analogues eluting at substantially different retention times compared with the majority of analogues, some adjustments to the gradient profile were made to better enable purity assessment comparison across samples. Also the composition of the channel B mobile phase component was in some of the analyses exchanged for a 90 v/v % Acetonitrile solvent solution in an attempt to better handle carry-over of material from one injection to the next in the sequence. This was however compensated for by recalculating the gradient profile appropriately.

Buffer:
50 mM Dinatriumphosphatdihydrat
184 mM Propylenglycol
58 mM Phenol
pH adjusted to 8.15 with $H_3PO_4$. In cases where pH was adjusted to 8.15 after re-suspension of analogues, 0.2 M NaOH was used.

Assay (XI)

Pharmacokinetic Study in Minipigs

The purpose of this study is to determine the pharmacokinetic properties in vivo of the glucagon derivatives after i.v. administration to minipigs. This is done in a pharmacokinetic (PK) study, whereamong other parameters the terminal half-life and the clearance of the derivative in question is determined. Increasing the terminal half-life and decreasing the clearance means that the compound of study is eliminated slower from the body. For glucagon analogues this entails an extended duration of pharmacological effect.

Male or female Göttingen minipigs were obtained from Ellegaard Göttingen Minipigs (Dalmose, Denmark) approximately 7-14 months of age and weighing from approximately 16-35 kg were used in the studies. The minipigs were housed either individually (pigs with permanent catheters) or in a group and fed restrictedly once or twice daily with SDS minipig diet (Special Diets Services, Essex, UK). In some studies two permanent central venous catheters were implanted in vena cava caudalis or cranialis in each animal after at least 2 weeks of acclimatisation. The animals were allowed 1 week recovery after the surgery, and were then used for repeated pharmacokinetic studies with a suitable wash-out period between successive glucagon derivative dosings. In other studies the animals acclimatized for 1 week, after which they were used for repeated pharmacokinetic studies with a suitable wash-out period between successive glucagon derivative dosings. On each dosing occasion these pigs were instrumented with a venflon in one ear vein through which the derivatives were dosed. Blood sampling was done by venipuncture in v. jugularis or v. cava cranialis The animals were either unfasted or fasted for approximately 18 h before dosing and from 0 to 4 h after dosing, but had ad libitum access to water during the whole period.

The glucagon derivatives were usually dissolved in 50 mM sodium phosphate, 145 mM sodium chloride, 0.05% tween 80, pH 7.4 to a concentration of usually from 20-60 nmol/ml. Intravenous injections (the volume corresponding to usually 2-3 nmol/kg, for example 0.1 ml/kg) of the compounds were given through one catheter or through the venflon, and blood was sampled at predefined time points for up till 13 days post dosing (preferably through the other catheter or by venipuncture). Blood samples (for example 0.8 ml) were collected in tubes with EDTA buffer (8 mM) (sometimes aprotinin 500 KIU/ml blood was added) and then centrifuged at 4° C. and 1942 G for 10 minutes. Plasma was pippetted into Micronic tubes on dry ice, and kept at −20° C. until analyzed for plasma concentration of the respective glucagon derivative using an appropriate quantitative assay like ELISA or LC-MS. Based on these measurements, time-plasma concentration profiles for the compound of study are plotted and a so-called non-compartmental pharmacokinetic analysis of the data is performed in WinNonlin v. 5.0 or Phoenix v. 6.2 (Pharsight Inc., Mountain View, Calif., USA) or other relevant software for PK analysis. For most compounds, the terminal part of the plasma-concentration profiles will be linear when drawn in a semi-logarithmic plot, reflecting that after the initial distribution, drug is removed from the body at a constant fractional rate. The rate (lambda Z or is equal to minus the slope of the terminal part of the plot. From this rate, also the terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance is defined as the dose (D) divided by area under the curve (AUC) on the plasmaconcentration versus time profile (Rowland, M and Tozer T N: Clinical Pharmacokinetics: Concepts and Applications, $3^{rd}$ edition, 1995 Williams Wilkins)

Assay (XII)
Effect of Glucagon Analogues on Body Weight in Diet-Induced Obesity (DIO) Rats The purpose of this assay is to asses the effect of glucagon analogues on body weight in diet-induced obesity (DIO) rats.

In brief, rats were fed a high fat diet for 10 weeks and obtained body weights of approximately 600 g. The DIO rats were then administered a daily subcutaneous dose of a glucagon analogue for three weeks. The body weight was measured each day in connection to the dosing.

Male Sprague Dawley rats, Taconic (Denmark), with a weight of approximately 325 g at arrival were housed three per cage and were provided ad libitum access to high fat diet (Research Diets, R12492, 60% calories from fat) and water. After 4 weeks on the high fat diet, the animals were randomised to be housed two per cage and after another week, a one-week study was initiated with daily subcutaneous dosing of glucagon analogues. Thereafter, the animals received four weeks of washout before the current study was initiated. After the washout period, the animals were randomly divided into 16 groups of 6 rats and one group of 10 rats that constituted the vehicle group. The animals were kept on a 12 hours light-dark cycle throughout the whole period.

The glucagon analogue were dissolved in 50 mM $Na_2HPO_4$, 145 mM NaCl og 0.05% Tween and the DIO rats were administered a daily subcutaneous dose of a glucagon analogue for three weeks (4 o'clock in the afternoon) as 0.5 ml/kg. The body weight was measured daily in connection to the dosing.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A method for treating obesity comprising administering to a patient in need thereof an effective amount of a glucagon peptide selected from the group consisting of

$N^{\epsilon 24}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy] ethoxy]acetyl]amino]butanoyl]-[Val$^{10}$,Leu$^{16}$,Glu$^{21}$,Lys$^{24}$,Leu$^{27}$,Ser$^{28}$]-Glucagon

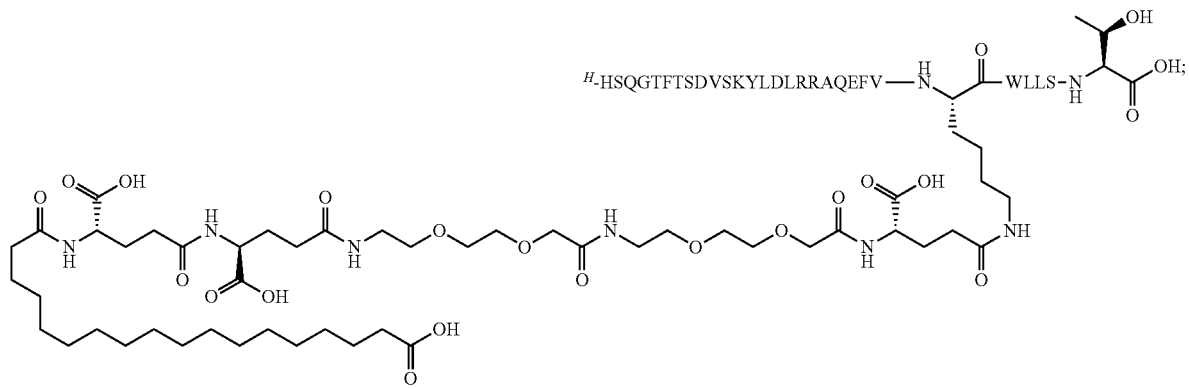

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Leu$^{16}$,Lys$^{24}$,Leu$^{27}$,Ser$^{28}$]-Glucagon

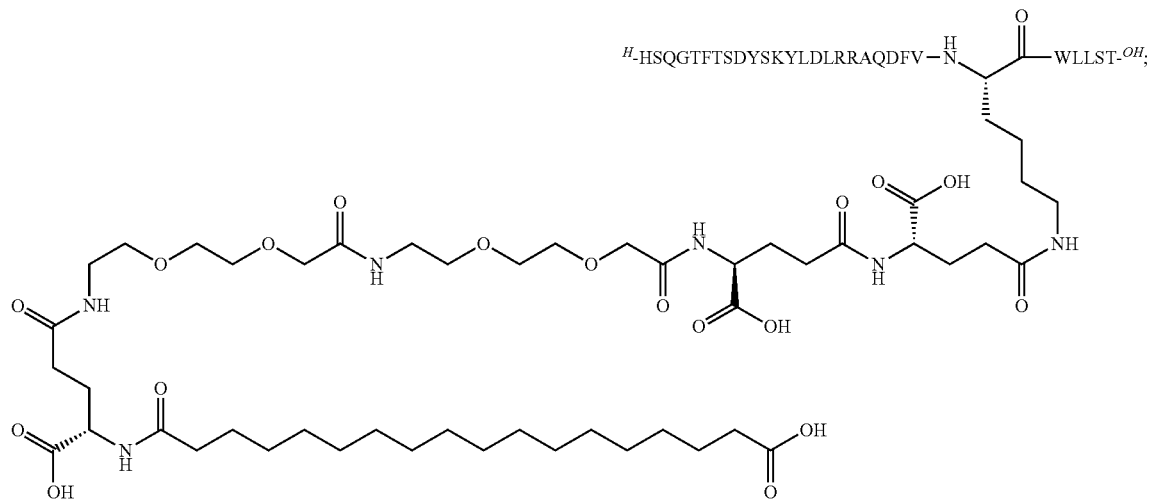

$N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Arg$^{12}$,Ala$^{16}$,Lys$^{24}$,Leu$^{27}$,Ser$^{28}$]-Glucagon

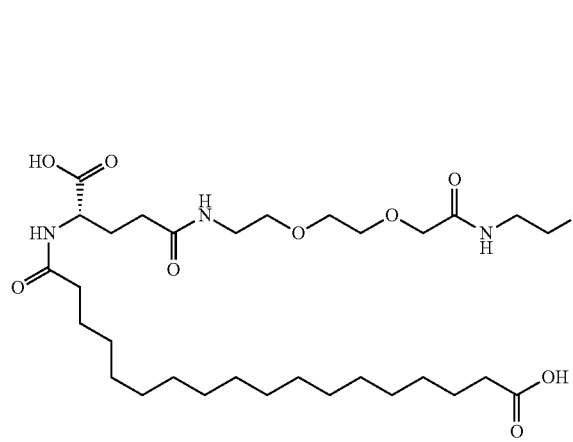

and $N^{\epsilon 24}$-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Leu$^{16}$,Lys$^{24}$,Leu$^{27}$, Ser$^{28}$]-Glucagon

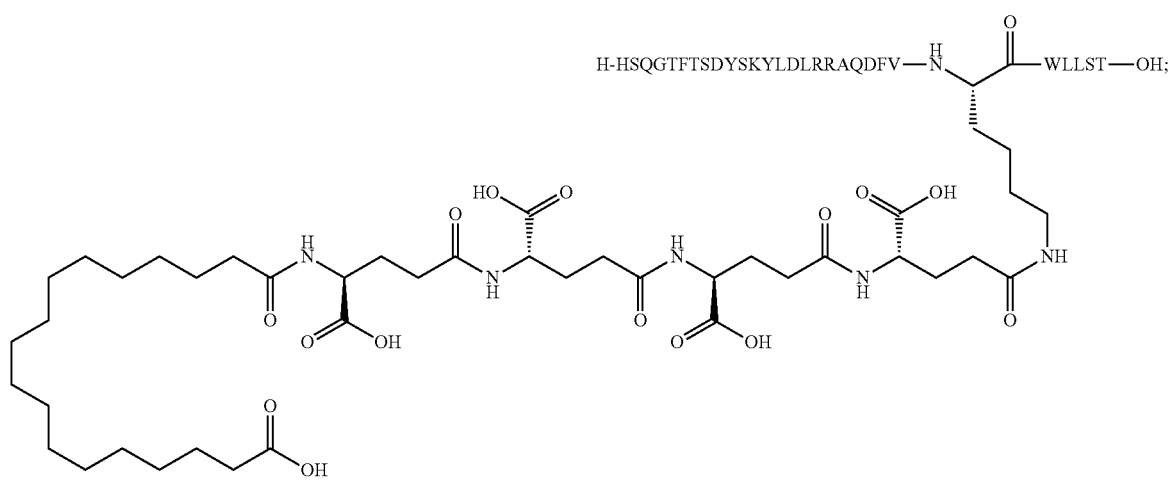

2. The method of claim 1, wherein the glucagon peptide is $N^{\epsilon 24}$-[(4S)-4-carboxy-4-[[2-[2-[2-[[2-[2-[2-[[(4S)-4-carboxy-4-[[(4S)-4-carboxy-4-(17- carboxyheptadecanoylamino)butanoyl]amino]butanoyl]amino]ethoxy]ethoxy]acetyl]amino]ethoxy]ethoxy]acetyl]amino]butanoyl]-[Val$^{10}$,Leu$^{16}$,Glu$^{21}$,Lys$^{24}$,Leu$^{27}$,Ser$^{28}$]-Glucagon

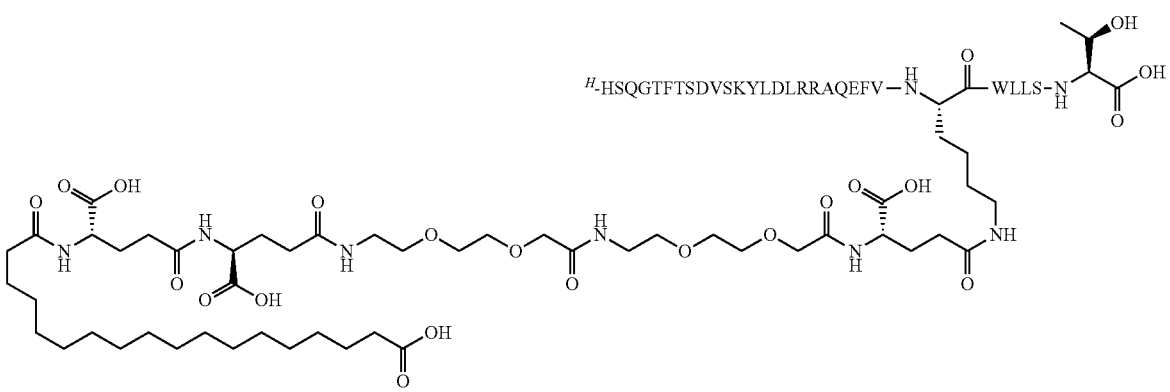

3. The method of claim 2, further comprising administering to the patient a GLP-1 compound selected from the group consisting of
N-epsilon26-((S)-4-Carboxy-4-hexadecanoylamino-butyryl)[Arg34]GLP-1-(7-37):

(compound G1)

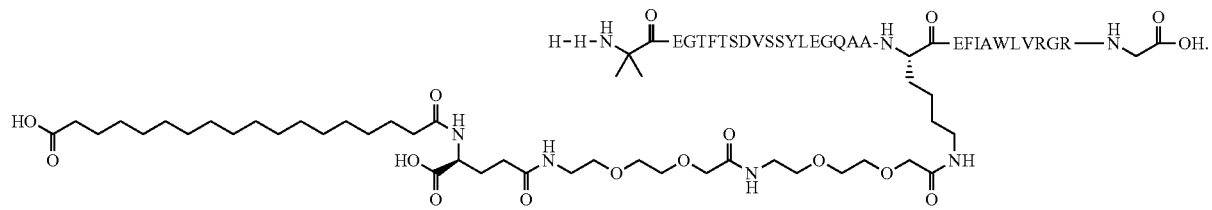

and
N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

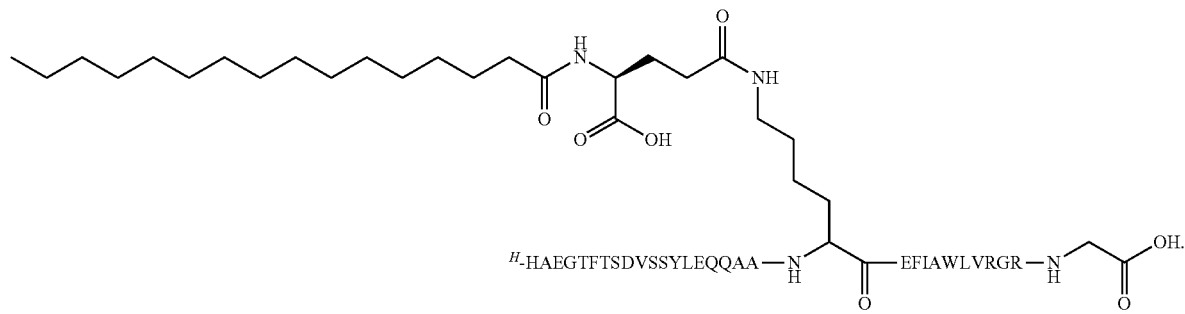

4. The method of claim 3, wherein the GLP-1 compound is N-epsilon26-((S)-4-Carboxy-4-hexadecanoylamino-butyryl)[Arg34]GLP-1-(7-37):

5. The method of claim 3, wherein the GLP-1 compound is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

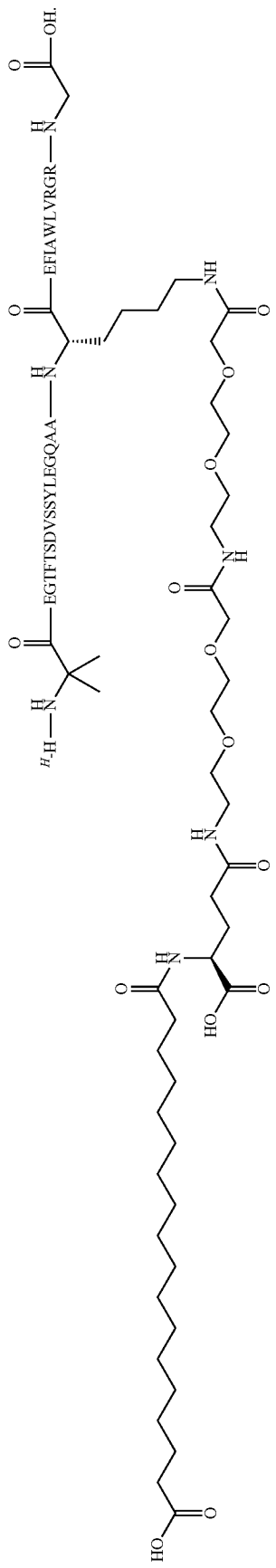

6. The method of claim 1, wherein said glucagon peptide is $N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino) butanoyl]amino]ethoxy]ethoxy]acetyl]amino]ethoxy] ethoxy]acetyl]amino]butanoyl]amino]butanoyl]-[Leu$^{16}$, Lys$^{24}$,Leu$^{27}$,Ser$^{28}$]-Glucagon

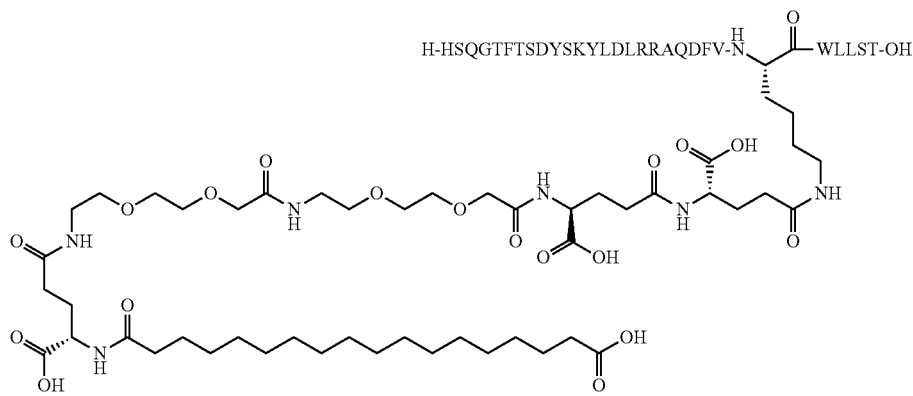

7. The method of claim 6, further comprising administering to the patient a GLP-1 compound selected from the group consisting of
N-epsilon26-((S)-4-Carboxy-4-hexadecanoylamino-butyryl)[Arg34]GLP-1-(7-37):

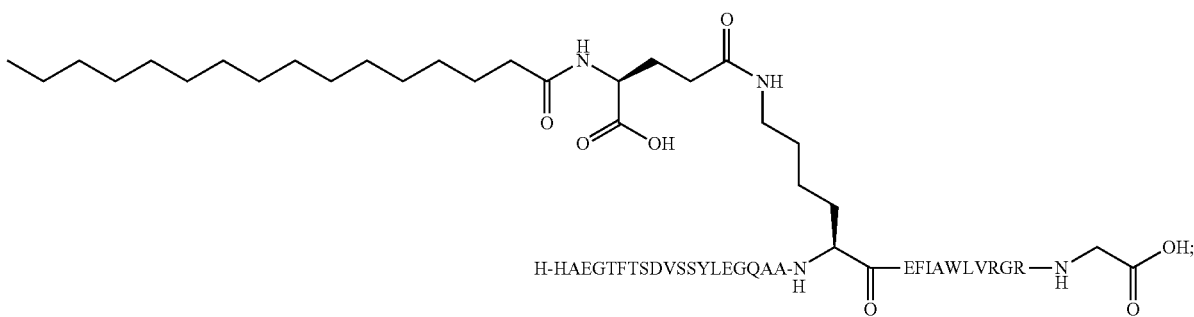

and
N-epsilon26-[2-(2-{2-[2-(2-{2-[(S)-4-Carboxy-4-(17-carboxyheptadecanoylamino)butyrylamino] ethoxy}ethoxy)acetylamino]ethoxy}ethoxy)acetyl] [Aib8,Arg34]GLP-1-(7-37):

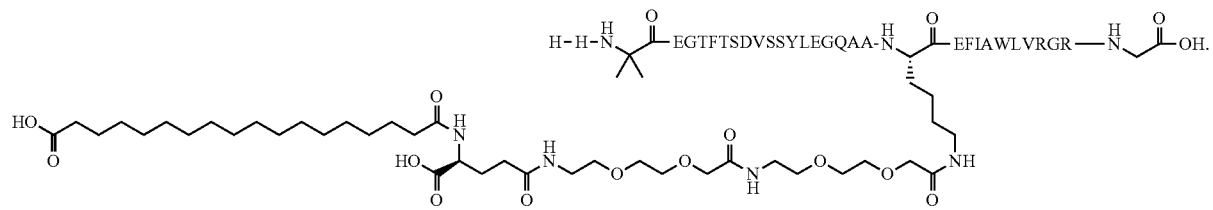

8. The method of claim 7, wherein the GLP-1 compound is N-epsilon26-((S)-4-Carboxy-4-hexadecanoylamino-butyryl)[Arg34]GLP-1-(7-37):
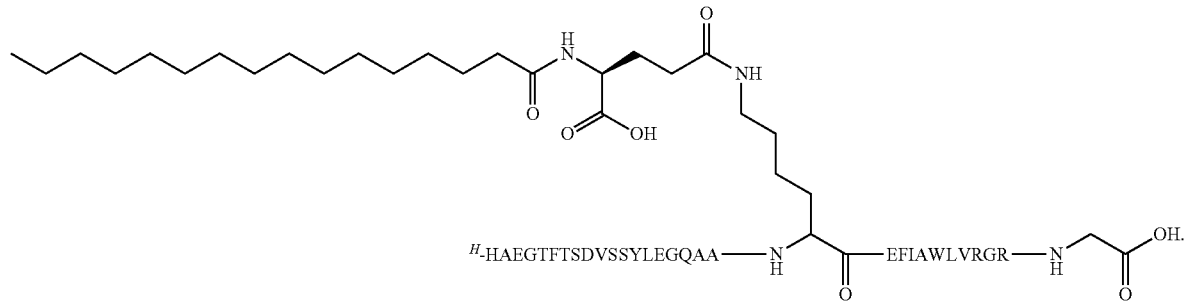
9. The method of claim 7, wherein the GLP-1 compound is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

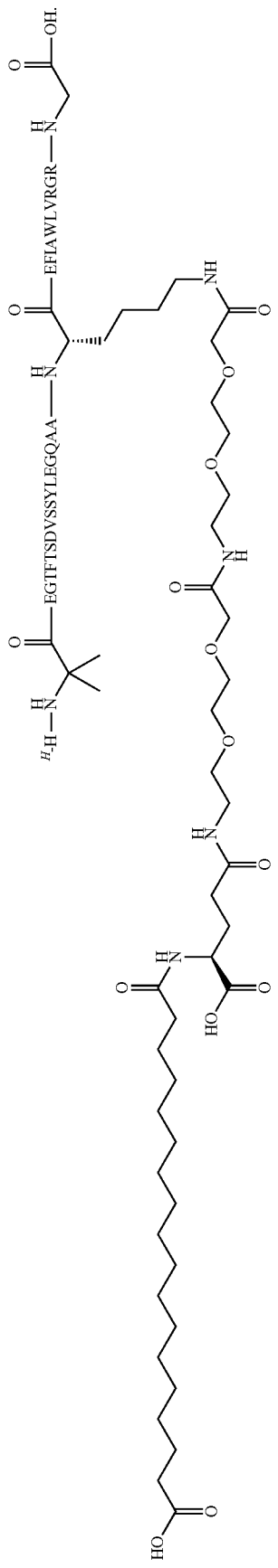

10. The method of claim 1, wherein said glucagon peptide is N^ε24-[(4S)-4-carboxy-4-[[(4S)-4-carboxy-4-[[2-[2-[2-[[2-[2-[2-[[(4S)-4-carboxy-4-(17-carboxyheptadecanoylamino) butanoyl]amino]ethoxy]ethoxy]acetyl]amino]ethoxy] ethoxy]acetyl]amino]butanoyl]amino]butanoyl]-[Arg¹², Ala¹⁶,Lys²⁴,Leu²⁷,Ser²⁸]-Glucagon

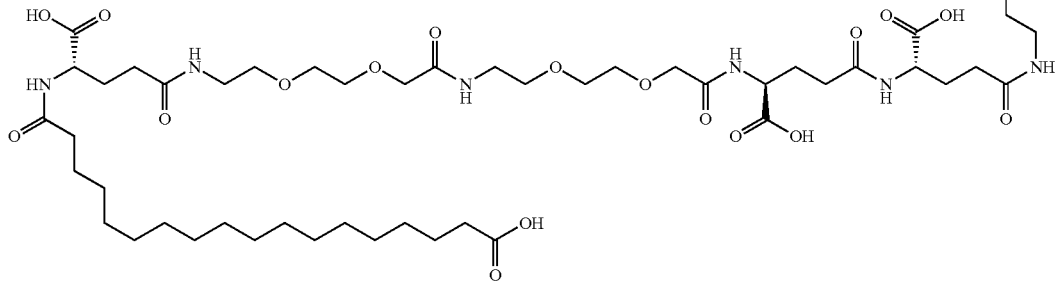

11. The method of claim 10, further comprising administering to the patient a GLP-1 compound selected from the group consisting of
N-epsilon26-((S)-4-Carboxy-4-hexadecanoylamino-butyryl)[Arg34]GLP-1-(7-37):

(compound G1)

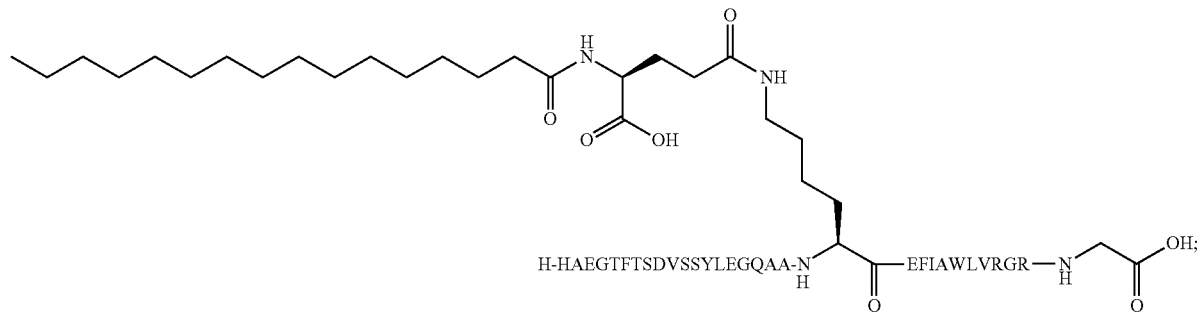

and
N-epsilon26-[2-(2-{2-[2-(2-{2-[(S)-4-Carboxy-4-(17-carboxyheptadecanoylamino)butyrylamino] ethoxy}ethoxy)acetylamino]ethoxy}ethoxy)acetyl] [Aib8,Arg34]GLP-1-(7-37):

(compound G3)

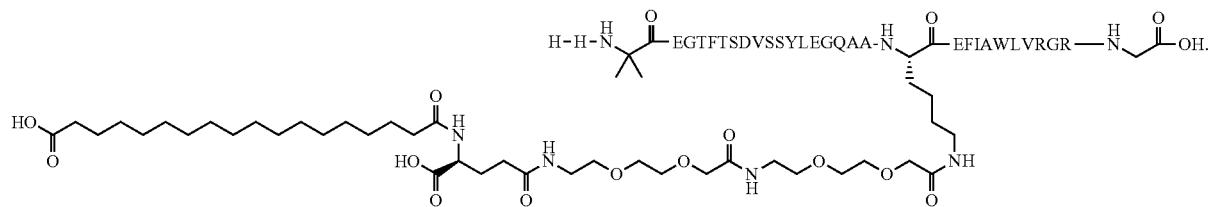

12. The method of claim 11, wherein the GLP-1 compound is N-epsilon26-((S)-4-Carboxy-4-hexadecanoylamino-butyryl)[Arg34]GLP-1-(7-37):
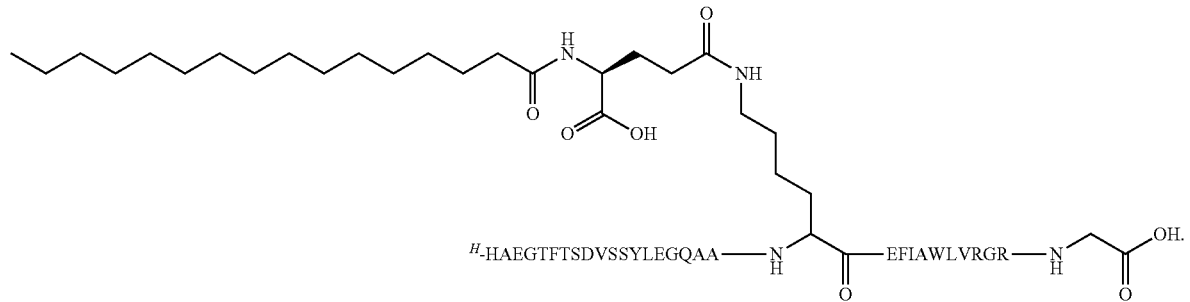
13. The method of claim 11, wherein the GLP-1 compound is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

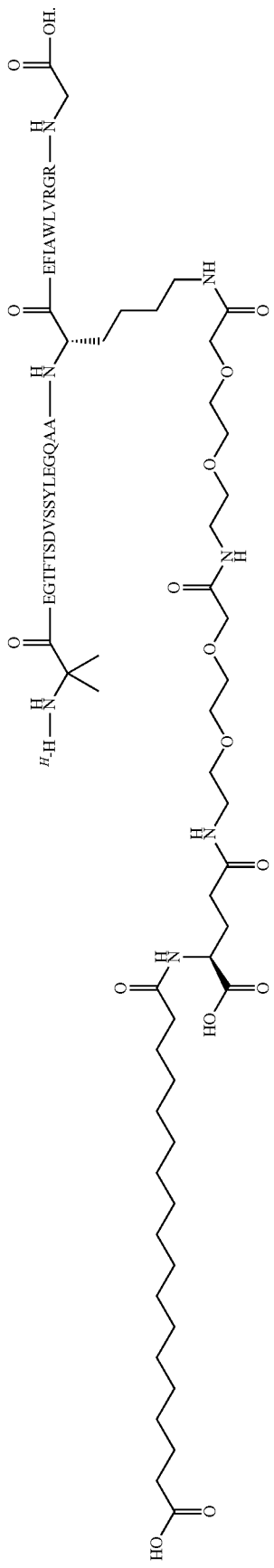

14. The method of claim 1, wherein said glucagon peptide is N^ε24-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Leu16,Lys24,Leu27,Ser28]-Glucagon

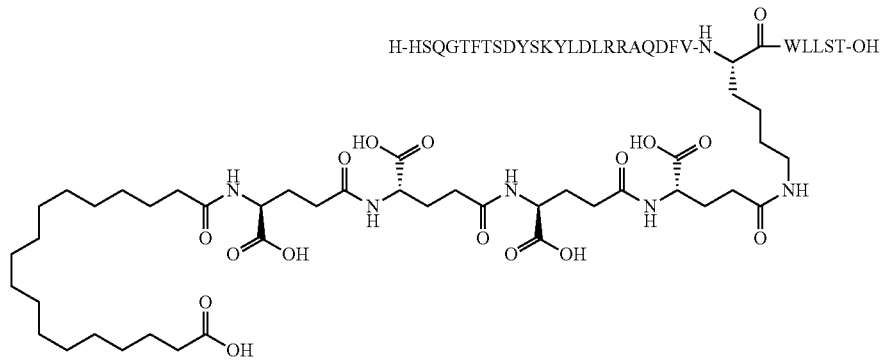

15. The method of claim 14, further comprising administering to the patient a GLP-1 compound selected from the group consisting of
N-epsilon26-((S)-4-Carboxy-4-hexadecanoylamino-butyryl)[Arg34]GLP-1-(7-37):

(compound G1)

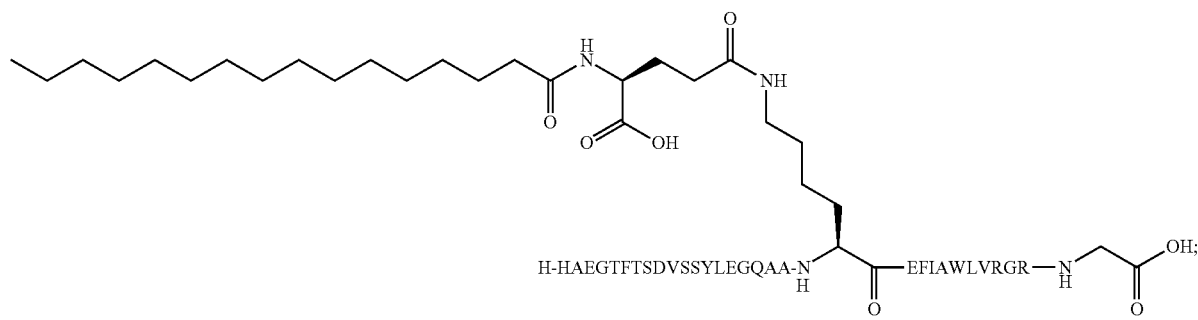

and
N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

(compound G3)

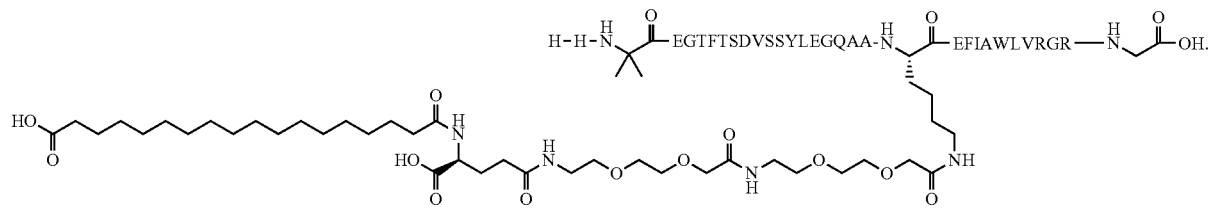

16. The method of claim 15, wherein the GLP-1 compound is N-epsilon26-((S)-4-Carboxy-4-hexadecanoylamino-butyryl)[Arg34]GLP-1-(7-37):
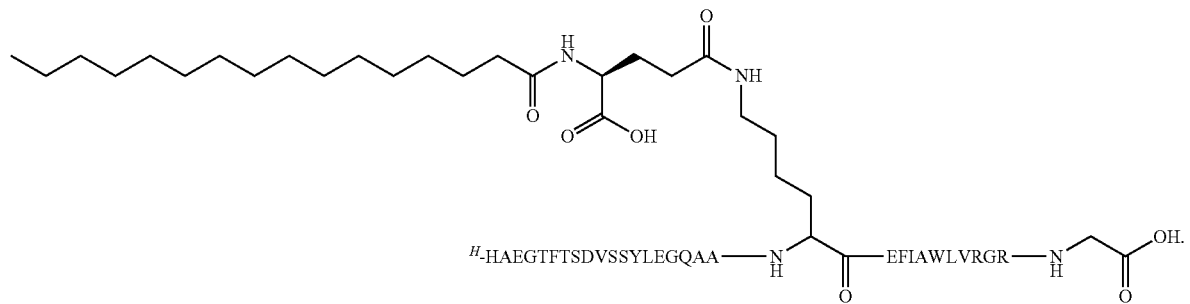
17. The method of claim 15, wherein the GLP-1 compound is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37):

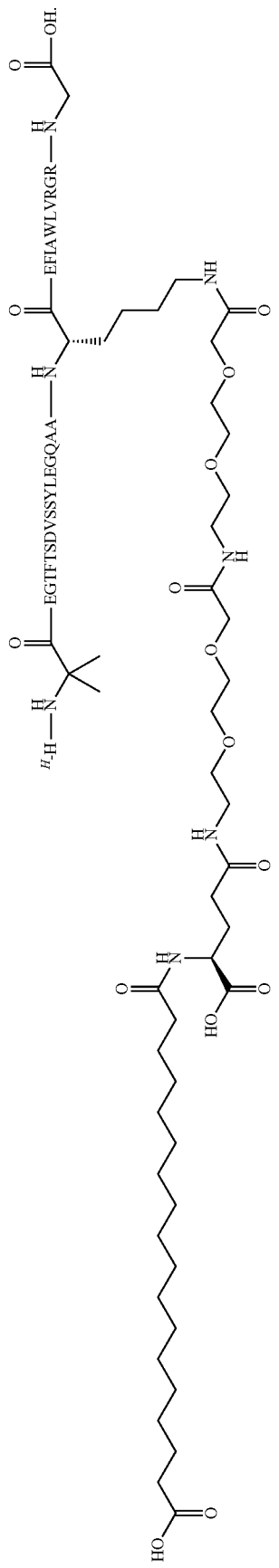

UNITED STATES PATENT AND TRADEMARK OFFICE
CERTIFICATE OF CORRECTION

PATENT NO. : 9,486,506 B2
APPLICATION NO. : 14/629682
DATED : November 8, 2016
INVENTOR(S) : Jesper F. Lau et al.

Page 1 of 1

It is certified that error appears in the above-identified patent and that said Letters Patent is hereby corrected as shown below:

In the Claims

In Column 194, Claim number 4, please replace the formula with the formula below:

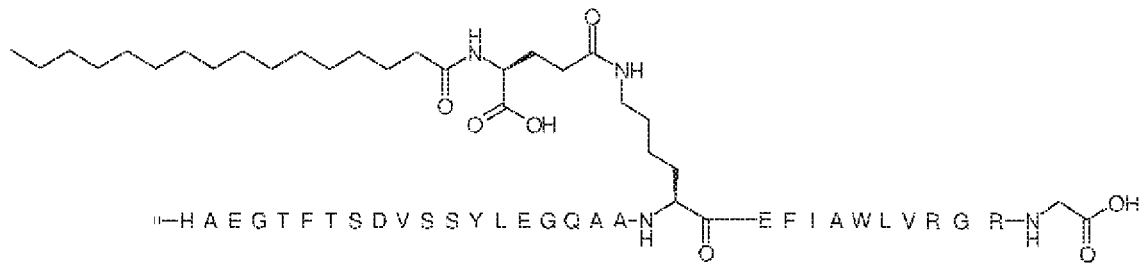

Signed and Sealed this
Twentieth Day of June, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 5

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
```

```
<212> TYPE: PRT
<213> ORGANISM: Heloderma suspectum

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
            35

<210> SEQ ID NO 4
<211> LENGTH: 29
<212> TYPE: PRT
<213> ORGANISM: Homo sapiens
<220> FEATURE:
<221> NAME/KEY: X3
<222> LOCATION: (3)..(3)
<223> OTHER INFORMATION: His
<220> FEATURE:
<221> NAME/KEY: X10
<222> LOCATION: (10)..(10)
<223> OTHER INFORMATION: Val
<220> FEATURE:
<221> NAME/KEY: X12
<222> LOCATION: (12)..(12)
<223> OTHER INFORMATION: Arg
<220> FEATURE:
<221> NAME/KEY: X15
<222> LOCATION: (15)..(15)
<223> OTHER INFORMATION: Glu
<220> FEATURE:
<221> NAME/KEY: X16
<222> LOCATION: (16)..(16)
<223> OTHER INFORMATION: Ala, Ile, Phe, Arg, Thr, Val, Leu, Glu, Trp or
      Tyr
<220> FEATURE:
<221> NAME/KEY: X17
<222> LOCATION: (17)..(17)
<223> OTHER INFORMATION: Lys
<220> FEATURE:
<221> NAME/KEY: X20
<222> LOCATION: (20)..(20)
<223> OTHER INFORMATION: Lys
<220> FEATURE:
<221> NAME/KEY: X21
<222> LOCATION: (21)..(21)
<223> OTHER INFORMATION: Glu
<220> FEATURE:
<221> NAME/KEY: X24
<222> LOCATION: (24)..(24)
<223> OTHER INFORMATION: Lys
<220> FEATURE:
<221> NAME/KEY: X27
<222> LOCATION: (27)..(27)
<223> OTHER INFORMATION: Leu
<220> FEATURE:
<221> NAME/KEY: X28
<222> LOCATION: (28)..(28)
<223> OTHER INFORMATION: Ser, Ile, Gly or Thr
<220> FEATURE:
<221> NAME/KEY: X29
<222> LOCATION: (29)..(29)
<223> OTHER INFORMATION: Val, Leu or Ile

<400> SEQUENCE: 4

His Ser Xaa Gly Thr Phe Thr Ser Asp Xaa Ser Xaa Tyr Leu Xaa Xaa
1               5                   10                  15

Xaa Arg Ala Xaa Xaa Phe Val Xaa Trp Leu Xaa Xaa Xaa
            20                  25

<210> SEQ ID NO 5
```

```
<211> LENGTH: 30
<212> TYPE: PRT
<213> ORGANISM: Homo sapiens
<220> FEATURE:
<221> NAME/KEY: X3
<222> LOCATION: (3)..(3)
<223> OTHER INFORMATION: His
<220> FEATURE:
<221> NAME/KEY: X10
<222> LOCATION: (10)..(10)
<223> OTHER INFORMATION: Val
<220> FEATURE:
<221> NAME/KEY: X12
<222> LOCATION: (12)..(12)
<223> OTHER INFORMATION: Arg
<220> FEATURE:
<221> NAME/KEY: X15
<222> LOCATION: (15)..(15)
<223> OTHER INFORMATION: Glu
<220> FEATURE:
<221> NAME/KEY: X16
<222> LOCATION: (16)..(16)
<223> OTHER INFORMATION: Ala, Ile, Phe, Arg, Thr, Val, Leu, Glu, Trp or
      Tyr
<220> FEATURE:
<221> NAME/KEY: X17
<222> LOCATION: (17)..(17)
<223> OTHER INFORMATION: Lys
<220> FEATURE:
<221> NAME/KEY: X20
<222> LOCATION: (20)..(20)
<223> OTHER INFORMATION: Lys
<220> FEATURE:
<221> NAME/KEY: X21
<222> LOCATION: (21)..(21)
<223> OTHER INFORMATION: Glu
<220> FEATURE:
<221> NAME/KEY: X24
<222> LOCATION: (24)..(24)
<223> OTHER INFORMATION: Lys
<220> FEATURE:
<221> NAME/KEY: X27
<222> LOCATION: (27)..(27)
<223> OTHER INFORMATION: Leu
<220> FEATURE:
<221> NAME/KEY: X28
<222> LOCATION: (28)..(28)
<223> OTHER INFORMATION: Ser, Ile, Gly or Thr
<220> FEATURE:
<221> NAME/KEY: X29
<222> LOCATION: (29)..(29)
<223> OTHER INFORMATION: Val, Leu or Ile
<220> FEATURE:
<221> NAME/KEY: X30
<222> LOCATION: (30)..(30)
<223> OTHER INFORMATION: Pro in this position can be present or absent.
      This peptide can have extra residues on an extension from 1 to 6
      amino acids.

<400> SEQUENCE: 5

His Ser Xaa Gly Thr Phe Thr Ser Asp Xaa Ser Xaa Tyr Leu Xaa Xaa
1               5                   10                  15

Xaa Arg Ala Xaa Xaa Phe Val Xaa Trp Leu Xaa Xaa Xaa Xaa
            20                  25                  30
```